United States Patent
Møller et al.

(10) Patent No.: US 12,209,110 B2
(45) Date of Patent: Jan. 28, 2025

(54) **CHIMERIC PROTEINS FOR INDUCING IMMUNITY TOWARDS INFECTION WITH *S. AUREUS***

(71) Applicant: Evaxion Biotech A/S, Hørsholm (DK)

(72) Inventors: Niels Iversen Møller, Hørsholm (DK); Andreas Holm Mattsson, Hørsholm (DK); Jens Kringelum, Hørsholm (DK)

(73) Assignee: Evaxion Biotech A/S, Hørsholm (DK)

( * ) Notice: Subject to any disclaimer, the term of this patent is extended or adjusted under 35 U.S.C. 154(b) by 106 days.

(21) Appl. No.: 17/816,145

(22) Filed: Jul. 29, 2022

(65) Prior Publication Data

US 2023/0045507 A1 Feb. 9, 2023

Related U.S. Application Data

(62) Division of application No. 16/319,729, filed as application No. PCT/EP2017/068694 on Jul. 24, 2017, now Pat. No. 11,414,464.

(30) Foreign Application Priority Data

Jul. 22, 2016 (EP) .................... 16180748

(51) Int. Cl.
  *A61K 39/085* (2006.01)
  *A61K 39/00* (2006.01)
  *A61P 31/04* (2006.01)
  *C07K 14/31* (2006.01)

(52) U.S. Cl.
  CPC ............ *C07K 14/31* (2013.01); *A61K 39/085* (2013.01); *A61P 31/04* (2018.01); *A61K 39/00* (2013.01); *A61K 2039/55505* (2013.01); *C07K 2319/00* (2013.01)

(58) Field of Classification Search
  None
  See application file for complete search history.

(56) References Cited

U.S. PATENT DOCUMENTS

| | | |
|---|---|---|
| 4,684,611 A | 8/1987 | Schilperoort et al. |
| 4,879,236 A | 11/1989 | Smith et al. |
| 4,952,500 A | 8/1990 | Finnerty et al. |
| 5,302,523 A | 4/1994 | Coffee et al. |
| 5,322,783 A | 6/1994 | Tomes et al. |
| 5,384,253 A | 1/1995 | Krzyzek et al. |
| 5,464,765 A | 11/1995 | Coffee et al. |
| 5,538,877 A | 7/1996 | Lundquist et al. |
| 5,538,880 A | 7/1996 | Lundquist et al. |
| 5,550,318 A | 8/1996 | Adams et al. |
| 5,563,055 A | 10/1996 | Townsend et al. |
| 5,580,859 A | 12/1996 | Felgner et al. |
| 5,589,466 A | 12/1996 | Felgner et al. |
| 5,591,616 A | 1/1997 | Hiei et al. |
| 5,610,042 A | 3/1997 | Chang et al. |
| 5,656,610 A | 8/1997 | Shuler et al. |
| 5,702,932 A | 12/1997 | Hoy et al. |
| 5,736,524 A | 4/1998 | Content et al. |
| 5,780,448 A | 7/1998 | Davis |
| 5,789,215 A | 8/1998 | Berns et al. |
| 5,871,986 A | 2/1999 | Boyce |
| 5,925,565 A | 7/1999 | Berlioz et al. |
| 5,935,819 A | 8/1999 | Eichner et al. |
| 5,945,100 A | 8/1999 | Fick |
| D417,274 S | 11/1999 | Selman |
| 5,981,274 A | 11/1999 | Tyrrell et al. |
| 5,994,624 A | 11/1999 | Trolinder et al. |
| 6,319,248 B1 | 11/2001 | Nahon |
| 6,645,205 B2 | 11/2003 | Ginn |
| 6,719,684 B2 | 4/2004 | Kim et al. |
| D506,550 S | 6/2005 | Greenberg |
| D575,399 S | 8/2008 | Matsumoto et al. |
| 8,088,063 B2 | 1/2012 | Fujikura et al. |
| D692,143 S | 10/2013 | shahidi bonjar |
| 8,545,853 B2 | 10/2013 | Filee et al. |
| D732,164 S | 6/2015 | Woloszko et al. |
| D810,935 S | 2/2018 | Bresco Torras et al. |
| 2002/0151868 A1 | 10/2002 | Taheri |
| 2006/0264708 A1 | 11/2006 | Horne, Jr. |
| 2008/0214897 A1 | 9/2008 | Matsuo |
| 2008/0269562 A1 | 10/2008 | Marescaux et al. |
| 2009/0182200 A1 | 7/2009 | Golden et al. |
| 2010/0018536 A1 | 1/2010 | Hershey et al. |
| 2011/0112563 A1 | 5/2011 | To et al. |
| 2012/0014983 A1 | 1/2012 | Filee et al. |
| 2013/0172828 A1 | 7/2013 | Kappel |
| 2014/0005639 A1 | 1/2014 | Rogers |
| 2014/0018749 A1 | 1/2014 | Senarith et al. |

(Continued)

FOREIGN PATENT DOCUMENTS

| | | |
|---|---|---|
| EP | 1769068 | 9/2005 |
| EP | 2192172 | 2/2010 |
| EP | 2853599 | 1/2015 |

(Continued)

OTHER PUBLICATIONS

Plotkin, S. et al., "Vaccines", W.B. Saunders Company, (1988).
Skolnick, J. et al., "From genes to protein structure and function: novel applications of computational approaches in genomic era", Trends Biotechnol., vol. 18(1), pp. 34-39, doi: 10.1016/s0167-7799(99)01398-0, (Jan. 2000).
Chen, X. et al., "Fusion protein linkers: property, design and functionality", Advanced Drug Delivery Rev., vol. 65(10), pp. 1357-1369, (2013).
Zhou, H. et al., "An immunogenicity study of a newly fusion protein Cna-FnBP vaccinated against *Staphylococcus aureus* infections in a mice model", Vaccine, vol. 24(22) pp. 4830-4837, XP02801722, (May 2006).

(Continued)

*Primary Examiner* — S. Devi
(74) *Attorney, Agent, or Firm* — McHale & Slavin, P.A.

(57) ABSTRACT

Disclosed is chimeric polypeptides derived from *S. aureus* proteins having SEQ ID NOs: 1-9 and 139-146. The chimeric polypeptides are useful as immunogens for providing protective immunity against *S. aureus* infection. Also disclosed are compositions, methods of treatment and prophylaxis, nucleic acids and vectors comprising the nucleic acids.

24 Claims, 18 Drawing Sheets

Specification includes a Sequence Listing.

(56) References Cited

U.S. PATENT DOCUMENTS

| | | |
|---|---|---|
| 2018/0185058 A1 | 7/2018 | Anand et al. |
| 2020/0000525 A1 | 1/2020 | Stigall et al. |

FOREIGN PATENT DOCUMENTS

| | | |
|---|---|---|
| WO | WO9014837 | 12/1990 |
| WO | WO9409699 | 5/1994 |
| WO | WO9506128 | 3/1995 |
| WO | WO2005081905 | 9/2005 |
| WO | WO2010081875 | 7/2010 |
| WO | WO2012136653 | 10/2012 |

OTHER PUBLICATIONS

Zou, Q. et al., "Evaluation of the protective immunity of a novel subunit fusion vaccine in a murine model of systemic MRSA infection", PLoS ONE, vol. 8(12), p. e81212, XP055414085, (Dec. 2013).

Agger, E. et al., "Catatonic liposomes formulated with synthetic mycobacterial cordfactor (CAF01): a versatile adjuvant for vaccines with different immunological requirements", PLoS ONE, vol. 3(9), p. e3116, (2008).

Yang, L. et al., "Protective efficacy of the chimeric *Staphylococcus aureus* vaccine candidate IC in sepsis and pneumonia models", Scientific Reports, vol. 6(1), pp. 1-13, XP055414062, (Feb. 2016).

Yu, L. et al., "Cross-protective effect of a novel multi-antigen-chimeric vaccine against *Streptococcus* and *Staphylococcus aureus* infection in mice", Journal of Medical Microbiology, vol. 63(pt 12), pp. 1732-1740, XP055414083, (Oct. 2014).

Robinson, H. et al., "DNA Vaccines", Seminars in Immunology, vol. 9(5), pp. 271-283, (1997).

Donnelly, J. et al., "DNA Vaccines", Annual Review of Immunology, vol. 15, pp. 617-648, (Apr. 1997).

David, M. et al., "Community-associated Methicillin-resistant *Staphlococcus aureus*: epidemiology and clinical consequences of an emerging epidemic", Clinical Microbiology Reviews, vol. 23(3), pp. 616-687, (Jul. 2010).

Zhang, F. et al., "Protection against *Staphylococcus aureus* colonization and infection by B- and T-cell-mediated mechanisms", American Society for Microbiology, vol. 9(5), e01949-18, pp. 1-12, (Sep./Oct. 2018).

Greenspan, N. et al., "Defining epitopes: it's not as easy as it seems", Nature Biotechnology, vol. 17, pp. 1-2, (Oct. 1999).

CHIMERIC PROTEINS FOR INDUCING IMMUNITY TOWARDS INFECTION WITH S. AUREUS

CROSS REFERENCE TO RELATED APPLICATIONS

In accordance with 37 C.F.R. § 1.76, a claim of priority is included in an Application Data Sheet filed concurrently herewith. Accordingly, the present invention claims priority as a divisional of U.S. patent application Ser. No. 16/319,729, filed Jan. 22, 2019, now U.S. Pat. No. 11,414,464, which is a § 371 of PCT/EP2017/068694, filed Jul. 24, 2017, which claims the benefit of the priority of the European Patent Application No. 16180748.2, filed Jul. 22, 2016, the contents of each are incorporated herein by reference.

REFERENCE TO AN ELECTRONIC SEQUENCE LISTING

The contents of the electronic sequence listing (4564159DIVSequencelisting.xml; Size: 304 KB; and Date of Creation: Jul. 29, 2022) is herein incorporated by reference in its entirety.

FIELD OF THE INVENTION

The present invention relates to the field of antimicrobial prophylaxis and therapy. In particular the present invention relates to novel recombinant chimeric polypeptides and polynucleotides derived from Staphylococcus aureus. The invention further relates to vectors comprising the polynucleotides, transformed host organisms expressing the polynucleotides, as well as prophylactic and therapeutic uses and methods. Finally, also methods of preparation are part of the invention.

BACKGROUND OF THE INVENTION

Bacterial infections are in most instances successfully treated by administration of antibiotics to patients in need thereof. However, due to careless or thoughtless use of powerful antibiotics, many pathological germs become resistant against antibiotics over time. One threatening example is Staphylococcus aureus. In particular in hospitals this bacterium is of relevance. So-called Methicillln Resistant S. Aureus (MRSA) strains jeopardize patient's survival in hospitals, in particular after surgery.

Vaccination is considered to be a very effective method of preventing infectious diseases in human and veterinary health care. Vaccination is the administration of effective amounts of antigenic material (the vaccine) to produce immunity to a disease/disease-causing pathogenic agent. Vaccines have contributed to the eradication of smallpox, the near eradication of polio, and the control of a variety of diseases, including rubella, measles, mumps, chickenpox, typhoid fever.

Before "the genomic era", vaccines were based on killed or live attenuated, microorganisms, or parts purified from them. Subunit vaccines are considered as a modern upgrade of these types of vaccine, as the subunit vaccines contain one or more protective antigens, which are more or less the weak spot of the pathogen. Hence, in order to develop subunit vaccines, it is critical to identify the proteins, which are important for inducing protection and to eliminate others.

An antigen is said to be protective if it is able to induce protection from subsequent challenge by a disease-causing infectious agent in an appropriate animal model following immunization.

The empirical approach to subunit vaccine development, which includes several steps, begins with pathogen cultivation, followed by purification into components, and then testing of antigens for protection. Apart from being time and labour consuming, this approach has several limitations that can lead to failure. It is not possible to develop vaccines using this approach for microorganisms, which cannot easily be cultured and only allows for the identification of the antigens, which can be obtained in sufficient quantities. The empirical approach has a tendency to focus on the most abundant proteins, which in some cases are not immunoprotective. In other cases, the antigen expressed during in vivo infection is not expressed during in vitro cultivation. Furthermore, antigen discovery by use of the empirical approach demands an extreme amount of proteins in order to discover the protective antigens, which are like finding needles in the haystack. This renders it a very expensive approach, and it limits the vaccine development around diseases, which is caused by pathogens with a large genome or disease areas, which perform badly in a cost-effective perspective.

The present applicant has previously filed patent applications relating to induction of immunity against Staphylococcus aureus. In international patent application publications WO 2012/136653 and WO 2015/053899 and in European patent application No. 16156786.2 are disclosed a number of polypeptides, nucleic acids, vectors, and compositions that are useful as vaccine agents.

OBJECT OF THE INVENTION

It is an object of embodiments of the invention to provide further polypeptides, nucleic acids, vectors, and compositions that are useful as vaccine agents that are able to induce protective immunity against infections with S. aureus. It is also an object of embodiments of the invention to provide useful tools for the recombinant production of such vaccine agents.

SUMMARY OF THE INVENTION

The present invention provides chimeric polypeptides that include antigenic material from several different proteins derived from S. aureus. These chimeric polypeptides are useful as (vaccine) immunogens per se but also in combination with any one of the immunogens disclosed in WO 2012/136653 and/or WO 2015/053899 and/or European patent application No. 16156786.2.

Hence, in a first aspect the present invention relates to a chimeric polypeptide comprising formula I $$a^1\text{-}A^1\text{-}L\text{-}A^2\text{-}a^1 \qquad (I)$$

wherein
  $A^1$ is selected from the group consisting of
    an amino acid sequence constituted by at least or exactly 5 contiguous amino acid residues present in any one of SEQ ID Nos: 1-9 and 139-146, and
    an amino acid sequence with at least 80% sequence identity with an amino acid sequence constituted by at least or exactly 5 contiguous amino acid residues present in any one of SEQ ID Nos: 1-9 and 139-146, A² is selected from the group consisting of
an amino acid sequence constituted by at least or exactly 5 contiguous amino acid residues present in any one of SEQ ID Nos: 1-9 and 139-146, and
an amino acid sequence with at least 80% sequence identity with an amino acid sequence constituted by at least or exactly 5 contiguous amino acid residues present in any one of SEQ ID Nos: 1-9 and 139-146,
L is an optional amino acid sequence,
a¹ is an optional amino acid sequence, and
b¹ is an optional amino acid sequence.

A second aspect of the invention relates to a chimeric polypeptide comprising at least 2 non-identical amino acid sequences, where each of said at least 2 non-identical amino add sequences consists of any one of SEQ ID NOs: 21-40, wherein 0, 1, 2, or 3 amino acid residues can be substituted.

A third aspect of the invention relates to an isolated nucleic acid fragment, which comprises
i) a nucleotide sequence encoding a chimeric polypeptide according to the first or second aspect of the invention as well as any embodiments of these aspects, or
ii) a nucleotide sequence consisting part of any one of SEQ ID NOs: 46-58 and 99-138, or the RNA equivalent thereof, that encodes a chimeric polypeptide,
iii) a nucleotide sequence consisting of at least or exactly or at most 10 consecutive nucleotides in part of any one of SEQ ID NOs: 46-58 and 99-138, or the RNA equivalent thereof, that encodes a chimeric polypeptide,
iv) a nucleotide sequence having a sequence identity of at least 60% with the nucleotide sequence in i) or ii),
v) a nucleotide sequence having a sequence identity of at least 60% with the nucleotide sequence in iii),
vi) a nucleotide sequence complementary to the nucleotide sequence in i)-v), or
vii) a nucleotide sequence which hybridizes under stringent conditions with the nucleotide sequence in i)-vi).

A fourth aspect of the invention relates to a vector comprising the nucleic acid of the third aspect of the invention or of any embodiments of the third aspect, such as a cloning vector or an expression vector.

A fifth aspect of the invention relates to a cell which is transformed so as to carry the vector of 1) the fourth aspect of the present invention or 2) any embodiments of the fourth aspect. Also part of this aspect is a cell line derived from such a transformed cell of the present invention.

A sixth aspect of the invention relates to a pharmaceutical composition comprising a chimeric polypeptide of the first or second aspect of the invention as well as any embodiments of these 2 aspects, a nucleic acid fragment of the third aspect of the invention or the embodiments of the 3$^{rd}$ aspect, a vector of the fourth aspect of the invention or of any embodiments thereof, or a cell of the fifth aspect of the invention and any embodiments of the fifth aspect, and a pharmaceutically acceptable carrier, vehicle or diluent.

A 7$^{th}$ aspects of the invention relates to a method for inducing immunity in an animal by administering at least once an immunogenically effective amount of a chimeric polypeptide of the first or second aspect of the invention as well as of embodiments of these 2 aspects, a nucleic acid fragment of the third aspect of the invention as well as any embodiment of the third aspect, a vector of the fourth aspect of the invention as well as any embodiment of the fourth aspect, a cell of the fifth aspect of the invention as well as any embodiment thereof, or a pharmaceutical composition of the sixth aspect of the invention as well as any embodiment thereof, so as to induce adaptive immunity against *S. aureus* in the animal.

An 8$^{th}$ aspect of the present invention relates to a method for the preparation of the chimeric polypeptide of the first aspect of the invention as well as any embodiment thereof, comprising
culturing a transformed cell of the fifth aspect of the invention as well as embodiments thereof (insofar as these relate to cells expressing the nucleic acid fragment of the invention) under conditions that facilitate that the transformed cell expresses the nucleic acid fragment of the third aspect of the invention and the embodiments thereof and subsequently recovering said chimeric polypeptide, or
preparing said chimeric polypeptide by means of solid or liquid phase peptide synthesis.

Finally, in separate aspect relating to the 7$^{th}$ aspect, the present invention also relates to the chimeric polypeptides of the invention, the nucleic acid or vector of the invention, the cells of the invention, or the pharmaceutical compositions of the invention for use as a pharmaceutical, in particular for use in the treatment, prophylaxis or amelioration of infection with *S. aureus*.

LEGENDS TO THE FIGURE

DETAILED DISCLOSURE OF THE INVENTION

Definitions

Figure 1A:
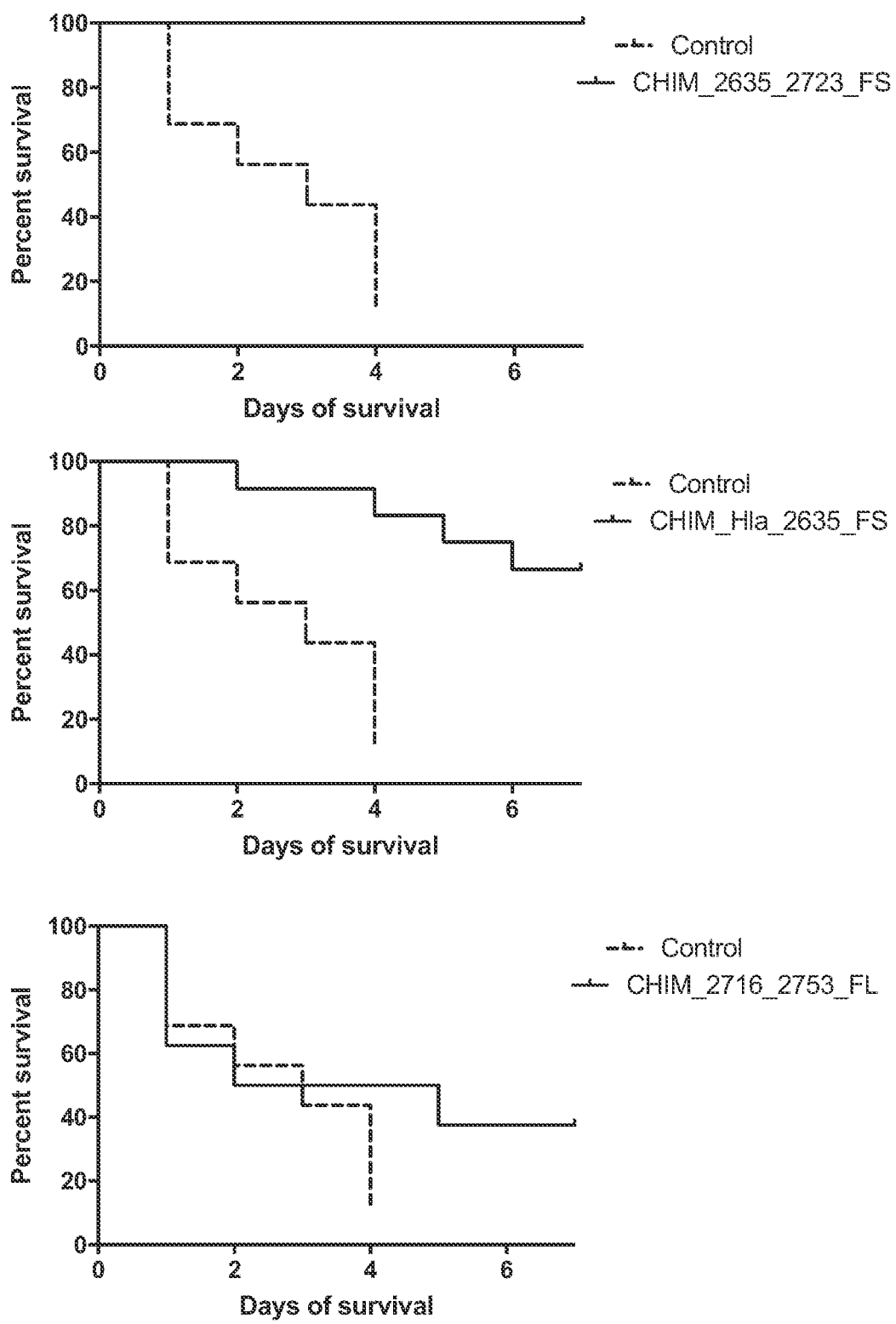
FIG. 1A shows survival plots after challenge infection in mice immunized with immunogens of the invention in a peritonitis model. Dotted lines indicates control, full lines indicates immunogen: Survival plots for CHIM_2635_2723_FS (top plot), CHIM_Hla_2635_FS (middle plot), and CHIM_2716_2753_FL (bottom plot).

The term "polypeptide" is in the present context intended to mean both short peptides of from 2 to 10 amino acid residues, oligopeptides of from 11 to 100 amino acid residues, and polypeptides of more than 100 amino acid residues. Furthermore, the term is also intended to include proteins, i.e. functional biomolecules comprising at least one polypeptide; when comprising at least two polypeptides, these may form complexes, be covalently linked, or may be non-covalently linked.

The polypeptide (s) in a protein can be glycosylated and/or lipidated and/or comprise prosthetic groups.

The term "subsequence" means any consecutive stretch of at least 3 amino acids or, when relevant, of at least 3 nucleotides, derived directly from a reference amino acid sequence or nucleic acid sequence, respectively The term "amino acid sequence" is the order in which amino acid residues, connected by peptide bonds, lie in the chain in peptides and proteins.

The term "adjuvant" or "immunological adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

"Sequence identity" is in the context of the present invention determined by comparing 2 aligned sequences of equal length (e.g. DNA, RNA or amino acid) according to the following formula: $(N_{ref}-N_{dif}) \cdot 100/N_{ref}$, wherein $N_{ref}$ is the number of residues in one of the 2 sequences and $N_{dif}$ is the number of residues which are non-identical in the two sequences when they are aligned over their entire lengths and in the same direction. So, two sequences 5'-ATTCG-GAAC-3' and 5'-ATACGGGAC-3' will provide the sequence identity 77.78% ($N_{ref}=9$ and $N_{dif}=2$). It will be understood that such a sequence identity determination requires that the two aligned sequences are aligned so that there are no overhangs between the two sequences: each amino acid in each sequence will have to be matched with a counterpart in the other sequence.

An "assembly of amino acids" means two or more amino acids bound together by physical or chemical means.

The "3D conformation" is the 3 dimensional structure of a biomolecule such as a protein. In monomeric polypeptides/proteins, the 3D conformation is also termed "the tertiary structure" and denotes the relative locations in 3 dimensional space of the amino acid residues forming the polypeptide.

"An immunogenic carrier" is a molecule or moiety to which an immunogen or a hapten can be coupled in order to enhance or enable the elicitation of an immune response against the immunogen/hapten. Immunogenic carriers are in classical cases relatively large molecules (such as tetanus toxoid, KLH, diphtheria toxoid etc.) which can be fused or conjugated to an immunogen/hapten, which is not sufficiently immunogenic in its own right—typically, the immunogenic carrier is capable of eliciting a strong cellular immune response against the combined substance constituted by the immunogen and the immunogenic carrier, and this in turn provides for improved responses against the immunogen antibody producing cells and cytotoxic cells. More recently, the large carrier molecules have to a certain extent been substituted by so-called promiscuous epitopes, i.e. shorter peptides that are recognized by a large fraction of MHC-haplotypes in a population, and which elicit antigen specific cellular immune responses.

An "immunogen" is a substance of matter which is capable of inducing an adaptive immune response in a host, whose immune system is exposed to the immunogen. As such, immunogens are a subset of the larger genus "antigens", which are substances that can be recognized specifically by the immune system but which are not necessarily capable of inducing immunity an antigen is, however, always capable of eliciting immunity, meaning that a host that has an established memory immunity against the antigen will mount a specific immune response against the antigen.

A "hapten" is a (typically) small molecule, which can neither induce nor elicit an immune response, but if conjugated to an immunogenic carrier, a specific adaptive immune response can be induced against a hapten upon exposure of the immune system with the hapten carrier conjugate.

An "adaptive immune response" is an immune response in response to exposure to an antigen or immunogen, where the immune response is specific for antigenic determinants of the antigen/immunogen—examples of adaptive immune responses are induction of antigen specific antibody production or antigen specific induction/activation of cellular immune responses.

A "protective, adaptive immune response" is an antigen-specific immune response induced in a subject as a reaction to immunization (artificial or natural) with an antigen, where the immune response is capable of protecting the subject against subsequent challenges with the antigen or a pathology-related agent that includes the antigen. Typically, prophylactic vaccination aims at establishing a protective adaptive immune response against one or several pathogens.

"Stimulation of the immune system" means that a substance or composition of matter exhibits a general, non-specific immunostimulatory effect. A number of adjuvants and putative adjuvants (such as certain cytokines) share the ability to stimulate the immune system. The result of using an immunostimulating agent is an increased "alertness" of the immune system meaning that simultaneous or subsequent immunization with an immunogen induces a significantly more effective immune response compared to isolated use of the immunogen.

Hybridization under "stringent conditions" is herein defined as hybridization performed under conditions by which a probe will hybridize to its target sequence, to a detectably greater degree than to other sequences. Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Specificity is typically the function of post-hybridization washes, the critical factors being the ionic strength and temperature of the final wash solution. Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature. Formulas are available in the art for the determination of melting temperatures.

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

"Specific binding" denotes binding between two substances which goes beyond binding of either substance to randomly chosen substances and also goes beyond simple association between substances that tend to aggregate because they share the same overall hydrophobicity or hydrophilicity. As such, specific binding usually involves a combination of electrostatic and other interactions between two conformationally complementary areas on the two substances, meaning that the substances can "recognize" each other in a complex mixture.

The term "vector" is used to refer to a carrier nucleic acid molecule into which a heterologous nucleic acid sequence can be inserted for introduction into a cell where it can be replicated and expressed. The term further denotes certain biological vehicles useful for the same purpose, e.g. viral and bacterial vectors—both these infectious agents are capable of introducing a heterologous nucleic acid sequence into a host and effect subsequence expression of a nucleic acid in the host.

The term "expression vector" refers to a vector containing a nucleic acid sequence coding for at least part of a gene product capable of being transcribed. In some cases, when the transcription product is an mRNA molecule, this is in turn translated into a protein, polypeptide, or peptide.

A "chimeric polypeptide" is a polypeptide as defined above, which is constituted by amino acid stretches derived from at least two different proteins, where these at least two stretches are fused to each other, optionally via a linker. By nature, a chimeric polypeptide does not occur in nature.

A "linker" or "peptide linker" is a stretch of amino acids that are interspersed between two peptides in a fusion polypeptide (such as a chimeric polypeptide). Linkers are widely used in recombinant biotechnology and are reviewed in Chen X et al. (2013), Advanced drug delivery reviews 65(10): 1357-1369. doi:10.1016/j.addr.2012.09.039. Typical linkers are flexible, meaning that they allow the joint polypeptides in a fusion construct to have a high degree of movement. Such flexible linkers are often rich in small, non-polar amino acid residues (such as glycine residues) but will often incorporate small polar amino acid residues such as serine or threonine residues, too. Such linkers are known as GS linkers.

Specific Embodiments of the Invention

The Chimeric Polypeptides of the Invention—the First and Second Aspects of the Invention Chimeric polypeptides of the first aspect of the invention comprise or consist of an amino acid sequence that has the general formula:

$$a^1\text{-}A^1\text{-}L\text{-}A^2\text{-}a^1 \tag{I}$$

This formula is generally defined above in the summary of the invention section. The core of the amino acid sequence is constituted by the 2 amino acid sequences $A^1$ and $A^2$, which are both—independently—derived from SEQ ID NOs: 1-9 and 139-146. L can be either a linker (see below) or absent, the latter meaning that $A^1$ and $A^2$ are joined directly, typically via a peptide bond. Both $a^1$ and $a^2$ are optional and can e.g. constitute various functional amino acid sequences or in certain embodiments amino acid sequences that occur adjacent to SEQ ID NOs: 1-9 or 139-146.

Typically, $A^1$ and $A^2$ are in important embodiments of the first aspect of the invention non-identical and it is preferred that they are not derived from the same sequence among SEQ ID NOs: 1-9 and 139-146.

Thus if $A^1$ is an amino acid sequence constituted by at least or exactly 5 contiguous amino acid residues present in SEQ ID NO: 1 or an amino acid sequence with at least 80% sequence identity with an amino acid sequence constituted by at least or exactly 5 contiguous amino acid residues present in SEQ ID NO: 1, then $A^2$ is an amino acid sequence with at least 80% sequence identity with any one of SEQ ID Nos: 2-9 and 139-146 or an amino acid sequence with at least 80% sequence identity with an amino acid sequence constituted by at least or exactly 5 contiguous amino acid residues present in any one of SEQ ID NOs: 2-9 and 139-146; and if $A^1$ is an amino acid sequence constituted by at least or exactly 5 contiguous amino acid residues present in SEQ ID NO: 2 or an amino acid sequence with at least 80% sequence identity with an amino acid sequence constituted by at least or exactly 5 contiguous amino acid residues present in SEQ ID NO: 2, then $A^2$ is an amino acid sequence constituted by at least or exactly 5 contiguous amino acid residues present in any one of SEQ ID Nos: 1, 3-9, and 139-146 or an amino acid sequence with at least 80% sequence identity with an amino acid sequence constituted by at least or exactly 5 contiguous amino acid residues present in any one of SEQ ID NOs: 1, 3-9, and 139-146; and if $A^1$ is an amino acid sequence constituted by at least or exactly 5 contiguous amino acid residues present in SEQ ID NO: 3 or an amino acid sequence with at least 80% sequence identity with an amino acid sequence constituted by at least or exactly 5 contiguous amino acid residues present in SEQ ID NO: 3, then $A^2$ is an amino acid sequence constituted by at least or exactly 5 contiguous amino acid residues present in any one of SEQ ID Nos: 1, 2, 4-9, and 139-146 or an amino acid sequence with at least 80% sequence identity with an amino acid sequence constituted by at least or exactly 5 contiguous amino acid residues present in any one of SEQ ID NOs: 1, 2, 4-9, and 139-146; and if $A^1$ is an amino acid sequence constituted by at least or exactly 5 contiguous amino acid residues present in SEQ ID NO: 4 or an amino acid sequence with at least 80% sequence identity with an amino acid sequence constituted by at least or exactly 5 contiguous amino acid residues present in SEQ ID NO: 4, then $A^2$ is an amino acid sequence constituted by at least or exactly 5 contiguous amino acid residues present in any one of SEQ ID Nos: 1-3, 5-9, and 139-146 or an amino acid sequence with at least 80% sequence identity with an amino acid sequence constituted by at least or exactly 5 contiguous amino acid residues present in any one of SEQ ID NOs: 1-3, 5-9, and 139-146; and if $A^1$ is an amino acid sequence constituted by at least or exactly 5 contiguous amino acid residues present in SEQ ID NO: 5 or an amino acid sequence with at least 80% sequence identity with an amino acid sequence constituted by at least or exactly 5 contiguous amino acid residues present in SEQ ID NO: 5, then $A^2$ is an amino acid sequence constituted by at least or exactly 5 contiguous amino acid residues present in any one of SEQ ID Nos: 1-4, 6-9, and 139-146 or an amino acid sequence with at least 80% sequence identity with an amino acid sequence constituted by at least or exactly 5 contiguous amino acid residues present in any one of SEQ ID NOs: 1-4, 6-9, and 139-146; and if $A^1$ is an amino acid sequence constituted by at least or exactly 5 contiguous amino acid residues present in SEQ ID NO: 6 or an amino acid sequence with at least 80% sequence identity with an amino acid sequence constituted by at least or exactly 5 contiguous amino acid residues present in SEQ ID NO: 6, then $A^2$ is an amino acid sequence constituted by at least or exactly 5 contiguous amino acid residues present in any one of SEQ ID Nos: 1-5, 7-9, and 139-146 or an amino acid sequence with at least 80% sequence identity with an amino acid sequence constituted by at least or exactly 5 contiguous amino acid residues present in any one of SEQ ID NOs: 1-5 and 7-9 and 139-146; and if $A^1$ is an amino acid sequence constituted by at least or exactly 5 contiguous amino acid residues present in SEQ ID NO: 7 or an amino acid sequence with at least 80% sequence identity with an amino acid sequence constituted by at least or exactly 5 contiguous amino acid residues present in SEQ ID NO: 7, then $A^2$ is an amino acid sequence constituted by at least or exactly 5 contiguous amino acid residues present in any one of SEQ ID Nos: 1-6, 8, 9, and 139-146 or an amino acid sequence with at least 80% sequence identity with an amino acid sequence constituted by at least or exactly 5 contiguous amino acid residues present in any one of SEQ ID NOs: 1-6, 8, 9, and 139-146; and if $A^1$ is an amino acid sequence constituted by at least or exactly 5 contiguous amino acid residues present in SEQ ID NO: 8 or an amino acid sequence with at least 80% sequence identity with an amino acid sequence constituted by at least or exactly 5 contiguous amino acid residues present in SEQ ID NO: 8, then $A^2$ is an amino acid sequence constituted by at least or exactly 5 contiguous amino acid residues present in any one of SEQ ID Nos: 1-7, 9, and 139-146 or an amino acid sequence with at least 80% sequence identity with an amino acid sequence constituted by at least or exactly 5 contiguous amino acid residues present in any one of SEQ ID NOs: 1-7, 9, and 139-146; and if $A^1$ is an amino acid sequence constituted by at least or exactly 5 contiguous amino acid residues present in SEQ ID NO: 9 or an amino acid sequence with at least 80% sequence identity with an amino acid sequence constituted by at least or exactly 5 contiguous amino add residues present in SEQ ID NO: 9, then $A^2$ is an amino acid sequence constituted by at least or exactly 5 contiguous amino acid residues present in any one of SEQ ID Nos: 1-8 and 139-146 or an amino acid sequence with at least 80% sequence identity with an amino acid sequence constituted by at least or exactly 5 contiguous amino acid residues present in any one of SEQ ID NOs: 1-8 and 139-146; and if $A^1$ is an amino acid sequence constituted by at least or exactly 5 contiguous amino acid residues present in SEQ ID NO: 139 or an amino acid sequence with at least 80% sequence identity with an amino acid sequence constituted by at least or exactly 5 contiguous amino acid residues present in SEQ ID NO: 139, then A² is an amino acid sequence constituted by at least or exactly 5 contiguous amino acid residues present in any one of SEQ ID Nos: 1-9 and 140-146 or an amino acid sequence with at least 80% sequence identity with an amino acid sequence constituted by at least or exactly 5 contiguous amino acid residues present in any one of SEQ ID NOs: 1-9 and 140-146; and if A¹ is an amino acid sequence constituted by at least or exactly 5 contiguous amino acid residues present in SEQ ID NO: 140 or an amino acid sequence with at least 80% sequence identity with an amino acid sequence constituted by at least or exactly 5 contiguous amino acid residues present in SEQ ID NO: 140, then A² is an amino acid sequence constituted by at least or exactly 5 contiguous amino acid residues present in any one of SEQ ID Nos: 1-9, 139, and 141-146 or an amino acid sequence with at least 80% sequence identity with an amino acid sequence constituted by at least or exactly 5 contiguous amino acid residues present in any one of SEQ ID NOs: 1-9, 139, and 141-146; and if A¹ is an amino acid sequence constituted by at least or exactly 5 contiguous amino acid residues present in SEQ ID NO: 141 or an amino acid sequence with at least 80% sequence identity with an amino acid sequence constituted by at least or exactly 5 contiguous amino acid residues present in SEQ ID NO: 141, then A² is an amino acid sequence constituted by at least or exactly 5 contiguous amino acid residues present in any one of SEQ ID Nos: 1-9 and 139, 140, and 142-146 or an amino acid sequence with at least 80% sequence identity with an amino acid sequence constituted by at least or exactly 5 contiguous amino acid residues present in any one of SEQ ID NOs: 1-9, 139, 140, and 142-146; and if A¹ is an amino acid sequence constituted by at least or exactly 5 contiguous amino acid residues present in SEQ ID NO: 142 or an amino acid sequence with at least 80% sequence identity with an amino acid sequence constituted by at least or exactly 5 contiguous amino acid residues present in SEQ ID NO: 142, then A² is an amino acid sequence constituted by at least or exactly 5 contiguous amino acid residues present in any one of SEQ ID Nos: 1-9 and 139-141 and 143-146 or an amino acid sequence with at least 80% sequence identity with an amino acid sequence constituted by at least or exactly 5 contiguous amino acid residues present in any one of SEQ ID NOs: 1-9 and 139-141 and 143-146; and if A¹ is an amino acid sequence constituted by at least or exactly 5 contiguous amino acid residues present in SEQ ID NO: 143 or an amino acid sequence with at least 80% sequence identity with an amino acid sequence constituted by at least or exactly 5 contiguous amino acid residues present in SEQ ID NO: 143, then A² is an amino acid sequence constituted by at least or exactly 5 contiguous amino acid residues present in any one of SEQ ID Nos: 1-9 and 139-142 and 144-146 or an amino acid sequence with at least 80% sequence identity with an amino acid sequence constituted by at least or exactly 5 contiguous amino acid residues present in any one of SEQ ID NOs: 1-9 and 139-142 and 144-146; and if A¹ is an amino acid sequence constituted by at least or exactly 5 contiguous amino acid residues present in SEQ ID NO: 144 or an amino add sequence with at least 80% sequence identity with an amino acid sequence constituted by at least or exactly 5 contiguous amino acid residues present in SEQ ID NO: 144, then A² is an amino acid sequence constituted by at least or exactly 5 contiguous amino acid residues present in any one of SEQ ID Nos: 1-9 and 139-143, 145, and 146 or an amino acid sequence with at least 80% sequence identity with an amino acid sequence constituted by at least or exactly 5 contiguous amino acid residues present in any one of SEQ ID NOs: 1-9 and 139-143, 145, and 146; and if A¹ is an amino acid sequence constituted by at least or exactly 5 contiguous amino acid residues present in SEQ ID NO: 145 or an amino acid sequence with at least 80% sequence identity with an amino acid sequence constituted by at least or exactly 5 contiguous amino acid residues present in SEQ ID NO: 145, then A² is an amino acid sequence constituted by at least or exactly 5 contiguous amino acid residues present in any one of SEQ ID Nos: 1-9, 139-144, and 146 or an amino acid sequence with at least 80% sequence identity with an amino acid sequence constituted by at least or exactly 5 contiguous amino acid residues present in any one of SEQ ID NOs: 1-9, 139-144, and 146; and if A¹ is an amino acid sequence constituted by at least or exactly 5 contiguous amino acid residues present in SEQ ID NO: 146 or an amino acid sequence with at least 80% sequence identity with an amino acid sequence constituted by at least or exactly 5 contiguous amino acid residues present in SEQ ID NO: 146, then A² is an amino acid sequence constituted by at least or exactly 5 contiguous amino acid residues present in any one of SEQ ID Nos: 1-9 and 139-145 or an amino acid sequence with at least 80% sequence identity with an amino acid sequence constituted by at least or exactly 5 contiguous amino acid residues present in any one of SEQ ID NOs: 1-9 and 139-145.

As Is clear from the claims, A¹ and A² can be modified independently in formula I but are defined in the same manner.

For instance, A¹ and A² are independently each an amino acid sequence with at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with an amino acid sequence constituted by at least or exactly 5 contiguous amino acid residues present in any one of SEQ ID NOs: 1-9 and 139-146. This applies to all embodiments of the first aspect of the invention discussed above.

Also the at least or exactly 5 contiguous amino acid residues present in any one of SEQ ID NOs: 1-9 and 139-146 in the definition of A¹ and A² are at least or exactly or at most 6, at least or exactly or at most 7, at least or exactly or at most 8, at least or exactly or at most 9, at least or exactly or at most 10, at least or exactly or at most 11, at least or exactly or at most 12, at least or exactly or at most 13, at least or exactly or at most 14, at least or exactly or at most 15, at least or exactly or at most 16, at least or exactly or at most 17, at least or exactly or at most 18, at least or exactly or at most 19, at least or exactly or at most 20, at least or exactly or at most 21, at least or exactly or at most 22, at least or exactly or at most 23, at least or exactly or at most 24, at least or exactly or at most 25, at least or exactly or at most 26, at least or exactly or at most 27, at least or exactly or at most 28, at least or exactly or at most 29, at least or exactly or at most 30, at least or exactly or at most 31, at least or exactly or at most 32, at least or exactly or at most 33, at least or exactly or at most 34, at least or exactly or at most 35, at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least or exactly or at most 54, at least or exactly or at most 55, at least or exactly or at most 56, at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64, at least or exactly or at most 65, at least or exactly or at most 66, at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, at least or exactly or at most 139, at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at most 165, at least or exactly or at most 166, at least or exactly or at most 167, at least or exactly or at most 168, at least or exactly or at most 169, at least or exactly or at most 170, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, or at least or exactly or at most 199 amino acid residues in any one of SEQ ID NOs: 1-9 and 139-146; or the at least or exactly 5 contiguous amino acid residues present in any one of SEQ ID NOs: 2-9 and 139-146 in the definition of $A^1$ and $A^2$ are at least or exactly or at most 200, at least or exactly or at most 201, or at least or exactly or at most 202 amino acid residues in any one of SEQ ID NOs: 2-9 and 139-146; or the at least or exactly 5 contiguous amino acid residues present in any one of SEQ ID NOs: 3-9 and 139-146 in the definition of $A^1$ and $A^2$ are at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most 224, at least or exactly or at most 225, at least or exactly or at most 226, at least or exactly or at most 227, at least or exactly or at most 228, at least or exactly or at most 229, at least or exactly or at most 230, at least or exactly or at most 231, at least or exactly or at most 232, at least or exactly or at most 233, at least or exactly or at most 234, at least or exactly or at most 235, at least or exactly or at most 236, at least or exactly or at most 237, at least or exactly or at most 238, at least or exactly or at most 239, at least or exactly or at most 240, at least or exactly or at most 241, at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253, at least or exactly or at most 254, at least or exactly or at most 255, at least or exactly or at most 256, at least or exactly or at most 257, at least or exactly or at most 258, at least or exactly or at most 259, or exactly or at most 260, at least or exactly or at most 261, at least or exactly or at most 262, at least or exactly or at most 263, at least or exactly or at most 264, at least or exactly or at most 265, at least or exactly or at most 266, at least or exactly or at most 267, at least or exactly or at most 268, at least or exactly or at most 269, at least or exactly or at most 270, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 286, at least or exactly or at most 287, at least or exactly or at most 288, at least or exactly or at most 289, at least or exactly or at most 290, at least or exactly or at most 291, at least or exactly or at most 292, or at least or exactly or at most 293 amino acid residues in any one of SEQ ID NOs: 3-9 and 139-146; or the at least or exactly 5 contiguous amino acid residues present in any one of SEQ ID NOs: 4-9 and 139-146 in the definition of $A^1$ and $A^2$ are at least or exactly or at most 294, at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, at least or exactly or at most 303, at least or exactly or at most 304, at least or exactly or at most 305, at least or exactly or at most 306, at least or exactly or at most 307, at least or exactly or at most 308, at least or exactly or at most 309, at least or exactly or at most 310, at least or exactly or at most 311, at least or exactly or at most 312, at least or exactly or at most 313, at least or exactly or at most 314, at least or exactly or at most 315, at least or exactly or at most 316, at least or exactly or at most 317, at least or exactly or at most 318, or at least or exactly or at most 319 amino acid residues in any one of SEQ ID NOs: 4-9 and 139-146; or the at least or exactly 5 contiguous amino acid residues present in any one of SEQ ID NOs: 4-9 and 140-146 in the definition of $A^1$ and $A^2$ are at least or exactly or at most 320, at least or exactly or at most 321, at least or exactly or at most 322, at least or exactly or at most 323, at least or exactly or at most 324, at least or exactly or at most 325, at least or exactly or at most 326, at least or exactly or at most 327, at least or exactly or at most 328, at least or exactly or at most 329, at least or exactly or at most 330, at least or exactly or at most 331, at least or exactly or at most 332, at least or exactly or at most 333, at least or exactly or at most 334, at least or exactly or at most 335, at least or exactly or at most 336, at least or exactly or at most 337, at least or exactly or at most 338, at least or exactly or at most 339, at least or exactly or at most 340, at least or exactly or at most 341, at least or exactly or at most 342, at least or exactly or at most 343, at least or exactly or at most 344, at least or exactly or at most 345, at least or exactly or at most 346, at least or exactly or at most 347, at least or exactly or at most 348, at least or exactly or at most 349, at least or exactly or at most 350, or at least or exactly or at most 351 amino acid residues in any one of SEQ ID NOs: 4-9 and 140-146; or the at least or exactly 5 contiguous amino acid residues present in any one of SEQ ID NOs: 5-9 and 140-146 in the definition of $A^1$ and $A^2$ are at least or exactly or at most 352, at least or exactly or at most 353, at least or exactly or at most 354, at least or exactly or at most 355, at least or exactly or at most 356, at least or exactly or at most 357, at least or exactly or at most 358, at least or exactly or at most 359, at least or exactly or at most 360, at least or exactly or at most 361, at least or exactly or at most 362, at least or exactly or at most 363, at least or exactly or at most 364, or at least or exactly or at most 365 amino acid residues in any one of SEQ ID NOs: 5-9 and 140-146; or the at least or exactly 5 contiguous amino acid residues present in any one of SEQ ID NOs: 6-9 and 140-146 in the definition of $A^1$ and $A^2$ are at least or exactly or at most 366, at least or exactly or at most 367, at least or exactly or at most 368, at least or exactly or at most 369, at least or exactly or at most 370, at least or exactly or at most 371, at least or exactly or at most 372, at least or exactly or at most 373, at least or exactly or at most 374, at least or exactly or at most 375, at least or exactly or at most 376, at least or exactly or at most 377, at least or exactly or at most 378, at least or exactly or at most 379, at least or exactly or at most 380, at least or exactly or at most 381, at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, or at least or exactly or at most 390 amino acid residues in any one of SEQ ID NOs: 6-9 and 140-146; or the at least or exactly 5 contiguous amino acid residues present in any one of SEQ ID NOs: 7-9 and 140-146 in the definition of $A^1$ and $A^2$ are at least or exactly or at most 391, at least or exactly or at most 392, at least or exactly or at most 393, at least or exactly or at most 394, at least or exactly or at most 395, at least or exactly or at most 396, at least or exactly or at most 397, at least or exactly or at most 398, at least or exactly or at most 399, at least or exactly or at most 400, at least or exactly or at most 401, at least or exactly or at most 402, at least or exactly or at most 403, or at least or exactly or at most 404, at least or exactly or at most 405, at least or exactly or at most 406, at least or exactly or at most 407, at least or exactly or at most 408, or at least or exactly or at most 409 amino acid residues in any one of SEQ ID NOs: 7-9 and 140-146; or the at least or exactly 5 contiguous amino acid residues present in any one of SEQ ID NOs: 8, 9 and 140-146 in the definition of $A^1$ and $A^2$ are at least or exactly or at most 410, at least or exactly or at most 411, or at least or exactly or at most 412 amino acid residues in any one of SEQ ID NO: 8, 9 and 140-146; or the at least or exactly 5 contiguous amino acid residues present in any one of SEQ ID NOs: 9 and 140-146 in the definition of $A^1$ and $A^2$ are at least or exactly or at most 413, at least or exactly or at most 414, at least or exactly or at most 415, at least or exactly or at most 416, at least or exactly or at most 417, at least or exactly or at most 418, at least or exactly or at most 419, at least or exactly or at most 420, at least or exactly or at most 421, at least or exactly or at most 422, at least or exactly or at most 423, at least or exactly or at most 424, at least or exactly or at most 425, at least or exactly or at most 426, at least or exactly or at most 427, at least or exactly or at most 428, at least or exactly or at most 429, at least or exactly or at most 430, at least or exactly or at most 431, at least or exactly or at most 432, at least or exactly or at most 433, at least or exactly or at most 434, at least or exactly or at most 435, at least or exactly or at most 436, at least or exactly or at most 437, at least or exactly or at most 438, at least or exactly or at most 439, at least or exactly or at most 440, at least or exactly or at most 441, at least or exactly or at most 442, at least or exactly or at most 443, at least or exactly or at most 444, at least or exactly or at most 445, at least or exactly or at most 446, at least or exactly or at most 447, at least or exactly or at most 448, at least or exactly or at most 449, at least or exactly or at most 450, at least or exactly or at most 451, at least or exactly or at most 452, at least or exactly or at most 453, at least or exactly or at most 454, at least or exactly or at most 455, at least or exactly or at most 456, at least or exactly or at most 457, at least or exactly or at most 458, at least or exactly or at most 459, at least or exactly or at most 460, at least or exactly or at most 461, at least or exactly or at most 462, at least or exactly or at most 463, at least or exactly or at most 464, at least or exactly or at most 465, at least or exactly or at most 466, at least or exactly or at most 467, at least or exactly or at most 468, at least or exactly or at most 469, at least or exactly or at most 470, at least or exactly or at most 471, at least or exactly or at most 472, at least or exactly or at most 473, at least or exactly or at most 474, at least or exactly or at most 475, at least or exactly or at most 476, at least or exactly or at most 477, at least or exactly or at most 478, at least or exactly or at most 479, at least or exactly or at most 480, at least or exactly or at most 481, at least or exactly or at most 482, at least or exactly or at most 483, at least or exactly or at most 484, at least or exactly or at most 485, at least or exactly or at most 486, at least or exactly or at most 487, at least or exactly or at most 488, at least or exactly or at most 489, at least or exactly or at most 490, at least or exactly or at most 491, at least or exactly or at most 492, at least or exactly or at most 493, at least or exactly or at most 494, at least or exactly or at most 495, at least or exactly or at most 496, at least or exactly or at most 497, at least or exactly or at most 498, at least or exactly or at most 499, at least or exactly or at most 500, at least or exactly or at most 501, at least or exactly or at most 502, at least or exactly or at most 503, at least or exactly or at most 504, at least or exactly or at most 505, at least or exactly or at most 506, at least or exactly or at most 507, at least or exactly or at most 508, at least or exactly or at most 509, at least or exactly or at most 510, at least or exactly or at most 511, at least or exactly or at most 512, at least or exactly or at most 513, at least or exactly or at most 514, or at least or exactly or at most 515 amino acid residues in any one of SEQ ID NO: 9 and 140-146; or the at least or exactly 5 contiguous amino acid residues present in any one of SEQ ID NOs: 9 and 141-146 in the definition of $A^1$ and $A^2$ are at least or exactly or at most 516, at least or exactly or at most 517, at least or exactly or at most 518, or at least or exactly or at most 519 amino acid residues in any one of SEQ ID NO: 9 and 141-146; or the at least or exactly 5 contiguous amino acid residues present in any one of SEQ ID NOs: 9 and 142-146 In the definition of $A^1$ and $A^2$ are at least or exactly or at most 520, at least or exactly or at most 521, at least or exactly or at most 522, at least or exactly or at most 523, at least or exactly or at most 524, at least or exactly or at most 525, at least or exactly or at most 526, at least or exactly or at most 527, at least or exactly or at most 528, at least or exactly or at most 529, at least or exactly or at most 530, at least or exactly or at most 531, at least or exactly or at most 532, at least or exactly or at most 533, at least or exactly or at most 534, at least or exactly or at most 535, at least or exactly or at most 536, at least or exactly or at most 537, at least or exactly or at most 538, at least or exactly or at most 539, at least or exactly or at most 540, at least or exactly or at most 541, at least or exactly or at most 542, at least or exactly or at most 543, at least or exactly or at most 544, at least or exactly or at most 545, at least or exactly or at most 546, at least or exactly or at most 547, at least or exactly or at most 548, at least or exactly or at most 549, at least or exactly or at most 550, at least or exactly or at most 551, at least or exactly or at most 552, at least or exactly or at most 553, at least or exactly or at most 554, at least or exactly or at most 555, at least or exactly or at most 556, at least or exactly or at most 557, at least or exactly or at most 558, at least or exactly or at most 559, at least or exactly or at most 560, at least or exactly or at most 561, at least or exactly or at most 562, at least or exactly or at most 563, at least or exactly or at most 564, at least or exactly or at most 565, at least or exactly or at most 566, at least or exactly or at most 567, at least or exactly or at most 568, at least or exactly or at most 569, at least or exactly or at most 570, at least or exactly or at most 571, at least or exactly or at most 572, at least or exactly or at most 573, at least or exactly or at most 574, at least or exactly or at most 575, at least or exactly or at most 576, at least or exactly or at most 577, at least or exactly or at most 578, at least or exactly or at most 579, at least or exactly or at most 580, at least or exactly or at most 581, at least or exactly or at most 582, at least or exactly or at most 583, at least or exactly or at most 584, at least or exactly or at most 585, at least or exactly or at most 586, at least or exactly or at most 587, at least or exactly or at most 588, at least or exactly or at most 589, at least or exactly or at most 590, at least or exactly or at most 591, or at least or exactly or at most 592 amino add residues in any one of SEQ ID NOs: 9 and 142-146; or the at least or exactly 5 contiguous amino acid residues present in any one of SEQ ID NOs: 142-146 in the definition of $A^1$ and $A^2$ are at least or exactly or at most 593, at least or exactly or at most 594, at least or exactly or at most 595, at least or exactly or at most 596, at least or exactly or at most 597, at least or exactly or at most 598, at least or exactly or at most 599, at least or exactly or at most 600, at least or exactly or at most 601, at least or exactly or at most 602, at least or exactly or at most 603, at least or exactly or at most 604, at least or exactly or at most 605, at least or exactly or at most 606, at least or exactly or at most 607, at least or exactly or at most 608, at least or exactly or at most 609, at least or exactly or at most 610, at least or exactly or at most 611, at least or exactly or at most 612, at least or exactly or at most 613, at least or exactly or at most 614, at least or exactly or at most 615, at least or exactly or at most 616, at least or exactly or at most 617, at least or exactly or at most 618, or at least or exactly or at most 619 amino acid residues in any one of SEQ ID NOs: 142-146; or the at least or exactly 5 contiguous amino acid residues present in any one of SEQ ID NOs: 143-146 in the definition of $A^1$ and $A^2$ are at least or exactly or at most 620, at least or exactly or at most 621, at least or exactly or at most 622, at least or exactly or at most 623, at least or exactly or at most 624, at least or exactly or at most 625, at least or exactly or at most 626, at least or exactly or at most 627, at least or exactly or at most 628, at least or exactly or at most 629, at least or exactly or at most 630, at least or exactly or at most 631, at least or exactly or at most 632, at least or exactly or at most 633, at least or exactly or at most 634, at least or exactly or at most 635, at least or exactly or at most 636, at least or exactly or at most 637, at least or exactly or at most 638, at least or exactly or at most 639, at least or exactly or at most 640, at least or exactly or at most 641, at least or exactly or at most 642, at least or exactly or at most 643, at least or exactly or at most 644, or at least or exactly or at most 645 amino acid residues in any one of SEQ ID NOs: 143-146; or the at least or exactly 5 contiguous amino acid residues present in any one of SEQ ID NOs: 144-146 in the definition of $A^1$ and $A^2$ are at least or exactly or at most 646, at least or exactly or at most 647, at least or exactly or at most 648, at least or exactly or at most 649, at least or exactly or at most 650, at least or exactly or at most 651, at least or exactly or at most 652, at least or exactly or at most 653, at least or exactly or at most 654, at least or exactly or at most 655, at least or exactly or at most 656, at least or exactly or at most 657, at least or exactly or at most 658, at least or exactly or at most 659, at least or exactly or at most 660, at least or exactly or at most 661, at least or exactly or at most 662, at least or exactly or at most 663, at least or exactly or at most 664, at least or exactly or at most 665, at least or exactly or at most 666, at least or exactly or at most 667, at least or exactly or at most 668, at least or exactly or at most 669, at least or exactly or at most 670, at least or exactly or at most 671, at least or exactly or at most 672, at least or exactly or at most 673, at least or exactly or at most 674, at least or exactly or at most 675, at least or exactly or at most 676, at least or exactly or at most 677, at least or exactly or at most 678, at least or exactly or at most 679, at least or exactly or at most 680, or at least or exactly or at most 681 amino acid residues in any one of SEQ ID NOs: 144-146; or the at least or exactly 5 contiguous amino acid residues present in any one of SEQ ID NO: 145 or 146 in the definition of $A^1$ and $A^2$ are at least or exactly or at most 682, at least or exactly or at most 683, at least or exactly or at most 684, at least or exactly or at most 685, at least or exactly or at most 686, at least or exactly or at most 687, at least or exactly or at most 688, at least or exactly or at most 689, at least or exactly or at most 690, at least or exactly or at most 691, at least or exactly or at most 692, at least or exactly or at most 693, at least or exactly or at most 694, at least or exactly or at most 695, at least or exactly or at most 696, at least or exactly or at most 697, at least or exactly or at most 698, at least or exactly or at most 699, at least or exactly or at most 700, at least or exactly or at most 701, at least or exactly or at most 702, at least or exactly or at most 703, at least or exactly or at most 704, at least or exactly or at most 705, at least or exactly or at most 706, at least or exactly or at most 707, at least or exactly or at most 708, at least or exactly or at most 709, at least or exactly or at most 710, at least or exactly or at most 711, at least or exactly or at most 712, at least or exactly or at most 713, at least or exactly or at most 714, at least or exactly or at most 715, at least or exactly or at most 716, at least or exactly or at most 717, at least or exactly or at most 718, at least or exactly or at most 719, at least or exactly or at most 720, at least or exactly or at most 721, at least or exactly or at most 722, at least or exactly or at most 723, at least or exactly or at most 724, at least or exactly or at most 725, at least or exactly or at most 726, at least or exactly or at most 727, at least or exactly or at most 728, at least or exactly or at most 729, at least or exactly or at most 730, at least or exactly or at most 731, at least or exactly or at most 732, at least or exactly or at most 733, at least or exactly or at most 734, at least or exactly or at most 735, at least or exactly or at most 736, at least or exactly or at most 737, at least or exactly or at most 738, at least or exactly or at most 739, at least or exactly or at most 740, at least or exactly or at most 741, at least or exactly or at most 742, at least or exactly or at most 743, at least or exactly or at most 744, at least or exactly or at most 745, at least or exactly or at most 746, at least or exactly or at most 747, at least or exactly or at most 748, at least or exactly or at most 749, at least or exactly or at most 750, at least or exactly or at most 751, at least or exactly or at most 752, at least or exactly or at most 753, at least or exactly or at most 754, at least or exactly or at most 755, at least or exactly or at most 756, at least or exactly or at most 757, at least or exactly or at most 758, at least or exactly or at most 759, at least or exactly or at most 760, at least or exactly or at most 761, at least or exactly or at most 762, at least or exactly or at most 763, at least or exactly or at most 764, at least or exactly or at most 765, at least or exactly or at most 766, at least or exactly or at most 767, at least or exactly or at most 768, or at least or exactly or at most 769 amino acid residues in SEQ ID NO: 145 or 146; or the at least or exactly 5 contiguous amino acid residues present in SEQ ID NO: 146 in the definition of $A^1$ and $A^2$ are at least or exactly or at most 770, at least or exactly or at most 771, at least or exactly or at most 772, at least or exactly or at most 773, at least or exactly or at most 774, at least or exactly or at most 775, at least or exactly or at most 776, at least or exactly or at most 777, at least or exactly or at most 778, at least or exactly or at most 779, at least or exactly or at most 780, at least or exactly or at most 781, at least or exactly or at most 782, at least or exactly or at most 783, at least or exactly or at most 784, at least or exactly or at most 785, at least or exactly or at most 786, at least or exactly or at most 787, at least or exactly or at most 788, at least or exactly or at most 789, at least or exactly or at most 790, at least or exactly or at most 791, at least or exactly or at most 792, at least or exactly or at most 793, at least or exactly or at most 794, at least or exactly or at most 795, at least or exactly or at most 796, at least or exactly or at most 797, at least or exactly or at most 798, at least or exactly or at most 799, at least or exactly or at most 800, at least or exactly or at most 801, at least or exactly or at most 802, at least or exactly or at most 803, at least or exactly or at most 804, at least or exactly or at most 805, at least or exactly or at most 806, at least or exactly or at most 807, at least or exactly or at most 808, at least or exactly or at most 809, at least or exactly or at most 810, at least or exactly or at most 811, at least or exactly or at most 812, at least or exactly or at most 813, at least or exactly or at most 814, at least or exactly or at most 815, at least or exactly or at most 816, at least or exactly or at most 817, at least or exactly or at most 818, at least or exactly or at most 819, at least or exactly or at most 820, at least or exactly or at most 821, at least or exactly or at most 822, at least or exactly or at most 823, at least or exactly or at most 824, at least or exactly or at most 825, at least or exactly or at most 826, at least or exactly or at most 827, at least or exactly or at most 828, at least or exactly or at most 829, at least or exactly or at most 830, at least or exactly or at most 831, at least or exactly or at most 832, at least or exactly or at most 833, at least or exactly or at most 834, at least or exactly or at most 835, at least or exactly or at most 836, at least or exactly or at most 837, at least or exactly or at most 838, at least or exactly or at most 839, at least or exactly or at most 840, at least or exactly or at most 841, at least or exactly or at most 842, at least or exactly or at most 843, at least or exactly or at most 844, at least or exactly or at most 845, at least or exactly or at most 846, at least or exactly or at most 847, at least or exactly or at most 848, at least or exactly or at most 849, at least or exactly or at most 850, at least or exactly or at most 851, at least or exactly or at most 852, at least or exactly or at most 853, at least or exactly or at most 854, at least or exactly or at most 855, at least or exactly or at most 856, at least or exactly or at most 857, at least or exactly or at most 858, at least or exactly or at most 859, at least or exactly or at most 860, at least or exactly or at most 861, at least or exactly or at most 862, at least or exactly or at most 863, at least or exactly or at most 864, at least or exactly or at most 865, at least or exactly or at most 866, at least or exactly or at most 867, at least or exactly or at most 868, at least or exactly or at most 869, at least or exactly or at most 870, at least or exactly or at most 871, at least or exactly or at most 872, at least or exactly or at most 873, at least or exactly or at most 874, at least or exactly or at most 875, at least or exactly or at most 876, at least or exactly or at most 877, at least or exactly or at most 878, at least or exactly or at most 879, at least or exactly or at most 880, at least or exactly or at most 881, at least or exactly or at most 882, at least or exactly or at most 883, at least or exactly or at most 884, at least or exactly or at most 885, at least or exactly or at most 886, at least or exactly or at most 887, at least or exactly or at most 888, at least or exactly or at most 889, at least or exactly or at most 890, at least or exactly or at most 891, at least or exactly or at most 892, at least or exactly or at most 893, at least or exactly or at most 894, at least or exactly or at most 895, at least or exactly or at most 896, at least or exactly or at most 897, at least or exactly or at most 898, at least or exactly or at most 899, at least or exactly or at most 900, at least or exactly or at most 901, at least or exactly or at most 902, at least or exactly or at most 903, at least or exactly or at most 904, at least or exactly or at most 905, at least or exactly or at most 906, at least or exactly or at most 907, at least or exactly or at most 908, at least or exactly or at most 909, at least or exactly or at most 910, at least or exactly or at most 911, at least or exactly or at most 912, at least or exactly or at most 913, at least or exactly or at most 914, at least or exactly or at most 915, at least or exactly or at most 916, at least or exactly or at most 917, at least or exactly or at most 918, at least or exactly or at most 919, at least or exactly or at most 920, at least or exactly or at most 921, at least or exactly or at most 922, at least or exactly or at most 923, at least or exactly or at most 924, at least or exactly or at most 925, at least or exactly or at most 926, at least or exactly or at most 927, at least or exactly or at most 928, at least or exactly or at most 929, at least or exactly or at most 930, at least or exactly or at most 931, at least or exactly or at most 932, at least or exactly or at most 933, at least or exactly or at most 934, at least or exactly or at most 935, at least or exactly or at most 936, at least or exactly or at most 937, at least or exactly or at most 938, at least or exactly or at most 939, at least or exactly or at most 940, at least or exactly or at most 941, at least or exactly or at most 942, at least or exactly or at most 943, at least or exactly or at most 944, at least or exactly or at most 945, at least or exactly or at most 946, at least or exactly or at most 947, at least or exactly or at most 948, at least or exactly or at most 949, at least or exactly or at most 950, at least or exactly or at most 951, at least or exactly or at most 952, at least or exactly or at most 953, at least or exactly or at most 954, at least or exactly or at most 955, at least or exactly or at most 956, at least or exactly or at most 957, at least or exactly or at most 958, at least or exactly or at most 959, at least or exactly or at most 960, at least or exactly or at most 961, at least or exactly or at most 962, at least or exactly or at most 963, at least or exactly or at most 964, at least or exactly or at most 965, at least or exactly or at most 966, at least or exactly or at most 967, at least or exactly or at most 968, at least or exactly or at most 969, at least or exactly or at most 970, at least or exactly or at most 971, at least or exactly or at most 972, at least or exactly or at most 973, at least or exactly or at most 974, at least or exactly or at most 975, at least or exactly or at most 976, at least or exactly or at most 977, at least or exactly or at most 978, at least or exactly or at most 979, at least or exactly or at most 980, at least or exactly or at most 981, at least or exactly or at most 982, at least or exactly or at most 983, at least or exactly or at most 984, at least or exactly or at most 985, at least or exactly or at most 986, at least or exactly or at most 987, at least or exactly or at most 988, at least or exactly or at most 989, at least or exactly or at most 990, at least or exactly or at most 991, at least or exactly or at most 992, at least or exactly or at most 993, at least or exactly or at most 994, at least or exactly or at most 995, at least or exactly or at most 996, at least or exactly or at most 997, at least or exactly or at most 998, at least or exactly or at most 999, at least or exactly or at most 1000, at least or exactly or at most 1001, at least or exactly or at most 1002, at least or exactly or at most 1003, at least or exactly or at most 1004, at least or exactly or at most 1005, at least or exactly or at most 1006, at least or exactly or at most 1007, at least or exactly or at most 1008, at least or exactly or at most 1009, at least or exactly or at most 1010, at least or exactly or at most 1011, at least or exactly or at most 1012, at least or exactly or at most 1013, at least or exactly or at most 1014, at least or exactly or at most 1015, at least or exactly or at most 1016, at least or exactly or at most 1017, at least or exactly or at most 1018, at least or exactly or at most 1019, at least or exactly or at most 1020, at least or exactly or at most 1021, at least or exactly or at most 1022, at least or exactly or at most 1023, at least or exactly or at most 1024, at least or exactly or at most 1025, at least or exactly or at most 1026, at least or exactly or at most 1027, at least or exactly or at most 1028, at least or exactly or at most 1029, at least or exactly or at most 1030, at least or exactly or at most 1031, at least or exactly or at most 1032, at least or exactly or at most 1033, at least or exactly or at most 1034, at least or exactly or at most 1035, at least or exactly or at most 1036, at least or exactly or at most 1037, at least or exactly or at most 1038, at least or exactly or at most 1039, at least or exactly or at most 1040, at least or exactly or at most 1041, at least or exactly or at most 1042, at least or exactly or at most 1043, at least or exactly or at most 1044, at least or exactly or at most 1045, at least or exactly or at most 1046, at least or exactly or at most 1047, at least or exactly or at most 1048, at least or exactly or at most 1049, at least or exactly or at most 1050, at least or exactly or at most 1051, at least or exactly or at most 1052, at least or exactly or at most 1053, at least or exactly or at most 1054, at least or exactly or at most 1055, at least or exactly or at most 1056, at least or exactly or at most 1057, at least or exactly or at most 1058, at least or exactly or at most 1059, at least or exactly or at most 1060, at least or exactly or at most 1061, at least or exactly or at most 1062, at least or exactly or at most 1063, at least or exactly or at most 1064, at least or exactly or at most 1065, at least or exactly or at most 1066, at least or exactly or at most 1067, at least or exactly or at most 1068, at least or exactly or at most 1069, at least or exactly or at most 1070, at least or exactly or at most 1071, at least or exactly or at most 1072, at least or exactly or at most 1073, at least or exactly or at most 1074, at least or exactly or at most 1075, at least or exactly or at most 1076, at least or exactly or at most 1077, at least or exactly or at most 1078, at least or exactly or at most 1079, at least or exactly or at most 1080, at least or exactly or at most 1081, at least or exactly or at most 1082, at least or exactly or at most 1083, at least or exactly or at most 1084, at least or exactly or at most 1085, at least or exactly or at most 1086, at least or exactly or at most 1087, at least or exactly or at most 1088, at least or exactly or at most 1089, at least or exactly or at most 1090, at least or exactly or at most 1091, at least or exactly or at most 1092, at least or exactly or at most 1093, at least or exactly or at most 1094, at least or exactly or at most 1095, at least or exactly or at most 1096, at least or exactly or at most 1097, at least or exactly or at most 1098, at least or exactly or at most 1099, at least or exactly or at most 1100, at least or exactly or at most 1101, at least or exactly or at most 1102, at least or exactly or at most 1103, at least or exactly or at most 1104, at least or exactly or at most 1105, at least or exactly or at most 1106, at least or exactly or at most 1107, at least or exactly or at most 1108, at least or exactly or at most 1109, at least or exactly or at most 1110, at least or exactly or at most 1111, at least or exactly or at most 1112, at least or exactly or at most 1113, at least or exactly or at most 1114, at least or exactly or at most 1115, at least or exactly or at most 1116, at least or exactly or at most 1117, at least or exactly or at most 1118, at least or exactly or at most 1119, at least or exactly or at most 1120, at least or exactly or at most 1121, at least or exactly or at most 1122, at least or exactly or at most 1123, at least or exactly or at most 1124, at least or exactly or at most 1125, at least or exactly or at most 1126, at least or exactly or at most 1127, at least or exactly or at most 1128, at least or exactly or at most 1129, at least or exactly or at most 1130, at least or exactly or at most 1131, at least or exactly or at most 1132, at least or exactly or at most 1133, at least or exactly or at most 1134, at least or exactly or at most 1135, at least or exactly or at most 1136, at least or exactly or at most 1137, at least or exactly or at most 1138, at least or exactly or at most 1139, at least or exactly or at most 1140, at least or exactly or at most 1141, at least or exactly or at most 1142, at least or exactly or at most 1143, at least or exactly or at most 1144, at least or exactly or at most 1145, at least or exactly or at most 1146, at least or exactly or at most 1147, at least or exactly or at most 1148, at least or exactly or at most 1149, at least or exactly or at most 1150, at least or exactly or at most 1151, at least or exactly or at most 1152, at least or exactly or at most 1153, at least or exactly or at most 1154, at least or exactly or at most 1155, at least or exactly or at most 1156, at least or exactly or at most 1157, at least or exactly or at most 1158, at least or exactly or at most 1159, at least or exactly or at most 1160, at least or exactly or at most 1161, at least or exactly or at most 1162, at least or exactly or at most 1163, at least or exactly or at most 1164, at least or exactly or at most 1165, at least or exactly or at most 1166, at least or exactly or at most 1167, at least or exactly or at most 1168, at least or exactly or at most 1169, at least or exactly or at most 1170, at least or exactly or at most 1171, at least or exactly or at most 1172, at least or exactly or at most 1173, at least or exactly or at most 1174, at least or exactly or at most 1175, at least or exactly or at most 1176, at least or exactly or at most 1177, at least or exactly or at most 1178, at least or exactly or at most 1179, at least or exactly or at most 1180, at least or exactly or at most 1181, at least or exactly or at most 1182, at least or exactly or at most 1183, at least or exactly or at most 1184, at least or exactly or at most 1185, at least or exactly or at most 1186, at least or exactly or at most 1187, at least or exactly or at most 1188, at least or exactly or at most 1189, at least or exactly or at most 1190, at least or exactly or at most 1191, at least or exactly or at most 1192, at least or exactly or at most 1193, at least or exactly or at most 1194, at least or exactly or at most 1195, at least or exactly or at most 1196, at least or exactly or at most 1197, at least or exactly or at most 1198, at least or exactly or at most 1199, at least or exactly or at most 1200, at least or exactly or at most 1201, at least or exactly or at most 1202, at least or exactly or at most 1203, at least or exactly or at most 1204, at least or exactly or at most 1205, at least or exactly or at most 1206, at least or exactly or at most 1207, at least or exactly or at most 1208, at least or exactly or at most 1209, at least or exactly or at most 1210, at least or exactly or at most 1211, at least or exactly or at most 1212, at least or exactly or at most 1213, at least or exactly or at most 1214, at least or exactly or at most 1215, at least or exactly or at most 1216, at least or exactly or at most 1217, at least or exactly or at most 1218, at least or exactly or at most 1219, at least or exactly or at most 1220, at least or exactly or at most 1221, at least or exactly or at most 1222, at least or exactly or at most 1223, at least or exactly or at most 1224, at least or exactly or at most 1225, at least or exactly or at most 1226, at least or exactly or at most 1227, at least or exactly or at most 1228, at least or exactly or at most 1229, at least or exactly or at most 1230, at least or exactly or at most 1231, at least or exactly or at most 1232, at least or exactly or at most 1233, at least or exactly or at most 1234, at least or exactly or at most 1235, at least or exactly or at most 1236, at least or exactly or at most 1237, at least or exactly or at most 1238, at least or exactly or at most 1239, at least or exactly or at most 1240, at least or exactly or at most 1241, at least or exactly or at most 1242, at least or exactly or at most 1243, at least or exactly or at most 1244, at least or exactly or at most 1245, at least or exactly or at most 1246, at least or exactly or at most 1247, at least or exactly or at most 1248, at least or exactly or at most 1249, at least or exactly or at most 1250, at least or exactly or at most 1251, at least or exactly or at most 1252, at least or exactly or at most 1253, at least or exactly or at most 1254, at least or exactly or at most 1255, at least or exactly or at most 1256, at least or exactly or at most 1257, at least or exactly or at most 1258, at least or exactly or at most 1259, at least or exactly or at most 1260, at least or exactly or at most 1261, at least or exactly or at most 1262, at least or exactly or at most 1263, at least or exactly or at most 1264, at least or exactly or at most 1265, at least or exactly or at most 1266, at least or exactly or at most 1267, at least or exactly or at most 1268, at least or exactly or at most 1269, at least or exactly or at most 1270, at least or exactly or at most 1271, at least or exactly or at most 1272, at least or exactly or at most 1273, at least or exactly or at most 1274, at least or exactly or at most 1275, at least or exactly or at most 1276, at least or exactly or at most 1277, at least or exactly or at most 1278, at least or exactly or at most 1279, at least or exactly or at most 1280, at least or exactly or at most 1281, at least or exactly or at most 1282, at least or exactly or at most 1283, at least or exactly or at most 1284, at least or exactly or at most 1285, at least or exactly or at most 1286, at least or exactly or at most 1287, at least or exactly or at most 1288, at least or exactly or at most 1289, at least or exactly or at most 1290, at least or exactly or at most 1291, at least or exactly or at most 1292, at least or exactly or at most 1293, at least or exactly or at most 1294, at least or exactly or at most 1295, at least or exactly or at most 1296, at least or exactly or at most 1297, at least or exactly or at most 1298, at least or exactly or at most 1299, at least or exactly or at most 1300, at least or exactly or at most 1301, at least or exactly or at most 1302, at least or exactly or at most 1303, at least or exactly or at most 1304, at least or exactly or at most 1305, at least or exactly or at most 1306, at least or exactly or at most 1307, at least or exactly or at most 1308, at least or exactly or at most 1309, at least or exactly or at most 1310, at least or exactly or at most 1311, at least or exactly or at most 1312, at least or exactly or at most 1313, at least or exactly or at most 1314, at least or exactly or at most 1315, at least or exactly or at most 1316, at least or exactly or at most 1317, at least or exactly or at most 1318, at least or exactly or at most 1319, at least or exactly or at most 1320, at least or exactly or at most 1321, at least or exactly or at most 1322, at least or exactly or at most 1323, at least or exactly or at most 1324, at least or exactly or at most 1325, at least or exactly or at most 1326, at least or exactly or at most 1327, at least or exactly or at most 1328, at least or exactly or at most 1329, at least or exactly or at most 1330, at least or exactly or at most 1331, at least or exactly or at most 1332, at least or exactly or at most 1333, at least or exactly or at most 1334, at least or exactly or at most 1335, at least or exactly or at most 1336, at least or exactly or at most 1337, at least or exactly or at most 1338, at least or exactly or at most 1339, at least or exactly or at most 1340, at least or exactly or at most 1341, at least or exactly or at most 1342, at least or exactly or at most 1343, at least or exactly or at most 1344, at least or exactly or at most 1345, at least or exactly or at most 1346, at least or exactly or at most 1347, at least or exactly or at most 1348, at least or exactly or at most 1349, at least or exactly or at most 1350, at least or exactly or at most 1351, at least or exactly or at most 1352, at least or exactly or at most 1353, at least or exactly or at most 1354, at least or exactly or at most 1355, at least or exactly or at most 1356, at least or exactly or at most 1357, at least or exactly or at most 1358, at least or exactly or at most 1359, at least or exactly or at most 1360, at least or exactly or at most 1361, at least or exactly or at most 1362, at least or exactly or at most 1363, at least or exactly or at most 1364, at least or exactly or at most 1365, at least or exactly or at most 1366, at least or exactly or at most 1367, at least or exactly or at most 1368, at least or exactly or at most 1369, at least or exactly or at most 1370, at least or exactly or at most 1371, at least or exactly or at most 1372, at least or exactly or at most 1373, at least or exactly or at most 1374, at least or exactly or at most 1375, at least or exactly or at most 1376, at least or exactly or at most 1377, at least or exactly or at most 1378, at least or exactly or at most 1379, at least or exactly or at most 1380, at least or exactly or at most 1381, at least or exactly or at most 1382, at least or exactly or at most 1383, at least or exactly or at most 1384, at least or exactly or at most 1385, at least or exactly or at most 1386, at least or exactly or at most 1387, at least or exactly or at most 1388, at least or exactly or at most 1389, at least or exactly or at most 1390, at least or exactly or at most 1391, at least or exactly or at most 1392, at least or exactly or at most 1393, at least or exactly or at most 1394, at least or exactly or at most 1395, at least or exactly or at most 1396, at least or exactly or at most 1397, at least or exactly or at most 1398, at least or exactly or at most 1399, at least or exactly or at most 1400, at least or exactly or at most 1401, at least or exactly or at most 1402, at least or exactly or at most 1403, at least or exactly or at most 1404, at least or exactly or at most 1405, at least or exactly or at most 1406, at least or exactly or at most 1407, at least or exactly or at most 1408, at least or exactly or at most 1409, at least or exactly or at most 1410, at least or exactly or at most 1411, at least or exactly or at most 1412, at least or exactly or at most 1413, at least or exactly or at most 1414, at least or exactly or at most 1415, at least or exactly or at most 1416, at least or exactly or at most 1417, at least or exactly or at most 1418, at least or exactly or at most 1419, at least or exactly or at most 1420, at least or exactly or at most 1421, at least or exactly or at most 1422, at least or exactly or at most 1423, at least or exactly or at most 1424, at least or exactly or at most 1425, at least or exactly or at most 1426, at least or exactly or at most 1427, at least or exactly or at most 1428, at least or exactly or at most 1429, at least or exactly or at most 1430, at least or exactly or at most 1431, at least or exactly or at most 1432, at least or exactly or at most 1433, at least or exactly or at most 1434, at least or exactly or at most 1435, at least or exactly or at most 1436, at least or exactly or at most 1437, at least or exactly or at most 1438, at least or exactly or at most 1439, at least or exactly or at most 1440, at least or exactly or at most 1441, at least or exactly or at most 1442, at least or exactly or at most 1443, at least or exactly or at most 1444, at least or exactly or at most 1445, at least or exactly or at most 1446, at least or exactly or at most 1447, at least or exactly or at most 1448, at least or exactly or at most 1449, at least or exactly or at most 1450, at least or exactly or at most 1451, at least or exactly or at most 1452, at least or exactly or at most 1453, at least or exactly or at most 1454, at least or exactly or at most 1455, at least or exactly or at most 1456, at least or exactly or at most 1457, at least or exactly or at most 1458, at least or exactly or at most 1459, at least or exactly or at most 1460, at least or exactly or at most 1461, at least or exactly or at most 1462, at least or exactly or at most 1463, at least or exactly or at most 1464, at least or exactly or at most 1465, at least or exactly or at most 1466, at least or exactly or at most 1467, at least or exactly or at most 1468, at least or exactly or at most 1469, at least or exactly or at most 1470, at least or exactly or at most 1471, at least or exactly or at most 1472, at least or exactly or at most 1473, at least or exactly or at most 1474, at least or exactly or at most 1475, at least or exactly or at most 1476, at least or exactly or at most 1477, at least or exactly or at most 1478, at least or exactly or at most 1479, at least or exactly or at most 1480, at least or exactly or at most 1481, at least or exactly or at most 1482, at least or exactly or at most 1483, at least or exactly or at most 1484, at least or exactly or at most 1485, at least or exactly or at most 1486, at least or exactly or at most 1487, at least or exactly or at most 1488, at least or exactly or at most 1489, at least or exactly or at most 1490, at least or exactly or at most 1491, at least or exactly or at most 1492, at least or exactly or at most 1493, at least or exactly or at most 1494, at least or exactly or at most 1495, at least or exactly or at most 1496, at least or exactly or at most 1497, at least or exactly or at most 1498, at least or exactly or at most 1499, at least or exactly or at most 1500, at least or exactly or at most 1501, at least or exactly or at most 1502, at least or exactly or at most 1503, at least or exactly or at most 1504, at least or exactly or at most 1505, at least or exactly or at most 1506, at least or exactly or at most 1507, at least or exactly or at most 1508, at least or exactly or at most 1509, at least or exactly or at most 1510, at least or exactly or at most 1511, at least or exactly or at most 1512, at least or exactly or at most 1513, at least or exactly or at most 1514, at least or exactly or at most 1515, at least or exactly or at most 1516, at least or exactly or at most 1517, at least or exactly or at most 1518, at least or exactly or at most 1519, at least or exactly or at most 1520, at least or exactly or at most 1521, at least or exactly or at most 1522, at least or exactly or at most 1523, at least or exactly or at most 1524, at least or exactly or at most 1525, at least or exactly or at most 1526, at least or exactly or at most 1527, at least or exactly or at most 1528, at least or exactly or at most 1529, at least or exactly or at most 1530, at least or exactly or at most 1531, at least or exactly or at most 1532, at least or exactly or at most 1533, at least or exactly or at most 1534, at least or exactly or at most 1535, at least or exactly or at most 1536, at least or exactly or at most 1537, at least or exactly or at most 1538, at least or exactly or at most 1539, at least or exactly or at most 1540, at least or exactly or at most 1541, at least or exactly or at most 1542, at least or exactly or at most 1543, at least or exactly or at most 1544, at least or exactly or at most 1545, at least or exactly or at most 1546, at least or exactly or at most 1547, at least or exactly or at most 1548, at least or exactly or at most 1549, at least or exactly or at most 1550, at least or exactly or at most 1551, at least or exactly or at most 1552, at least or exactly or at most 1553, at least or exactly or at most 1554, at least or exactly or at most 1555, at least or exactly or at most 1556, at least or exactly or at most 1557, at least or exactly or at most 1558, at least or exactly or at most 1559, at least or exactly or at most 1560, at least or exactly or at most 1561, at least or exactly or at most 1562, at least or exactly or at most 1563, at least or exactly or at most 1564, at least or exactly or at most 1565, at least or exactly or at most 1566, at least or exactly or at most 1567, at least or exactly or at most 1568, at least or exactly or at most 1569, at least or exactly or at most 1570, at least or exactly or at most 1571, at least or exactly or at most 1572, at least or exactly or at most 1573, at least or exactly or at most 1574, at least or exactly or at most 1575, at least or exactly or at most 1576, at least or exactly or at most 1577, at least or exactly or at most 1578, at least or exactly or at most 1579, at least or exactly or at most 1580, at least or exactly or at most 1581, at least or exactly or at most 1582, at least or exactly or at most 1583, at least or exactly or at most 1584, at least or exactly or at most 1585, at least or exactly or at most 1586, at least or exactly or at most 1587, at least or exactly or at most 1588, at least or exactly or at most 1589, at least or exactly or at most 1590, at least or exactly or at most 1591, at least or exactly or at most 1592, at least or exactly or at most 1593, at least or exactly or at most 1594, at least or exactly or at most 1595, at least or exactly or at most 1596, at least or exactly or at most 1597, at least or exactly or at most 1598, at least or exactly or at most 1599, at least or exactly or at most 1600, at least or exactly or at most 1601, at least or exactly or at most 1602, at least or exactly or at most 1603, at least or exactly or at most 1604, at least or exactly or at most 1605, at least or exactly or at most 1606, at least or exactly or at most 1607, at least or exactly or at most 1608, at least or exactly or at most 1609, at least or exactly or at most 1610, at least or exactly or at most 1611, at least or exactly or at most 1612, at least or exactly or at most 1613, at least or exactly or at most 1614, at least or exactly or at most 1615, at least or exactly or at most 1616, at least or exactly or at most 1617, at least or exactly or at most 1618, at least or exactly or at most 1619, at least or exactly or at most 1620, at least or exactly or at most 1621, at least or exactly or at most 1622, at least or exactly or at most 1623, at least or exactly or at most 1624, at least or exactly or at most 1625, at least or exactly or at most 1626, at least or exactly or at most 1627, at least or exactly or at most 1628, at least or exactly or at most 1629, at least or exactly or at most 1630, at least or exactly or at most 1631, at least or exactly or at most 1632, at least or exactly or at most 1633, at least or exactly or at most 1634, at least or exactly or at most 1635, at least or exactly or at most 1636, at least or exactly or at most 1637, at least or exactly or at most 1638, at least or exactly or at most 1639, at least or exactly or at most 1640, at least or exactly or at most 1641, at least or exactly or at most 1642, at least or exactly or at most 1643, at least or exactly or at most 1644, at least or exactly or at most 1645, at least or exactly or at most 1646, at least or exactly or at most 1647, at least or exactly or at most 1648, at least or exactly or at most 1649, at least or exactly or at most 1650, at least or exactly or at most 1651, at least or exactly or at most 1652, at least or exactly or at most 1653, at least or exactly or at most 1654, at least or exactly or at most 1655, at least or exactly or at most 1656, at least or exactly or at most 1657, at least or exactly or at most 1658, at least or exactly or at most 1659, at least or exactly or at most 1660, at least or exactly or at most 1661, at least or exactly or at most 1662, at least or exactly or at most 1663, at least or exactly or at most 1664, at least or exactly or at most 1665, at least or exactly or at most 1666, at least or exactly or at most 1667, at least or exactly or at most 1668, at least or exactly or at most 1669, at least or exactly or at most 1670, at least or exactly or at most 1671, at least or exactly or at most 1672, at least or exactly or at most 1673, at least or exactly or at most 1674, at least or exactly or at most 1675, at least or exactly or at most 1676, at least or exactly or at most 1677, at least or exactly or at most 1678, at least or exactly or at most 1679, at least or exactly or at most 1680, at least or exactly or at most 1681, at least or exactly or at most 1682, at least or exactly or at most 1683, at least or exactly or at most 1684, at least or exactly or at most 1685, at least or exactly or at most 1686, at least or exactly or at most 1687, at least or exactly or at most 1688, at least or exactly or at most 1689, at least or exactly or at most 1690, at least or exactly or at most 1691, at least or exactly or at most 1692, at least or exactly or at most 1693, at least or exactly or at most 1694, at least or exactly or at most 1695, at least or exactly or at most 1696, at least or exactly or at most 1697, at least or exactly or at most 1698, at least or exactly or at most 1699, at least or exactly or at most 1700, at least or exactly or at most 1701, at least or exactly or at most 1702, at least or exactly or at most 1703, at least or exactly or at most 1704, at least or exactly or at most 1705, at least or exactly or at most 1706, at least or exactly or at most 1707, at least or exactly or at most 1708, at least or exactly or at most 1709, at least or exactly or at most 1710, at least or exactly or at most 1711, at least or exactly or at most 1712, at least or exactly or at most 1713, at least or exactly or at most 1714, at least or exactly or at most 1715, at least or exactly or at most 1716, at least or exactly or at most 1717, at least or exactly or at most 1718, at least or exactly or at most 1719, at least or exactly or at most 1720, at least or exactly or at most 1721, at least or exactly or at most 1722, at least or exactly or at most 1723, at least or exactly or at most 1724, at least or exactly or at most 1725, at least or exactly or at most 1726, at least or exactly or at most 1727, at least or exactly or at most 1728, at least or exactly or at most 1729, at least or exactly or at most 1730, at least or exactly or at most 1731, at least or exactly or at most 1732, at least or exactly or at most 1733, at least or exactly or at most 1734, at least or exactly or at most 1735, at least or exactly or at most 1736, at least or exactly or at most 1737, at least or exactly or at most 1738, at least or exactly or at most 1739, at least or exactly or at most 1740, at least or exactly or at most 1741, at least or exactly or at most 1742, at least or exactly or at most 1743, at least or exactly or at most 1744, at least or exactly or at most 1745, at least or exactly or at most 1746, at least or exactly or at most 1747, at least or exactly or at most 1748, at least or exactly or at most 1749, at least or exactly or at most 1750, at least or exactly or at most 1751, at least or exactly or at most 1752, at least or exactly or at most 1753, at least or exactly or at most 1754, at least or exactly or at most 1755, at least or exactly or at most 1756, at least or exactly or at most 1757, at least or exactly or at most 1758, at least or exactly or at most 1759, at least or exactly or at most 1760, at least or exactly or at most 1761, at least or exactly or at most 1762, at least or exactly or at most 1763, at least or exactly or at most 1764, at least or exactly or at most 1765, at least or exactly or at most 1766, at least or exactly or at most 1767, at least or exactly or at most 1768, at least or exactly or at most 1769, at least or exactly or at most 1770, at least or exactly or at most 1771, at least or exactly or at most 1772, at least or exactly or at most 1773, at least or exactly or at most 1774, at least or exactly or at most 1775, at least or exactly or at most 1776, at least or exactly or at most 1777, at least or exactly or at most 1778, at least or exactly or at most 1779, at least or exactly or at most 1780, at least or exactly or at most 1781, at least or exactly or at most 1782, at least or exactly or at most 1783, at least or exactly or at most 1784, at least or exactly or at most 1785, at least or exactly or at most 1786, at least or exactly or at most 1787, at least or exactly or at most 1788, at least or exactly or at most 1789, at least or exactly or at most 1790, at least or exactly or at most 1791, at least or exactly or at most 1792, at least or exactly or at most 1793, at least or exactly or at most 1794, at least or exactly or at most 1795, at least or exactly or at most 1796, at least or exactly or at most 1797, at least or exactly or at most 1798, at least or exactly or at most 1799, at least or exactly or at most 1800, at least or exactly or at most 1801, at least or exactly or at most 1802, at least or exactly or at most 1803, at least or exactly or at most 1804, at least or exactly or at most 1805, at least or exactly or at most 1806, at least or exactly or at most 1807, at least or exactly or at most 1808, at least or exactly or at most 1809, at least or exactly or at most 1810, at least or exactly or at most 1811, at least or exactly or at most 1812, at least or exactly or at most 1813, at least or exactly or at most 1814, at least or exactly or at most 1815, at least or exactly or at most 1816, at least or exactly or at most 1817, at least or exactly or at most 1818, at least or exactly or at most 1819, at least or exactly or at most 1820, at least or exactly or at most 1821, at least or exactly or at most 1822, at least or exactly or at most 1823, at least or exactly or at most 1824, at least or exactly or at most 1825, at least or exactly or at most 1826, at least or exactly or at most 1827, at least or exactly or at most 1828, at least or exactly or at most 1829, at least or exactly or at most 1830, at least or exactly or at most 1831, at least or exactly or at most 1832, at least or exactly or at most 1833, at least or exactly or at most 1834, at least or exactly or at most 1835, at least or exactly or at most 1836, at least or exactly or at most 1837, at least or exactly or at most 1838, at least or exactly or at most 1839, at least or exactly or at most 1840, at least or exactly or at most 1841, at least or exactly or at most 1842, at least or exactly or at most 1843, at least or exactly or at most 1844, at least or exactly or at most 1845, at least or exactly or at most 1846, at least or exactly or at most 1847, at least or exactly or at most 1848, at least or exactly or at most 1849, at least or exactly or at most 1850, at least or exactly or at most 1851, at least or exactly or at most 1852, at least or exactly or at most 1853, at least or exactly or at most 1854, at least or exactly or at most 1855, at least or exactly or at most 1856, at least or exactly or at most 1857, at least or exactly or at most 1858, at least or exactly or at most 1859, at least or exactly or at most 1860, at least or exactly or at most 1861, at least or exactly or at most 1862, at least or exactly or at most 1863, at least or exactly or at most 1864, at least or exactly or at most 1865, at least or exactly or at most 1866, at least or exactly or at most 1867, at least or exactly or at most 1868, at least or exactly or at most 1869, at least or exactly or at most 1870, at least or exactly or at most 1871, at least or exactly or at most 1872, at least or exactly or at most 1873, at least or exactly or at most 1874, at least or exactly or at most 1875, at least or exactly or at most 1876, at least or exactly or at most 1877, at least or exactly or at most 1878, at least or exactly or at most 1879, at least or exactly or at most 1880, at least or exactly or at most 1881, at least or exactly or at most 1882, at least or exactly or at most 1883, at least or exactly or at most 1884, at least or exactly or at most 1885, at least or exactly or at most 1886, at least or exactly or at most 1887, at least or exactly or at most 1888, at least or exactly or at most 1889, at least or exactly or at most 1890, at least or exactly or at most 1891, at least or exactly or at most 1892, at least or exactly or at most 1893, at least or exactly or at most 1894, at least or exactly or at most 1895, at least or exactly or at most 1896, at least or exactly or at most 1897, at least or exactly or at most 1898, at least or exactly or at most 1899, at least or exactly or at most 1900, at least or exactly or at most 1901, at least or exactly or at most 1902, at least or exactly or at most 1903, at least or exactly or at most 1904, at least or exactly or at most 1905, at least or exactly or at most 1906, at least or exactly or at most 1907, at least or exactly or at most 1908, at least or exactly or at most 1909, at least or exactly or at most 1910, at least or exactly or at most 1911, at least or exactly or at most 1912, at least or exactly or at most 1913, at least or exactly or at most 1914, at least or exactly or at most 1915, at least or exactly or at most 1916, at least or exactly or at most 1917, at least or exactly or at most 1918, at least or exactly or at most 1919, at least or exactly or at most 1920, at least or exactly or at most 1921, at least or exactly or at most 1922, at least or exactly or at most 1923, at least or exactly or at most 1924, at least or exactly or at most 1925, at least or exactly or at most 1926, at least or exactly or at most 1927, at least or exactly or at most 1928, at least or exactly or at most 1929, at least or exactly or at most 1930, at least or exactly or at most 1931, at least or exactly or at most 1932, at least or exactly or at most 1933, at least or exactly or at most 1934, at least or exactly or at most 1935, at least or exactly or at most 1936, at least or exactly or at most 1937, at least or exactly or at most 1938, at least or exactly or at most 1939, at least or exactly or at most 1940, at least or exactly or at most 1941, at least or exactly or at most 1942, at least or exactly or at most 1943, at least or exactly or at most 1944, at least or exactly or at most 1945, at least or exactly or at most 1946, at least or exactly or at most 1947, at least or exactly or at most 1948, at least or exactly or at most 1949, at least or exactly or at most 1950, at least or exactly or at most 1951, at least or exactly or at most 1952, at least or exactly or at most 1953, at least or exactly or at most 1954, at least or exactly or at most 1955, at least or exactly or at most 1956, at least or exactly or at most 1957, at least or exactly or at most 1958, at least or exactly or at most 1959, at least or exactly or at most 1960, at least or exactly or at most 1961, at least or exactly or at most 1962, at least or exactly or at most 1963, at least or exactly or at most 1964, at least or exactly or at most 1965, at least or exactly or at most 1966, at least or exactly or at most 1967, at least or exactly or at most 1968, at least or exactly or at most 1969, at least or exactly or at most 1970, at least or exactly or at most 1971, at least or exactly or at most 1972, at least or exactly or at most 1973, at least or exactly or at most 1974, at least or exactly or at most 1975, at least or exactly or at most 1976, at least or exactly or at most 1977, at least or exactly or at most 1978, at least or exactly or at most 1979, at least or exactly or at most 1980, at least or exactly or at most 1981, at least or exactly or at most 1982, at least or exactly or at most 1983, at least or exactly or at most 1984, at least or exactly or at most 1985, at least or exactly or at most 1986, at least or exactly or at most 1987, at least or exactly or at most 1988, at least or exactly or at most 1989, at least or exactly or at most 1990, at least or exactly or at most 1991, at least or exactly or at most 1992, at least or exactly or at most 1993, at least or exactly or at most 1994, at least or exactly or at most 1995, at least or exactly or at most 1996, at least or exactly or at most 1997, at least or exactly or at most 1998, at least or exactly or at most 1999, at least or exactly or at most 2000, at least or exactly or at most 2001, at least or exactly or at most 2002, at least or exactly or at most 2003, at least or exactly or at most 2004, at least or exactly or at most 2005, at least or exactly or at most 2006, at least or exactly or at most 2007, at least or exactly or at most 2008, at least or exactly or at most 2009, at least or exactly or at most 2010, at least or exactly or at most 2011, at least or exactly or at most 2012, at least or exactly or at most 2013, at least or exactly or at most 2014, at least or exactly or at most 2015, at least or exactly or at most 2016, at least or exactly or at most 2017, at least or exactly or at most 2018, at least or exactly or at most 2019, at least or exactly or at most 2020, at least or exactly or at most 2021, at least or exactly or at most 2022, at least or exactly or at most 2023, at least or exactly or at most 2024, at least or exactly or at most 2025, at least or exactly or at most 2026, at least or exactly or at most 2027, at least or exactly or at most 2028, at least or exactly or at most 2029, at least or exactly or at most 2030, at least or exactly or at most 2031, at least or exactly or at most 2032, at least or exactly or at most 2033, at least or exactly or at most 2034, at least or exactly or at most 2035, at least or exactly or at most 2036, at least or exactly or at most 2037, at least or exactly or at most 2038, at least or exactly or at most 2039, at least or exactly or at most 2040, at least or exactly or at most 2041, at least or exactly or at most 2042, at least or exactly or at most 2043, at least or exactly or at most 2044, at least or exactly or at most 2045, at least or exactly or at most 2046, at least or exactly or at most 2047, at least or exactly or at most 2048, at least or exactly or at most 2049, at least or exactly or at most 2050, at least or exactly or at most 2051, at least or exactly or at most 2052, at least or exactly or at most 2053, at least or exactly or at most 2054, at least or exactly or at most 2055, at least or exactly or at most 2056, at least or exactly or at most 2057, at least or exactly or at most 2058, at least or exactly or at most 2059, at least or exactly or at most 2060, at least or exactly or at most 2061, at least or exactly or at most 2062, at least or exactly or at most 2063, at least or exactly or at most 2064, at least or exactly or at most 2065, or at least or exactly or at most 2066 amino acid residues in SEQ ID NO: 146.

Another way to phrase this is that for each of the definitions of $A^1$ and $A^2$ the number of the contiguous amino acid residues derived from SEQ ID NO: 1-9 and 139-146 is at least or exactly or at most N-n, where N is the length of the sequence ID in question and n is any integer ranging from N-5 and 0; that is, the at least 5 contiguous amino acids can be at least any number between 5 and the length of the reference sequence minus one, in increments of one.

In the embodiments of the first aspect of the invention discussed above, the at least or exactly 5 contiguous amino acid residues present in any one of SEQ ID NOs: 1-9 and 139-146 in the definition of $A^1$ and $A^2$ can independently commence at any one of amino acid residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, and 194 in any one of SEQ ID NOs: 1-9 and 139-146, with the proviso that the number of the selected commencing amino acid residue satisfies the formula N≤L−n+1, where N is the number of the selected residue, L is the number of amino acid residues in the sequence selected from SEQ ID NOs: 1-9 and 139-146 from which the at least 5 contiguous amino acid residues are selected, and n is the number of contiguous amino acid residues, or the at least or exactly 5 contiguous amino acid residues present in any one of SEQ ID NOs: 2-9 and 139-146 in the definition of $A^1$ and $A^2$ can independently commence at any one of amino acid residues 195, 196, 197, and 198 in any one of SEQ ID NOs: 2-9 and 139-146, with the proviso that the number of the selected commencing amino acid residue satisfies the formula N≤L−n+1, where N is the number of the selected residue, L is the number of amino acid residues in the sequence selected from SEQ ID NOs: 2-9 and 139-146 from which the at least 5 contiguous amino acid residues are selected, and n is the number of contiguous amino acid residues; or the at least or exactly 5 contiguous amino acid residues present in any one of SEQ ID NOs: 3-9 and 139-146 in the definition of $A^1$ and $A^2$ can independently commence at any one of amino acid residues 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, and 289 in any one of SEQ ID NOs: 3-9 and 139-146, with the proviso that the number of the selected commencing amino acid residue satisfies the formula N≤L−n+1, where N is the number of the selected residue, L is the number of amino acid residues in the sequence selected from SEQ ID NOs: 3-9 and 139-146 from which the at least 5 contiguous amino acid residues are selected, and n is the number of contiguous amino acid residues; or the least or exactly 5 contiguous amino acid residues present in any one of SEQ ID NOs: 4-9 and 139-146 in the definition of $A^1$ and $A^2$ can independently commence at any one of amino acid residues 290, 291, 292, 293, 294, 295, 296, 297, 298, 299, 300, 301, 302, 303, 304, 305, 306, 307, 308, 309, 310, 311, 312, 313, 314, and 315 in any one of SEQ ID NOs: 4-9 and 139-146, with the proviso that the number of the selected commencing amino acid residue satisfies the formula N≤L−n+1, where N is the number of the selected residue, L is the number of amino acid residues in the sequence selected from SEQ ID NOs: 4-9 and 139-146 from which the at least 5 contiguous amino acid residues are selected, and n is the number of contiguous amino acid residues; or the at least or exactly 5 contiguous amino acid residues present in any one of SEQ ID NOs: 4-9 and 140-146 in the definition of $A^1$ and $A^2$ can independently commence at any one of amino acid residues 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, and 347 in any one of SEQ ID NOs: 4-9 and 140-146, with the proviso that the number of the selected commencing amino acid residue satisfies the formula N≤L−n+1, where N is the number of the selected residue, L is the number of amino acid residues in the sequence selected from SEQ ID NOs: 4-9 and 140-146 from which the at least 5 contiguous amino acid residues are selected, and n is the number of contiguous amino acid residues; or the at least or exactly 5 contiguous amino acid residues present in any one of SEQ ID NOs: 5-9 and 140-146 in the definition of $A^1$ and $A^2$ can independently commence at any one of amino acid residues 348, 349, 350, 351, 352, 353, 354, 355, 356, 357, 358, 359, 360, and 361$^{in}$ any one of SEQ ID NOs: 5-9 and 140-146, with the proviso that the number of the selected commencing amino acid residue satisfies the formula N≤L−n+1, where N is the number of the selected residue, L is the number of amino acid residues in the sequence selected from SEQ ID NOs: 5-9 and 140-146 from which the at least 5 contiguous amino acid residues are selected, and n is the number of contiguous amino acid residues; or the at least or exactly 5 contiguous amino acid residues present in any one of SEQ ID NOs: 6-9 and 140-146 in the definition of $A^1$ and $A^2$ can independently commence at any one of amino acid residues 362, 363, 364, 365, 366, 367, 368, 369, 370, 371, 372, 373, 374, 375, 376, 377, 378, 379, 380, 381, 382, 383, 384, 385, and 386 in any one of SEQ ID NOs: 6-9 and 140-146, with the proviso that the number of the selected commencing amino acid residue satisfies the formula N≤L−n+1, where N is the number of the selected residue, L is the number of amino acid residues in the sequence selected from SEQ ID NOs: 6-9 and 140-146 from which the at least 5 contiguous amino acid residues are selected, and n is the number of contiguous amino acid residues; or the at least or exactly 5 contiguous amino acid residues present in any one of SEQ ID NOs: 7-9 and 140-146 in the definition of $A^1$ and $A^2$ can independently commence at any one of amino acid residues 387, 388, 389, 390, 391, 392, 393, 394, 395, 396, 397, 398, 399, 400, 401, 402, 403, 404, and 405 in any one of SEQ ID NOs: 7-9 and 140-146, with the proviso that the number of the selected commencing amino acid residue satisfies the formula N≤L−n+1, where N is the number of the selected residue, L is the number of amino acid residues in the sequence selected from SEQ ID NOs: 7-9 and 140-146 from which the at least 5 contiguous amino acid residues are selected, and n is the number of contiguous amino acid residues; or the at least or exactly 5 contiguous amino acid residues present in any one of SEQ ID NOs: 8, 9 and 140-146 in the definition of $A^1$ and $A^2$ can independently commence at any one of amino acid residues 406, 407, and 408 in any one of SEQ ID NOs: 8, 9 and 140-146, with the proviso that the number of the selected commencing amino acid residue satisfies the formula N≤L−n+1, where N is the number of the selected residue, L is the number of amino acid residues in the sequence selected from SEQ ID NOs: 8, 9 and 140-146 from which the at least 5 contiguous amino acid residues are selected, and n is the number of contiguous amino acid residues; or the at least or exactly 5 contiguous amino acid residues present in any one of SEQ ID NOs: 9 and 140-146 in the definition of $A^1$ and $A^2$ can independently commence at any one of amino acid residues 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, and 511 in any one of SEQ ID NOs: 9 and 140-146, with the proviso that the number of the selected commencing amino acid residue satisfies the formula N≤L−n+1, where N is the number of the selected residue, L is the number of amino acid residues in the sequence selected from SEQ ID NOs: 9 and 140-146 from which the at least 5 contiguous amino acid residues are selected, and n is the number of contiguous amino acid residues; or the at least or exactly 5 contiguous amino acid residues present in any one of SEQ ID NOs: 9 and 141-146 in the definition of $A^1$ and $A^2$ can independently commence at any one of amino acid residues 512, 513, 514, and 515 in any one of SEQ ID NOs: 9 and 141-146, with the proviso that the number of the selected commencing amino acid residue satisfies the formula N≤L−n+1, where N is the number of the selected residue, L is the number of amino acid residues in the sequence selected from SEQ ID NOs: 9 and 141-146 from which the at least 5 contiguous amino acid residues are selected, and n is the number of contiguous amino acid residues; or the at least or exactly 5 contiguous amino acid residues present in any one of SEQ ID NOs: 9 and 142-146 in the definition of $A^1$ and $A^2$ can independently commence at any one of amino acid residues 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, and 588 in any one of SEQ ID NOs: 9 and 142-146, with the proviso that the number of the selected commencing amino acid residue satisfies the formula N≤L−n+1, where N is the number of the selected residue in SEQ ID NOs: 9 and 142-146, and n is the number of contiguous amino acid residues; or the at least or exactly 5 contiguous amino acid residues present in any one of SEQ ID NOs: 142-146 in the definition of $A^1$ and $A^2$ can independently commence at any one of amino acid residues 589, 590, 591, 592, 593, 594, 595, 596, 597, 598, 599, 600, 601, 602, 603, 604, 605, 606, 607, 608, 609, 610, 611, 61.2, 613, 614, and 615 in any one of SEQ ID NOs: 142-146, with the proviso that the number of the selected commencing amino acid residue satisfies the formula N≤L−n+1, where N is the number of the selected residue in SEQ ID NO: 142-146, and n is the number of contiguous amino acid residues; or the at least or exactly 5 contiguous amino acid residues present in any one of SEQ ID NOs: 143-146 in the definition of $A^1$ and $A^2$ can independently commence at any one of amino acid residues 616, 617, 618, 619, 620, 621, 622, 623, 624, 625, 626, 627, 628, 629, 630, 631, 632, 633, 634, 635, 636, 637, 638, 639, 640, and 641 in any one of SEQ ID NOs: 143-146, with the proviso that the number of the selected commencing amino acid residue satisfies the formula N≤L−n+1, where N is the number of the selected residue in SEQ ID NO: 143-146, and n is the number of contiguous amino acid residues; or the at least or exactly 5 contiguous amino acid residues present in any one of SEQ ID NOs: 144-146 in the definition of $A^1$ and $A^2$ can independently commence at any one of amino acid residues 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, and 677 in any one of SEQ ID NOs: 144-146, with the proviso that the number of the selected commencing amino acid residue satisfies the formula N≤L−n+1, where N is the number of the selected residue in SEQ ID NO: 144-146, and n is the number of contiguous amino acid residues; or the at least or exactly 5 contiguous amino acid residues present in any one of SEQ ID NOs: 145 or 146 in the definition of $A^1$ and $A^2$ can independently commence at any one of amino acid residues 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, and 765 in any one of SEQ ID NOs: 145 or 146, with the proviso that the number of the selected commencing amino acid residue satisfies the formula N≤L−n+1, where N is the number of the selected residue in SEQ ID NO: 142-146, and n is the number of contiguous amino acid residues; or the at least or exactly 5 contiguous amino acid residues present in SEQ ID NO: 146 in the definition of $A^1$ and $A^2$ can independently commence at any one of amino acid residues 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1641, 1642, 1643, 1644, 1645, 1646, 1647, 1648, 1649, 1650, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, 1731, 1732, 1733, 1734, 1735, 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, 1963, 1964, 1965, 1966, 1967, 1968, 1969, 1970, 1971, 1972, 1973, 1974, 1975, 1976, 1977, 1978, 1979, 1980, 1981, 1982, 1983, 1984, 1985, 1986, 1987, 1988, 1989, 1990, 1991, 1992, 1993, 1994, 1995, 1996, 1997, 1998, 1999, 2000, 2001, 2002, 2003, 2004, 2005, 2006, 2007, 2008, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062 in SEQ ID NO 146, with the proviso that the number of the selected commencing amino acid residue satisfies the formula N≤L−n+1, where N is the number of the selected residue in SEQ ID NO: 146, and n is the number of contiguous amino acid residues.

For instance, if the number of the contiguous amino acid residues defined for $A^1$ and $A^2$ is exactly 30 and the sequence in question is SEQ ID NO: 1, the N-terminal first residue can hence not be higher numbered than 199−30+1=170, meaning that the 30 amino acid residues in that case will be constituted by amino acid residues 170-199 of SEQ ID NO: 1.

The chimeric polypeptide as disclosed in any of the embodiments above may include an amino acid sequence $A^1$ and $A^2$, which can be any suitable fusion partner. In certain embodiments $A^1$ and $A^2$ is selected from the group consisting of
1) a methionine residue,
2) an amino acid sequence located, or directly linked, N-terminally to the amino acid sequence selected from any one of SEQ ID NOs: 1-9 from which $A^1$ and $A^2$ is derived,
3) an amino acid sequence that comprises or constitutes a purification tag,
4) an amino acid sequence that comprises or constitutes an immunogenic carrier molecule,
5) an amino acid sequence that exerts adjuvant activity; and
6) any combination of 1-5.

This means that when $A^1$ and $A^2$ is an amino acid sequence (as in 2-6) then $A^1$ and $A^2$ further may include an N-terminal methionine residue, cf. option 1.

The chimeric polypeptide may also include an amino acid sequence $a^2$, which can be any suitable fusion partner. In certain embodiments, $a^2$ is selected from the group consisting of
  i) an amino acid sequence located, or directly linked, C-terminally to the amino add sequence selected from any one of SEQ ID NOs: 1-9 from which $A^2$ is derived,
  ii) an amino acid sequence that comprises or constitutes a purification tag,
  iii) an amino acid sequence that comprises or constitutes an immunogenic carrier molecule,
  iv) an amino acid sequence that exerts adjuvant activity, and
  v) any combination of i-iv.

In the definition of the chimeric polypeptide in any of the embodiments described above L may constitute a linker. Typical linkers are flexible, and the ones that art particularly preferred are linkers that comprise glycine and/or serine residues. In particular, the linker may be any linker disclosed in Chen X et al. (2013), Advanced drug delivery reviews 65(10): 1357-1369. doi:10.1016/j.addr.2012.09.039. Particularly preferred linkers comprise or consist of the amino acid sequence GSGGGA (SEQ ID NO: 10) or GSGG-GAGSGGGA (SEQ ID NO: 11).

A further embodiment of the first aspect is that one or more of the amino acid sequences derived from SEQ ID NOs: 21-40 (see the second aspect of the invention) can be introduced into chimeric polypeptides of the first aspect of the present invention. Thus, such sequences can be part of or constitute $a^1$, L, and/or $a^2$ in formula I.

The presently exemplified chimeric polypeptides of the first aspect of the invention are those that comprise or consist of the amino acid sequence SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20, or SEQ ID NO: 59, or SEQ ID NO: 60, or SEQ ID NO: 61, or SEQ ID NO: 62, or SEQ ID NO: 63, or SEQ ID NO: 64, or SEQ ID NO: 65, or SEQ ID NO: 66, or SEQ ID NO: 67, or SEQ ID NO: 68, or SEQ ID NO: 69, or SEQ ID NO: 70, or SEQ ID NO: 71, or SEQ ID NO: 72, or SEQ ID NO: 73, or SEQ ID NO: 74, or SEQ ID NO: 75, or SEQ ID NO: 76, or SEQ ID NO: 77, or SEQ ID NO: 78, or SEQ ID NO: 79, or SEQ ID NO: 80, or SEQ ID NO: 81, or SEQ ID NO: 82, or SEQ ID NO: 83, or SEQ ID NO: 84, or SEQ ID NO: 85, or SEQ ID NO: 86.

The chimeric polypeptide of the second aspect of the invention focusses on inclusion of MHC Class II binding peptides derived from *S. aureus* into peptide constructs. As shown in the example below, the present inventors have identified 20 *S. aureus* derived peptides (SEQ ID NOs: 21-40) that exert binding to multiple MHC Class II molecules (DRB1*01:01; DRB1*04:01; and DRB5*01:01), and these have been introduced into chimeric peptide constructs. Hence, the second aspect of the invention relates to a chimeric polypeptide comprising at least 2 non-identical amino acid sequences, where each of said at least 2 non-identical amino acid sequences consists of any one of SEQ ID NOs: 21-40, wherein 0, 1, 2, or 3 amino acid residues can be substituted. In other words, each of SEQ ID NOs 21-40 can be modified with up to 3 amino acid substitutions, thereby providing for features such as increased stability of binding to MHC Class II, broader population coverage, changed solubility in either water or organic solvents, and increased stability towards proteolytic breakdown.

The chimeric polypeptide of the second aspect typically comprises at least or exactly 3 or at least or exactly 4 or at least or exactly 5 or at least or exactly 6 or at least or exactly 7 or at least or exactly 8 or at least or exactly 9 or at least or exactly 10 or at least or exactly 11 or at least or exactly 11 or at least or exactly 12 or at least or exactly 13 or at least or exactly 14 or at least or exactly 15 or at least or exactly 16 or at least or exactly 17 or at least or exactly 18 or at least or exactly 19 or at least or exactly 20 of said non-identical amino acid sequences. In particularly interesting embodiments of the second aspect, 2 or more of said at least 2 non-identical amino acid sequences are not derivable from the same of SEQ ID NOs: 21-40 by introducing 0, 1, 2, or 3 amino acid substitutions. This means that 2 or more of the non-identical amino acid sequences are unrelated in the sense that their sequences cannot be arrived at when starting out with one and the same of SEQ ID NOs: 21-40 and introducing 0, 1, 2, or 3 amino acid substitutions. In an embodiment, 3 or 4 or 5 or 6 or 7 or 8 or 9 or 10 or 11 or 12 or 13 or 14 or 15 or 16 or 17 or 19 or 20 of said at least 2 non-identical amino acid sequences are not derivable from the same of SEQ ID NOs: 21-40 by introducing 0, 1, 2, or 3 amino acid substitutions. "Derivable from SEQ ID NO: 21-40" thus means that if an amino acid sequence can be defined by introducing 0, 1, 2 or 3 amino acid substitutions in a sequence selected from one of SEQ ID NOs: 21-40, then this amino acid sequence is derivable from that sequence selected from SEQ ID NOs: 21-40.

In some embodiments of the 2$^{nd}$ aspect of the invention, including the embodiments disclosed above, the chimeric polypeptide includes amino acid sequences derivable from the group consisting of SEQ ID NO: 21, 23, 26, 27, 30, 33, 34, 38, and 40, but none derivable from the group selected from SEQ ID NOs: 22, 24, 25, 28, 29, 31, 32, 35-37, and 39. Alternatively, some embodiments relate to chimeric polypeptide that do not include amino acid sequences derivable from the group consisting of SEQ ID NO: 21, 23, 26, 27, 30, 33, 34, 38, and 40, but does include amino acid sequences derivable from the groups selected from SEQ ID NOs: 22, 24, 25, 28, 29, 31, 32, 35-37, and 39.

The chimeric polypeptide of the second aspect can include that the individual sequences derived from SEQ ID NOs: 21-40 are directly jointed, but in important embodiments some or all of the sequences are separated. One possibility is to separate via use of peptide linkers (cf. above for details) but another possibility is to use a scaffold protein or polypeptide, where the sequences derived from SEQ ID NOs: 21-40 are introduced via insertion and/or substitution in the scaffold's amino acid sequence. A particularly interesting linker for use in the second aspect is SEQ ID NO: 45 (-GPGPG-), cf. SEQ ID NOs: 41 and 42. With respect to the scaffold protein, it may be any suitable scaffold. In the present application, the protein having the NCBI identifier: 53721566 has been used as scaffold, cf. SEQ ID NOs: 43 and 44.

A further embodiment of the second aspect is that one or more of the amino acid sequences derived from SEQ ID NOs: 21-40 can be introduced into chimeric polypeptides of the first aspect of the present invention. Thus, such sequences can be part of or constitute a$^1$, L, and/or a$^2$ in formula I. Thus, in such embodiments, A$^1$ and/or A$^2$ can constitute scaffolds as discussed herein.

The chimeric polypeptide of the invention is in certain embodiments also covalently linked (i.e. fused or conjugated) to an immunogenic carrier molecule; or, phrased otherwise, the polypeptide of the invention also includes such an immunogenic carrier molecule in addition to the chimeric polypeptides of the present invention. The immunogenic carrier molecule is a typically polypeptide that induces T-helper lymphocyte responses in a majority of humans, such as immunogenic carrier proteins selected from the group consisting of keyhole limpet hemocyanino or a fragment thereof, tetanus toxoid or a fragment thereof, dipththeria toxoid or a fragment thereof. Other suitable carrier molecules are discussed infra. One further fusion partner, which is preferably incorporated is a "His tag", i.e. a stretch of amino acids, which is rich or only consists of histidinyl residues so as to facilitate protein purification.

In preferred embodiments, the polypeptide of the invention detailed above is capable of inducing an adaptive immune response against the chimeric polypeptide in a mammal, in particular in a human being. Preferably, the adaptive immune response is a protective adaptive immune response against infection with S. aureus, in particular multi-resistant S. aureus. The polypeptide may in these cases induce a humeral and/or a cellular immune response.

It is believed that the presently presented T-helper epitopes are inventive in their own right.

Hence, related to the second aspect of the invention—and part of the invention—is a peptide selected from SEQ ID NOs. 21-40 and peptides having an amino acid sequence set forth in any one of SEQ ID NOs: 21-40 wherein 1, 2, or 3 amino acids have been substituted. Also included in the invention is peptides having up to 30 amino acid residues and comprising 1) an amino acid selected from SEQ ID NOs. 21-40 2) an amino acid sequence set forth in any one of SEQ ID NOs: 21-40 wherein 1, 2, or 3 amino acids have been substituted.

Nucleic Acid Fragments of the Invention; Third Aspect

The nucleic acid fragment of the invention referred to above preferably is a DNA fragment or an RNA fragment. Exemplary DNA fragments are provided as SEQ ID NOs: 46-54 (DNA encoding SEQ ID NOs: 12-20, i.e. exemplary polypeptides of the first aspect of the invention) and as SEQ ID NOs: 55-58 (DNA encoding SEQ ID NOs: 41-44, i.e. exemplary polypeptides of the second aspect of the present invention). The RNA equivalents of these sequences are also encompassed by the present invention (i.e. SEQ ID NOs: 46-58, where T is exchanged with U in the sequence notation). Also the complimentary sequences are embraced by the present invention.

Since the presently disclosed chimeric polypeptides can be encoded by a plethora of nucleic acid sequences due to the degeneracy of the genetic code, the skilled person will understand that none single nucleic acid sequence is particularly preferred as long as it encodes a chimeric polypeptide of the present invention. Rather, the skilled person will design suitable coding sequences that are codon optimised with respect to e.g. the expression system wherein recombinant production of the polypeptide is to take place.

Nevertheless, the sequence identity with the nucleotide sequence in i) or ii) or iii) in the definition of the nucleic acid fragment of the invention is preferably at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

It will be understood that the nucleic acid fragments of the invention may be used for both production, carrier and vaccine purposes—the latter will require that the sequences are included in expression vectors that may lead to production of immunogenic proteins in the host animal receiving the vector.

Fourth Aspect—Vectors of the Invention

It will be understood that the nucleic acid fragments of the invention may be used for both production, carrier and vaccine purposes—the latter will require that the sequences are included in expression vectors that may lead to production of immunogenic proteins in the mammal receiving the vector. Or put differently, the nucleic acid is comprised in a vector capable of expressing the nucleic acid in man upon administration.

Such a vector of the invention often comprises in operable linkage and in the 5'-3' direction, an expression control region comprising an enhancer/promoter for driving expression of the nucleic acid, an optional signal peptide coding sequence, a nucleotide sequence of the invention, and optionally a terminator. Hence, such a vector constitutes an expression vector useful for effecting production in cells of the polypeptide of the invention. Since the polypeptides of the invention are protozoan of origin, recombinant production has to be effected in host cells that can express the coding nucleic acid. Bacterial host cells may be used. However, if the vector is to drive expression in eukaryotic cell (as would be the case for a nucleic acid vaccine vector), the expression control region should be adapted to this particular use.

For production purposes it is therefore often convenient that the expression control region drives expression in a prokaryotic cell such as a bacterium, e.g. in *E. coli*, or in a eukaryotic cell such as a plant cell, an insect cell, or a mammalian cell. For vaccine purposes, the expression control region has to be able to drive expression in a mammalian, preferably human, cell.

Also, for production purposes, it is practical that the vector is capable of integrating the nucleic acid into the genome of a host cell—this is particularly useful if the vector is use in the production of stably transformed cells, where the progeny will also include the genetic information introduced via the vector. Alternatively, vectors incapable of being integrated into the genome of a piscine host cell are useful in e.g. nucleic acid vaccination.

An interesting production system is the use of plants. For instance, proteins can be produced at low cost in plants using an *Agrobacterium* transfection system to genetically modify plants to express genes that encode the protein of interest. One commercially available platform are those provided by iBio CMO LLC (8800 HSC Pkwy, Bryan, TX 77807, USA) and iBio, Inc (9 Innovation Way, Suite 100, Newark, DE 19711, USA) and disclosed in e.g. EP 2 853 599, EP 1 769 068, and EP 2 192 172. Hence, in such systems the vector is an *Agrobacterium* vector or other vector suitable for transfection of plants.

The vector is typically selected from the group consisting of a virus, such as a virus which is non-pathogenic in mammals and in particular in humans, a bacterium such as a bacterium which is non-pathogenic in mammals such as humans, a plasmid, a minichromosome, and a cosmid.

Interesting vectors are viral vectors (in particular those useful as vaccine agents in humans). These may be selected from the group consisting of a retrovirus vector, such as a lentivirus vector, an adenovirus vector, an adeno-associated virus vector, and a pox virus vector. Certain pox virus vectors are preferred, in particular vaccinia virus vectors. A particularly preferred vaccinia virus vector is a modified vaccinia Ankara (MVA) vector.

Polypeptides of the invention may as indicated be encoded by a nucleic acid molecule comprised in a vector. A nucleic acid sequence can be "heterologous," which means that it is in a context foreign to the cell in which the vector is being introduced, which includes a sequence homologous to a sequence in the cell but in a position within the host cell where it is ordinarily not found.

Vectors include naked DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques. In addition to encoding the polypeptides of this invention, a vector of the present invention may encode polypeptide sequences such as a "tag" or immunogenicity enhancing peptide (e.g. an immunogenic carrier or a fusion partner that stimulates the immune system, such as a cytokine or active fragment thereof). Useful vectors encoding such fusion proteins include pIN vectors, vectors encoding a stretch of histidines, and pGEX vectors, for use in generating glutathione S-transferase (GST) soluble fusion proteins for later purification and separation or cleavage.

Vectors of the invention may be used in a host cell to produce a polypeptide of the invention that may subsequently be purified for administration or the vector may be purified for direct administration for expression of the protein (as is the case when administering a nucleic acid vaccine).

Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural state. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including polymerase chain reaction in connection with the compositions disclosed herein.

It may be important to employ a promoter and/or enhancer that effectively direct(s) the expression of the DNA segment in the cell type or organism chosen for expression. Those of skill in the art of molecular biology generally know the use of promoters, enhancers, and cell type combinations for protein expression. The promoters employed may be constitutive, tissue-specific, or inducible and in certain embodiments may direct high level expression of the introduced DNA segment under specified conditions, such as large-scale production of recombinant proteins or peptides.

Examples of inducible elements, which are regions of a nucleic acid sequence that can be activated in response to a specific stimulus, include but are not limited to Immunoglobulin Heavy Chain, Immunoglobulin Light Chain, T Cell Receptor, HLA DQα and/or DQβ, β-Interferon, Interleukin-2, Interleukin-2 Receptor, MHC Class II 5, MHC Class II HLA-DRα, β-Actin, Muscle Creatine Kinase (MCK), Pre-albumin (Transthyretin), Elastase I, Metallothionein (MTII), Collagenase, Albumin, α-Fetoprotein, γ-Globin, β-Globin, c-fos, c-HA-ras, Insulin, Neural Cell Adhesion Molecule (NCAM), α1-Antitrypain, H2B (TH2B) Histone, Mouse and/or Type I Collagen, Glucose-Regulated Proteins (GRP94 and GRP78), Rat Growth Hormone, Human Serum Amyloid A (SAA), Troponin I (TN I), Platelet-Derived Growth Factor (PDGF), Duchenne Muscular Dystrophy, SV40, Polyoma, Retroviruses, Papilloma Virus, Hepatitis B Virus, Human Immunodeficiency Virus, Cytomegalovirus (CMV) IE, and Gibbon Ape Leukemia Virus.

Inducible Elements include MT II—Phorbol Ester (TFA)/Heavy metals; MMTV (mouse mammary tumor virus)—Glucocorticoids; β-Interferon—poly(rl)x/poly(rc); Adenovirus 5 E2—EIA; Collagenase—Phorbol Ester (TPA); Stromelysin—Phorbol Ester (TPA); SV40—Phorbol Ester (TPA); Murine MX Gene—Interferon, Newcastle Disease Virus; GRP78 Gene—A23187; α-2-Macroglobulin—IL-6; Vimentin—Serum; MHC Class I Gene H-2κb—Interferon; HSP70-E1A/SV40 Large T Antigen; Proliferin—Phorbol Ester/TPA; Tumor Necrosis Factor—PMA; and Thyroid Stimulating Hormonea Gene—Thyroid Hormone.

Also contemplated as useful in the present invention are the dectin-1 and dectin-2 promoters. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

The particular promoter that is employed to control the expression of peptide or protein encoding polynucleotide of the invention is not believed to be critical, so long as it is capable of expressing the polynucleotide in a targeted cell. Where a piscine cell is targeted (as is the case in nucleic acid vaccination), it is preferable to position the polynucleotide coding region adjacent to and under the control of a promoter that is capable of being expressed in a piscine cell. Generally speaking, such a promoter might include either a bacterial, piscine or viral promoter as long as the promoter is effective in piscine cells.

In various embodiments—in particular those where recombinant production of the polypeptide of the invention is the aim—the human cytomegalovirus (CMV) immediate early gene promoter, the SV40 early promoter, and the Rous sarcoma virus long terminal repeat can be used to obtain high level expression of a related polynucleotide to this invention. The use of other viral or mammalian cellular or bacterial phage promoters, which are well known in the art, to achieve expression of polynucleotides is contemplated as well.

In embodiments in which a vector is administered to humans for expression of the protein, it is contemplated that a desirable promoter for use with the vector is one that is not down-regulated by cytokines or one that is strong enough that even if down-regulated, it produces an effective amount of the protein/polypeptide of the current invention in humans to elicit an immune response. Non-limiting examples of these are CMV IE and RSV LTR. In other embodiments, a promoter that is up-regulated in the presence of cytokines is employed. The MHC I promoter increases expression in the presence of IFN-γ.

Tissue specific promoters can be used, particularly if expression is in cells in which expression of an antigen is desirable, such as dendritic cells and macrophages. The mammalian MHC I and MHC II promoters are examples of such tissue-specific promoters in man and it is contemplated that corresponding piscine promoters will be effective.

2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic and may be operable in bacteria or mammalian cells. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector. Frequently, a vector is linearized or fragmented using a restriction enzyme that cuts within the MCS to enable exogenous sequences to be ligated to the vector. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. If relevant in the context of vectors of the present invention, vectors containing genomic eukaryotic sequences may require donor and/or acceptor splicing sites to ensure proper processing of the transcript for protein expression.

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (poly A) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

Terminators contemplated for use in the invention include any known terminator of transcription described herein or known to one of ordinary skill in the art, including but not limited to, for example, the bovine growth hormone terminator or viral termination sequences, such as the SV40 terminator. In certain embodiments, the termination signal may be a lack of transcribable or translatable sequence, such as due to a sequence truncation.

6. Polyadenylation Signals

In expression, particularly eukaryotic expression (as is relevant in nucleic acid vaccination), one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, markers that confer resistance to neomycin, puromycin, hygromycin, DHFR, GPT, zeocin or histidinol are useful selectable markers. In addition to markers conferring a phenotype that allows for the discrimination of transformants based on the implementation of conditions, other types of markers including screenable markers such as GFP for colorimetric analysis. Alternatively, screenable enzymes such as herpes simplex virus thymidine kinase (tk) or chloramphenicol acetyltransferase (CAT) may be utilized. One of skill in the art would also know how to employ immunologic markers that can be used in conjunction with FACS analysis. The marker used is not believed to be important, so long as it is capable of being expressed simultaneously with the nucleic acid encoding a protein of the invention. Further examples of selectable and screenable markers are well known to one of skill in the art.

The Transformed Cells of the Invention—Fifth Aspect

Transformed cells of the invention are useful as organisms for producing the polypeptide of the invention, but also as simple "containers" of nucleic acids and vectors of the invention.

Certain transformed cells of the invention are capable of replicating the nucleic acid fragment defined for option i) of the third aspect of the invention. Preferred transformed cells of the invention are capable of expressing the nucleic acid fragment defined for option i).

For recombinant production it is convenient, but not a prerequisite that the transformed cell according is prokaryotic, such as a bacterium, but generally both prokaryotic cells and eukaryotic cells may be used.

Suitable prokaryotic cells are bacterial cells selected from the group consisting of *Escherichia* (such as *E. coli*), *Bacillus* [e.g. *Bacillus subtilis*], *Salmonella*, and *Mycobacterium* [preferably non-pathogenic, e.g. *M. bovis* BCG].

Eukaryotic cells can be in the form of yeasts (such as *Saccharomyces cerevisiae*) and protozoans. Alternatively, the transformed eukaryotic cells are derived from a multicellular organism such as a fungus, an insect cell, a plant cell, or a mammalian cell.

For production purposes, it is advantageous that the transformed cell of the invention is is stably transformed by having the nucleic acid defined above for option i) stably integrated into its genome, and in certain embodiments it is also preferred that the transformed cell secretes or carries on its surface the polypeptide of the invention, since this facilitates recovery of the polypeptides produced. A particular version of this embodiment is one where the transformed cell is a bacterium and secretion of the polypeptide of the invention is into the periplasmic space.

As noted above, stably transformed cells are preferred—these i.a. allows that cell lines comprised of transformed cells as defined herein may be established—such cell lines are particularly preferred aspects of the invention.

Further Details on Cells and Cell Lines are Presented in the Following:

Suitable cells for recombinant nucleic acid expression of the nucleic acid fragments of the present invention are prokaryotes and eukaryotes. Examples of prokaryotic cells include *E. coli*; members of the *Staphylococcus* genus, such as *S. epidermidis*; members of the *Lactobacillus* genus, such as *L. plantarum*; members of the *Lactococcus* genus, such as *L. lactis*; members of the *Bacillus* genus, such as *B. subtilis*; members of the *Corynebacterium* genus such as *C. glutamicum*; and members of the *Pseudomonas* genus such as *Ps. fluorescens*. Examples of eukaryotic cells include mammalian cells; insect cells; yeast cells such as members of the *Saccharomyces* genus (e.g. *S. cerevisiae*), members of the *Pichia* genus (e.g. *P. pastoris*), members of the *Hansenula* genus (e.g. *H. polymorpha*), members of the *Kluyveromyces* genus (e.g. *K. lactis* or *K. fragilis*) and members of the *Schizosaccharomyces* genus (e.g. *S. pombe*).

Techniques for recombinant gene production, introduction into a cell, and recombinant gene expression are well known in the art. Examples of such techniques are provided in references such as Ausubel, Current Protocols in Molecular Biology, John Wiley, 1987-2002, and Sambrook et al., Molecular Cloning, A Laboratory Manual, 2 nd Edition, Cold Spring Harbor Laboratory Press, 1989.

As used herein, the terms "cell," "cell line," and "cell culture" may be used interchangeably. All of these terms also include their progeny, which includes any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org) or from other depository institutions such as Deutsche Sammlung vor Micrroorganismen and Zelikulturen (DSM).

An appropriate host can be determined by one of skill in the art based on the vector backbone and the desired result. A plasmid or cosmid, for example, can be introduced into a prokaryote host cell for replication of many vectors or expression of encoded proteins. Bacterial cells used as host cells for vector replication and/or expression include *Staphylococcus* strains, DH5α, JMI 09, and KC8, as well as a number of commercially available bacterial hosts such as SURE® Competent Cells and SOLOP ACK™ Gold Cells (STRATAGENE®, La Jolla, CA). Alternatively, bacterial cells such as *E. coli* LE392 could be used as host cells for phage viruses. Appropriate yeast cells include *Saccharomyces cerevisiae, Saccharomyces pombe*, and *Pichia pastoris*.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ Baculovirus expression system from CLONTECH®

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Methods of Gene Transfer

Suitable methods for nucleic acid delivery to effect expression of compositions of the present invention are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859), including microinjection (U.S. Pat. No. 5,789,215); by electroporation (U.S. Pat. No. 5,384,253); by calcium phosphate precipitation; by using DEAE dextran followed by polyethylene glycol; by direct sonic loading; by liposome mediated transfection; by microprojectile bombardment (PCT Application Nos. WO 94/09699 and 95/06128; U.S. Pat. Nos. 5,610,042; 5,322,783 5,563,055, 5,550,318, 5,538,877 and 5,538,880); by agitation with silicon carbide fibers (U.S. Pat. Nos. 5,302,523 and 5,464,765); by *Agrobacterium* mediated transformation (U.S. Pat. Nos. 5,591,616 and 5,563,055); or by PEG mediated transformation of protoplasts (U.S. Pat. Nos. 4,684,611 and 4,952,500); by desiccation/inhibition mediated DNA uptake. Through the application of techniques such as these, organelle(s), cell(s), tissue(s) or organism(s) may be stably or transiently transformed.

Compositions of the Invention; Vaccines

Compositions, in particular vaccines, according to the invention are prophylactic but may also be used therapeutically.

Such vaccines comprise immunising antigen(s), immunogen(s), polypeptide(s), protein(s) or nucleic acid(s), usually in combination with "pharmaceutically acceptable carriers", which include any carrier that does not itself induce the production of antibodies harmful to the individual receiving the composition.

In some embodiments of the invention, the pharmaceutical compositions such as vaccines include merely one single antigen, immunogen, polypeptide, protein, nucleic acid or vector of the invention, but in other embodiments, the pharmaceutical compositions comprise "cocktails" of the antigens or of the immunogens or of the polypeptides or of the protein or of the nucleic acids or of the vectors of the invention.

In particularly interesting embodiments, the pharmaceutical composition is a vector mentioned herein, which encodes and can effect expression of at least 2 nucleic acid fragments of the invention.

Another interesting embodiment of a pharmaceutical composition comprises RNA as the active principle, i.e. at least one mRNA encoding a polypeptide of the invention.

An embodiment of a pharmaceutical composition of the invention at least 2 (such as 2, 3, 4, 5, 6, 7, 8, 9, or 10) distinct chimeric polypeptides of the invention described above.

Another embodiment of the pharmaceutical composition of the invention comprises at least 2 (such as 2, 3, 4, 5, 6, 7, 8, 9, or 10) distinct nucleic acid molecules (such as DNA and RNA) each encoding a chimeric polypeptide of the invention.

Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles.

Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, H. pylori, etc. pathogen, cf. the description of immunogenic carriers supra.

The pharmaceutical compositions of the invention thus typically contain an immunological adjuvant, which is commonly an aluminium based adjuvant or one of the other adjuvants described in the following:

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (WO 90/14837; Chapter 10 in Vaccine design: the subunit and adjuvant approach, eds. Powell & Newman, Plenum Press 1995), containing 5% Squalene, 0.5% TWEEN 80, and 0.5% SPAN 85 (optionally containing various amounts of MTP-PE (see below), although not required) formulated into submicron particles using a microfluidizer such as Model 110Y microfluidizer (Microfluidics, Newton, MA), (b) SAF, containing 10% Squalane, 0.4% TWEEN 80, 5% PLURONIC blocked polymer L121, and thr-MDP (see below) either microfluidized into a submicron emulsion or vortexed to generate a larger particle size emulsion, and (c) Ribi adjuvant system (RAS), (Ribi Immunochem, Hamilton, MT) containing 2% Squalene, 0.2% TWEEN 80, and one or more bacterial cell wall components from the group consisting of monophosphoryl lipid A (MPL), trehalose dimycolate (TDM), and cell wall skeleton (CWS), preferably MPL+CWS (Detox™); (3) saponin adjuvants such as STIMULON (Cambridge Bioscience, Worcester, MA) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12, etc.), interferons (eg. gamma interferon), macrophage colony stimulating factor (M-CSF), tumor necrosis factor (TNF), etc.; and (6) other substances that act as immunostimulating agents to enhance the effectiveness of the composition. Alum and MFS9™ adjuvants are preferred together with CFA and IFA.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2''-2'-dipalmitoyl-sn-glycero-3-hydroxyphosphoryloxy)-ethylamine (MTP-PE), etc.

Another possibility for a polypeptide vaccine formulation is to include the vaccine polypeptide(s) of the present invention in a virus-like particle, i.e. a non-infectious self-assembling structure composed of envelope or capsid proteins, where the protein(s) of the invention are incorporated. The effect is multiple presentations of the polypeptides of the invention on the surface of the VLP, which in turn provides for improved immune recognition of the polypeptides. Hence, VLPs exert immunological adjuvant effects, too.

The immunogenic compositions (e.g. the immunising antigen or immunogen or polypeptide or protein or nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. non-human primate, primate, etc.), the capacity of the individual's immune system to synthesize antibodies or generally mount an immune response, the degree of protection desired, the formulation of the vaccine, the treating doctor's assessment of the medical situation, and other relevant factors. It is expected that the amount of immunogen will fall in a relatively broad range that can be determined through routine trials. However, for the purposes of protein vaccination, the amount administered per immunization is typically in the range between 0.5 µg and 500 mg (however, often not higher than 5,000 µg). The amount of polypeptide of the invention can therefore be between 1 and 400 µg, between 2 and 350 µg, between 4 and 300 µg, between 5 and 250 µg, and between 10 and 200 µg. Hence, the composition will typically contain between 0.1-500 µg of protein of the invention per g of vaccine composition.

The immunogenic compositions are conventionally administered parenterally, eg, by injection, either subcutaneously, Intramuscularly, or transdermally/transcutaneously (eg. WO98/20734). Additional formulations suitable for other modes of administration include oral and pulmonary formulations, suppositories, and transdermal applications. In the case of nucleic acid vaccination, also the intravenous or intraarterial routes may be applicable.

Dosage treatment may be a single dose schedule or a multiple dose schedule. The vaccine may be administered in conjunction with other immunoregulatory agents.

As an alternative to protein-based vaccines, DNA vaccination (also termed nucleic acid vaccination or gene vaccination) may be used [eg. Robinson & Torres (1997) Seminars in Immunol 9: 271-283; Donnelly et al. (1997) Avnu Rev Immunol 15: 617-648; later herein].

A further aspect of the invention is as mentioned above the recognition that combination vaccines can be provided, wherein 2 or more chimeric polypeptide antigens disclosed herein are combined to enhance the immune response by the vaccinated individual, including to optimize initial immune response and duration of immunity. For the purposes of this aspect of the invention, multiple antigenic fragments derived from the same, longer protein can also be used, such as the use of a combination of different lengths of polypeptide sequence fragments from one protein.

Thus, embodiments of the invention relate to a composition (or the use as a vaccine thereof) comprising 2 distinct (i.e. non-identical) proteinaceous immunogens disclosed herein.

Immunization Methods

The method of this aspect of the invention generally relates to induction of immunity and as such also entails methods that are prophylactic as well as therapeutic.

When immunization methods entail that a chimeric polypeptide of the Invention or a composition comprising such a chimeric polypeptide is administered the animal (e.g. the human) typically receives between 0.5 and 5,000 µg of the polypeptide of the invention per administration, cf. the above indications concerning dosages.

In preferred embodiments, the immunization scheme includes that the a primary administration of the chimeric polypeptide(s), the nucleic acids/vectore, or the composition(s) of the invention, but it may be necessary to follow up with one or more booster administrations.

Preferred embodiments comprise that the administration is for the purpose of inducing protective immunity against S. aureus. In this embodiment it is particularly preferred that the protective immunity is effective in reducing the risk of attracting infection with S. aureus.

As mentioned herein, the some vaccines of the invention induce humoral immunity, so it is preferred that the administration is for the purpose of inducing antibodies specific for S. aureus.

But, as also mentioned the immunization method may also be useful in antibody production, so in other embodiments the administration is for the purpose of inducing antibodies specific for S. aureus wherein B-lymphocytes producing said antibodies are subsequently recovered from the animal and used for preparation of monoclonal antibodies.

Compositions for immunization can as mentioned above comprise polypeptides, nucleic acids, or vectors of the invention. The pharmaceutical compositions will comprise a therapeutically effective amount thereof.

The term "therapeutically effective amount" or "prophylactically effective amount" as used herein refers to an amount of a therapeutic agent to treat, ameliorate, or prevent a desired disease or condition, or to exhibit a detectable preventative effect in a group of mammals such as humans The effect can be detected by, for example, chemical markers or antigen levels. Reference is made to the ranges for dosages of immunologically effective amounts of polypeptides, cf. above. However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the animal to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Example 1

Identification of Amino Acid Sequences Binding to MHC Class II Molecules

A number of 15-mer peptides were initially identified in silico from the S. aureus proteomes. Also, a number of putative scaffold proteins were identified, leaving out potentially toxic or otherwise harmful scaffold proteins. The initial 15-mer peptides were selected based on the probability that they would bind several MHC Class II allelic variants and also based on their degree of non-similarity with the human proteome. Finally, each 15-mer was mapped to a proteome and evaluated relative to normalized expression data of the proteome member in S. aureus. The total number of 15-mer peptides selected was 50.

The 50 selected peptides were subsequently tested in vitro for MHC Class II binding: As the peptide: MHCII complex stability has been proven to be the main driver of immunogenicity, the 50 selected epitopes were subjected to analysis by Immunitrack (Biocenter of Copenhagen, Ole Maaloes Vej 5, DK-2200 Copenhagen N, Denmark) by measuring the stability of the peptide:DRB1*01:01 complex, the peptide:DRB1*04:01 complex, and the peptide:DRB5*01:01 complex.

12 out the 50 tested peptides did not form complexes with one or more of the 3 alleles. From the remaining 38 epitopes 20 (SEQ ID NOs: 21-40) were categorized as forming stable or very stable complexes with all 3 alleles and were used for building epitope constructs.

Finally the 9 epitopes having SEQ ID NOs: 21, 23, 26, 27, 30, 33, 34, 38, and 40, and the 11 epitopes having SEQ ID NOs: 22, 24, 25, 28, 29, 31, 32, 35-37, and 39 were compiled into multiple different constructs using either an epitope on a string strategy (epitope-linker-epitope- . . . -) or by replacing known epitopes in the NCBI 53721566 protein with the nearest (in BLOSUM space) identified S. aureus epitope.

The constructs were finally submitted to 3 different solubility prediction servers and the 4 most soluble constructs were ordered from Genscript. The amino acid sequences of the resulting chimeric proteins are set forth in SEQ ID NOs: 41-44 (41 and 42 are "epitopes on a string" constructs, 43 and 44 are "epitopes in scaffold" constructs). For recombinant production, a start codon encoded Met was introduced in the N-terminus of the epitope on a string constructs (not shown in the SEQ ID NOs: 41 and 42).

Hence, 4 *S. aureus* T-helper cell epitope constructs were developed. Formalized together with the adjuvant CAF01 (Agger E M et al. PLoS ONE. 2008; 3(9): e3116) the constructs can elicit a Th1/Th17 response important for recurrent skin infection in humans, thereby supplementing the primarily antibody driven protection induced by protein vaccines.

Example 2—General Experimental Setup

Proteins of the Invention were tested in two animal models: a skin abscess model and a sepsis model. In the following the general experimental details are provided.
1. Murine Mode of Subcutaneous Skin Abscess Induced by *S. aureus* USA300

A number of polypeptides of the present invention were tested for their ability to interfere with subcutaneous skin abscess formation caused by *S. aureus* USA300; see the examples below.

Abbreviations Used

BHI Brain-heart infusion
BW Body weight
DPBS Dulbecco's Phosphate-Buffered Saline
CFU Colony forming units
LB Luria-Bertani
ns Not significant
ON Over night
p.i. Post infection
rpm Revolutions per minute
SC Subcutaneous administration
TSA Tryptic Soy Agar
D Study Day Materials and Methods Microorganism:
 *S. aureus* USA300 [*Staphylococcus aureus* subsp. *aureus* Rosenbach (ATCC® BAA-1717™)], Strain Designations: TCH1516 [USA300-HOU-MR]
Animals:
 Female BALB/c Mice, obtained from Charles River Italy. Mice were 5 weeks at arrival. After arrival, the mice we acclimatized for 5 days. The mice were kept at 22° C.±2 and a relative humidity of 55%±10 in cages from TECNIPLAST S.p.A. Italy, (type III, polysulfone cage with a 3-4 cm thick Scobis Duo, Mucedola, Italy with provision of one cotton nestlet for nestmaking and a Des Res paper shelter (Lillico Serving Biotechnology, UK), as well as with ASPEN BLOCKS, MEDIUM (20×20×100 mm), LBS (Serving Biotechnology, UK). Air was changed 15-20 times per hour, and the lighting cycle was 12 hours light (7:00 to 19:00)/12 hours dark (19:00 to 7:00). The mice received ad libitum pelleted food for mice (SDS VRF 1 (P), UK) and ad libitum drinking water. At day 1 in all experiments, the mice were grouped randomly. Each mouse was identified by a number, as well as by a tail mark within the cage. Each single cage had a tag, indicating experiment number, progressive cage and animal numbers. All animals were subjected to a detailed physical examination by a veterinarian to ensure that they were in a good state of health prior to start of the study.

In the study in Example 3, the mice were female Tg (HLA-DRA/H2-Ea, HLA-DRB1*0401/H2-Eb) 1Kito from Taconic, USA. Other procedures were otherwise as described in the present example.
Materials Used:
 Narkamon (100 mg/mL ketamine chloride), Bioveta, a. s. Czech Republic, serial no 095322A, Exp. date March 2017
 Rompun 2%, Bayer, Leverkusen, Germany
 Forane, ABBOTT, USA
 Microtainer tubes, BD, ref. no. 365950.
 CAF01 adjuvant (Agger E M et al. PLoS ONE. 2008; 3(9): e3116)
Bacterial Inoculum:
 *S. aureus* USA300 was plated on blood agar TSA plate. The next day, one 50 mL Falcon tube containing 20 ml of LB broth was inoculated with one colony of *S. aureus* USA300 grown on blood agar. Bacterial culture was incubated in orbital shaker at 200 rpm/37° C./ON. After the overnight growth in liquid broth, bacteria were subcultured by diluting 1 mL of ON bacterial suspension in 100 ml of LB broth in an Erlenmeyer flask. Bacterial culture was incubated in orbital shaker till mid log phase at 200 rpm/37° C. Mid-log bacterial cultures were centrifuged 3× at 5000 g for 10 min at 4° C. and washed each time with sterile DPBS (without Ca and Mg). Pellet was finally re suspended in 10× lower volume of sterile PBS (10 mL). One-hundred 100 microliter µL of prepared bacterial suspensions were given SC per animal (confirmed inoculum size was $5.6 \times 10^9$ cfu/animal). Actual inoculum size was confirmed by plating prepared suspensions on surface of Tryptic Soy Agar plate supplemented with 5% defibrinated sheep blood. Plates were incubated at 37° C. ON and colonies counted.
Immunization and Blood Sampling
 Mice were immunized on D0, D14 and D28.
 Each mouse was immunized with an SC injection of 100 µL of formulation/injection site. The amount of each protein in the formulation was 20 µg/mouse.
 At D1 and D37 blood was obtained for serum preparation from all mice by puncturing the tail vein after warming in warming cabinet for 5 min/38° C. Sample size of whole blood was ≤100 µL. After collection, blood was centrifuged at 3500 rpm/15 min. Obtained serum samples were stored at −80° C.
Challenge Infection
 Blinding procedure: One day prior to challenge, cages were labelled by a person not involved in the study and the cages were mixed in order. Original labels were marked with the assigned letter and kept away from the researchers performing the measurements. When the challenge had finished and all data collected, the cages/animals were revealed.
 D41_preparing mice for the challenge: Mice were anaesthetized with ketamine+xylazine IP injection, the fur was shaved from the back of the mouse (3×4 cm), and the shaved area was disinfected with Pursept A, Schülz, Germany.
 D42_challenge: Animals were weighed, 100 µL of bacterial suspension was injected SC into the middle of the shaved area, under light ketamine+xylazine anaesthesia, and mice were observed for 3-5 hours post challenge to ensure that all mice have recovered from anaesthesia.
 D43-D52 (D1-D10 post challenge)_Abscess measurements, clinical observations and body weight recordings following challenge: Abscess measurement was performed on 7 time points in total, on study days 43, 44, 45, 46, 47, 48 and 52 (days 1, 2, 3, 4, 5, 6 and 10 following challenge). The measurements were performed under Isoflurane anesthesia using caliper and the values of width and length were captured in Excel spread sheet tables. Mice were monitored once daily for clinical signs and body weights were recorded on the day of challenge (day 42) and then on day 46 and 52. Data were collected into prepared Excel table.

D52_Terminal procedures: At D52 mice were weighed and euthanized by CO2 asfixion.

Read-Outs

Abscess area (mm$^2$) (7 time points in total)
Body weights at D0, D42, D46 and D52

Data Analysis

Data was processed using Microsoft Excel SW. Statistical analyses and graphical presentation were performed using GraphPad Prism software (version 5.04). Differences between groups were considered statistically significant when $p<0.05$.

Animal Welfare

All animal related research was conducted in accordance with 2010/63/EU and National legislation regulating the use of laboratory animals in scientific research and for other purposes (Official Gazette 55/13). An Institutional Committee on Animal Research Ethics (CARE-Zg) oversees that animal related procedures are not compromising the animal welfare.

2. Murine Model of Peritonitis

Female NMRI mice were immunized with recombinant peptides in combination with the adjuvant CAF01 (cf. above). As control, the adjuvant alone was administered. Each mouse was immunized subcutaneously three times at approximately two week intervals. At each immunization the mice were immunized with a formulation of 100 µL CAF01 mixed with 20 µg peptide; protein was added to the adjuvant in small portions, and the tube gently flicked before adding additional protein. When the protein was mixed with the adjuvant 10 mM tris (pH 7.2) was added to attain a total injection volume of 200 µL per ani-mal.

Blood samples were collected from each animal approximately ten days after the last immunization for analysis of antibody titre. Blood samples were collected by tail vein puncture following a short exposure under a heat lamp. The blood was collected in Eppendorf tubes containing 5 µL 0.5 M EDTA and the sample mixed vigorously. The tubes were centrifuged at 1800×g for 10 minutes and the plasma fraction transferred to a new tube and stored at −80° C.

Four days before challenge, temperature transponders (BMDS, cat. no. IPTT-300) were inserted into each mouse. The mice were briefly anaesthetized by inhalation of isoflurane, and a temperature transponder inserted underneath the skin on the lower back or side of the mouse. Using a compatible wireless scanner (BMDS Smart Probe; BMDS, cat. no. DAS-7007s) body temperature could be registered when placing the scanner close to the transponders underneath the skin of the mouse.

Preparation of Bacterial Inoculum

The bacteria used in the animal model of peritonitis were prepared in advance and frozen at −80° C. in aliquots; bacterial matter was streaked out on a blood agar plate and incubated at 37° C. overnight. The following day, a single colony of S. aureus was used for the inoculation of 30 mL tryptic soy broth (TSB) media. The culture was incubated overnight at 37° C., with continuous shaking. The following day 1 L of TSB media was inoculated with 10 mL of the overnight culture and incubated at 37° C. under continuous shaking for 6 hours. The bacterial suspension was centrifuged at 3000×g for 10 minutes and the pellet washed twice in 400 mL sterile PBS. After each wash the bacterial suspension was centrifuged at 3000×g for 10 minutes. The bacterial pellet was resuspended in 10-15 mL PBS and glycerol added to a final concentration of 16%. The suspension was thoroughly mixed, aliquoted in 1 mL aliquots and stored at −80° C. The number of colony forming units (CFU) per mL was determined for the frozen stock, as aliquots were thawed on ice and serially diluted in sterile saline. The dilutions were plated on TSB agar plates and incubated overnight at 37° C. The number of CFU per mL was established the following day. The procedure was repeated with an additional aliquot to confirm homogeny among the aliquots. Immediately prior to challenge, aliquots were thawed and diluted in sterile saline to the desired number of CFU.

Challenge Setup

The mice were housed at the Biomedical Laboratory at the University of Southern Denmark.

The animals were kept in an environment characterized by a 12-hours light-dark cycle and temperature and humidity control. The mice had access to food and water ad libitum. The experimental procedures were carried out in accordance with the guidelines of the Danish National Animal Ethics Committee (license number 2015-15-0201-00680).

The experiments were performed in class 2 certified facilities at the Biomedical Laboratory. Each mouse was challenged intraperitoneally with $3.0 \times 10^9$ CFU S. aureus strain MRSA252 (lot #4). The seven days following the challenge, the mice were assessed daily to register symptoms and development of disease. To ensure a consistent evaluation of all animals, each animal was scored individually following the criteria for clinical symptoms set forth here:

0: No symptoms.
1: Decreased spontaneous activity, slightly ruffled fur, weight loss maximum 10%.
2: Decreased provoked activity, ruffled fur, weight loss maximum 15%.
3: Symptoms like 1 or 2 and/or semi-closed eyes, decreased food and water uptake, weight loss maximum 20%.
4: No activity when provoked, cold to the touch, no uptake of food and water, weight loss maximum 20%.

The mice were individually assessed on their physical appearance and behaviour, noting the presence or absence of the given characteristics.

Apart from the registration of clinical symptoms, body weight and temperature of each animal was registered daily following challenge. The weight loss was calculated as a percentage of the body weight registered prior to challenge. Animals were euthanized if either of the following humane endpoints were reached: a body temperature below 34° C. or a weight loss above 20% of the initial body weight. Additionally, mice scored 3 over three successive days, without signs of improvements such as weight gain, or 4 once were euthanized.

Example 3

Subcutaneous Skin Abscess Testing of Immunogens of the Present Invention

The proteins having SEQ ID NOs: 41-44 were subjected to the skin abscess testing described above in Example 2. One group of mice received a cocktail of the proteins having SEQ ID NOs: 41 and 44 ("Eden" group), the other group received a cocktail of the proteins having SEQ ID NOs. 42 and 43 ("NonEden" group). The mice received 50 µg of protein per injection (25 µg of each protein in the cocktail).

The most striking read-out of this study was that the Eden group which was vaccinated with the two immunogens having SEQ ID NO: 41 and 44 exhibited a mean abscess area expressed in mm² which was significantly (p<0.05) smaller than both the nonEden group receiving SEQ ID NO: 42 and 43 and a control group receiving adjuvant only.

| | Mean abscess area (mm²) | | | | | | |
|---|---|---|---|---|---|---|---|
| Group | Day 43 | Day 44 | Day 45 | Day 46 | Day 47 | Day 48 | Day 52 |
| Eden | 404.0 | 330.3 | 307.8 | 295.4 | 283.4 | 257.5 | 117.5 |
| NonEden | 433.2 | 419.3 | 371.3 | 360.6 | 349.8 | 309.4 | 154.2 |
| Control | 487.7 | 461.4 | 423.2 | 371.5 | 359.2 | 322.9 | 181.2 |

Adjuvant Control

The mean abscess areas in the group treated with CAF01 alone slowly decreased from 488 mm² (D1 p.i.) to 181 mm² (D10 p.i.).

EDEN and NonEDEN Formulations

In the EDEN immunized group, a maximal mean abscess area was observed at D1 p.i. (404 mm²) and gradually decreased to 117 mm² on D10 p.i. Significantly smaller abscess areas were observed on D2 and D3 p.i., as compared to CAF01 adjuvant control. A decrease in the mean abscess area of 17% was observed already at D1 p.i. A further reduction in the mean abscess area was observed on D2 p.i. (28%) whilst a 35% of decrease on the last study day was observed, as compared to CAF01 adjuvant control mean abscess area values.

Maximum mean abscess areas in the NonEDEN CD4+ construct immunized group was reached at D1 p.i. (433 mm²) after which it gradually decreased to 154 mm² at D10 p.i. A decrease in the mean abscess areas ranged from 11% on D1 p.i. to 15% at the end of the study (D10 p.i.), when compared to CAF01 adjuvant control mean abscess area values. However, these differences in mean abscess areas were not significant.

In conclusion, subcutaneous immunization with EDEN construct formulation (a mixture of SEQ ID NO: 41 and SEQ ID NO: 44) exhibited protective effect against *S. aureus* USA300 subcutaneous skin abscess formation in female Tg (HLA-DRA/H2-Ea, HLA-DRB1*0401/H2-Eb) 1Kito mice.

Example 4

Subcutaneous Skin Abscess Testing of Immunogens of the Present Invention

In a series of experiments, the following constructs of the invention were tested in the skin abscess model detailed in Example 2:
1. CHIM_0992_0735_FS, CHIM_0992_0735_FL, CHIM_0735_0992_FL and CHIM_0992_2753_FS Formulations (Containing SEQ ID NOs. 12, 60, 59, and 64, Respectively);

The recorded data for these formulations were as follows:

| | Average body weight (g) (mean ± SD) | | | | |
|---|---|---|---|---|---|
| Day | SEQ ID NO: 12 | SEQ ID NO: 60 | SEQ ID NO: 59 | SEQ ID NO: 64 | CAF01 |
| 0 | 17.4 ± 1.1 | 17.4 ± 1.1 | 17.5 ± 0.6 | 17.5 ± 1.3 | 17.4 ± 1.0 |
| 42 | 19.3 ± 1.0 | 19.0 ± 1.2 | 19.7 ± 1.1 | 20.0 ± 1.0 | 18.9 ± 1.6 |
| 46 | 18.1 ± 1.0 | 17.8 ± 1.2 | 18.4 ± 1.3 | 18.4 ± 1.2 | 17.7 ± 1.3 |
| 52 | 19.5 ± 1.0 | 19.2 ± 1.3 | 19.7 ± 1.1 | 19.4 ± 1.2 | 18.9 ± 1.6 |

| Group (SEQ ID NO:) | D43 | D44 | D45 | D46 | D47 | D48 | D52 |
|---|---|---|---|---|---|---|---|
| 12 | 209.9 | 187.5 | 170.9 | 154.9 | 134.5 | 111.4 | 74.6 |
| 60 | 349.2 | 282.8 | 257.9 | 233.7 | 215.2 | 200.9 | 142.0 |
| 59 | 391.7 | 338.0 | 320.2 | 301.3 | 273.6 | 260.4 | 178.1 |
| 64 | 295.3 | 268.0 | 247.6 | 225.2 | 198.9 | 179.2 | 132.8 |
| CAF01 (control) | 329.8 | 308.6 | 259.6 | 226.0 | 202.7 | 173.3 | 121.7 |

Bold letters: statistical significant reduction vs. control

Observations:

In the CHIM_0992_0735_FS immunized group, a maximum mean abscess area was reached on D1 p.i. (210 mm²) and was significantly smaller compared to the CAF01 control group (36%). The mean abscess area gradually decreased to 75 mm² at D10 p.i., corresponding to 39% reduction as compared to the CAF01 adjuvant control mean abscess area value. Significantly smaller abscess areas were observed between D1 (36%) and D2 (39%) as compared to the CAF01 adjuvant control group.

A maximum mean abscess area in the CHIM_0992_0735_FL immunized group was reached at D1 p.i. (349 mm²) and when compared to the CAF01 control group, it was increased for 6%. The mean abscess area gradually decreased to 142 mm² at D10 p.i., increased for 17%, when compared to CAF01 adjuvant control mean abscess area value.

In the CHIM_0735_0992_FL immunized group, a maximum mean abscess area was reached at D1 p.i. (392 mm²) after which it gradually decreased to 178 mm² at 010 p.i. An Increase in the mean abscess areas ranged from 19% on D1 p.i. to 46% at the end of the study (D10 p.i.) was observed as compared to CAF01 adjuvant control mean abscess area value.

The mean abscess areas in the CHIM_0992_2753_FS immunized group reached maximum value on D1 p.i. (295 mm²), and gradually decreased to a value of 133 mm² on D10 p.i. When compared to the CAF01 adjuvant control mean abscess area values, mean abscess areas ranged from decrease of 10% on D1 p.i. to increase of 9% at the end of the study (D10 p.i.).

A transient body weight loss was observed in all groups following challenge, with no statistical significance compared to the CAF01 control group.

Conclusion

Single protein immunization with CHIM_0992_0735_FS resulted in statistically significant protection against *S. aureus* USA300 induced skin abscess formation on day 1 and day 2 post challenge, when compared to the CAF01 adjuvant control group, as revealed by the abscess areas measured during the 10-day period following SC challenge.

Immunization with the single protein CHIM_0992_0735_FL and CHIM_0992_2753_FS showed no protective effect against S. aureus USA300 induced skin abscess formation since abscess areas were similar to CAF01 control group during the whole course of the infection (10 days). In addition, immunization with single protein CHIM_0735_0992_FL showed no protective effect against S. aureus USA300 induced skin abscess formation, since abscess areas were increased when compared to the CAF01 adjuvant control group during the 10-day period following SC challenge.

In conclusion, immunization with the single protein CHIM_0992_0735_FS showed statistically significant protective effect on day 1 and day 2 following challenge with S. aureus USA300. Subcutaneous immunization with CHIM_0992_0735_FL, CHIM_0735_0992_FL and CHIM_0992_2753_FS as single protein formulations exhibited no significant protective effect in the same model.

2. M2863_SAR0992-1-409, USA300HOU_2637-28-439, and SAR0992-1-409 Formulations (Containing SEQ ID NOs. 85, 98, and 89, Respectively):

The data obtained with these 3 protein formulations (SEQ ID NOs: 85, 98, and 89) provided no conclusive data, since animals immunized with did no exhibit any significant difference from control immunized animals.

3. Hla_H35L-27-319, SAR2635-1-199, CHIM_Hla_2753_FS, and CHIM_Hla_0735_FS Formulations (Containing SEQ ID NOs: 83, 93, 80, and 78, Respectively):

The recorded data for these formulations were as follows:

| | Average body weight (g) (mean ± SD) | | | | |
|---|---|---|---|---|---|
| Day | SEQ ID NO: 83 | SEQ ID NO: 93 | SEQ ID NO: 80 | SEQ ID NO: 78 | CAF01 |
| 0 | 17.4 ± 1.3 | 18.3 ± 1.2 | 18.0 ± 1.1 | 17.9 ± 1.1 | 17.7 ± 1.6 |
| 42 | 18.9 ± 1.1 | 20.1 ± 0.9 | 19.4 ± 1.6 | 19.3 ± 1.3 | 18.9 ± 1.8 |
| 46 | 18.0 ± 1.3 | 18.6 ± 1.4 | 18.7 ± 1.6 | 18.7 ± 1.3 | 17.5 ± 1.8 |
| 52 | 18.9 ± 1.5 | 18.6 ± 1.4 | 19.8 ± 1.2 | 19.8 ± 1.6 | 17.9 ± 2.0 |

| Group (SEQ ID NO:) | D43 | D44 | D45 | D46 | D47 | D48 | D52 |
|---|---|---|---|---|---|---|---|
| 83 | 124.7 | 111.2 | 99.4 | 98.5 | 93.4 | 76.0 | 38.8 |
| 93 | 569.6 | 703.1 | 660.5 | 584.8 | 546.4 | 509.8 | 433.8 |
| 80 | 135.6 | 109.4 | 105.7 | 97.3 | 79.0 | 66.9 | 43.3 |
| 78 | 109.9 | 78.3 | 73.8 | 66.4 | 56.9 | 45.9 | 28.3 |
| CAF01 (control) | 536.3 | 578.0 | 569.5 | 531.5 | 481.8 | 451.9 | 366.0 |

Bold letters: statistical significant reduction vs. control

Observations:

In the SAR2635-1-199 immunized group, a maximal mean abscess area was reached at D2 p.i. (703 mm$^2$) and was significantly higher compared to the CAF01 control group (22%). The mean abscess area gradually decreased to 434 mm$^2$ at D10 p.i. When compared to CAF01 adjuvant control mean abscess area value, it was increased for 19% (not statistically significant).

A maximal mean abscess area in the Hla_H35L-27-319-immunized group was reached at D1 p.i. (125 mm$^2$) after which it gradually decreased to 39 mm$^2$ at D10 p.i. Decreases in the mean abscess areas ranged from 77% on 01 p.i. to 89% at the end of the study (D10 p.i.), when compared to CAF01 adjuvant control mean abscess area values and were statistically significant during the whole post-challenge course.

The mean abscess areas in the CHIM_Hla_2753_FS* immunized group reached a maximal value on D1 (136 mm$^2$), and gradually decreased to a value of 43 mm$^2$ on D10. Significantly smaller abscess areas were observed between D1 (75%) and D10 (88%) as compared to the CAF01 adjuvant control group.

The mean abscess areas in the CHIM_Hla_0735_FS immunized group reached a maximal value on D1 p.i. (110 mm$^2$), and gradually decreased to a value of 28 mm$^2$ at D10 p.i. When compared with CAF01, statistically significant decreases in the abscess areas between D1 (β0%) and D10 (92%) were observed.

Conclusions

A transient body weight loss was observed in all groups following challenge. An evident improvement in clinical status of the protein immunized animals was noticed up to D52, as revealed by the statistically significant increases in body weights in CHIM_Hla_2753_FS* and CHIM_Hla_0735_FS immunized groups on D52.

Immunization with Hla_H35L-27-319, CHIM_Hla_2753_FS or CHIM_Hla_0735_FS as single protein formulations resulted in statistically significant protection against S. aureus USA300 induced skin abscess formation, when compared to the CAF01 adjuvant control, as revealed by the abscess areas measured during the 10 day period following SC challenge.

Single protein immunization with SAR2635-1-199 demonstrated no protective effect against S. aureus USA300 induced skin abscess formation, when compared to the CAF01 adjuvant control group, since mean abscess areas measured during the 10 day period following SC challenge were similar between these two groups. However, it should be noted that the group immunized with SAR2635-1-199 included only 11 mice in the abscess measurements since 5 mice had died during the course of the experiment (either during the challenge preparation phase or following the challenge).

In conclusion, subcutaneous vaccination with Hla-_H35L-27-319, CHIM_Hla_2753_FS or CHIM_Hla_0735_FS as single protein formulations exhibited protective effect against S. aureus USA300 subcutaneous skin abscess formation in female BALB/c mice. However, immunization with SAR2635-1-199 formulation showed no protective effect in the same model.

4. CHIM_1262_2496_RS, CHIM_2716_2753_FL, CHIM_2723_2753_S_FS, and CHIM_2723_2753_L_FS Formulations (Containing SEQ ID NOs: 65, 14, 77, and 15, Respectively):

Subcutaneous immunization with CHIM_2723_2753_S_FS, CHIM_1262_2496_RS, CHIM_2716_2753_FL or CHIM_2723_2753_L_FS as single protein formulation exhibited no significant protective effect against S. aureus USA 300 subcutaneous skin abscess formation in female BALB/c mice.

5. CHIM_2723_2635_FS, CHIM_2723_2635_RL, CHIM_2635_2723_FS, and CHIM_Hla_2635_FS Formulations (Containing SEQ ID NOs: 74, 75, 70, and 79, Respectively):

The recorded data for these formulations were as follows:

| | Average body weight (g) (mean ± SD) | | | | |
|---|---|---|---|---|---|
| Day | SEQ ID NO: 74 | SEQ ID NO: 75 | SEQ ID NO: 70 | SEQ ID NO: 79 | CAF01 |
| 0 | 18.2 ± 1.2 | 17.6 ± 1.1 | 17.8 ± 0.8 | 18.2 ± 1.0 | 18.1 ± 0.9 |
| 42 | 18.3 ± 1.4 | 18.2 ± 0.9 | 19.1 ± 0.8 | 19.7 ± 1.1 | 18.6 ± 0.8 |
| 46 | 18.7 ± 1.6 | 17.9 ± 1.6 | 18.9 ± 0.8 | 19.7 ± 0.8 | 18.4 ± 1.0 |
| 52 | 19.8 ± 1.6 | 18.6 ± 1.2 | 19.8 ± 0.9 | 20.7 ± 0.9 | 18.8 ± 1.3 |

| Group (SEQ ID NO:) | D43 | D44 | D45 | D46 | D47 | D48 | D52 |
|---|---|---|---|---|---|---|---|
| 74 | 261.6 | 220.5 | 216.2 | 207.8 | 190.7 | 167.2 | 78.1 |
| 75 | 402.6 | 391.4 | 379.8 | 371.0 | 347.8 | 318.7 | 201.3 |
| 70 | 312.3 | 272.6 | 265.6 | 257.6 | 237.1 | 211.7 | 86.5 |
| 79 | 24.8 | 31.6 | 20.7 | 17.4 | 18.9 | 9.7 | 3.8 |
| CAF01 (control) | 412.0 | 402.5 | 389.5 | 367.3 | 335.2 | 296.2 | 161.3 |

Bold letters: statistical significant reduction vs. control

Observations:

In the CHIM_2723_2635_FS immunized group, a maximum mean abscess area was reached at D1 p.i. (262 mm$^2$) and gradually decreased to 78 mm$^2$ at D10 p.i. Significantly smaller abscess areas were observed from D1 until D6 p.i., as compared to CAF01 adjuvant control. A decrease in the mean abscess area of 37% was observed already at D1 p.i. A reduction in the mean abscess area continued at D2 p.i. (45%) and ended with a 52% of decrease on the last study day, when compared to CAF01 adjuvant control mean abscess area value.

A maximum mean abscess area in the CHIM_2723_2635_RL*-immunized group was reached at D1 p.i. (403 mm$^2$) after which it gradually decreased to 201 mm$^2$ at D10 p.i. A change in the mean abscess areas ranged from 2% reduction on D1 p.i. to 25% increase at the end of the study (D10 p.i.), when compared to the CAF01 adjuvant control mean abscess area value (not statistically significant).

The mean abscess areas in the CHIM_2635_2723_FS immunized group reached maximum value at D1 (312 mm$^2$), and gradually decreased to value of 87 mm$^2$ at D10. Significantly smaller mean abscess areas were observed on D2 (32%) and D3 (32%) as compared to the CAF01 adjuvant control group.

In the CHIM_Hla_2635_FS immunized group, only three animals developed measurable abscesses after challenge with *S. aureus* USA300 on D42. The mean abscess areas reached maximum value on D2 p.i. (32 mm$^2$), and gradually decreased to value of 3.8 mm$^2$ on D10 p.i. When compared to the CAF01 immunized group, a statistically significant decrease in abscess areas between D1 (94%) and D6 (97%) was observed.

Conclusions

Immunization with CHIM_2723_2635_FS, CHIM_2635_2723_FS or CHIM_Hla_2635_FS as single protein formulations, resulted in statistically significant protection against *S. aureus* USA300 induced skin abscess formation, when compared to the CAF01 adjuvant control, as revealed by the abscess areas measured during the 10 day period following SC challenge.

Immunization with the single protein CHIM_2723_2635_RL* showed no protective effect against *S. aureus* USA300 induced skin abscess formation, since abscess areas were similar to the CAF01 Control group during the whole course of the infection (10 days).

Although immunizations with CHIM_2723_2635_FS, CHIM_2635_2723_FS or CHIM_Hla_2635_FS as single antigens demonstrated significant protective effects when compared to the CAF01 Control treated group, CHIM_Hla_2635_FS formulation showed superior protective effect compared to the other two. Namely, only three animals of sixteen in this group formed abscesses following bacterial infection.

In conclusion, subcutaneous immunization with CHIM_2723_2635_FS, CHIM_2635_2723_FS or CHIM_Hla_2635_FS as single protein formulations exhibited protective effect against *S. aureus* USA300 subcutaneous skin abscess formation in female BALB/c mice. Immunization with CHIM_Hla_2635_FS showed superior protective effect in comparison to the other single protein vaccines tested in this study.

6. CHIM_2496_1816_FS, CHIM_2716_1816_FS, CHIM2119_1816_FS, and CHIM_1816_2119_FL Formulations (Containing SEQ ID NOs: 69, 71, 68, and 67, Respectively):

The recorded data for these formulations were as follows:

| | Average body weight (g) (mean ± SD) | | | | |
|---|---|---|---|---|---|
| Day | SEQ ID NO: 69 | SEQ ID NO: 71 | SEQ ID NO: 68 | SEQ ID NO: 67 | CAF01 |
| 0 | 18.8 ± 0.9 | 18.4 ± 1.0 | 18.3 ± 2.2 | 18.0 ± 1.1 | 18.1 ± 1.2 |
| 42 | 19.7 ± 1.2 | 19.5 ± 1.0 | 20.0 ± 1.5 | 19.1 ± 1.1 | 19.7 ± 1.0 |
| 46 | 19.0 ± 1.1 | 18.9 ± 1.2 | 19.2 ± 1.8 | 18.3 ± 1.1 | 18.7 ± 1.2 |
| 52 | 19.4 ± 1.4 | 19.7 ± 1.3 | 19.7 ± 1.9 | 19.0 ± 1.3 | 19.2 ± 1.7 |

| Group (SEQ ID NO:) | D43 | D44 | D45 | D46 | D47 | D48 | D52 |
|---|---|---|---|---|---|---|---|
| 69 | 318.13 | 323.09 | 316.27 | 318.96 | 293.22 | 267.49 | 151.96 |
| 71 | 238.85 | 251.02 | 238.70 | 234.58 | 211.71 | 184.19 | 101.06 |
| 68 | 285.08 | 290.30 | 282.47 | 271.78 | 249.21 | 198.54 | 106.84 |
| 67 | 349.23 | 367.45 | 343.32 | 342.03 | 323.58 | 271.68 | 170.51 |
| CAF01 (control) | 407.94 | 415.30 | 409.76 | 374.86 | 348.01 | 296.51 | 187.48 |

Bold letters: statistical significant reduction vs. control.

Observations:

In the CHIM_2496_1816_FS vaccinated group, maximum mean abscess area was reached at D2 p.i. (323.09 mm$^2$) and gradually decreased to 151.96 mm$^2$ at D10 p.i. A reduction in the mean abscess areas ranged from 22% on D1 p.i. to 10% at the D6 p.i. and ended with 19% (D10 p.i.), when compared to CAF01 adjuvant control mean abscess area values.

Significantly smaller abscess areas were observed from D1 (238.85 mm$^2$) until D5 (211.71 mm$^2$) p.i. in CHIM_2716_1816_FS vaccine group, as compared to CAF01 adjuvant control. A decrease in the mean abscess area of 41% was observed already at D1 p.i. Reduction in the mean abscess area started from D3 p.i. (42%) and ended with 46% of decrease at the last study day, as compared to CAF01 adjuvant control mean abscess area values.

A maximal mean abscess area in the CHIM_2119_1816_FS vaccine group was reached at D2 p.i. (290.30 mm$^2$) after which it gradually decreased to 106.64 mm$^2$ at D10 p.i. A reduction in the mean abscess areas ranged from 30% on D1 p.i. to 33% at the D6 p.i. and ended with 43% (D10 p.i.), when compared to CAF01 adjuvant control mean abscess area values.

The mean abscess areas in the CHIM_1816_0.2119_FL vaccinated group reached maximal value at D2 (367.45 mm$^2$), and gradually decreased to value of 170.51 mm$^2$ at D10. When compared to CAF01 adjuvant control mean abscess area values, a reduction in the mean abscess areas ranged from 14% on D1 p.i. and ended with 9% (D10 p.i.).

Conclusions

A transient body weight loss was observed in all groups following infection. Slight improvement in clinical status and body weight was noticed in all groups up to D52.

Vaccination with CHIM_2496_1816_FS and CHIM_1816_2119_FL single protein vaccine resulted in poor protection of *S. aureus* USA300 induced skin abscess formation, when compared to the respective CAF01 adjuvant control, as revealed by the abscess areas measured during the 10 day period following SC infection. Vaccination with CHIM_2119_1816_FS single protein vaccine resulted in moderate protection of *S. aureus* USA300 induced skin abscess formation, when compared to the respective CAF01 adjuvant control. There was no statistically significant difference in the abscess areas between CHIM_2496_1816_FS, CHIM_2119_1816_FS and CHIM_1816_2119_FL and Control CAF01 group during the whole course of the infection (10 days).

Vaccination with CHIM_2716_1816_FS single protein vaccine resulted in strong, statistically significant protection of *S. aureus* USA300 induced skin abscess formation, when compared to the respective CAF01 adjuvant control.

In conclusion, subcutaneous vaccination with CHIM_2496_1816_FS, CHIM_2119_1816_FS and CHIM_1816_2119_FL single protein vaccine exhibited protective effect against *S. aureus* USA 300 subcutaneous skin abscess formation in BALB/c female mice but it was not statistically significant. In addition, vaccination with CHIM_2716_1816_FS vaccine showed statistically significant and strong protective effect against *S. aureus* USA 300 subcutaneous skin abscess formation in BALB/c female mice.

7. CHIM_0992_2635_FL, CHIM_0992_2635_FS, CHIM_1507_2119_FS, and CHIM_2716_2119_FS Formulations (Containing SEQ ID NOs: 17, 63, 66, and 72, Respectively):

The recorded data for these formulations were as follows:

| | Average body weight (g) (mean ± SD) | | | | |
|---|---|---|---|---|---|
| Day | SEQ ID NO: 17 | SEQ ID NO: 63 | SEQ ID NO: 66 | SEQ ID NO: 72 | CAF01 |
| 0 | 17.5 ± 1.4 | 17.8 ± 1.4 | 16.9 ± 1.4 | 17.6 ± 1.7 | 16.7 ± 1.4 |
| 42 | 18.1 ± 1.7 | 18.8 ± 1.6 | 18.5 ± 1.5 | 19.5 ± 1.5 | 18.5 ± 1.4 |
| 46 | 17.7 ± 1.2 | 18.1 ± 1.6 | 17.5 ± 1.2 | 18.8 ± 1.8 | 17.1 ± 1.5 |
| 52 | 18.4 ± 1.3 | 18.8 ± 1.8 | 18.6 ± 1.4 | 19.1 ± 1.8 | 16.9 ± 1.6 |

| Group (SEQ ID NO:) | D43 | D44 | D45 | D46 | D47 | D48 | D52 |
|---|---|---|---|---|---|---|---|
| 17 | 286.13 | 303.19 | 283.50 | 291.77 | 295.73 | 276.92 | 174.86 |
| 63 | 358.61 | 409.00 | 412.30 | 411.31 | 388.71 | 330.55 | 231.54 |
| 66 | 345.42 | 366.00 | 313.73 | 316.09 | 294.27 | 249.55 | 169.63 |
| 72 | 346.48 | 350.47 | 303.86 | 293.63 | 273.11 | 222.99 | 142.87 |
| CAF01 (control) | 465.22 | 503.18 | 459.02 | 471.18 | 428.15 | 396.98 | 250.19 |

Bold letters: statistical significant reduction vs. control.

Observations:

In CHIM_0992_2635_FL-vaccinated group, a maximal mean abscess area was reached at D2 p.i. (303.19 mm$^2$) and gradually decreased to 174.86 mm$^2$ at D10 p.i. Significantly smaller abscess areas were observed from D1 until D5 p.i. In CHIM_0992_2635_FL vaccinated group, as compared to CAF01 adjuvant control. A decrease in the mean abscess area of 38% was observed already at D1 p.i. A reduction in the mean abscess area started from D2 p.i. (40%) and ended with a 30% of decrease on the last study day, when compared to CAF01 adjuvant control mean abscess area values.

A maximum mean abscess area in the CHIM_0992_2635_FS vaccine group was reached at D3 p.i. (412.30 mm$^2$) after which it gradually decreased to 231.54 mm$^2$ at D10 p.i. A reduction in the mean abscess areas ranged from 23% on D1 p.i. to 7% at the end of the study (D10 p.i.), when compared to CAF01 adjuvant control mean abscess area values.

The mean abscess areas in the CHIM_1507_2119_FS vaccinated group reached maximal value at D2 (366 mm$^2$), and gradually decreased to value of 169.63 mm$^2$ at D10. Significantly smaller abscess areas were observed between D2 (27%) and D6 (37%) as compared to CAF01 adjuvant control.

The mean abscess areas in the CHIM_2716_2119_FS vaccinated group reached maximal value on D2 p.i. (350.47 mm$^2$), and gradually decreased to value of 142.87 mm$^2$ at D10 p.i. When compared with CAF01, a statistically significant decrease in abscess areas between D2 (30%) and D6 (44%) was observed.

Conclusions

A transient body weight loss was observed in all groups following infection. However, it was less pronounced in the protein-vaccinated animals. In addition, an evident improvement in clinical status of the protein vaccinated animals was noticed up to D52.

Vaccination with CHIM_0992_2635_FL, CHIM_1507_2119_FS and CHIM_2716_2119_FS single protein vaccine resulted in strong, significant protection of *S. aureus* USA300 induced skin abscess formation, when compared to respective CAF01 adjuvant controls, as revealed by the abscess areas measured during the 10 day period following SC infection. There was no statistically significant difference in the abscess areas between CHIM_0992_2635_FS and Control CAF01 groups during the whole course of the infection (10 days).

Although vaccinations with these three single proteins resulted in significant protection when compared to Control CAF01 vaccinated group, CHIM_2716_2119_FS vaccine showed superior protective effect to other single proteins vaccines applied.

In conclusion, subcutaneous vaccination with CHIM_0992_2635_FL, CHIM_1507_2119_FS and CHIM_2716_2119_FS single protein vaccine exhibited protective effect against *S. aureus* USA 300 subcutaneous skin abscess formation in BALB/c female mice. In addition, vaccination with CHIM_2716_2119_FS vaccine showed superior protective effect to the other single proteins vaccines applied.

Example 5

Peritonitis Testing of Immunogens of the Present Invention

Figure 1B:
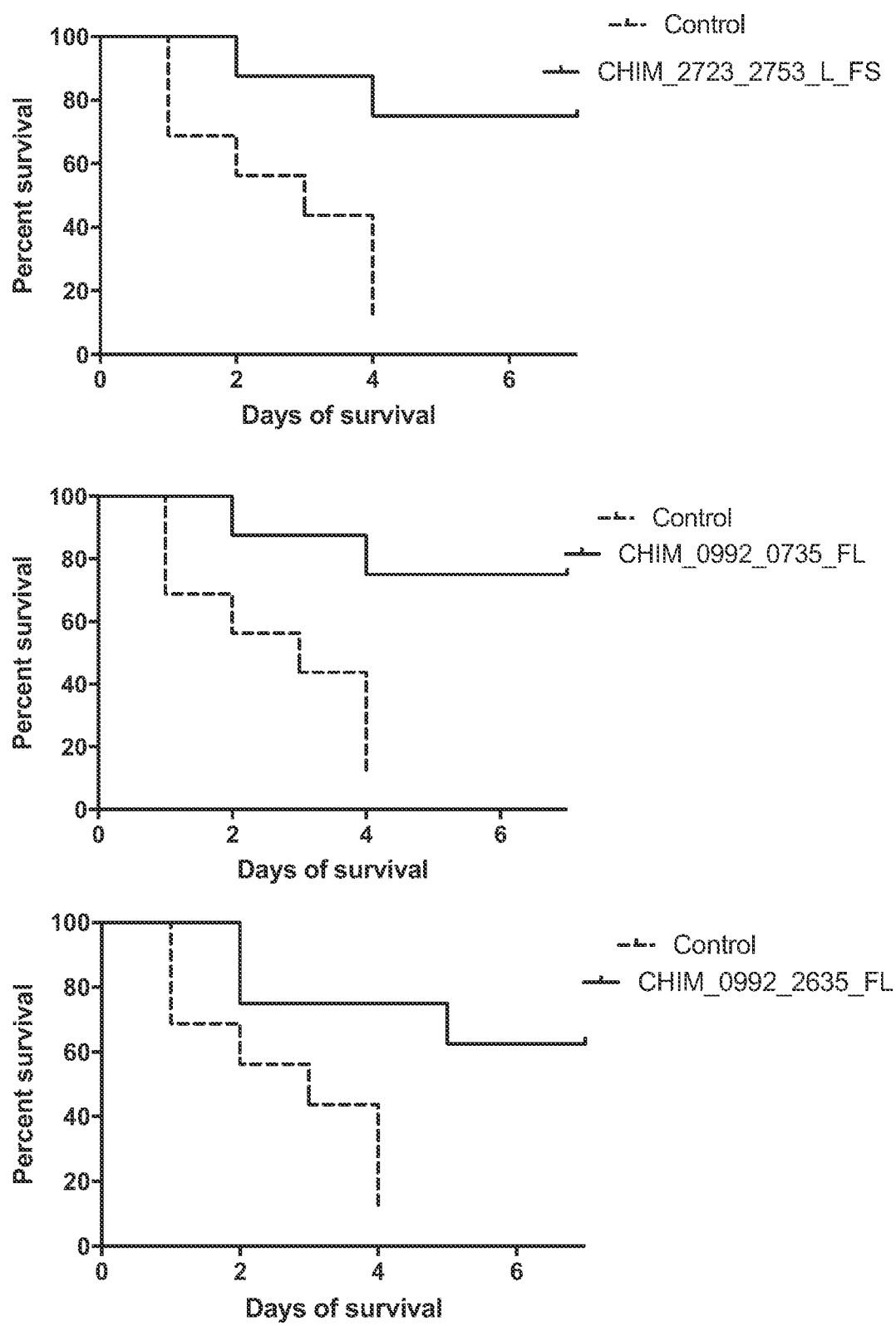
FIG. 1B shows survival plots after challenge infection in mice immunized with immunogens of the invention in a peritonitis model. Dotted lines indicates control, full lines indicates immunogen: Survival plots for CHIM_2723_2753_L_FL (top plot), CHIM_0992_0735_FL (middle plot), and CHIM_0992_2635_FL (bottom plot).
Figure 1C:
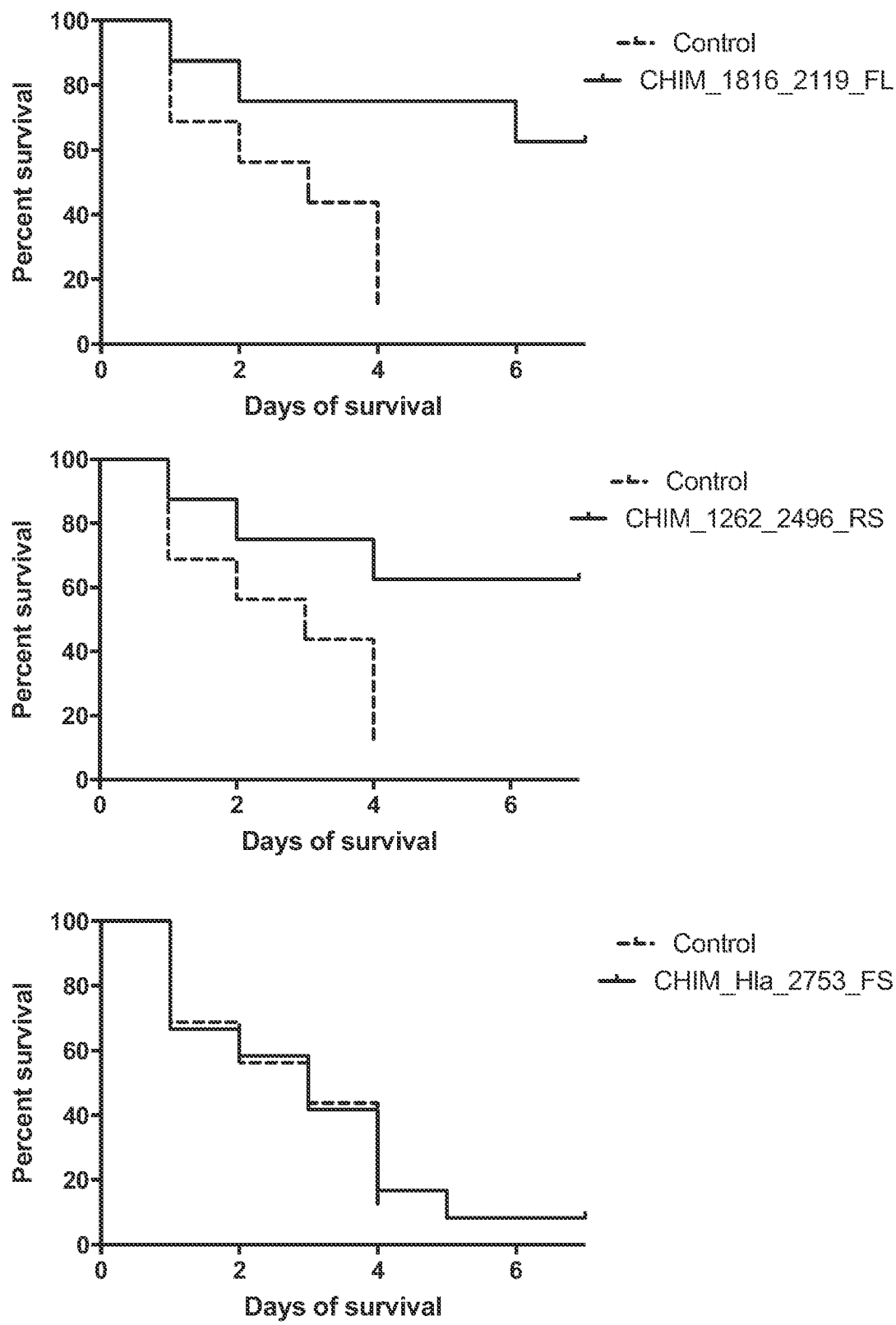
FIG. 1C shows survival plots after challenge infection in mice immunized with immunogens of the invention in a peritonitis model. Dotted lines indicates control, full lines indicates immunogen: Survival plots for CHIM_1816_2119_FL (top plot), CHIM_1262_2496_RS (middle plot), and CHIM_Hla_2753_FS (bottom plot).
Figure 2A:
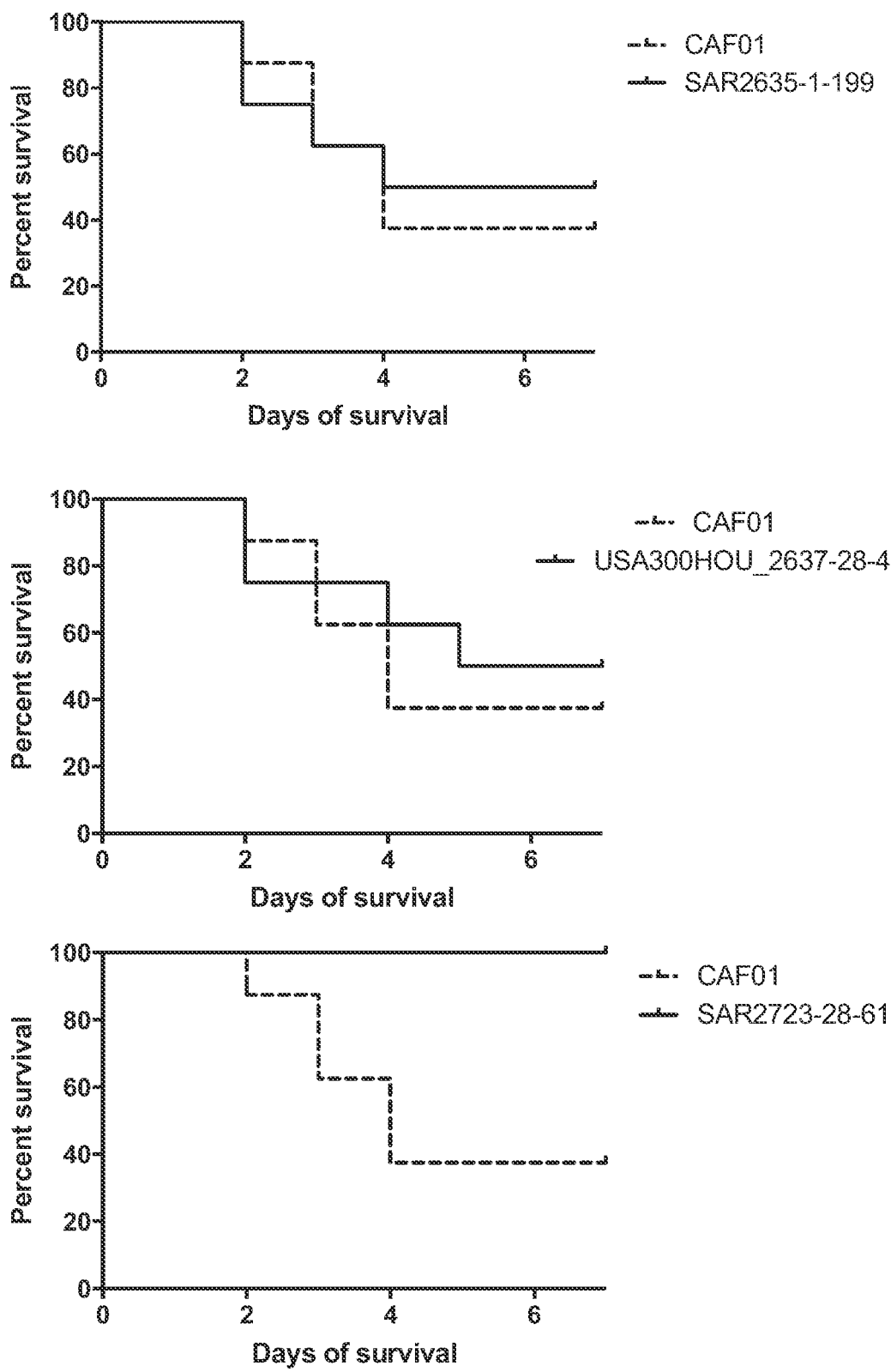
FIG. 2A shows survival plots after challenge infection in mice immunized with immunogens of the invention in a peritonitis model. Dotted lines indicates control, full lines indicates immunogen: Survival plots for SAR2635-1-199 (top plot), USA300HOU_2637-28-439 (middle plot), and SAR2723-28-619 (bottom plot).
Figure 2B:
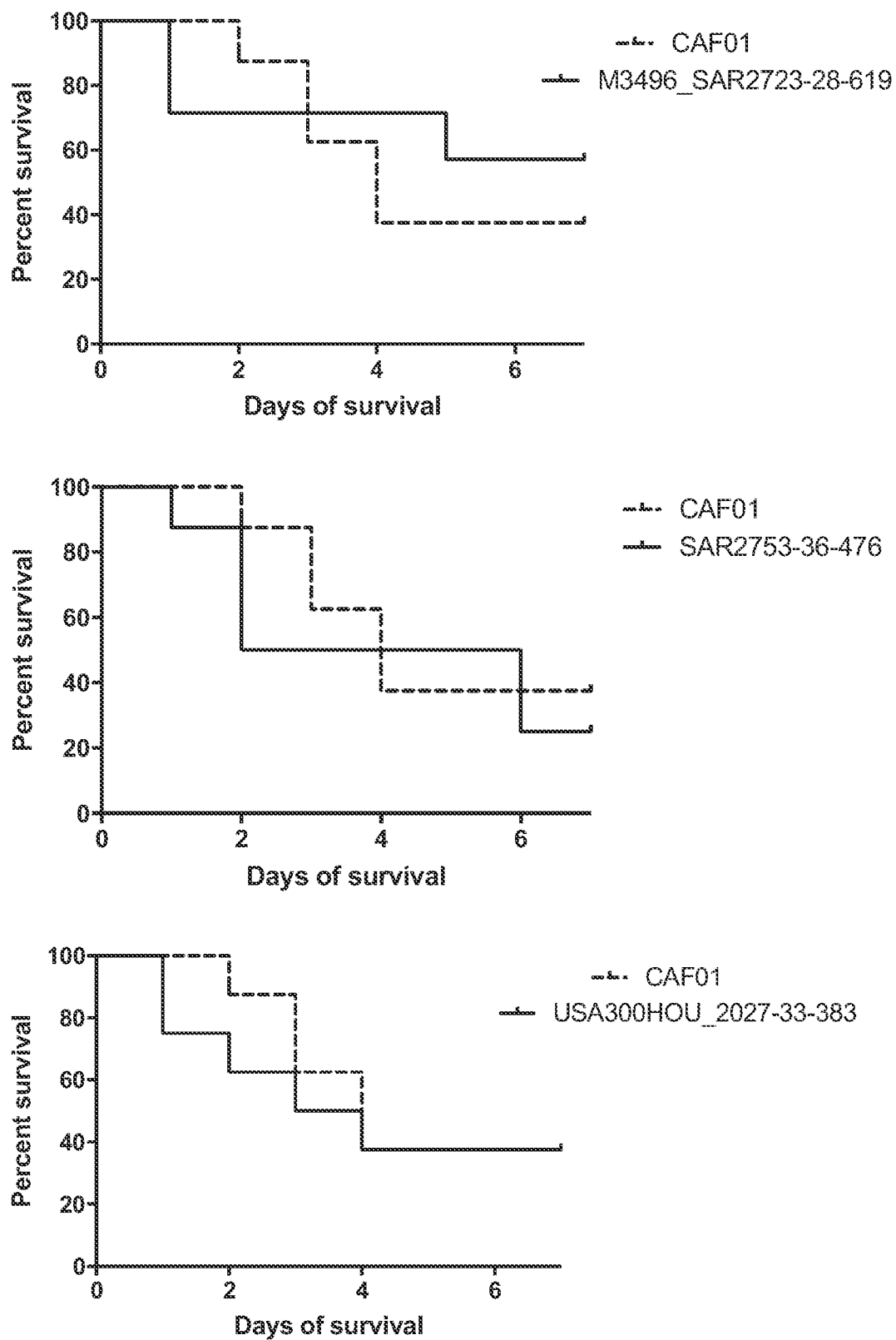
FIG. 2B shows survival plots after challenge infection in mice immunized with immunogens of the invention in a peritonitis model. Dotted lines indicates control, full lines indicates immunogen: Survival plots for M3496_SAR2723-28-619 (top plot), SAR2753-36-476 (middle plot), and USA300HOU_2027-33-383 (bottom plot).
Figure 2C:
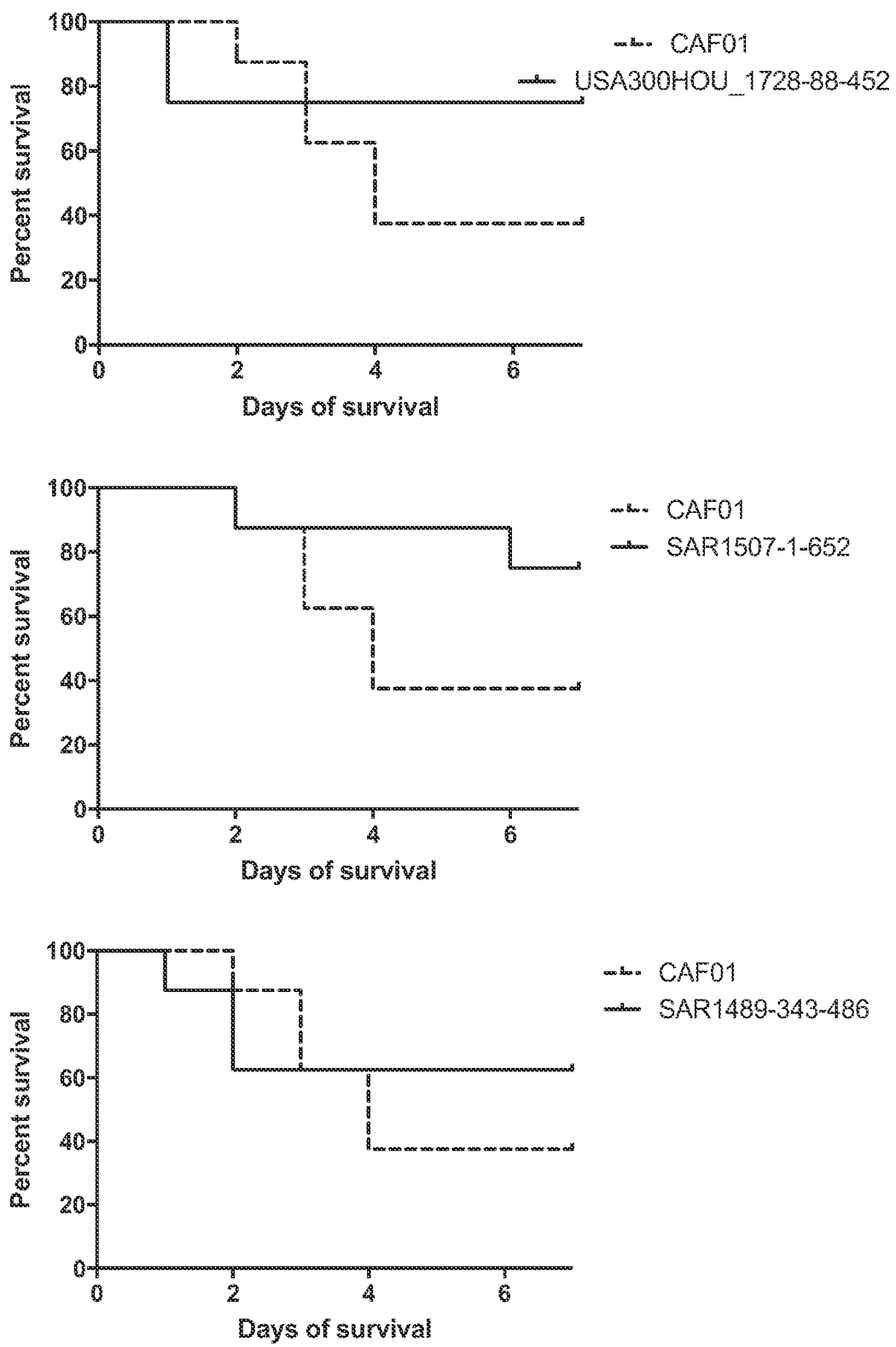
FIG. 2C shows survival plots after challenge infection in mice immunized with immunogens of the invention in a peritonitis model. Dotted lines indicates control, full lines indicates immunogen: Survival plots for USA300HOU_1728-88-452 (top plot), SAR1507-1-652 (middle plot), and SAR1489-343-486 (bottom plot).
Figure 2D:
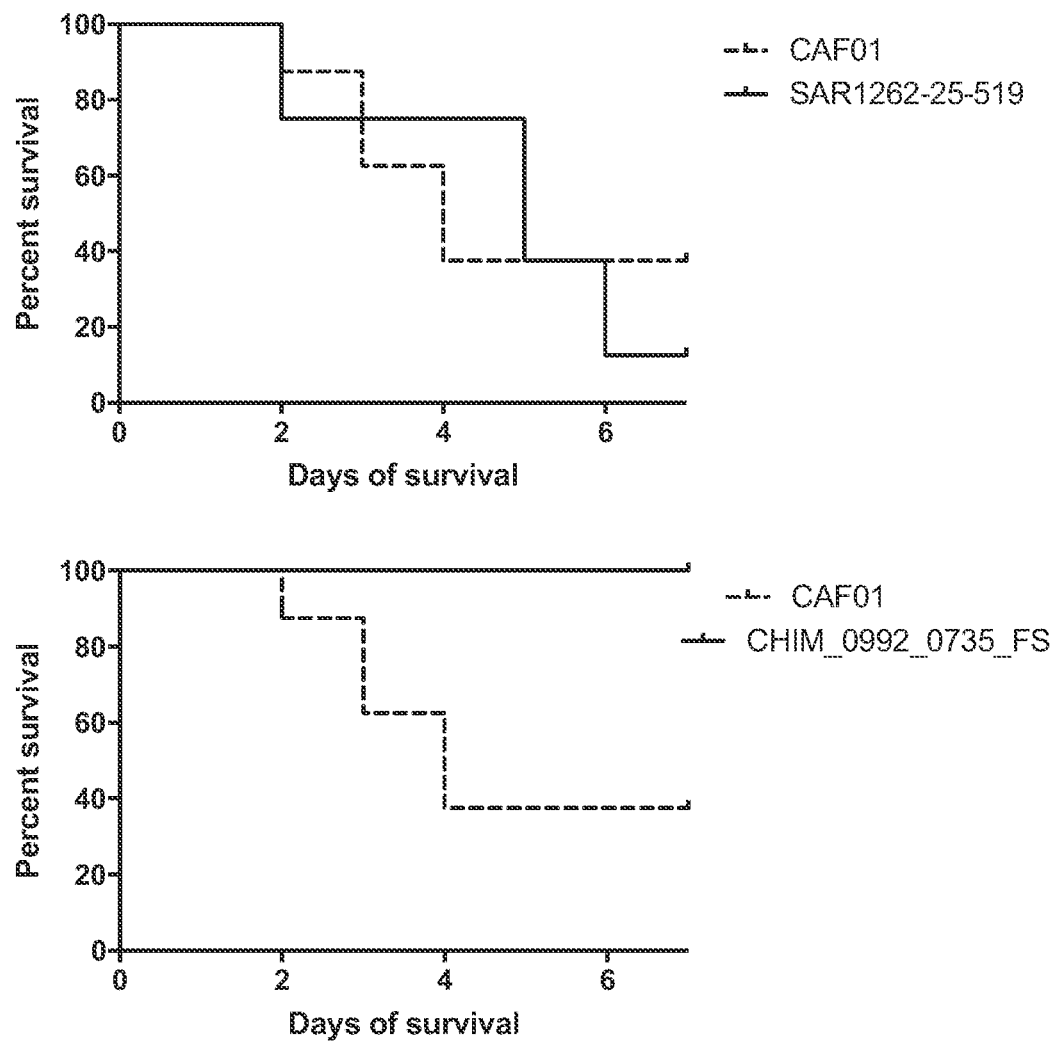
FIG. 2D shows survival plots after challenge infection in mice immunized with immunogens of the invention in a peritonitis model. Dotted lines indicates control, full lines indicates immunogen: Survival plots for SAR1262-25-519 (top plot) and CHIM_0992_0735_FS (bottom plot).

A number of the immunogens disclosed herein were tested in the peritonitis model described in Example 2 above:

1. CHIM_2635_2723_FS, CHIM_Hla_2635_FS, CHIM_2716_2753_FL, CHIM_2723_2753_L_FS, CHIM_0992_0735_FL, CHIM_0992_2635_FL, CHIM_1816_2119_FL, CHIM_1262_2496_RS, and CHIM_Hla_2753_FS Formulations (Containing SEQ ID NOs: 13, 79, 73, 76, 60, 62, 67, 65, and 80, Respectively):

Survival of animals is provided for each of the immunogens in the survival plots in FIG. 1A-FIG. 1C. The results from the experiment show that immunization with either of CHIM_2635_2723_FS, CHIM_Hla_2635_FS, CHIM_2723_2753_L_FL, CHIM_0992_0735_FL, CHIM_0992_2635_FL, CHIM_1816_2119_FL, and CHIM_1262_2496_RS protected mice significantly against a lethal infection with S. aureus MRSA252 as compared to immunization with adjuvant alone.

2. SAR2635-1-199, USA300HOU 2637-28-439, SAR2723-28-619, M3496 SAR2723-28-619, SAR2753-36-476, USA300HOU 2027-33-383, USA300HOU_1728-88-452, SAR1507-1-652, SAR1489-343-486, SAR1262-25-519, and CHIM_0992_0735 FS Formulations (Containing SEQ ID NOS: 93, 98, 94, 86, 95, 97, 96, 92, 91, 90, and 12, Respectively:

Survival of animals is provided for each of the immunogens in the survival plots in FIG. 2A-FIG. 2D. The results from the experiments show that immunization with either SAR2723-28-619 or CHIM_0992_0735_FS protected mice against a lethal challenge with S. aureus MRSA252 as compared to immunization with adjuvant alone.

Figure 3A:
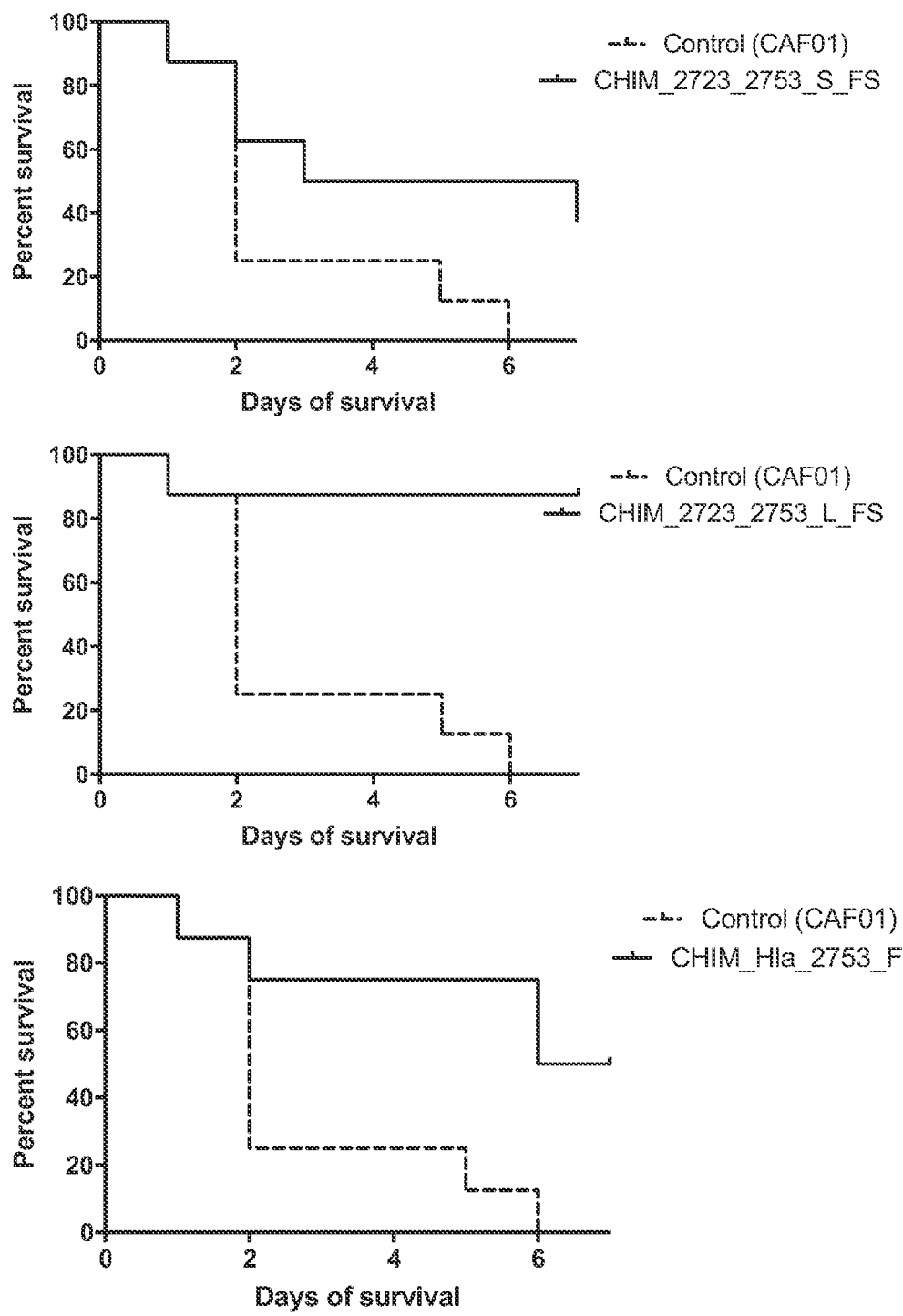
FIG. 3A shows survival plots after challenge infection in mice immunized with immunogens of the invention in a peritonitis model. Dotted lines indicates control, full lines indicates immunogen: Survival plots for CHIM_2723_2753_S_FS (top plot), CHIM_2723_2753_L_FS (middle plot), and CHIM_Hla_2753_FS (bottom plot).
Figure 3B:
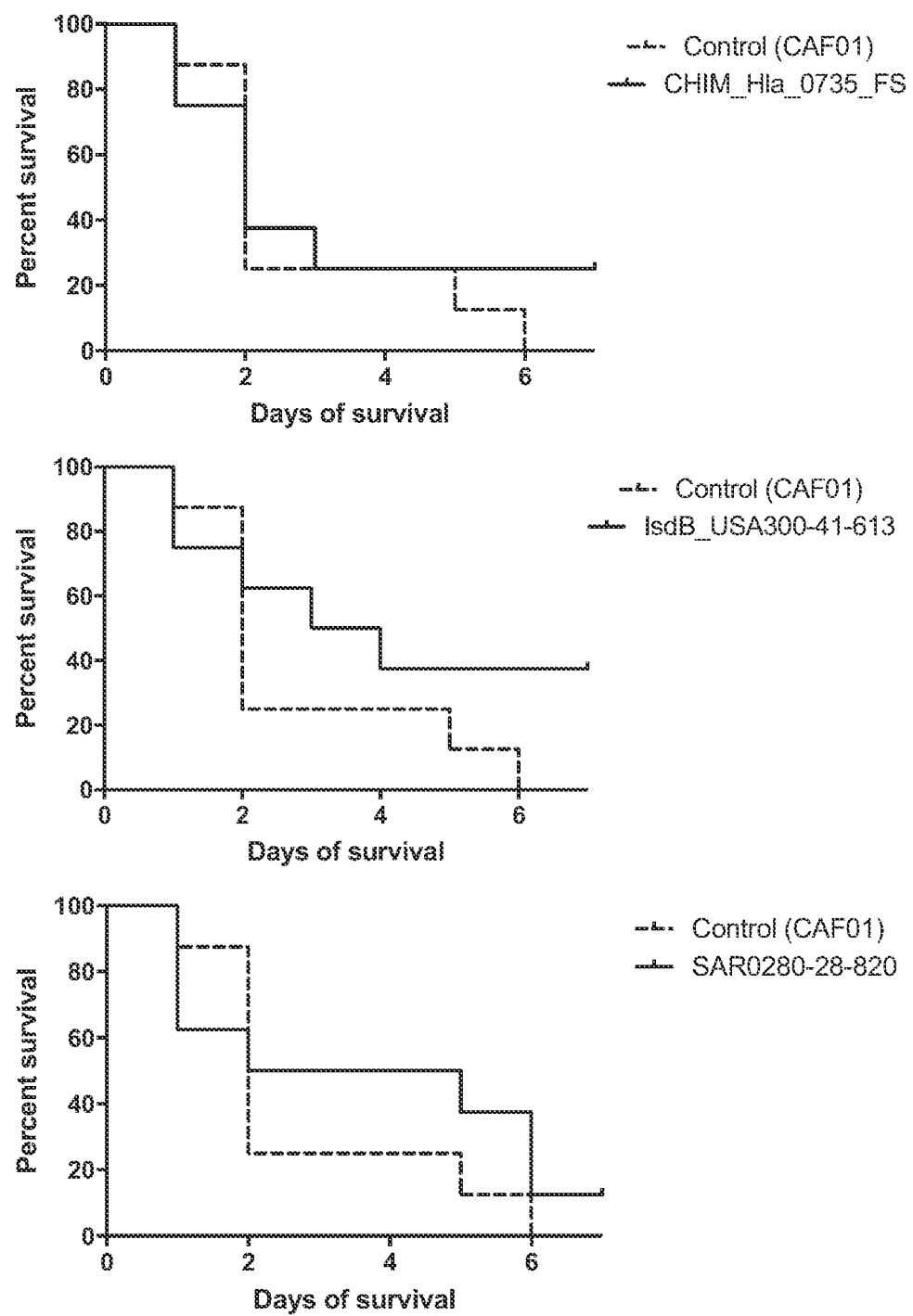
FIG. 3B shows survival plots after challenge infection in mice immunized with immunogens of the invention in a peritonitis model. Dotted lines indicates control, full lines indicates immunogen: Survival plots for CHIM_Hla_0735_FS (top plot), IsdB_USA300-41-613 (middle plot), and SAR0280-28-820 (bottom plot).
Figure 3C:
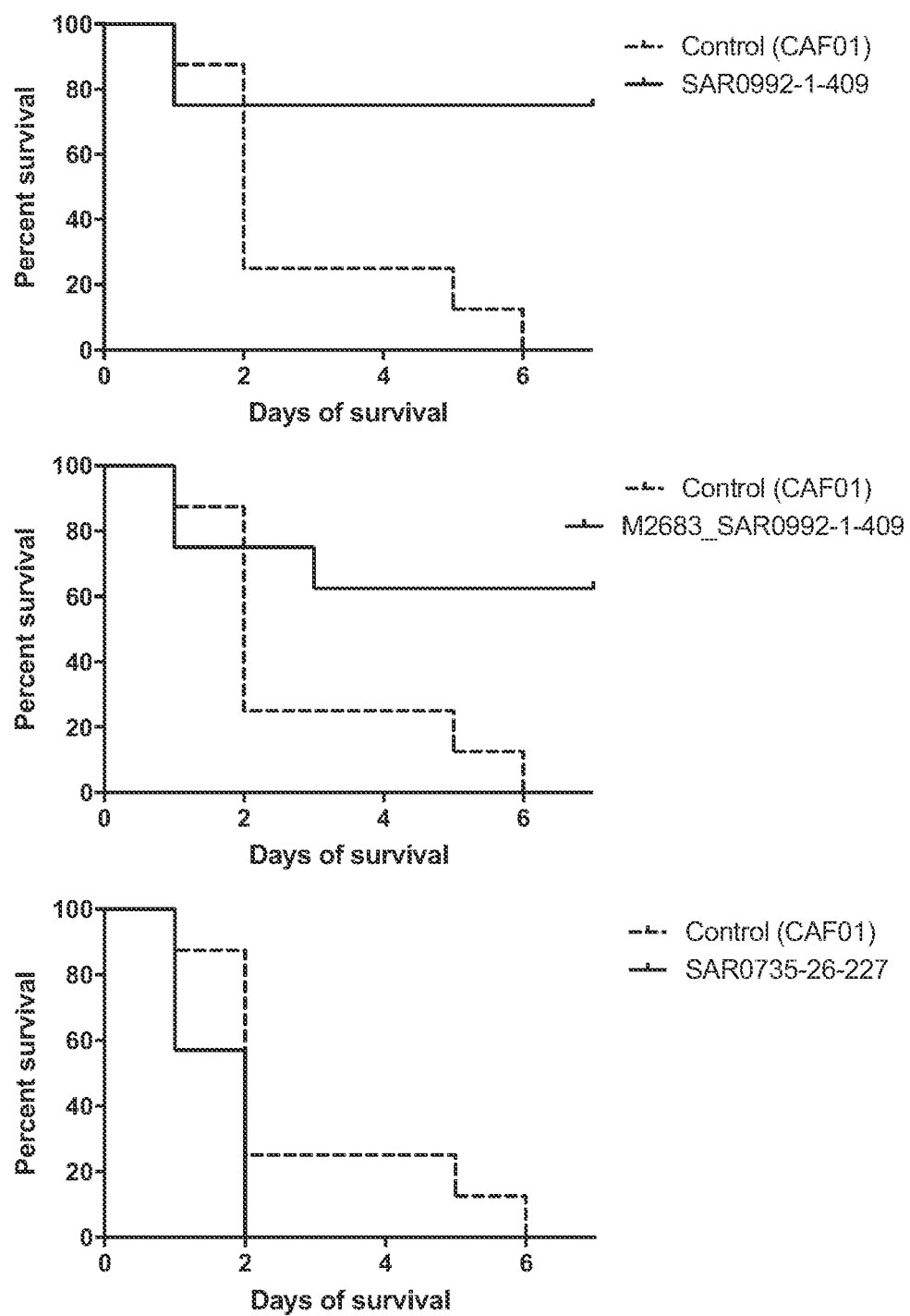
FIG. 3C shows survival plots after challenge infection in mice immunized with immunogens of the invention in a peritonitis model. Dotted lines indicates control, full lines indicates immunogen: Survival plots for SAR0992-1-409 (top plot), M2683_SAR0992-1-409 (middle plot), and SAR0735-26-227 (bottom plot).
Figure 4A:
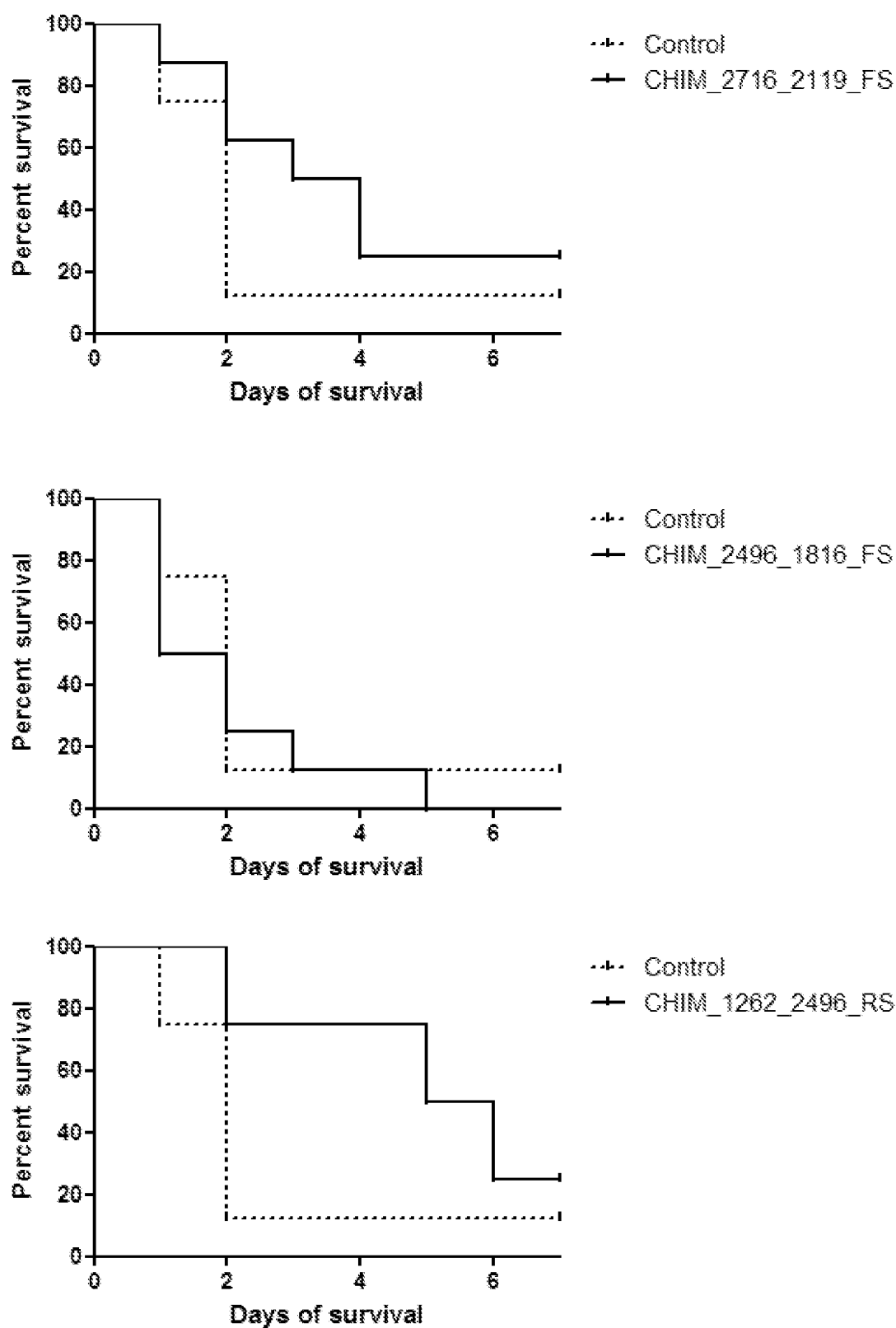
FIG. 4A shows survival plots after challenge infection in mice immunized with immunogens of the invention in a peritonitis model. Dotted lines indicates control, full lines indicates immunogen: Survival plots for CHIM_2119_1816_FS (top plot), CHIM_1816_2119_FL (middle plot), and CHIM_2716_2119_FS (bottom plot).
Figure 4B:
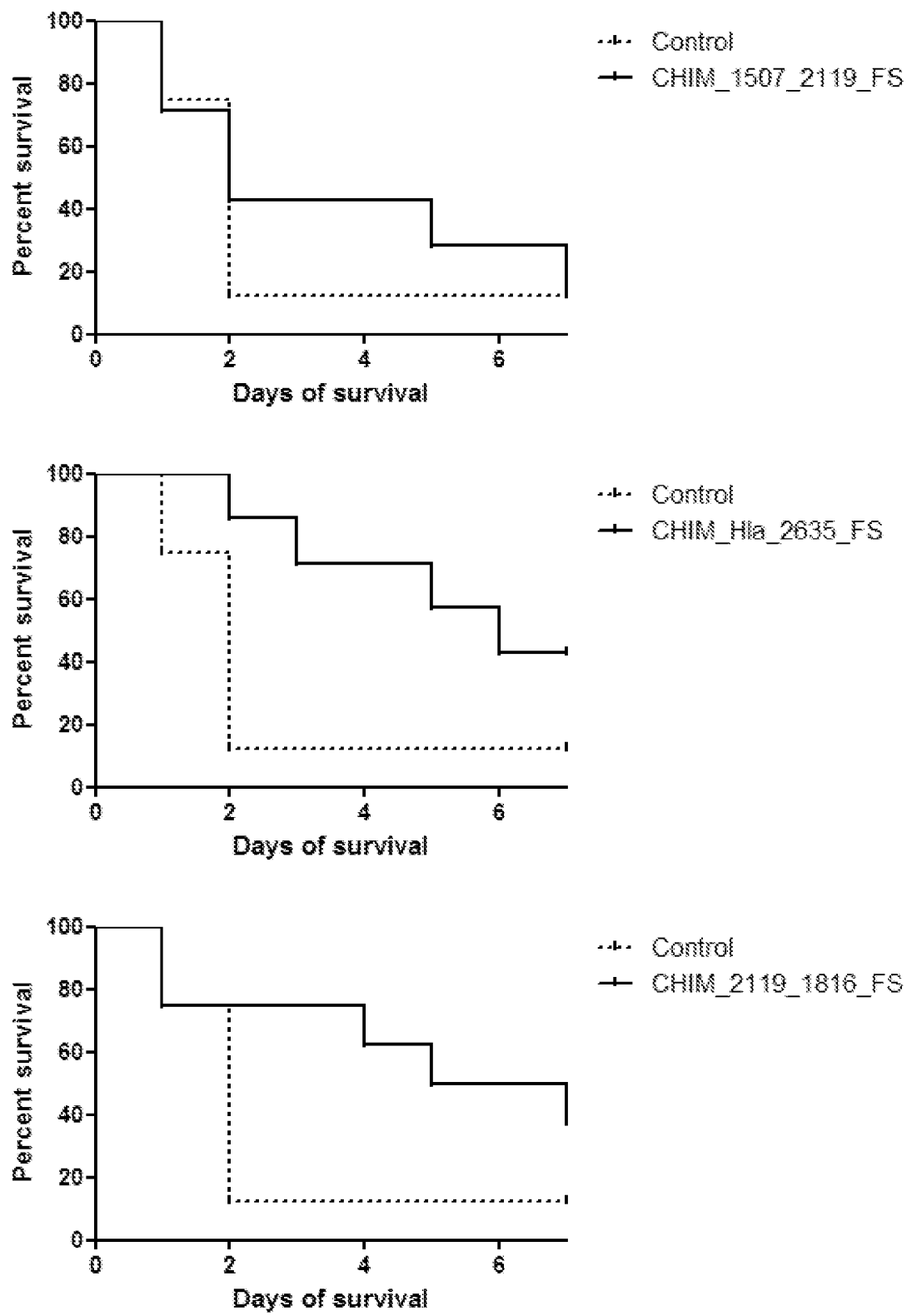
FIG. 4B shows survival plots after challenge infection in mice immunized with immunogens of the invention in a peritonitis model. Dotted lines indicates control, full lines indicates immunogen: Survival plots for CHIM_2496_1816_FS (top plot), CHIM_1262_2496_RS (middle plot), and CHIM_1507_2119_FS (bottom plot).
Figure 4C:
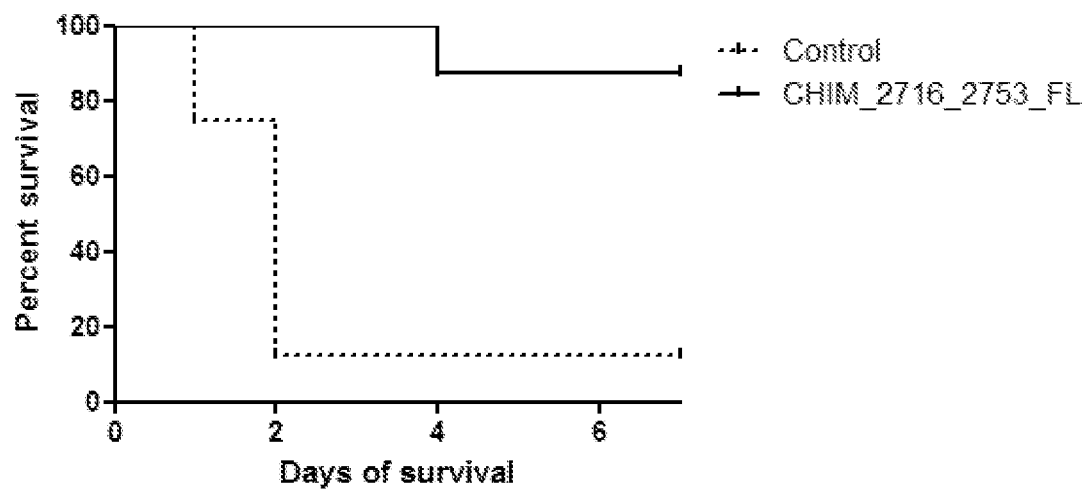
FIG. 4C shows survival plots after challenge infection in mice immunized with immunogens of the invention in a peritonitis model. Dotted lines indicates control, full lines indicates immunogen: Survival plots for CHIM_Hla_2635_FS (top plot), CHIM_2716_2753_FL (middle plot), and HL461_SAR2753-291-476 (bottom plot).
Figure 4C:
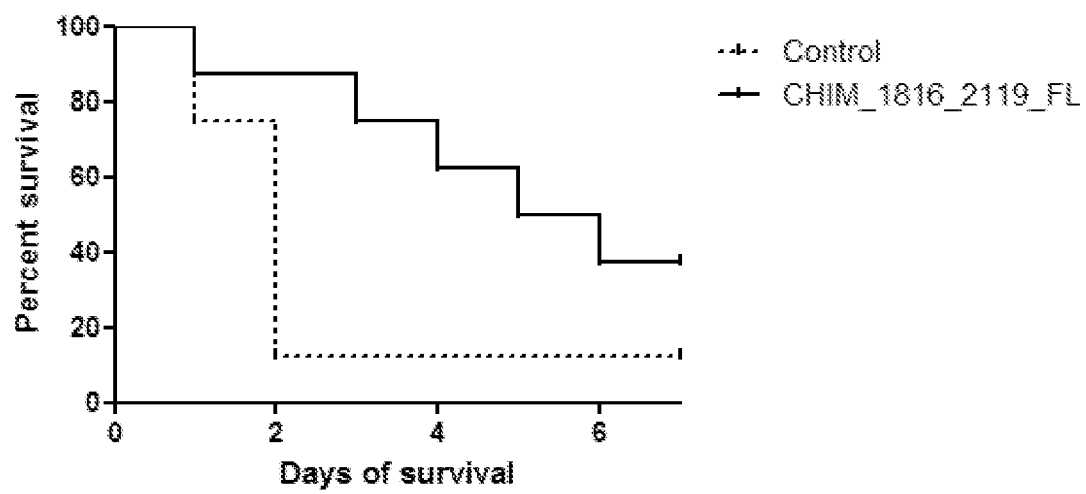
Figure 4C:
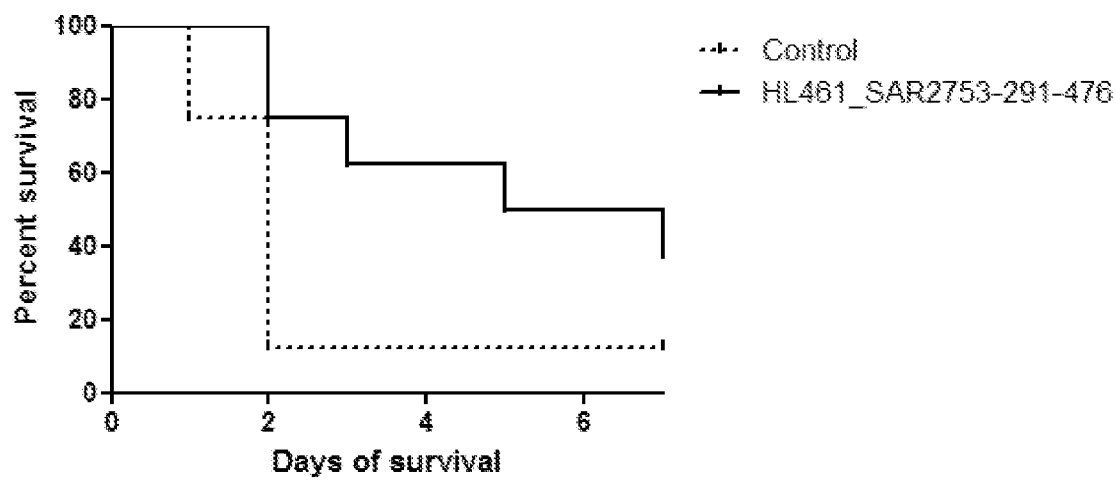
Figure 4D:
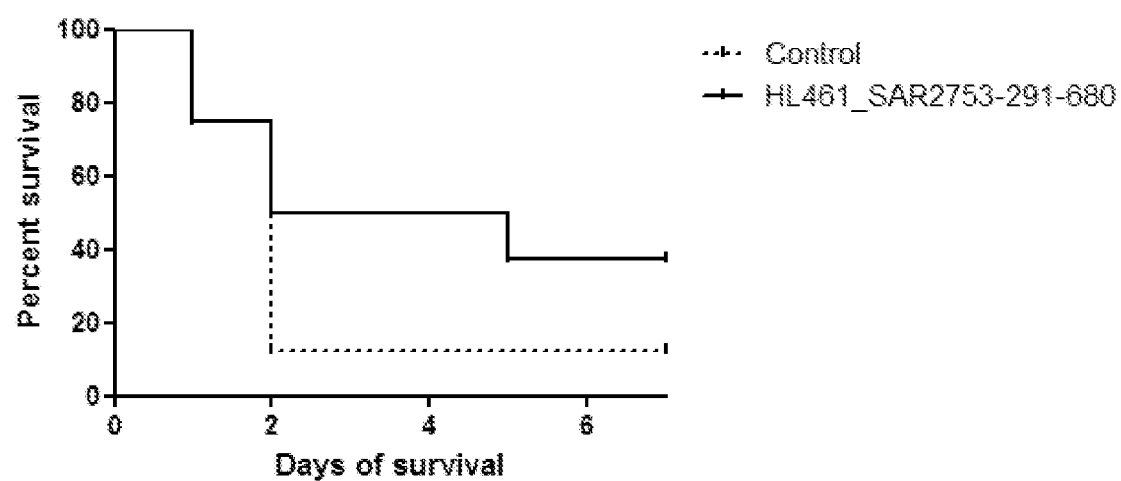
FIG. 4D shows survival plots after challenge infection in mice immunized with immunogens of the invention in a peritonitis model. Dotted lines indicates control, full lines indicates immunogen: Survival plot for HL461_SAR2753_291-680.
Figure 5A:
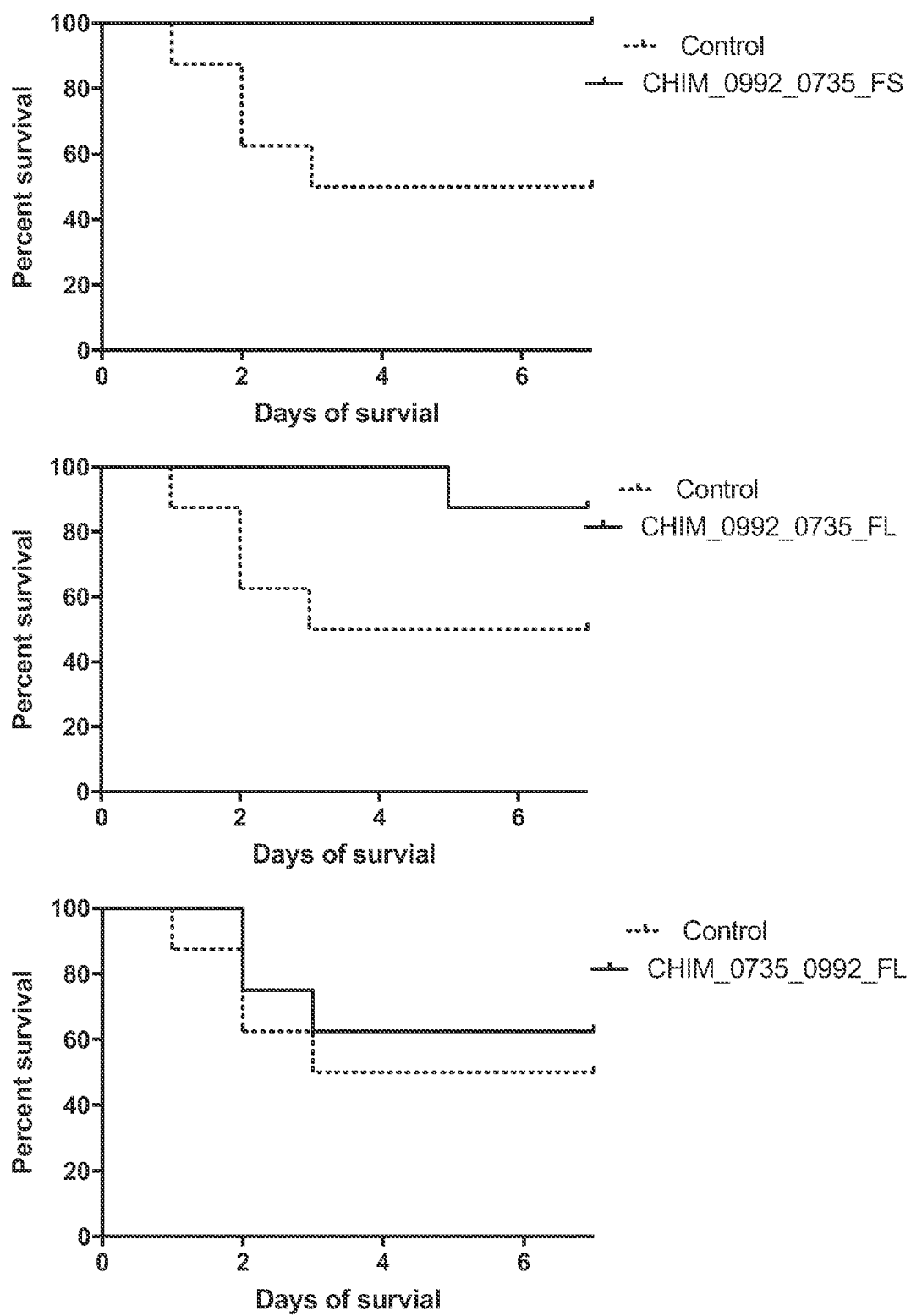
FIG. 5A shows survival plots after challenge infection in mice immunized with immunogens of the invention in a peritonitis model. Dotted lines indicates control, full lines indicates immunogen: Survival plots for CHIM_0992_0735_FS (top plot), CHIM_0992_0735_FL (middle plot), and CHIM_0735_0992_FL (bottom plot).
Figure 5B:
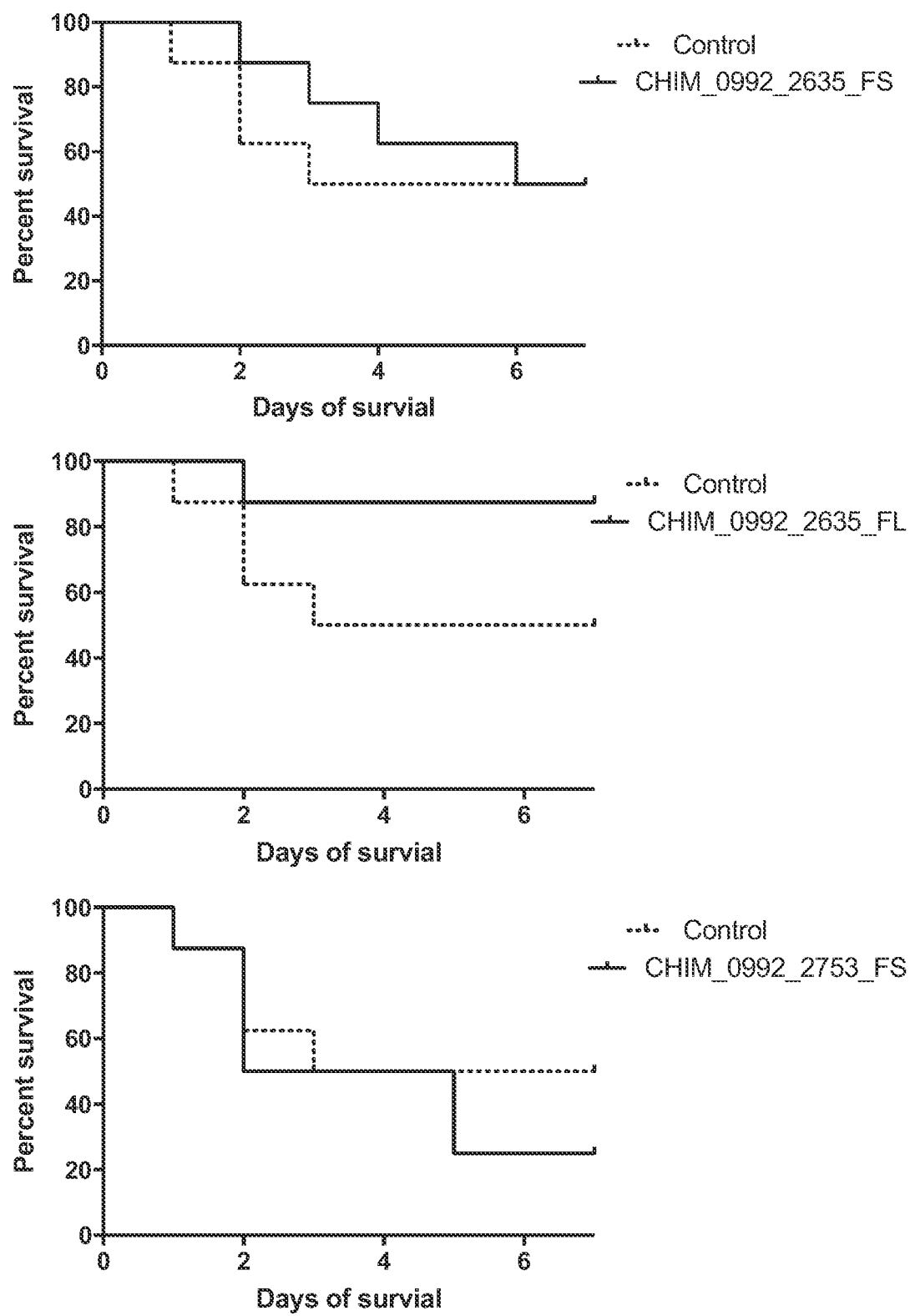
FIG. 5B shows survival plots after challenge infection in mice immunized with immunogens of the invention in a peritonitis model. Dotted lines indicates control, full lines indicates immunogen: Survival plots for CHIM_0992_2635_FS (top plot), CHIM_0992_2635_FL (middle plot), and CHIM_0992_2753_FS (bottom plot).
Figure 5C:
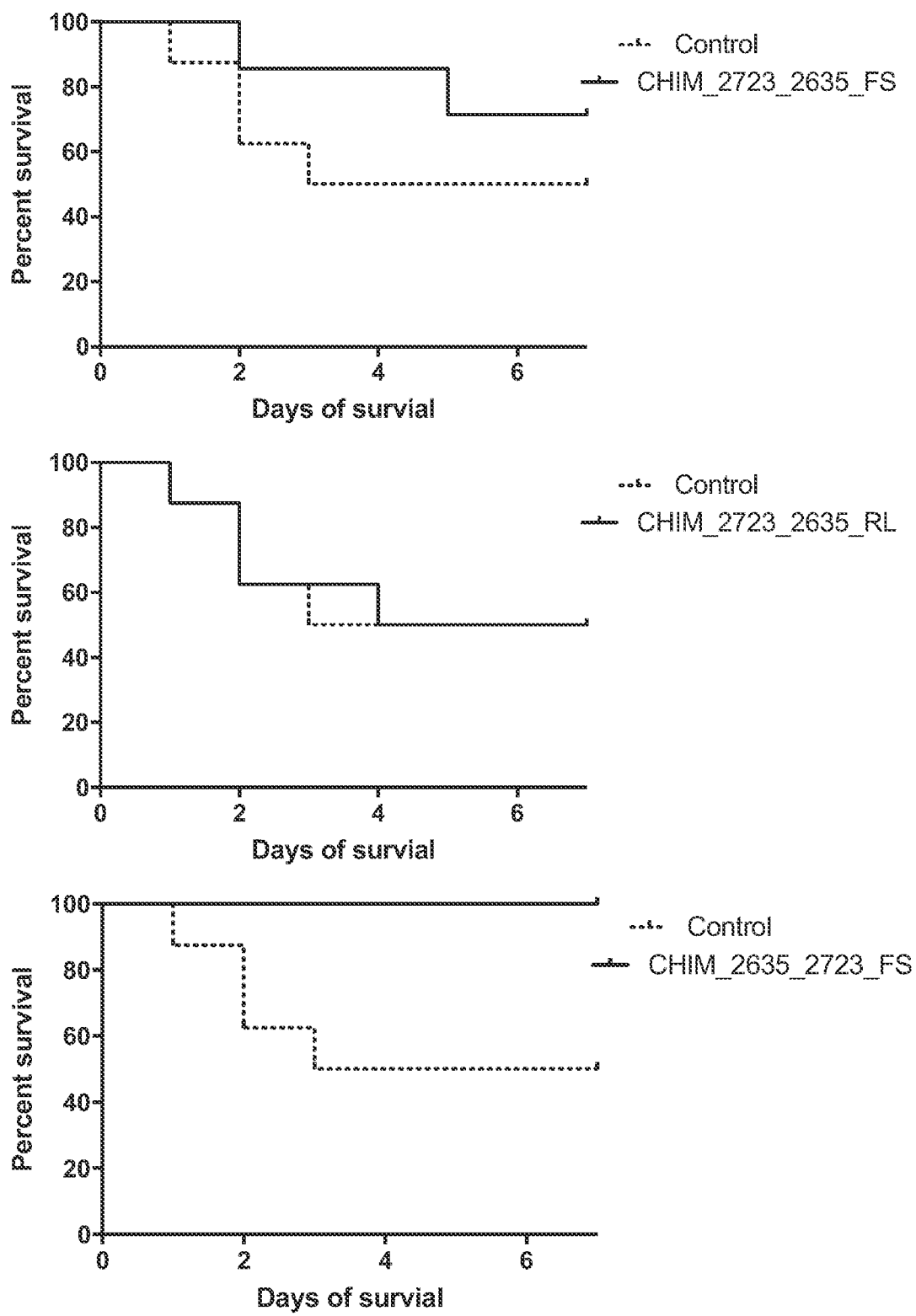
FIG. 5C shows survival plots after challenge infection in mice immunized with immunogens of the invention in a peritonitis model. Dotted lines indicates control, full lines indicates immunogen: Survival plots for CHIM_2723_2635_FS (top plot), CHIM_2723_2635_RL (middle plot), and CHIM_2635_2723_FS (bottom plot).
Figure 5D:
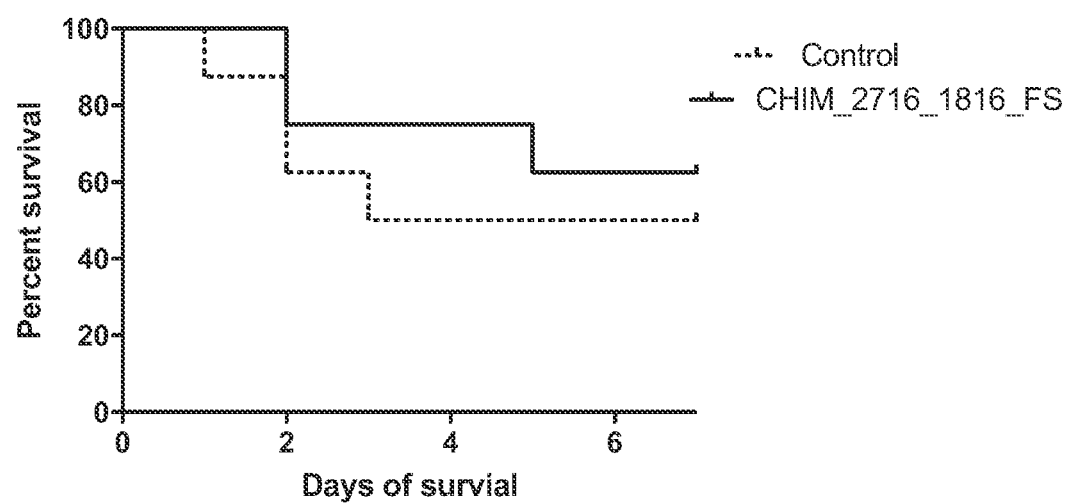
FIG. 5D shows survival plots after challenge infection in mice immunized with immunogens of the invention in a peritonitis model. Dotted lines indicates control, full lines indicates immunogen: Survival plot for CHIM_2716_1816_FS.

3. CHIM_2723_2753_S_FS, CHIM_2723_2753_L_FS, CHIM_Hla_2753_FS, CHIM_Hla_0735_FS, IsdB_USA300-41-613, SAR0280-28-820, SAR0992-1-409, M2683 SAR0992-1-409 and SAR0735-26-227 Formulations (Containing SEQ ID NOs: 77, 15, 80, 78, 84, 87, 89, 85, and 88, Respectively):

Survival of animals is provided for each of the immunogens in the survival plots in FIG. 3A-FIG. 3C. The results show that immunization with either CHIM_2723_2753_L_FS, CHIM_Hla_2753_FS, SAR0992-1-409 or M2683_SAR0992-1-409 protected mice against a lethal challenge with S. aureus MRSA252. Immunization with the other antigens did not result in significant protection compared to the control group.

4. CHIM_2119_1816 FS, CHIM_1816_2119_FL, CHIM_2716_2119 FS, CHIM_2496_1816_FS, CHIM_1262_2496_RS, CHIM_1507_2119_FS, CHIM_HLa_2635_FS, CHIM_2716_2753_FL, HL461_SAR2753-291-476, and HL461_SAR2753_291-680 Formulations (Containing SEQ ID NOS: 68, 67, 72, 69, 65, 66, 79, 73, 82, and 81, Respectively):

Survival of animals is provided for each of the immunogens in the survival plots in FIG. 4A-FIG. 4D. The results show that immunization with either CHIM_HLA_2635 or CHIM_2716_2753_FL in combination with the adjuvant CAF01 had a protective effect, resulting in survival of a significant number of the immunized animals.

5. CHIM_0992_0735_FS, CHIM_0992_0735_FL, CHIM_0735_0992_FL, CHIM_0992_2635_FS, CHIM_0992_2635_FL, CHIM_0992_2753_FS, CHIM_2723_2635_FS, CHIM_2723_2635_RL, CHIM_2635_2723_FS and CHIM_2716_1816_FS Formulations (Containing SEQ ID NOs: 61, 60, 59, 63, 62, 64, 74, 75, 13, and 71, Respectively):

Survival of animals is provided for each of the immunogens in the survival plots in FIG. 5A-FIG. 5D. The results show that immunization with either CHIM_0992_0735_FS or CHIM_2635_2723_FS protected mice against a lethal infection with S. aureus MRSA252 when compared to adjuvant alone.

```
                                                         SEQ ID NO: 1
MTEKEKMLAE KWYDANFDQD LINERARAKD ICFELNHTKP SDKNKRKELI DELFQTTTDN

VSISIPFDTD YGWNVKLGKN VYVNTNCYFM DGGQITIGDN VFIGPNCGFY TATHPLNFHH

RNEGFEKAGP INIGSNTWFG GHVAVLPGVT IGEGSVIGAG SVVTKDIPPH SLAVGNPCKV

VRKIDNEVPS EALNDETLN

SEQ ID NO: 2
KRIKQHPDVQ KVTDATSKVA SKTSAAISNT ASDVKEYVGD KKQDFENKRE LKKFAREHDP

AYIEKKGEKL AKQNRKDADK MNKILQKNIE KRHKEEQKAR EKNEIQRIKD MKKSQKYEVK

AGLTPNKLDE KTEKKGDKLA EKNRKEIAKM NKKLQKNIEK RHKEEQKRQQ EADKARIKSF

KKYKDYVAKS ASQQNKENNT EA

SEQ ID NO: 3
ADSDINIKTG TTDIGSNTTV KTGDLVTYDK ENGMLKKVFY SFIDDKNHNK KLLVIRTKGT

IAGQYRVYSE EGANKSGLAW PSAFKVQLQL PDNEVAQISD YYPRNSIDTK EYMSTLTYGF

NGNVTGDDTG KIGGLIGANV SIGHTLKYVQ PDFKTILESP TDKKVGWKVI FNNMVNQNWG

PYDRDSWNPV YGNQLFMKTR NGSMKAADNF LDPNKASSLL SSGFSPDFAT VITMDRKASK

QQTNIDVIYE RVRDDYQLHW TSTNWKGTNT KDKWIDRSSE RYKIDWEKEE MTN
```

```
                                                      SEQ ID NO: 4
AKDNLNGEKP TTNLNHNVTS PSVNSEMNNN ETGTPHESNQ AGNEGTGSNS RDANPDSNNV

KPDSNNQNPS PDSKPDPNNP NPGPNPKPDP DKPKPNPEPK PDPKPDPDKP KPNPDPKPDP

DKPKPNPDPK PDPDKPKPNP DPKPDPNPNP KPDPNKPNPN PSPNPNQPGD SNQSGGSKNG

GTWNPNASDG SNQGQWQPNG NQGNSQNPTG NDFVSQRFLA LANGAYKYNP YILNQINQLG

KEYGEVTDED IYNIIRKQNF SGNAYLNGLQ QQSNYFRFQY FNPLKSERYY RNLDEQVLAL

ITGEIGSMPD LKKPEDKPDS KQRSFEPHEK DDFTVVKKQE DNKKSASTAY S

SEQ ID NO: 5
GFLNKSKNEQ AALKAQQAAI KEEASANNLS DTSQEAQEIQ EAKREAQAEA DKSVAVSNKE

SKAVALKAQQ AAIKEEASAN NLSDTSQEAQ EIQEAKKEAQ AETDKSAAVS NEEPKAVALK

AQQAAIKEEA SANNLSDISQ EAQEVQEAKK EAQAEKDSDT LTKDASAAKV EVSKPESQAE

RLANAAKQKQ AKLTPGSKES QLTEALFAEK PVAKNDLKEI PQLVTKKNDV SETETVNIDN

KDTVKQKEAK FENGVITRKA DEKTTNNTAV DKKSGKQSKK TTPSNKRNAS KASTNKTSGQ

KKQHNKKSSQ GAKKQSSSSK STQKNNQTSN KNSKTTNAKS SNASKTPNAK VEKAKSKIEK

RTFND

SEQ ID NO: 6
KVAKQGQYKN QDPIVLVHGF NGFTDDINPS VLAHYWGGNK MNIRQDLEEN GYKAYEASIS

AFGSNYDRAV ELYYYIKGGR VDYGAAHAAK YGHERYGKTY EGIYKDWKPG QKVHLVGHSM

GGQTIRQLEE LLRNGSREEI EYQKKHGGEI SPLFKGNNDN MISSITTLGT PHNGTHASDL

AGNEALVRQI VFDIGKMFGN KNSRVDFGLA QWGLKQKPNE SYIDYVKRVK QSNLWKSKDN

GFYDLTREGA TDLNRKTSLN PNIVYKTYTG EATHKALNSD RQKADLNMFF PFVITGNLIG

KATEKEWREN DGLVSVISSQ HPFNQAYTNA TDKIQKGIWQ VTPTKHDWDH VDFVGQDSSD

TVRTREELQD FWHHLADDLV KTEKVTDTKQ

SEQ ID NO: 7
MDIGKKHVIP KSQYRRKRRE FFHNEDREEN LNQHQDKQNI DNTTSKKADK QIHKDSIDKH

ERFKNSLSSH LEQRNRDVNE NKAEESKSNQ DSKSAYNRDH YLTDDVSKKQ NSLDSVQDT

EKSKYYEQNS EATLSTKSTD KVESTEMRKL SSDKNKVGHE EQHVLSKPSE HDKETRIDSE

SSRTDSDSSM QTEKIKKDSS DGNKSSNLKS EVISDKSNTV PKLSESDDEV NNQKPLTLPE

EQKLKRQQSQ NEQTKTYTYG DSEQNDKSNH ENDLSHHIPS ISDDKDNVMR ENHIVDDNPD

NDINTPSLSK TDDDRKLDEK IHVEDKHKQN ADSSETVGYQ SQSTASHRST EKRNISINDH

DKLNGQKTNT KTSANNNQKK ATSKLNKGRA TNNNYSDILK KFWMMYWPK

SEQ ID NO: 8
IDSKNKPANS DIKFEVTQKS DAVKALKELP KSENVKNIYQ DYAVTDVKTD KKGFTHYTLQ

PSVDGVHAPD KEVKVHADKS GKVVLINGDT DAKKVKPTNK VTLSKDDAAD KAFKAVKIDK

NKAKNLKDKV IKENKVEIDG DSNKYVYNVE LITVTPEISH WKVKIDAQTG EILEKMNLVK

EAAETGKGKG VLGDTKDINI NSIDGGFSLE DLTHQGKLSA FSFNDQTGQA TLITNEDENF

VKDEQRAGVD ANYYAKQTYD YYKDTFGRES YDNQGSPIVS LTHVNNYGGQ DNRNNAAWIG

DKMIYGDGDG RTFTSLSGAN DVVAHELTHG VTQETANLEY KDQSGALNES FSDVFGYFVD

DEDFLMGEDV YTPGKEGDAL RSMSNPEQFG QPAHMKDYVF TEKDNGGVHT NS

SEQ ID NO: 9
DTPQKDTTAK TTSHDSKKSN DDETSKDTTS KDIDKADNNN TSNQDNNDKK FKTIDDSTSD

SNNIIDFIYK NLPQTNINQL LTKNKYDDNY SLTTLIQNLF NLNSDISDYE QPRNGEKSTN

DSNKNSDNSI KNDTDTQSSK QDKADNQKAP KSNNTKPSTS NKQPNSPKPT QPNQSNSQPA
```

-continued

SDDKANQKSS SKDNQSMSDS ALDSILDQYS EDAKKTQKDY ASQSKKDKNE KSNTKNPQLP

TQDELKHKSK PAQSFNNDVN QKDTRATSLF ETDPSISNND DSGQFNVVDS KDTRQFVKSI

AKDAHRIGQD NDIYASVMIA QAILESDSGR SALAKSPNHN LFGIKGAFEG NSVPFNTLEA

DGNKLYSINA GFRKYPSTKE SLKDYSDLIK NGIDGNRTIY KPTWKSEADS YKDATSHLSK

TYATDPNYAK KLNSIIKHYQ LTQFDDERMP DLDKYERSIK DYDDSSDEFK PFREVSDSMP

YPHGQCTWYV YNRMKQFGTS ISGDLGDAHN WNNRAQYRDY QVSHTPKRHA AVVFEAGQFG

ADQHYGHVAF VEKVNSDGSI VISESNVKGL GIISHRTINA AAAEELSYIT GK

SEQ ID NO: 10
GSGGGA

SEQ ID NO: 11
GSGGGAGSGG GA

SEQ ID NO: 12
MDIGKKHVIP KSQYRRKRRE FFHNEDREEN LNQHQDKQNI DNTTSKKADK QIHKDSIDKH

ERFKNSLSSH LEQRNRDVNE NKAEESKSNQ DSKSAYNRDH YLTDDVSKKQ NSLDSVDQDT

EKSKYYEQNS EATLSTKSTD KVESTEMRKL SSDKNKVGHE EQHVLSKPSE HDKETRIDSE

SSRTDSDSSM QTEKIKKDSS DGNKSSNLKS EVISDKSNTV PKLSESDDEV NNQKPLTLPE

EQKLKRQQSQ NEQTKTYTYG DSEQNDKSNH ENDLSHHIPS ISDDKDNVMR ENHIVDDNPD

NDINTPSLSK TDDDRKLDEK IHVEDKHKQN ADSSETVGYQ SQSTASHRST EKRNISINDH

DKLNGQKTNT KTSANNNQKK ATSKLNKGRA TNNNYSDILK KFWMMYWPKG SGGGAKRIKQ

HPDVQKVTDA TSKVASKTSA AISNTASDVK EYVGDKKQDF ENKRELKKFA REHDPAYIEK

KGEKLAKQNR KDADKMNKIL QKNIEKRHKE EQKAREKNEI QRIKDMKKSQ KYEVKAGLTP

NKLDEKTEKK GDKLAEKNRK EIAKMNKKLQ KNIEKRHKEE QKRQQEADKA RIKSFKKYKD

YVAKSASQQN KENNTEA

SEQ ID NO: 13
MTEKEKMLAE KWYDANFDQD LINERARAKD ICFELNHTKP SDKNKRKELI DELFQTTTDN

VSISIPFDTD YGWNVKLGKN VYVNTNCYFM DGGQITIGDN VFIGPNCGFY TATHPLNFHH

RNEGFEKAGP INIGSNTWFG GHVAVLPGVT IGEGSVIGAG SVVTKDIPPH SLAVGNPCKV

VRKIDNEVPS EALNDETLNG SGGGADTPQK DTTAKTTSHD SKKSNDDETS KDTTSKDIDK

ADNNNTSNQD NNDKKFKTID DSTSDSNNII DFIYKNLPQT NINQLLTKNK YDDNYSLTTL

IQNLFNLNSD ISDYEQPRNG EKSTNDSNKN SDNSIKNDTD TQSSKQDKAD NQKAPKSNNT

KPSTSNKQPN SPKPTQPNQS NSQPASDDKA NQKSSSKDNQ SMSDSALDSI LDQYSEDAKK

TQKDYASQSK KDKNEKSNTK NPQLPTQDEL KHKSKPAQSF NNDVNQKDTR ATSLFETDPS

ISNNDDSGQF NVVDSKDTRQ FVKSIAKDAH RIGQDNDIYA SVMIAQAILE SDSGRSALAK

SPNHNLFGIK GAFEGNSVPF NTLEADGNKL YSINAGFRKY PSTKESLKDY SDLIKNGIDG

NRTIYKPTWK SEADSYKDAT SHLSKTYATD PNYAKKLNSI IKHYQLTQFD DERMPDLDKY

ERSIKDYDDS SDEFKPFREV SDSMPYPHGQ CTWYVYNRMK QFGTSISGDL GDAHNWNNRA

QYRDYQVSHT PKRHAAVVFE AGQFGADQHY GHVAFVEKVN SDGSIVISES NVKGLGIISH

RTINAAAEEE LSYITGK

SEQ ID NO: 14
IDSKNKPANS DIKFEVTQKS DAVKALKELP KSENVKNIYQ DYAVTDVKTD KKGFTHYTLQ

PSVDGVHAPD KEVKVHADKS GKVVLINGDT DAKKVKPTNK VTLSKDDAAD KAFKAVKIDK

NKAKNLKDKV IKENKVEIDG DSNKYVYNVE LITVTPEISH WKVKIDAQTG EILEKMNLVK

EAAETGKGKG VLGDTKDINI NSIDGGFSLE DLTHQGKLSA FSFNDQTGQA TLITNEDENF

```
                                             -continued
VKDEQRAGVD ANYYAKQTYD YYKDTFGRES YDNQGSPIVS LTHVNNYGGQ DNRNNAAWIG

DKMIYGDGDG RTFTSLSGAN DVVAHELTHG VTQETANLEY KDQSGALNES FSDVFGYFVD

DEDFLMGEDV YTPGKEGDAL RSMSNPEQFG QPAHMKDYVF TEKDNGGVHT NSGSGGGAGS

GGGAKVAKQG QYKNQDPIVL VHGFNGFTDD INPSVLAHYW GGNKMNIRQD LEENGYKAYE

ASISAFGSNY DRAVELYYYI KGGRVDYGAA HAAKYGHERY GKTYEGIYKD WKPGQKVHLV

GHSMGGQTIR QLEELLRNGS REEIEYQKKH GGEISPLFKG NNDNMISSIT TLGTPHNGTH

ASDLAGNEAL VRQIVFDIGK MFGNKNSRVD FGLAQWGLKQ KPNESYIDYV KRVKQSNLWK

SKDNGFYDLT REGATDLNRK TSLNPNIVYK TYTGEATHKA LNSDRQKADL NMFFPFVITG

NLIGKATEKE WRENDGLVSV ISSQHPFNQA YTNATDKIQK GIWQVTPTKH DWDHVDFVGQ

DSSDTVRTRE ELQDFWHHLA DDLVKTEKVT DTKQ

SEQ ID NO: 15
DTPQKDTTAK TTSHDSKKSN DDETSKDTTS KDIDKADNNN TSNQDNNDKK FKTIDDSTSD

SNNIIDFIYK NLPQTNINQL LTKNKYDDNY SLTTLIQNLF NLNSDISDYE QPRNGEKSTN

DSNKNSDNSI KNDTDTQSSK QDKADNQKAP KSNNTKPSTS NKQPNSPKPT QPNQSNSQPA

SDDKANQKSS SKDNQSMSDS ALDSILDQYS EDAKKTQKDY ASQSKKDKNE KSNTKNPQLP

TQDELKHKSK PAQSFNNDVN QKDTRATSLF ETDPSISNND DSGQFNVVDS KDTRQFVKSI

AKDAHRIGQD NDIYASVMIA QAILESDSGR SALAKSPNHN LFGIKGAFEG NSVPFNTLEA

DGNKLYSINA GFRKYPSTKE SLKDYSDLIK NGIDGNRTIY KPTWKSEADS YKDATSHLSK

TYATDPNYAK KLNSIIKHYQ LTQFDDERMP DLDKYERSIK DYDDSSDEFK PFREVSDSMP

YPHGQCTWYV YNRMKQFGTS ISGDLGDAHN WNNRAQYRDY QVSHTPKRHA AVVFEAGQFG

ADQHYGHVAF VEKVNSDGSI VISESNVKGL GIISHRTINA AAAEELSYIT GKGSGGGAKV

AKQGQYKNQD PIVLVHGFNG FTDDINPSVL AHYWGGNKMN IRQDLEENGY KAYEASISAF

GSNYDRAVEL YYYIKGGRVD YGAAHAAKYG HERYGKTYEG IYKDWKPGQK VHLVGHSMGG

QTIRQLEELL RNGSREEIEY QKKHGGEISP LFKGNNDNMI SSITTLGTPH NGTHASDLAG

NEALVRQIVF DIGKMFGNKN SRVDFGLAQW GLKQKPNESY IDYVKRVKQS NLWKSKDNGF

YDLTREGATD LNRKTSLNPN IVYKTYTGEA THKALNSDRQ KADLNMFFPF VITGNLIGKA

TEKEWRENDG LVSVISSQHP FNQAYTNATD KIQKGIWQVT PTKHDWDHVD FVGQDSSDTV

RTREELQDFW HHLADDLVKT EKVTDTKQ

SEQ ID NO: 16
AKDNLNGEKP TTNLNHNVTS PSVNSEMNNN ETGTPHESNQ AGNEGTGSNS RDANPDSNNV

KPDSNNQNPS PDSKPDPNNP NPGPNPKPDP DKPKPNPEPK PDPKPDPDKP KPNPDPKPDP

DKPKPNPDPK PDPDKPKPNP DPKPDPNPNP KPDPNKPNPN PSPNPNQPGD SNQSGGSKNG

GTWNPNASDG SNQGWQPNG NQGNSQNPTG NDFVSQRFLA LANGAYKYNP YILNQINQLG

KEYGEVTDED IYNIIRKQNF SGNAYLNGLQ QQSNYFRFQY FNPLKSERYY RNLDEQVLAL

ITGEIGSMPD LKKPEDKPDS KQRSFEPHEK DDFTVVKKQE DNKKSASTAY SGSGGGAGFL

NKSKNEQAAL KAQQAAIKEE ASANNLSDTS QEAQEIQEAK REAQAEDKS VAVSNKESKA

VALKAQQAAI KEEASANNLS DTSQEAQEIQ EAKKEAQAET DKSAAVSNEE PKAVALKAQQ

AAIKEEASAN NLSDISQEAQ EVQEAKKEAQ AEKDSDTLTK DASAAKVEVS KPESQAERLA

NAAKQKQAKL TPGSKESQLT EALFAEKPVA KNDLKEIPQL VTKKNDVSET ETVNIDNKDT

VKQKEAKFEN GVITRKADEK TTNNTAVDKK SGKQSKKTTP SNKRNASKAS TNKTSGQKKQ

HNKKSSQGAK KQSSSSKSTQ KNNQTSNKNS KTTNAKSSNA SKTPNAKVEK AKSKIEKRTF

ND
```

SEQ ID NO: 17
MDIGKKHVIP KSQYRRKRRE FFHNEDREEN LNQHQDKQNI DNTTSKKADK QIHKDSIDKH
ERFKNSLSSH LEQRNRDVNE NKAEESKSNQ DSKSAYNRDH YLTDDVSKKQ NSLDSVDQDT
EKSKYYEQNS EATLSTKSTD KVESTEMRKL SSDKNKVGHE EQHVLSKPSE HDKETRIDSE
SSRTDSDSSM QTEKIKKDSS DGNKSSNLKS EVISDKSNTV PKLSESDDEV NNQKPLTLPE
EQKLKRQQSQ NEQTKTYTYG DSEQNDKSNH ENDLSHHIPS ISDDKDNVMR ENHIVDDNPD
NDINTPSLSK TDDDRKLDEK IHVEDKHKQN ADSSETVGYQ SQSTASHRST EKRNISINDH
DKLNGQKTNT KTSANNNQKK ATSKLNKGRA TNNNYSDILK KFWMMYWPKG SGGGAGSGGG
AMTEKEKMLA EKWYDANFDQ DLINERARAK DICFELNHTK PSDKNKRKEL IDELFQTTTD
NVSISIPFDT DYGWNVKLGK NVYVNTNCYF MDGGQITIGD NVFIGPNCGF YTATHPLNFH
HRNEGFEKAG PINIGSNTWF GGHVAVLPGV TIGEGSVIGA GSVVTKDIPP HSLAVGNPCK
VVRKIDNEVP SEALNDETLN

SEQ ID NO: 18
ADSDINIKTG TTDIGSNTTV KTGDLVTYDK ENGMLKKVFY SFIDDKNHNK KLLVIRTKGT
IAGQYRVYSE EGANKSGLAW PSAFKVQLQL PDNEVAQISD YYPRNSIDTK EYMSTLTYGF
NGNVTGDDTG KIGGLIGANV SIGHTLKYVQ PDFKTILESP TDKKVGWKVI FNNMVNQNWG
PYDRDSWNPV YGNQLFMKTR NGSMKAADNF LDPNKASSLL SSGFSPDFAT VITMDRKASK
QQTNIDVIYE RVRDDYQLHW TSTNWKGTNT KDKWIDRSSE RYKIDWEKEE MTNGSGGGAM
TEKEKMLAEK WYDANFDQDL INERARAKDI CFELNHTKPS DKNKRKELID ELFQTTTDNV
SISIPFDTDY GWNVKLGKNV YVNTNCYFMD GGQITIGDNV FIGPNCGFYT ATHPLNFHHR
NEGFEKAGPI NIGSNTWFGG HVAVLPGVTI GEGSVIGAGS VVTKDIPPHS LAVGNPCKVV
RKIDNEVPSE ALNDETLN

SEQ ID NO: 19
ADSDINIKTG TTDIGSNTTV KTGDLVTYDK ENGMLKKVFY SFIDDKNHNK KLLVIRTKGT
IAGQYRVYSE EGANKSGLAW PSAFKVQLQL PDNEVAQISD YYPRNSIDTK EYMSTLTYGF
NGNVTGDDTG KIGGLIGANV SIGHTLKYVQ PDFKTILESP TDKKVGWKVI FNNMVNQNWG
PYDRDSWNPV YGNQLFMKTR NGSMKAADNF LDPNKASSLL SSGFSPDFAT VITMDRKASK
QQTNIDVIYE RVRDDYQLHW TSTNWKGTNT KDKWIDRSSE RYKIDWEKEE MTNGSGGGAK
VAKQGQYKNQ DPIVLVHGFN GFTDDINPSV LAHYWGGNKM NIRQDLEENG YKAYEASISA
FGSNYDRAVE LYYYIKGGRV DYGAAHAAKY GHERYGKTYE GIYKDWKPGQ KVHLVGHSMG
GQTIRQLEEL LRNGSREEIE YQKKHGGEIS PLFKGNNDNM ISSITTLGTP HNGTHASDLA
GNEALVRQIV FDIGKMFGNK NSRVDFGLAQ WGLKQKPNES YIDYVKRVKQ SNLWKSKDNG
FYDLTREGAT DLNRKTSLNP NIVYKTYTGE ATHKALNSDR QKADLNMFFP FVITGNLIGK
ATEKEWREND GLVSVISSQH PFNQAYTNAT DKIQKGIWQV TPTKHDWDHV DFVGQDSSDT
VRTREELQDF WHHLADDLVK TEKVTDTKQ

SEQ ID NO: 20
ADSDINIKTG TTDIGSNTTV KTGDLVTYDK ENGMLKKVFY SFIDDKNHNK KLLVIRTKGT
IAGQYRVYSE EGANKSGLAW PSAFKVQLQL PDNEVAQISD YYPRNSIDTK EYMSTLTYGF
NGNVTGDDTG KIGGLIGANV SIGHTLKYVQ PDFKTILESP TDKKVGWKVI FNNMVNQNWG
PYDRDSWNPV YGNQLFMKTR NGSMKAADNF LDPNKASSLL SSGFSPDFAT VITMDRKASK
QQTNIDVIYE RVRDDYQLHW TSTNWKGTNT KDKWIDRSSE RYKIDWEKEE MTNGSGGGAK
RIKQHPDVQK VTDATSKVAS KTSAAISNTA SDVKEYVGDK KQDFENKREL KKFAREHDPA

-continued

YIEKKGEKLA KQNRKDADKM NKILQKNIEK RHKEEQKARE KNEIQRIKDM KKSQKYEVKA
GLTPNKLDEK TEKKGDKLAE KNRKEIAKMN KKLQKNIEKR HKEEQKRQQE ADKARIKSFK
KYKDYVAKSA SQQNKENNTE A

EPINFILKSSTKLKA
SEQ ID NO: 21

FLKLFRITNPIARGL
SEQ ID NO: 22

GLYFVAMNNLKAAGQ
SEQ ID NO: 23

IIKKLFRLPAIKRFE
SEQ ID NO: 24

ILLGYFVAQRALVKA
SEQ ID NO: 25

KADALKAITALKLQM
SEQ ID NO: 26

KHQIRMLSIPRDTIS
SEQ ID NO: 27

KRIFKMSPIHHHFEL
SEQ ID NO: 28

KTLFVALNNKARIPE
SEQ ID NO: 29

LDQIIAQANLRLATM
SEQ ID NO: 30

LMGIRAFRKLLPNIP
SEQ ID NO: 31

MHFIAISINHRTADV
SEQ ID NO: 32

QRHFQIGYNRAARII
SEQ ID NO: 33

SSNVYMFKTALKLAG
SEQ ID NO: 34

STFIYKIANERLFSR
SEQ ID NO: 35

SVTIIKSLQAIRVPF
SEQ ID NO: 36

TSQFHVLRALRLAQK
SEQ ID NO: 37

VLFYLRSNKRQIIEK
SEQ ID NO: 38

WKRIGRLKSIPIFMY
SEQ ID NO: 39

YFRFQYFNPLKSERY
SEQ ID NO: 40

SEQ ID NO: 41
VLFYLRSNKR QIIEKGPGPG EPINFILKSS TKLKAGPGPG GLYFVAMNNL KAAGQGPGPG
KADALKAITA LKLQMGPGPG KHQIRMLSIP RDTISGPGPG LDQIIAQANL RLATMGPGPG
QRHFQIGYNR AARIIGPGPG SSNVYMFKTA LKLAGGPGPG YFRFQYFNPL KSERY

SEQ ID NO: 42
TSQFHVLRAL RLAQKGPGPG FLKLFRITNP IARGLGPGPG IIKKLFRLPA IKRFEGPGPG
ILLGYFVAQR ALVKAGPGPG KRIFKMSPIH HHFELGPGPG KTLFVALNNK ARIPEGPGPG
LMGIRAFRKL LPNIPGPGPG MHFIAISINH RTADVGPGPG STFIYKIANE RLFSRGPGPG
SVTIIKSLQA IRVPFGPGPG WKRIGRLKSI PIFMY

SEQ ID NO: 43
```
MSSLPVGPVA WSDGMLIETQ HFQQLKRIFK MSPIHHHFEL SNHGWGFTLL DLDQDGLGLG
RLMGIRAFRK LLPNIPFSLP SDDPLPPPLE TELAQAGDIA CLALQAARTG GPEMAFGDVE
LASRYRAVST EVPDLAVGLD APGTPFLKLF RITNPIARGL WKRIGRLKSI PIFMYRVAGR
NASRTVSLDP RFIPPKTLFV ALNNKARIPE ELQSTSVTII KSLQAIRVPF TGGGVADLIE
ILLGYFVAQR ALVKANLDAF DPLPPMHFIA ISINHRTADV VLPGVDEELA DRELGYDHDD
LQTSFTSQFH VLRALRLAQK ETPVLPLRFE DRGDQVHICI VDKQWNLKKL IFAFSIIKKL
FRLPAIKRFE TKLGAVEQIQ KLVDLQLPGA RLNALPNPPR QIPYYAQSTY FEVESTDPFW
KQTLAGSAMA LRIVGDFPST FIYKIANERL FSR
```

SEQ ID NO: 44
```
MSSLPVGPVA WSDGMLIETQ HFQQLERHLA HQASLRLGQT SNHGWGFTLL DLDQDGLGLG
RLGLRSSNVY MFKTALKLAG SDDPLPPPLE TELAQAGDIA CLALQAARTG GPEMAFGDVE
LASRYRAVST EVPDLAVGLD APGTPRRLTI ETGQLVTRLC WKSQVLFYLR SNKRQIIEKR
NASRTVSLDP RFIPPEPINF ILKSSTKLKA ELQSTQRHFQ IGYNRAARII TGGGVADLIE
LLLRQLDQII AQANLRLATM DPLPPGLYFV AMNNLKAAGQ VLPGVDEELA DRELGYDHDD
LQTSFEPLAM MLRQALARVI ETPVLPLRFE DRGDQVHICI VDKQWNLKKL IFAFSKADAL
KAITALKLQM TKLGAVEQIQ KLVDLQLPGA RLNALPNPPR QIPYYAQSTY FEVESKHQIR
MLSIPRDTIS LRIVGDYFRF QYFNPLKSER YVA
```

SEQ ID NO: 45
```
GPGPG
```

SEQ ID NO: 59
```
KRIKQHPDVQ KVTDATSKVA SKTSAAISNT ASDVKEYVGD KKQDFENKRE LKKFAREHDP
AYIEKKGEKL AKQNRKDADK MNKILQKNIE KRHKEEQKAR EKNEIQRIKD MKKSQKYEVK
AGLTPNKLDE KTEKKGDKLA EKNRKEIAKM NKKLQKNIEK RHKEEQKRQQ EADKARIKSF
KKYKDYVAKS ASQQNKENNT EAGSGGGAGS GGGAMDIGKK HVIPKSQYRR KRREFFHNED
REENLNQHQD KQNIDNTTSK KADKQIHKDS IDKHERFKNS LSSHLEQRNR DVNENKAEES
KSNQDSKSAY NRDHYLTDDV SKKQNSLDSV DQDTEKSKYY EQNSEATLST KSTDKVESTE
MRKLSSDKNK VGHEEQHVLS KPSEHDKETR IDSESSRTDS DSSMQTEKIK KDSSDGNKSS
NLKSEVISDK SNTVPKLSES DDEVNNQKPL TLPEEQKLKR QQSQNEQTKT YTYGDSEQND
KSNHENDLSH HIPSISDDKD NVMRENHIVD DNPDNDINTP SLSKTDDDRK LDEKIHVEDK
HKQNADSSET VGYQSQSTAS HRSTEKRNIS INDHDKLNGQ KTNTKTSANN NQKKATSKLN
KGRATNNNYS DILKKFWMMY WPK
```

SEQ ID NO: 60
```
MDIGKKHVIP KSQYRRKRRE FFHNEDREEN LNQHQDKQNI DNTTSKKADK QIHKDSIDKH
ERFKNSLSSH LEQRNRDVNE NKAEESKSNQ DSKSAYNRDH YLTDDVSKKQ NSLDSVDQDT
EKSKYYEQNS EATLSTKSTD KVESTEMRKL SSDKNKVGHE EQHVLSKPSE HDKETRIDSE
SSRTDSDSSM QTEKIKKDSS DGNKSSNLKS EVISDKSNTV PKLSESDDEV NNQKPLTLPE
EQKLKRQQSQ NEQTKTYTYG DSEQNDKSNH ENDLSHHIPS ISDDKDNVMR ENHIVDDNPD
NDINTPSLSK TDDDRKLDEK IHVEDKHKQN ADSSETVGYQ SQSTASHRST EKRNISINDH
DKLNGQKTNT KTSANNNQKK ATSKLNKGRA TNNNYSDILK KFWMMYWPKG SGGGAGSGGG
AKRIKQHPDV QKVTDATSKV ASKTSAAISN TASDVKEYVG DKKQDFENKR ELKKFAREHD
PAYIEKKGEK LAKQNRKDAD KMNKILQKNI EKRHKEEQKA REKNEIQRIK DMKKSQKYEV
```

```
KAGLTPNKLD EKTEKKGDKL AEKNRKEIAK MNKKLQKNIE KRHKEEQKRQ QEADKARIKS

FKKYKDYVAK SASQQNKENN TEA
```

SEQ ID NO: 61
```
MDIGKKHVIP KSQYRRKRRE FFHNEDREEN LNQHQDKQNI DNTTSKKADK QIHKDSIDKH

ERFKNSLSSH LEQRNRDVNE NKAEESKSNQ DSKSAYNRDH YLTDDVSKKQ NSLDSVDQDT

EKSKYYEQNS EATLSTKSTD KVESTEMRKL SSDKNKVGHE EQHVLSKPSE HDKETRIDSE

SSRTDSDSSM QTEKIKKDSS DGNKSSNLKS EVISDKSNTV PKLSESDDEV NNQKPLTLPE

EQKLKRQQSQ NEQTKTYTYG DSEQNDKSNH ENDLSHHIPS ISDDKDNVMR ENHIVDDNPD

NDINTPSLSK TDDDRKLDEK IHVEDKHKQN ADSSETVGYQ SQSTASHRST EKRNISINDH

DKLNGQKTNT KTSANNNQKK ATSKLNKGRA TNNNYSDILK KFWMMYWPKG SGGGAKRIKQ

HPDVQKVTDA TSKVASKTSA AISNTASDVK EYVGDKKQDF ENKRELKKFA REHDPAYIEK

KGEKLAKQNR KDADKMNKIL QKNIEKRHKE EQKAREKNEI QRIKDMKKSQ KYEVKAGLTP

NKLDEKTEKK GDKLAEKNRK EIAKMNKKLQ KNIEKRHKEE QKRQQEADKA RIKSFKKYKD

YVAKSASQQN KENNTEA
```

SEQ ID NO: 62
```
MDIGKKHVIP KSQYRRKRRE FFHNEDREEN LNQHQDKQNI DNTTSKKADK QIHKDSIDKH

ERFKNSLSSH LEQRNRDVNE NKAEESKSNQ DSKSAYNRDH YLTDDVSKKQ NSLDSVDQDT

EKSKYYEQNS EATLSTKSTD KVESTEMRKL SSDKNKVGHE EQHVLSKPSE HDKETRIDSE

SSRTDSDSSM QTEKIKKDSS DGNKSSNLKS EVISDKSNTV PKLSESDDEV NNQKPLTLPE

EQKLKRQQSQ NEQTKTYTYG DSEQNDKSNH ENDLSHHIPS ISDDKDNVMR ENHIVDDNPD

NDINTPSLSK TDDDRKLDEK IHVEDKHKQN ADSSETVGYQ SQSTASHRST EKRNISINDH

DKLNGQKTNT KTSANNNQKK ATSKLNKGRA TNNNYSDILK KFWMMYWPKG SGGGAGSGGG

AMTEKEKMLA EKWYDANFDQ DLINERARAK DICFELNHTK PSDKNKRKEL IDELFQTTTD

NVSISIPFDT DYGWNVKLGK NVYVNTNCYF MDGGQITIGD NVFIGPNCGF YTATHPLNFH

HRNEGFEKAG PINIGSNTWF GGHVAVLPGV TIGEGSVIGA GSVVTKDIPP HSLAVGNPCK

VVRKIDNEVP SEALNDETLN
```

SEQ ID NO: 63
```
MDIGKKHVIP KSQYRRKRRE FFHNEDREEN LNQHQDKQNI DNTTSKKADK QIHKDSIDKH

ERFKNSLSSH LEQRNRDVNE NKAEESKSNQ DSKSAYNRDH YLTDDVSKKQ NSLDSVDQDT

EKSKYYEQNS EATLSTKSTD KVESTEMRKL SSDKNKVGHE EQHVLSKPSE HDKETRIDSE

SSRTDSDSSM QTEKIKKDSS DGNKSSNLKS EVISDKSNTV PKLSESDDEV NNQKPLTLPE

EQKLKRQQSQ NEQTKTYTYG DSEQNDKSNH ENDLSHHIPS ISDDKDNVMR ENHIVDDNPD

NDINTPSLSK TDDDRKLDEK IHVEDKHKQN ADSSETVGYQ SQSTASHRST EKRNISINDH

DKLNGQKTNT KTSANNNQKK ATSKLNKGRA TNNNYSDILK KFWMMYWPKG SGGGAMTEKE

KMLAEKWYDA NFDQDLINER ARAKDICFEL NHTKPSDKNK RKELIDELFQ TTTDNVSISI

PFDTDYGWNV KLGKNVYVNT NCYFMDGGQI TIGDNVFIGP NCGFYTATHP LNFHHRNEGF

EKAGPINIGS NTWFGGHVAV LPGVTIGEGS VIGAGSVVTK DIPPHSLAVG NPCKVVRKID

NEVPSEALND ETLN
```

SEQ ID NO: 64
```
MDIGKKHVIP KSQYRRKRRE FFHNEDREEN LNQHQDKQNI DNTTSKKADK QIHKDSIDKH

ERFKNSLSSH LEQRNRDVNE NKAEESKSNQ DSKSAYNRDH YLTDDVSKKQ NSLDSVDQDT

EKSKYYEQNS EATLSTKSTD KVESTEMRKL SSDKNKVGHE EQHVLSKPSE HDKETRIDSE
```

-continued

```
SSRTDSDSSM QTEKIKKDSS DGNKSSNLKS EVISDKSNTV PKLSESDDEV NNQKPLTLPE

EQKLKRQQSQ NEQTKTYTYG DSEQNDKSNH ENDLSHHIPS ISDDKDNVMR ENHIVDDNPD

NDINTPSLSK TDDDRKLDEK IHVEDKHKQN ADSSETVGYQ SQSTASHRST EKRNISINDH

DKLNGQKTNT KTSANNNQKK ATSKLNKGRA TNNNYSDILK KFWMMYWPKG SGGGAKVAKQ

GQYKNQDPIV LVHGFNGFTD DINPSVLAHY WGGNKMNIRQ DLEENGYKAY EASISAFGSN

YDRAVELYYY IKGGRVDYGA AHAAKYGHER YGKTYEGIYK DWKPGQKVHL VGHSMGGQTI

RQLEELLRNG SREEIEYQKK HGGEISPLFK GNNDNMISSI TTLGTPHNGT HASDLAGNEA

LVRQIVFDIG KMFGNKNSRV DFGLAQWGLK QKPNESYIDY VKRVKQSNLW KSKDNGFYDL

TREGATDLNR KTSLNPNIVY KTYTGEATHK ALNSDRQKAD LNMFFPFVIT GNLIGKATEK

EWRENDGLVS VISSQHPFNQ AYTNATDKIQ KGIWQVTPTK HDWDHVDFVG QDSSDTVRTR

EELQDFWHHL ADDLVKTEKV TDTKQ
                                                    SEQ ID NO: 65
RNLLLQKQSQ ARQTAEDIVN QAHKEADNIK KEKLLEAKEE NQILREQTEA ELRERRSELQ

RQETRLLQKE ENLERKSDLL DKKDEILEQK ESKIEEKQQQ VDAKESSVQT LIMKHEQELE

RISGLTQEEA INEQLQRVEE ELSQDIAVLV KEKEKEAKEK VDKTAKELLA TAVQRLAADH

TSESTVSVVN LPNDEMKGRI IGREGRNIRT LETLTGIDLI IDDTPEAVIL SGFDPIRREI

ARTALVNLVS DGRIHPGRIE DMVEKARKEV DDIIREAGEQ ATFEVNAHNM HPDLVKIVGR

LNYRTSYGQN VLKHSIEVAH LASMLAAELG EDETLAKRAG LLHDVGKAID HEVEGSHVEI

GVELAKKYGE NETVINAIHS HHGDVEPTSI ISILVAAADA LSAARPGARK ETLENYIRRL

ERLETLSESY DGVEKAFAIQ AGREIRVIVS PEEIDDLKSY RLARDIKNQI EDELQYPGHI

KVTVVRETRA VEYAKKPEPK PAPAPKPACG NDDGKDKDGK VTIKTTVYPL QSFAEQIGGK

HVKVSSIYPA GTDLHSYEPT QKDILSASKS DLFMYTGDNL DPVAKKVAST IKDKDKKLSL

EDKLDKAKLL TDQHEHGEEH EHEGHDHEKE EHHHHGGYDP HVWLDPKINQ TFAKEIKDEL

VKKDPKHKDD YEKNYKKLND DLKKIDNDMK QVTKDKQGNA VFISHESIGY LADRYGFVQK

GIQNMNAEDP SQKELTKIVK EIRDSNAKYI LYEDNVANKV TETIRKETDA KPLKFYNMES

LNKEQQKKDN ITYQSLMKSN IENIGKALDS GVKVKDDKAE SKHDKAISDG YFKDEQVKDR

ELSDYAGEWQ SVYPYLKDGT LDEVMEHKAE NDPKKSAKDL KAYYDKGYKT DITNIDIKGN

EITFTKDGKK HTGKYEYNGK KTLKYPKGNR GVRFMFKLVD GNDKDLPKFI QFSDHNIAPK

KAEHFHIFMG NDNDALLKEM DNWPTYYPSK LNKDQIKEEM LAH
                                                    SEQ ID NO: 66
MNEKVEGMTL ELKLDHLGVQ EGMKGLKRQL GVVNSEMKAN LSAFDKSEKS MEKYQARIKG

LNDRLKVQKK MYSQVEDELK QVNANYQKAK SSVKDVEKAY LKLVEANKKE KLALDKSKEA

LKSSNTELKK AENQYKRTNQ RKQDAYQKLK QLRDAEQKLK NSNQATTAQL KRASDAVQKQ

SAKHKALVEQ YKQEGNQVQK LKVQNDNLSK SNDKIESSYA KTNTKLKQTE KEFNDLNNTI

KNHSANVAKA ETAVNKEKAA LNNLERSIDK ASSEMKTFNK EQMIAQSHFG KLASQADVMS

KKFSSIGDKM TSLGRTMTMG VSTPITLGLG AALKTSADFE GQMSRVGAIA QASSKDLKSM

SNQAVDLGAK TSKSANEVAK GMEELAALGF NAKQTMEAMP GVISAAEASG AEMATTATVM

ASAINSFGLK ASDANHVADL LARSANDSAA DIQYMGDALK YAGTPAKALG VSIEDTSAAI

EVLSNSGLEG SQAGTALRAS FIRLANPSKN TAKEMKKLGI HLSDAKGQFV GMGELIRQFQ

DNMKGMTREQ KLATVATIVG TEAASGFLAL IEAGPDKINS YSKSLKNSNG ESKKAADLMK

DNLKGALEQL GGAFESLAIE VGKDLTPMIR AGAEGLTKLV DGFTHLPGWV RKGSGGGAAK

DNLNGEKPTT NLNHNVTSPS VNSEMNNNET GTPHESNQAG NEGTGSNSRD ANPDSNNVKP
```

```
                                    -continued
DSNNQNPSPD SKPDPNNPNP GPNPKPDPDK PKPNPEPKPD PKPDPDKPKP NPDPKPDPDK

PKPNPDPKPD PDKPKPNPDP KPDPNPNPKP DPNKPNPNPS PNPNQPGDSN QSGGSKNGGT

WNPNASDGSN QGQWQPNGNQ GNSQNPTGND FVSQRFLALA NGAYKYNPYI LNQINQLGKE

YGEVTDEDIY NIIRKQNFSG NAYLNGLQQQ SNYFRFQYFN PLKSERYYRN LDEQVLALIT

GEIGSMPDLK KPEDKPDSKQ RSFEPHEKDD FTVVKKQEDN KKSASTAYS

SEQ ID NO: 67
GFLNKSKNEQ AALKAQQAAI KEEASANNLS DTSQEAQEIQ EAKREAQAEA DKSVAVSNKE

SKAVALKAQQ AAIKEEASAN NLSDTSQEAQ EIQEAKKEAQ AETDKSAAVS NEEPKAVALK

AQQAAIKEEA SANNLSDISQ EAQEVQEAKK EAQAEKDSDT LTKDASAAKV EVSKPESQAE

RLANAAKQKQ AKLTPGSKES QLTEALFAEK PVAKNDLKEI PQLVTKKNDV SETETVNIDN

KDTVKQKEAK FENGVITRKA DEKTTNNTAV DKKSGKQSKK TTPSNKRNAS KASTNKTSGQ

KKQHNKKSSQ GAKKQSSSSK STQKNNQTSN KNSKTTNAKS SNASKTPNAK VEKAKSKIEK

RTFNDGSGGG AGSGGGAAKD NLNGEKPTTN LNHNVTSPSV NSEMNNNETG TPHESNQAGN

EGTGSNSRDA NPDSNNVKPD SNNQNPSPDS KPDPNNPNPG PNPKPDPDKP KPNPEPKPDP

KPDPDKPKPN PDPKPDPDKP KPNPDPKPDP DKPKPNPDPK PDPNPNPKPD PNKPNPNPSP

NPNQPGDSNQ SGGSKNGGTW NPNASDGSNQ GQWQPNGNQG NSQNPTGNDF VSQRFLALAN

GAYKYNPYIL NQINQLGKEY GEVTDEDIYN IIRKQNFSGN AYLNGLQQQS NYFRFQYFNP

LKSERYYRNL DEQVLALITG EIGSMPDLKK PEDKPDSKQR SFEPHEKDDF TVVKKQEDNK

KSASTAYS

SEQ ID NO: 68
AKDNLNGEKP TTNLNHNVTS PSVNSEMNNN ETGTPHESNQ AGNEGTGSNS RDANPDSNNV

KPDSNNQNPS PDSKPDPNNP NPGPNPKPDP DKPKPNPEPK PDPKPDPDKP KPNPDPKPDP

DKPKPNPDPK PDPDKPKPNP DPKPDPNPNP KPDPNKPNPN PSPNPNQPGD SNQSGGSKNG

GTWNPNASDG SNQGQWQPNG NQGNSQNPTG NDFVSQRFLA LANGAYKYNP YILNQINQLG

KEYGEVTDED IYNIIRKQNF SGNAYLNGLQ QQSNYFRFQY FNPLKSERYY RNLDEQVLAL

ITGEIGSMPD LKKPEDKPDS KQRSFEPHEK DDFTVVKKQE DNKKSASTAY SGSGGGAGFL

NKSKNEQAAL KAQQAAIKEE ASANNLSDTS QEAQEIQEAK REAQAEDKS VAVSNKESKA

VALKAQQAAI KEEASANNLS DTSQEAQEIQ EAKKEAQAET DKSAAVSNEE PKAVALKAQQ

AAIKEEASAN NLSDISQEAQ EVQEAKKEAQ AEKDSDTLTK DASAAKVEVS KPESQAERLA

NAAKQKQAKL TPGSKESQLT EALFAEKPVA KNDLKEIPQL VTKKNDVSET ETVNIDNKDT

VKQKEAKFEN GVITRKADEK TTNNTAVDKK SGKQSKKTTP SNKRNASKAS TNKTSGQKKQ

HNKKSSQGAK KQSSSSKSTQ KNNQTSNKNS KTTNAKSSNA SKTPNAKVEK AKSKIEKRTF

ND

SEQ ID NO: 69
ACGNDDGKDK DGKVTIKTTV YPLQSFAEQI GGKHVKVSSI YPAGTDLHSY EPTQKDILSA

SKSDLFMYTG DNLDPVAKKV ASTIKDKDKK LSLEDKLDKA KLLTDQHEHG EEHEHEGHDH

EKEEHHHHGG YDPHVWLDPK INQTFAKEIK DELVKKDPKH KDDYEKNYKK LNDDLKKIDN

DMKQVTKDKQ GNAVFISHES IGYLADRYGF VQKGIQNMNA EDPSQKELTK IVKEIRDSNA

KYILYEDNVA NKVTETIRKE TDAKPLKFYN MESLNKEQQK KDNITYQSLM KSNIENIGKA

LDSGVKVKDD KAESKHDKAI SDGYFKDEQV KDRELSDYAG EWQSVYPYLK DGTLDEVMEH

KAENDPKKSA KDLKAYYDKG YKTDITNIDI KGNEITFTKD GKKHTGKYEY NGKKTLKYPK

GNRGVRFMFK LVDGNDKDLP KFIQFSDHNI APKKAEHFHI FMGNDNDALL KEMDNWPTYY
```

```
PSKLNKDQIK EEMLAHGSGG GAGFLNKSKN EQAALKAQQA AIKEEASANN LSDTSQEAQE

IQEAKREAQA EADKSVAVSN KESKAVALKA QQAAIKEEAS ANNLSDTSQE AQEIQEAKKE

AQAETDKSAA VSNEEPKAVA LKAQQAAIKE EASANNLSDI SQEAQEVQEA KKEAQAEKDS

DTLTKDASAA KVEVSKPESQ AERLANAAKQ KQAKLTPGSK ESQLTEALFA EKPVAKNDLK

EIPQLVTKKN DVSETETVNI DNKDTVKQKE AKFENGVITR KADEKTTNNT AVDKKSGKQS

KKTTPSNKRN ASKASTNKTS GQKKQHNKKS SQGAKKQSSS SKSTQKNNQT SNKNSKTTNA

KSSNASKTPN AKVEKAKSKI EKRTFND

SEQ ID NO: 70
MTEKEKMLAE KWYDANFDQD LINERARAKD ICFELNHTKP SDKNKRKELI DELFQTTTDN

VSISIPFDTD YGWNVKLGKN VYVNTNCYFM DGGQITIGDN VFIGPNCGFY TATHPLNFHH

RNEGFEKAGP INIGSNTWFG GHVAVLPGVT IGEGSVIGAG SVVTKDIPPH SLAVGNPCKV

VRKIDNEVPS EALNDETLNG SGGGADTPQK DTTAKTTSHD SKKSNDDETS KDTTSKDIDK

ADNNNTSNQD NNDKKFKTID DSTSDSNNII DFIYKNLPQT NINQLLTKNK YDDNYSLTTL

IQNLFNLNSD ISDYEQPRNG EKSTNDSNKN SDNSIKNDTD TQSSKQDKAD NQKAPKSNNT

KPSTSNKQPN SPKPTQPNQS NSQPASDDKA NQKSSSKDNQ SMSDSALDSI LDQYSEDAKK

TQKDYASQSK KDKNEKSNTK NPQLPTQDEL KHKSKPAQSF NNDVNQKDTR ATSLFETDPS

ISNNDDSGQF NVVDSKDTRQ FVKSIAKDAH RIGQDNDIYA SVMIAQAILE SDSGRSALAK

SPNHNLFGIK GAFEGNSVPF NTLEADGNKL YSINAGFRKY PSTKESLKDY SDLIKNGIDG

NRTIYKPTWK SEADSYKDAT SHLSKTYATD PNYAKKLNSI IKHYQLTQFD DERMPDLDKY

ERSIKDYDDS SDEFKPFREV SDSMPYPHGQ CTWYVYNRMK QFGTSISGDL GDAHNWNNRA

QYRDYQVSHT PKRHAAVVFE AGQFGADQHY GHVAFVEKVN SDGSIVISES NVKGLGIISH

RTINAAAAEE LSYITGK

SEQ ID NO: 71
IDSKNKPANS DIKFEVTQKS DAVKALKELP KSENVKNIYQ DYAVTDVKTD KKGFTHYTLQ

PSVDGVHAPD KEVKVHADKS GKVVLINGDT DAKKVKPTNK VTLSKDDAAD KAFKAVKIDK

NKAKNLKDKV IKENKVEIDG DSNKYVYNVE LITVTPEISH WKVKIDAQTG EILEKMNLVK

EAAETGKGKG VLGDTKDINI NSIDGGFSLE DLTHQGKLSA FSFNDQTGQA TLITNEDENF

VKDEQRAGVD ANYYAKQTYD YYKDTFGRES YDNQGSPIVS LTHVNNYGGQ DNRNNAAWIG

DKMIYGDGDG RTFTSLSGAN DVVAHELTHG VTQETANLEY KDQSGALNES FSDVFGYFVD

DEDFLMGEDV YTPGKEGDAL RSMSNPEQFG QPAHMKDYVF TEKDNGGVHT NSGSGGGAGF

LNKSKNEQAA LKAQQAAIKE EASANNLSDT SQEAQEIQEA KREAQAEADK SVAVSNKESK

AVALKAQQAA IKEEASANNL SDTSQEAQEI QEAKKEAQAE TDKSAAVSNE EPKAVALKAQ

QAAIKEEASA NNLSDISQEA QEVQEAKKEA QAEKDSDTLT KDASAAKVEV SKPESQAERL

ANAAKQKQAK LTPGSKESQL TEALFAEKPV AKNDLKEIPQ LVTKKNDVSE TETVNIDNKD

TVKQKEAKFE NGVITRKADE KTTNNTAVDK KSGKQSKKTT PSNKRNASKA STNKTSGQKK

QHNKKSSQGA KKQSSSSKST QKNNQTSNKN SKTTNAKSSN ASKTPNAKVE KAKSKIEKRT

END

SEQ ID NO: 72
IDSKNKPANS DIKFEVTQKS DAVKALKELP KSENVKNIYQ DYAVTDVKTD KKGFTHYTLQ

PSVDGVHAPD KEVKVHADKS GKVVLINGDT DAKKVKPTNK VTLSKDDAAD KAFKAVKIDK

NKAKNLKDKV IKENKVEIDG DSNKYVYNVE LITVTPEISH WKVKIDAQTG EILEKMNLVK

EAAETGKGKG VLGDTKDINI NSIDGGFSLE DLTHQGKLSA FSFNDQTGQA TLITNEDENF
```

```
VKDEQRAGVD ANYYAKQTYD YYKDTFGRES YDNQGSPIVS LTHVNNYGGQ DNRNNAAWIG

DKMIYGDGDG RTFTSLSGAN DVVAHELTHG VTQETANLEY KDQSGALNES FSDVFGYFVD

DEDFLMGEDV YTPGKEGDAL RSMSNPEQFG QPAHMKDYVF TEKDNGGVHT NSGSGGGAAK

DNLNGEKPTT NLNHNVTSPS VNSEMNNNET GTPHESNQAG NEGTGSNSRD ANPDSNNVKP

DSNNQNPSPD SKPDPNNPNP GPNPKPDPDK PKPNPEPKPD PKPDPDKPKP NPDPKPDPDK

PKPNPDPKPD PDKPKPNPDP KPDPNPNPKP DPNKPNPNPS PNPNQPGDSN QSGGSKNGGT

WNPNASDGSN QGQWQPNGNQ GNSQNPTGND FVSQRFLALA NGAYKYNPYI LNQINQLGKE

YGEVTDEDIY NIIRKQNFSG NAYLNGLQQQ SNYFRFQYFN PLKSERYYRN LDEQVLALIT

GEIGSMPDLK KPEDKPDSKQ RSFEPHEKDD FTVVKKQEDN KKSASTAYS
                                                                SEQ ID NO: 73
IDSKNKPANS DIKFEVTQKS DAVKALKELP KSENVKNIYQ DYAVTDVKTD KKGFTHYTLQ

PSVDGVHAPD KEVKVHADKS GKVVLINGDT DAKKVKPTNK VTLSKDDAAD KAFKAVKIDK

NKAKNLKDKV IKENKVEIDG DSNKYVYNVE LITVTPEISH WKVKIDAQTG EILEKMNLVK

EAAETGKGKG VLGDTKDINI NSIDGGFSLE DLTHQGKLSA FSFNDQTGQA TLITNEDENF

VKDEQRAGVD ANYYAKQTYD YYKDTFGRES YDNQGSPIVS LTHVNNYGGQ DNRNNAAWIG

DKMIYGDGDG RTFTSLSGAN DVVAHELTHG VTQETANLEY KDQSGALNES FSDVFGYFVD

DEDFLMGEDV YTPGKEGDAL RSMSNPEQFG QPAHMKDYVF TEKDNGGVHT NSGSGGGAGS

GGGAKVAKQG QYKNQDPIVL VHGFNGFTDD INPSVLAHYW GGNKMNIRQD LEENGYKAYE

ASISAFGSNY DRAVELYYYI KGGRVDYGAA HAAKYGHERY GKTYEGIYKD WKPGQKVHLV

GHSMGGQTIR QLEELLRNGS REEIEYQKKH GGEISPLFKG NNDNMISSIT TLGTPHNGTH

ASDLAGNEAL VRQIVFDIGK MFGNKNSRVD FGLAQWGLKQ KPNESYIDYV KRVKQSNLWK

SKDNGFYDLT REGATDLNRK TSLNPNIVYK TYTGEATHKA LNSDRQKADL NMFFPFVITG

NLIGKATEKE WRENDGLVSV ISSQHPFNQA YTNATDKIQK GIWQVTPTKH DWDHVDFVGQ

DSSDTVRTRE ELQDFWHHLA DDLVKTEKVT DTKQ
                                                                SEQ ID NO: 74
DTPQKDTTAK TTSHDSKKSN DDETSKDTTS KDIDKADNNN TSNQDNNDKK FKTIDDSTSD

SNNIIDFIYK NLPQTNINQL LTKNKYDDNY SLTTLIQNLF NLNSDISDYE QPRNGEKSTN

DSNKNSDNSI KNDTDTQSSK QDKADNQKAP KSNNTKPSTS NKQPNSPKPT QPNQSNSQPA

SDDKANQKSS SKDNQSMSDS ALDSILDQYS EDAKKTQKDY ASQSKKDKNE KSNTKNPQLP

TQDELKHKSK PAQSFNNDVN QKDTRATSLF ETDPSISNND DSGQFNVVDS KDTRQFVKSI

AKDAHRIGQD NDIYASVMIA QAILESDSGR SALAKSPNHN LFGIKGAFEG NSVPFNTLEA

DGNKLYSINA GFRKYPSTKE SLKDYSDLIK NGIDGNRTIY KPTWKSEADS YKDATSHLSK

TYATDPNYAK KLNSIIKHYQ LTQFDDERMP DLDKYERSIK DYDDSSDEFK PFREVSDSMP

YPHGQCTWYV YNRMKQFGTS ISGDLGDAHN WNNRAQYRDY QVSHTPKRHA AVVFEAGQFG

ADQHYGHVAF VEKVNSDGSI VISESNVKGL GIISHRTINA AAAEELSYIT GKGSGGGAMT

EKEKMLAEKW YDANFDQDLI NERARAKDIC FELNHTKPSD KNKRKELIDE LFQTTTDNVS

ISIPFDTDYG WNVKLGKNVY VNTNCYFMDG GQITIGDNVF IGPNCGFYTA THPLNFHHRN

EGFEKAGPIN IGSNTWFGGH VAVLPGVTIG EGSVIGAGSV VTKDIPPHSL AVGNPCKVVR

KIDNEVPSEA LNDETLN
                                                                SEQ ID NO: 75
DTPQKDTTAK TTSHDSKKSN DDETSKDTTS KDIDKADNNN TSNQDNNDKK FKTIDDSTSD

SNNIIDFIYK NLPQTNINQL LTKNKYDDNY SLTTLIQNLF NLNSDISDYE QPRNGEKSTN
```

```
DSNKNSDNSI KNDTDTQSSK QDKADNQKAP KSNNTKPSTS NKQPNSPKPT QPNQSNSQPA

SDDKANQKSS SKDNQSMSDS ALDSILDQYS EDAKKTQKDY ASQSKKDKNE KSNTKNPQLP

TQDELKHKSK PAQSFNNDVN QKDTRATSLF ETDPSISNND DSGQFNVVDS KDTRQFVKSI

AKDAHRIGQD NDIYASVMIA QAILESDSGR SALAKSPNHN LFGIKGAFEG NSVPFNTLEA

DGNKLYSINA GFRKYPSTKE SLKDYSDLIK NGIDGNRTIY KPTWKSEADS YKDATSHLSK

TYATDPNYAK KLNSIIKHYQ LTQFDDERMP DLDKYERSIK DYDDSSDEFK PFREVSDSMP

YPHGQCTWYV YNRMKQFGTS ISGDLGDAHN WNNRAQYRDY QVSHTPKRHA AVVFEAGQFG

ADQHYGHVAF VEKVNSDGSI VISESNVKGL GIISHRTINA AAAEELSYIT GKKPEPKPAP

APKPMTEKEK MLAEKWYDAN FDQDLINERA RAKDICFELN HTKPSDKNKR KELIDELFQT

TTDNVSISIP FDTDYGWNVK LGKNVYVNTN CYFMDGGQIT IGDNVFIGPN CGFYTATHPL

NFHHRNEGFE KAGPINIGSN TWFGGHVAVL PGVTIGEGSV IGAGSVVTKD IPPHSLAVGN

PCKVVRKIDN EVPSEALNDE TLN
                                                     SEQ ID NO: 76
DTPQKDTTAK TTSHDSKKSN DDETSKDTTS KDIDKADNNN TSNQDNNDKK FKTIDDSTSD

SNNIIDFIYK NLPQTNINQL LTKNKYDDNY SLTTLIQNLF NLNSDISDYE QPRNGEKSTN

DSNKNSDNSI KNDTDTQSSK QDKADNQKAP KSNNTKPSTS NKQPNSPKPT QPNQSNSQPA

SDDKANQKSS SKDNQSMSDS ALDSILDQYS EDAKKTQKDY ASQSKKDKNE KSNTKNPQLP

TQDELKHKSK PAQSFNNDVN QKDTRATSLF ETDPSISNND DSGQFNVVDS KDTRQFVKSI

AKDAHRIGQD NDIYASVMIA QAILESDSGR SALAKSPNHN LFGIKGAFEG NSVPFNTLEA

DGNKLYSINA GFRKYPSTKE SLKDYSDLIK NGIDGNRTIY KPTWKSEADS YKDATSHLSK

TYATDPNYAK KLNSIIKHYQ LTQFDDERMP DLDKYERSIK DYDDSSDEFK PFREVSDSMP

YPHGQCTWYV YNRMKQFGTS ISGDLGDAHN WNNRAQYRDY QVSHTPKRHA AVVFEAGQFG

ADQHYGHVAF VEKVNSDGSI VISESNVKGL GIISHRTINA AAAEELSYIT GKGSGGGAKV

AKQGQYKNQD PIVLVHGFNG FTDDINPSVL AHYWGGNKMN IRQDLEENGY KAYEASISAF

GSNYDRAVEL YYYIKGGRVD YGAAHAAKYG HERYGKTYEG IYKDWKPGQK VHLVGHSMGG

QTIRQLEELL RNGSREEIEY QKKHGGEISP LFKGNNDNMI SSITTLGTPH NGTHASDLAG

NEALVRQIVF DIGKMFGNKN SRVDFGLAQW GLKQKPNESY IDYVKRVKQS NLWKSKDNGF

YDLTREGATD LNRKTSLNPN IVYKTYTGEA THKALNSDRQ KADLNMFFPF VITGNLIGKA

TEKEWRENDG LVSVISSQHP FNQAYTNATD KIQKGIWQVT PTKHDWDHVD FVGQDSSDTV

RTREELQDFW HHLADDLVKT EKVTDTKQ
                                                     SEQ ID NO: 77
DTPQKDTTAK TTSHDSKKSN DDETSKDTTS KDIDKADNNN TSNQDNNDKK FKTIDDSTSD

SNNIIDFIYK NLPQTNINQL LTKNKYDDNY SLTTLIQNLF NLNSDISDYE QPRNGEKSTN

DSNKNSDNSI KNDTDTQSSK QDKADNQKAP KSNNTKPSTS NKQPNSPKPT QPNQSNSQPA

SDDKANQKSS SKDNQSMSDS ALDSILDQYS EDAKKTQKDY ASQSKKDKNE KSNTKNPQLP

TQDELKHKSK PAQSFNNDVN QKDTRATSLF ETDPSISNND DSGQFNVVDS KDTRQFVKSI

AKDAHRIGQD NDIYASVMIA QAILESDSGR SALAKSPNHN LFGIKGAFEG NSVPFNTLEA

DGNKLYSINA GFRKYPSTKE SLKDYSDLIK NGIDGNRTIY KPTWKSEADS YKDATSHLSK

TYATDPNYAK KLNSIIKHYQ LTQFDDERMP DLDKYERSIK DYDDSSDEFK PFREVSDSMP

YPHGQCTWYV YNRMKQFGTS ISGDLGDAHN WNNRAQYRDY QVSHTPKRHA AVVFEAGQFG

ADQHYGHVAF VEKVNSDGSI VISESNVKGL GIISHRTINA AAAEELSYIT GKGSGGGAKV
```

```
AKQGQYKNQD PIVLVHGFNG FTDDINPSVL AHYWGGNKMN IRQDLEENGY KAYEASISAF
GSNYDRAVEL YYYIKGGRVD YGAAHAAKYG HERYGKTYEG IYKDWKPGQK VHLVGHSMGG
QTIRQLEELL RNGSREEIEY QKKHGGEISP LFKGNNDNMI SSITTLGTPH NGTHASDLAG
NEAL
                                                     SEQ ID NO: 78
ADSDINIKTG TTDIGSNTTV KTGDLVTYDK ENGMLKKVFY SFIDDKNHNK KLLVIRTKGT
IAGQYRVYSE EGANKSGLAW PSAFKVQLQL PDNEVAQISD YYPRNSIDTK EYMSTLTYGF
NGNVTGDDTG KIGGLIGANV SIGHTLKYVQ PDFKTILESP TDKKVGWKVI FNNMVNQNWG
PYDRDSWNPV YGNQLFMKTR NGSMKAADNF LDPNKASSLL SSGFSPDFAT VITMDRKASK
QQTNIDVIYE RVRDDYQLHW TSTNWKGTNT KDKWIDRSSE RYKIDWEKEE MTNGSGGGAK
RIKQHPDVQK VTDATSKVAS KTSAAISNTA SDVKEYVGDK KQDFENKREL KKFAREHDPA
YIEKKGEKLA KQNRKDADKM NKILQKNIEK RHKEEQKARE KNEIQRIKDM KKSQKYEVKA
GLTPNKLDEK TEKKGDKLAE KNRKEIAKMN KKLQKNIEKR HKEEQKRQQE ADKARIKSFK
KYKDYVAKSA SQQNKENNTE A
                                                     SEQ ID NO: 79
ADSDINIKTG TTDIGSNTTV KTGDLVTYDK ENGMLKKVFY SFIDDKNHNK KLLVIRTKGT
IAGQYRVYSE EGANKSGLAW PSAFKVQLQL PDNEVAQISD YYPRNSIDTK EYMSTLTYGF
NGNVTGDDTG KIGGLIGANV SIGHTLKYVQ PDFKTILESP TDKKVGWKVI FNNMVNQNWG
PYDRDSWNPV YGNQLFMKTR NGSMKAADNF LDPNKASSLL SSGFSPDFAT VITMDRKASK
QQTNIDVIYE RVRDDYQLHW TSTNWKGTNT KDKWIDRSSE RYKIDWEKEE MTNGSGGGAM
TEKEKMLAEK WYDANFDQDL INERARAKDI CFELNHTKPS DKNKRKELID ELFQTTTDNV
SISIPFDTDY GWNVKLGKNV YVNTNCYFMD GGQITIGDNV FIGPNCGFYT ATHPLNFHHR
NEGFEKAGPI NIGSNTWFGG HVAVLPGVTI GEGSVIGAGS VVTKDIPPHS LAVGNPCKVV
RKIDNEVPSE ALNDETLN
                                                     SEQ ID NO: 80
ADSDINIKTG TTDIGSNTTV KTGDLVTYDK ENGMLKKVFY SFIDDKNHNK KLLVIRTKGT
IAGQYRVYSE EGANKSGLAW PSAFKVQLQL PDNEVAQISD YYPRNSIDTK EYMSTLTYGF
NGNVTGDDTG KIGGLIGANV SIGHTLKYVQ PDFKTILESP TDKKVGWKVI FNNMVNQNWG
PYDRDSWNPV YGNQLFMKTR NGSMKAADNF LDPNKASSLL SSGFSPDFAT VITMDRKASK
QQTNIDVIYE RVRDDYQLHW TSTNWKGTNT KDKWIDRSSE RYKIDWEKEE MTNGSGGGAK
VAKQGQYKNQ DPIVLVHGFN GFTDDINPSV LAHYWGGNKM NIRQDLEENG YKAYEASISA
FGSNYDRAVE LYYYIKGGRV DYGAAHAAKY GHERYGKTYE GIYKDWKPGQ KVHLVGHSMG
GQTIRQLEEL LRNGSREEIE YQKKHGGEIS PLFKGNNDNM ISSITTLGTP HNGTHASDLA
GNEALVRQIV FDIGKMFGNK NSRVDFGLAQ WGLKQKPNES YIDYVKRVKQ SNLWKSKDNG
FYDLTREGAT DLNRKTSLNP NIVYKTYTGE ATHKALNSDR QKADLNMFFP FVITGNLIGK
ATEKEWREND GLVSVISSQH PFNQAYTNAT DKIQKGIWQV TPTKHDWDHV DFVGQDSSDT
VRTREELQDF WHHLADDLVK TEKVTDTKQ
                                                     SEQ ID NO: 81
KVAKQGQYKN QDPIVLVHGF NGFTDDINPS VLAHYWGGNK MNIRQDLEEN GYKAYEASIS
AFGSNYDRAV ELYYYIKGGR VDYGAAHAAK YGHERYGKTY EGIYKDWKPG QKVHLVGHSM
GGQTIRQLEE LLRNGSREEI EYQKKHGGEI SPLFKGNNDN MISSITTLGT PHNGTHASDL
AGNEALVRQI VFDIGKMFGN KNSRVDFGLA QWGLKQKPNE SYIDYVKRVK QSNLWKSKDN
GFYDLTREGA TDLNRKTSLN PNIVYKTYTG EATHKALNSD RQKADLNMFF PFVITGNLIG
```

```
KATEKEWREN DGLVSVISSQ HPFNQAYTNA TDKIQKGIWQ VTPTKHDWDH VDFVGQDSSD

TVRTREELQD FWHHLADDLV KTEKVTDTKQ
```

SEQ ID NO: 82
```
KVAKQGQYKN QDPIVLVHGF NGFTDDINPS VLAHYWGGNK MNIRQDLEEN GYKAYEASIS

AFGSNYDRAV ELYYYIKGGR VDYGAAHAAK YGHERYGKTY EGIYKDWKPG QKVHLVGHSM

GGQTIRQLEE LLRNGSREEI EYQKKHGGEI SPLFKGNNDN MISSITTLGT PHNGTHASDL

AGNEAL
```

SEQ ID NO: 83
```
ADSDINIKTG TTDIGSNTTV KTGDLVTYDK ENGMLKKVFY SFIDDKNHNK KLLVIRTKGT

IAGQYRVYSE EGANKSGLAW PSAFKVQLQL PDNEVAQISD YYPRNSIDTK EYMSTLTYGF

NGNVTGDDTG KIGGLIGANV SIGHTLKYVQ PDFKTILESP TDKKVGWKVI FNNMVNQNWG

PYDRDSWNPV YGNQLFMKTR NGSMKAADNF LDPNKASSLL SSGFSPDFAT VITMDRKASK

QQTNIDVIYE RVRDDYQLHW TSTNWKGTNT KDKWIDRSSE RYKIDWEKEE MTN
```

SEQ ID NO: 84
```
AAEETGGTNT EAQPKTEAVA SPTTTSEKAP ETKPVANAVS VSNKEVEAPT SETKEAKEVK

EVKAPKETKE VKPAAKATNN TYPILNQELR EAIKNPAIKD KDHSAPNSRP IDFEMKKKDG

TQQFYHYASS VKPARVIFTD SKPEIELGLQ SGQFWRKFEV YEGDKKLPIK LVSYDTVKDY

AYIRFSVSNG TKAVKIVSST HFNNKEEKYD YTLMEFAQPI YNSADKFKTE EDYKAEKLLA

PYKKAKTLER QVYELNKIQD KLPEKLKAEY KKKLEDTKKA LDEQVKSAIT EFQNVQPTNE

KMTDLQDTKY VVYESVENNE SMMDTFVKHP IKTGMLNGKK YMVMETTNDD YWKDFMVEGQ

RVRTISKDAK NNTRTIIFPY VEGKTLYDAI VKVHVKTIDY DGQYHVRIVD KEAFTKANTD

KSNKKEQQDN SAKKEATPAT PSKPTPSPVE KESQKQDSQK DDNKQLPSVE KENDASSESG

KDKTPATKPT KGEVESSSTT PTKVVSTTQN VAKPTTASSK TTKDVVQTSA GSSEAKDSAP

LQKANIKNTN DGHTQSQNNK NTQENKAKSL PQT
```

SEQ ID NO: 85
```
MDIGKKHVIP KSQYRRKRRE FFHNEDREEN LNQHQDKQNI DNTTSKKADK QIHKDSIDKH

ERFKNSLSSH LEQRNRDVNE NKAEESKSNQ DSKSAYNRDH YLTDDVSKKQ NSLDSVDQDT

EKSKYYEQNS EATLSTKSTD KVESTEMRKL SSDKNKVGHE EQHVLSKPSE HDKETRIDSE

SSRTDSDSSM QTEKIKKDSS DGNKSSNLKS EVISDKSNTV PKLSESDDEV NNQKPLTLPE

EQKLKRQQSQ NEQTKTYTYG DSEQNDKSNH ENDLSHHIPS ISDDKDNVMR ENHIVDDNPD

NDINTPSLSK TDDDRKLDEK IHVEDKHKQN ADSSETVGYQ SQSTASHRST EKRNISINDH

DKLNGQKTNT KTSANNNQKK ATSKLNKGRA TNNNYSDILK KFWMMYWPK
```

SEQ ID NO: 86
```
DTPQKDTTAK TTSHDSKKSN DDETSKDTTS KDIDKADNNN TSNQDNNDKK FKTIDDSTSD

SNNIIDFIYK NLPQTNINQL LTKNKYDDNY SLTTLIQNLF NLNSDISDYE QPRNGEKSTN

DSNKNSDNSI KNDTDTQSSK QDKADNQKAP KSNNTKPSTS NKQPNSPKPT QPNQSNSQPA

SDDKANQKSS SKDNQSMSDS ALDSILDQYS EDAKKTQKDY ASQSKKDKNE KSNTKNPQLP

TQDELKHKSK PAQSFNNDVN QKDTRATSLF ETDPSISNND DSGQFNVVDS KDTRQFVKSI

AKDAHRIGQD NDIYASVMIA QAILESDSGR SALAKSPNHN LFGIKGAFEG NSVPFNTLEA

DGNKLYSINA GFRKYPSTKE SLKDYSDLIK NGIDGNRTIY KPTWKSEADS YKDATSHLSK

TYATDPNYAK KLNSIIKHYQ LTQFDDERMP DLDKYERSIK DYDDSSDEFK PFREVSDSMP

YPHGQCTWYV YNRMKQFGTS ISGDLGDAHN WNNRAQYRDY QVSHTPKRHA AVVFEAGQFG

ADQHYGHVAF VEKVNSDGSI VISESNVKGL GIISHRTINA AAAEELSYIT GK
```

```
                                                      SEQ ID NO: 87
QTKYGDQSEK GSQSVSNKNN KIHIAIVNED QPTTYNGKKV ELGQAFIKRL ANEKNYKFET

VTRNVAESGL KNGGYQVMIV IPENFSKLAM QLDAKTPSKI SLQYKTAVGQ KEEVAKNTEK

VVSNVLNDFN KNLVEIYLTS IIDNLHNAQK NVGAIMTREH GVNSKFSNYL LNPINDFPEL

FTDTLVNSIS ANKDITKWFQ TYNKSLLSAN SDTFRVNTDY NVSTLIEKQN SLFDEHNTAM

DKMLQDYKSQ KDSVELDNYI NALKQMDSQI DQQSSMQDTG KEEYKQTVKE NLDKLREIIQ

SQESPFSKGM IEDYRKQLTE SLQDELANNK DLQDALNSIK MNNAQFAENL EKQLHDDIVK

EPDSDTTFIY NMSKQDFIAA GLNEDEANKY EAIVKEAKRY KNEYNLKKPL AEHINLTDYD

NQVAQDTSSL INDGVKVQRT ETIKSNDINQ LTVATDPHFN FEGDIKINGK KYDIKDQSVQ

LDTSNKEYKV EVNGVAKLKK DAEKDFLKDK TMHLQLLFGQ ANRQDEPNDK KATSVVDVTL

NHNLDGRLSK DALSQQLSAL SRFDAHYKMY TDTKGREDKP FDNKRLIDMM VDQVINDMES

FKDDKVAVLH QIDSMEENSD KLIDDILNNK KNTTKNKEDI SKLIDQLENV KKTFAEEPQE

PKIDKGKNDE FNTMSSNLDK EISRISEKST QLLSDTQESK TIADSVSGQL NQLDNNVNKL

HATGRALGVR ANDLNRQMAK NDKDNELFAK EFKKVLQNSK DGDRQNQALK AFMSNPVQKK

NLENVLANNG NTD

SEQ ID NO: 88
KRIKQHPDVQ KVTDATSKVA SKTSAAISNT ASDVKEYVGD KKQDFENKRE LKKFAREHDP

AYIEKKGEKL AKQNRKDADK MNKILQKNIE KRHKEEQKAR EKNEIQRIKD MKKSQKYEVK

AGLTPNKLDE KTEKKGDKLA EKNRKEIAKM NKKLQKNIEK RHKEEQKRQQ EADKARIKSF

KKYKDYVAKS ASQQNKENNT EA

SEQ ID NO: 89
MDIGKKHVIP KSQYRRKRRE FFHNEDREEN LNQHQDKQNI DNTTSKKADK QIHKDSIDKH

ERFKNSLSSH LEQRNRDVNE NKAEESKSNQ GSKSAYNKDH YLTDDVSKKQ NSLDSVDQDT

EKSKYYEQNT EATLSTNSTD KVESTDMRKL SSDKNKVGHE EQHVLSKPSE HDKETRIDFE

SSRTDSDSSM QTEKIKKDSS DGNKSSNLKS EVISDKSNSV PILSESDDEV NNQKPLTLPE

EQKLKRQQSQ NEQTKTYTYG DSEQNDKSNH ENDLSHHTPS ISDDKDYVMR EDHIVDDNPD

NDINTPSLSK IDDDRKLDEK IHVEDKHKQN ADSSETVGYQ SQSSASHRST EKRNMAINDH

DKLNGQKPNT KTSANNNQKK ATSKLNKGRA TNNNYSAILK KFWMMYWPK

SEQ ID NO: 90
RNLLLQKQSQ ARQTAEDIVN QAHKEADNIK KEKLLEAKEE NQILREQTEA ELRERRSELQ

RQETRLLQKE ENLERKSDLL DKKDEILEQK ESKIEEKQQQ VDAKESSVQT LIMKHEQELE

RISGLTQEEA INEQLQRVEE ELSQDIAVLV KEKEKEAKEK VDKTAKELLA TAVQRLAADH

TSESTVSVVN LPNDEMKGRI IGREGRNIRT LETLTGIDLI IDDTPEAVIL SGFDPIRREI

ARTALVNLVS DGRIHPGRIE DMVEKARKEV DDIIREAGEQ ATFEVNAHNM HPDLVKIVGR

LNYRTSYGQN VLKHSIEVAH LASMLAAELG EDETLAKRAG LLHDVGKAID HEVEGSHVEI

GVELAKKYGE NETVINAIHS HHGDVEPTSI ISILVAAADA LSAARPGARK ETLENYIRRL

ERLETLSESY DGVEKAFAIQ AGREIRVIVS PEEIDDLKSY RLARDIKNQI EDELQYPGHI

KVTVVRETRA VEYAK

SEQ ID NO: 91
NNHNNGTKEN KIANTNKNNA DESKDKDTSK DASKDKSKST DSDKSKDDQD KATKDESDND

QNNANQANNQ AQNNQNQQQA NQNQQQQQQR QGGGQRHTVN GQENLYRIAI QYYGSGSPEN

VEKIRRANGL SGNNIRNGQQ IVIP
```

```
                                                 SEQ ID NO: 92
MNEKVEGMTL ELKLDHLGVQ EGMKGLKRQL GVVNSEMKAN LSAFDKSEKS MEKYQARIKG

LNDRLKVQKK MYSQVEDELK QVNANYQKAK SSVKDVEKAY LKLVEANKKE KLALDKSKEA

LKSSNTELKK AENQYKRTNQ RKQDAYQKLK QLRDAEQKLK NSNQATTAQL KRASDAVQKQ

SAKHKALVEQ YKQEGNQVQK LKVQNDNLSK SNDKIESSYA KTNTKLKQTE KEFNDLNNTI

KNHSANVAKA ETAVNKEKAA LNNLERSIDK ASSEMKTFNK EQMIAQSHFG KLASQADVMS

KKFSSIGDKM TSLGRTMTMG VSTPITLGLG AALKTSADFE GQMSRVGAIA QASSKDLKSM

SNQAVDLGAK TSKSANEVAK GMEELAALGF NAKQTMEAMP GVISAAEASG AEMATTATVM

ASAINSFGLK ASDANHVADL LARSANDSAA DIQYMGDALK YAGTPAKALG VSIEDTSAAI

EVLSNSGLEG SQAGTALRAS FIRLANPSKN TAKEMKKLGI HLSDAKGQFV GMGELIRQFQ

DNMKGMTREQ KLATVATIVG TEAASGFLAL IEAGPDKINS YSKSLKNSNG ESKKAADLMK

DNLKGALEQL GGAFESLAIE VGKDLTPMIR AGAEGLTKLV DGFTHLPGWV RK
                                                 SEQ ID NO: 93
MTEKEKMLAE KWYDANFDQD LINERARAKD ICFELNHTKP SDKNKRKELI DELFQTTTDN

VSISIPFDTD YGWNVKLGKN VYVNTNCYFM DGGQITIGDN VFIGPNCGFY TATHPLNFHH

RNEGFEKAGP INIGSNTWFG GHVAVLPGVT IGEGSVIGAG SVVTKDIPPH SLAVGNPCKV

VRKIDNEVPS EALNDETLN
                                                 SEQ ID NO: 94
DTPQKDTTAK TTSHDSKKST DDETSKDTTS KDIDKADNNN TSNQDNNDKK VKTIDDSTSD

SNNIIDFIYK NLPQTNINQL LTKNKYDDNY SLTTLIQNLF NLNSDISDYE QPRNGEKSTN

DSNKNSDNSI KNDTDTQSSK QDKADNQKAP KSNNTKPSTS NKQPNSPKPT QPNQSNSQPA

SDDKVNQKSS SKDNQSMSDS ALDSILDQYS EDAKKTQKDY ASQSKKDKNE KSNTKNPQLP

TQDELKHKSK PAQSFNNDVN QKDTRATSLF ETDPSISNND DSGQFNVVDS KDTRQFVKSI

AKDAHRIGQD NDIYASVMIA QAILESDSGR SALAKSPNHN LFGIKGAFEG NSVPFNTLEA

DGNQLYSINA GFRKYPSTKE SLKDYSDLIK NGIDGNRTIY KPTWKSEADS YKDATSHLSK

TYATDPNYAK KLNSIIKHYQ LTQFDDERMP DLDKYERSIK DYDDSSDEFK PFREVSDNMP

YPHGQCTWYV YNRMKQFGTS ISGDLGDAHN WNNRAQYRDY QVSHTPKRHA AVVFEAGQFG

ADQHYGHVAF VEKVNSDGSI VISESNVKGL GIISHRTINA AAAEELSYIT GK
                                                 SEQ ID NO: 95
AEKQVNMGNS QEDTVTAQSI GDQQTRENAN YQRENGVDEQ QHTENLTKNL HNDKTISEEN

HRKTDDLNKD QLKDDKKSSL NNKNIQRDTT KNNNANPRDV NQGLEQAIND GKQSKVASQQ

QSKEADNSQD LNANNNLPSQ SRTKVSPSLN KSDQTSQREI VNETEIEKVQ PQQKNQANDK

ITDHNFNNEQ EVKPQKDEKT LSVSDLKNNQ KSPVEPTKDN DKKNGLNLLK SSAVATLPNK

GTKELTAKAK GDQTNKVAKQ GQYKNQDPIV LVHGFNGFTD DINPSVLAHY WGGNKMNIRQ

DLEENGYKAY EASISAFGSN YDRAVELYYY IKGGRVDYGA AHAAKYGHER YGKTYEGIYK

DWKPGQKVHL VGHSMGGQTI RQLEELLRNG SREEIEYQKK HSGEISPLFK GNNDNMISSI

TTLGTPHNGT HASDLAGNEA L
                                                 SEQ ID NO: 96
GFLNKSKNEQ AALKAQQAAI KEEASANNLS DTSQEAQEIQ EAKREAQAEA DKSVAVSNKE

SKAVALKAQQ AAIKEEASAN NLSDTSQEAQ EIQEAKKEAQ AETDKSAAVS NEEPKAVALK

AQQAAIKEEA SANNLSDISQ EAQEVQEAKK EAQAEKDSDT LTKDASAAKV EVSKPESQAE

RLANAAKQKQ AKLTPGSKES QLTEALFAEK PVAKNDLKEI PQLVTKKNDV SETETVNIDN

KDTVKQKEAK FENGVITRKA DEKTTNNTAV DKKSGKQSKK TTPSNKRNAS KASTNKTSGQ
```

-continued

KKQHNKKSSQ GAKKQSSSSK STQKNNQTSN KNSKTTNAKS SNASKTPNAK VEKAKSKIEK

RTFND

SEQ ID NO: 97

KDNLNGEKPT TNLNHNITSP SVNSEMNNNE TGTPHESNQT GNEGTGSNSR DANPDSNNVK

PDSNNQNPST DSKPDPNNQN PSPNPKPDPD NPKPKPDPKP DPDKPKPNPD PKPDPDNPKP

NPDPKPDPNK PNPDPKPDPD KPKPNPNPKP DPNKPNPNPS PDPDQPGDSN HSGGSKNGGT

WNPNASDGSN QGQWQPNGNQ GNSQNPTGND FVSQRFLALA NGAYKYNPYI LNQINKLGKD

YGEVTDEDIY NIIRKQNFSG NAYLNGLQQQ SNYFRFQYFN PLKSERYYRN LDEQVLALIT

GEIGSMPDLK KPEDKPDSKQ RSFEPHEKDD FTVVKKQEDN KKSASTAYSK S

SEQ ID NO: 98

IDSKNKPANS DIKFEVTQKS DAVKALKELP KSENVKNIYQ DYAVTDVKTD KKGFTHYTLQ

PSVDGVHAPD KEVKVHADKS GKVVLINGDT DAKKVKPTNK VTLSKDDAAD KAFKAVKIDK

NKAKNLKDKV IKENKVEIDG DSNKYVYNVE LITVTPEISH WKVKIDAQTG EILEKMNLVK

EAAETGKGKG VLGDTKDINI NSIDGGFSLE DLTHQGKLSA FSFNDQTGQA TLITNEDENF

VKDEQRAGVD ANYYAKQTYD YYKDTFGRES YDNQGSPIVS LTHVNNYGGQ DNRNNAAWIG

DKMIYGDGDG RTFTSLSGAN DVVAHELTHG VTQETANLEY KDQSGALNES FSDVFGYFVD

DEDFLMGEDV YTPGKEGDAL RSMSNPEQFG QPAHMKDYVF TEKDNGGVHT NS

The DNA sequences encoding SEQ ID NOs: 12-20 and 41-44 are set forth in SEQ ID NO: 46-58 in the same order. The DNA sequence encoding SEQ ID NOs: 59-98 are set forth in SEQ ID NOs: 99-138.

The following table provides the amino acid sequence information relative to constructs disclosed and tested herein:

| Construct name | SEQ ID NO |
| --- | --- |
| CHIM_0992_0735_FS | 12 |
| CHIM_2635_2723_FS | 13 |
| CHIM_2716_2753_FL | 14 |
| CHIM_2723_2753_L_FS | 15 |
| CHIM_2119_1816_FS | 16 |
| CHIM_0992_2635_FL | 17 |
| CHIM_Hla_2635_FS | 18 |
| CHIM_Hla_2753_FS | 19 |
| CHIM_Hla_0735_FS | 20 |
| CHIM_0735_0992_FL | 59 |
| CHIM_0992_0735_FL | 60 |
| CHIM_0992_0735_FS | 61 |
| CHIM_0992_2635_FL | 62 |
| CHIM_0992_2635_FS | 63 |
| CHIM_0992_2753_FS | 64 |
| CHIM_1262_2496_RS | 65 |
| CHIM_1507_2119_FS | 66 |
| CHIM_1816_2119_FL | 67 |
| CHIM_2119_1816_FS | 68 |
| CHIM_2496_1816_FS | 69 |
| CHIM_2635_2723_FS | 70 |
| CHIM_2716_1816_FS | 71 |
| CHIM_2716_2119_FS | 72 |
| CHIM_2716_2753_FL | 73 |
| CHIM_2723_2635_FS | 74 |
| CHIM_2723_2635_RL | 75 |
| CHIM_2723_2753_L_FL | 76 |
| CHIM_2723_2753_S_FS | 77 |
| CHIM_Hla_0735_FS | 78 |
| CHIM_Hla_2635_FS | 79 |
| CHIM_Hla_2753_FS | 80 |
| HL461_SAR2753_291-680 | 81 |
| HL461_SAR2753-291-476 | 82 |
| Hla_H35L-27-319 | 83 |
| IsdB_USA300-41-613 | 84 |
| M2863_SAR0992-1-409 | 85 |
| M3496_SAR2723-28-619 | 86 |
| SAR0280-28-820 | 87 |
| SAR0735-26-227 | 88 |
| SAR0992-1-409 | 89 |
| SAR1262-25-519 | 90 |
| SAR1489-343-486 | 91 |
| SAR1507-1-652 | 92 |
| SAR2635-1-199 | 93 |
| SAR2723-28-619 | 94 |
| SAR2753-36-476 | 95 |
| USA300HOU_1728-88-452 | 96 |
| USA300HOU_2027-33-383 | 97 |
| USA300HOU_2637-28-439 | 98 |

The invention claimed is:

1. A chimeric polypeptide comprising formula I $$a^1\text{-}A^1\text{-}L\text{-}A^2\text{-}a^1 \quad (I)$$

wherein $A^1$ is an amino acid sequence constituted by at least or exactly 35 contiguous amino acid residues present in SEQ ID NO: 7 or an amino acid sequence with at least 80% sequence identity with an amino acid sequence constituted by at least or exactly 35 contiguous amino acid residues present in SEQ ID NO: 7, and $A^2$ is an amino acid sequence constituted by at least or exactly 35 contiguous amino acid residues present in SEQ ID NO: 2 or an amino acid sequence with at least 80% sequence identity with an amino acid sequence constituted by at least or exactly 35 contiguous amino acid residues present in SEQ ID NO: 2, L is an optional amino acid sequence, $a^1$ is an optional amino acid sequence, and $a^2$ is an optional amino acid sequence.

2. The chimeric polypeptide according to claim 1, wherein $A^1$ and $A^2$ is an amino acid sequence with at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with an amino acid sequence constituted by at least or exactly 35 contiguous amino acid residues present in SEQ ID NO: 7 or SEQ ID NO: 2.

3. The chimeric polypeptide according to claim 1, wherein the at least or exactly 35 contiguous amino acid residues present in SEQ ID NO: 7 or SEQ ID NO: 2 in the definition of $A^1$ and/or $A^2$ are at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least or exactly or at most 54, at least or exactly or at most 55, at least or exactly or at most 56, at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64, at least or exactly or at most 65, at least or exactly or at most 66, at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, at least or exactly or at most 139, at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at most 165, at least or exactly or at most 166, at least or exactly or at most 167, at least or exactly or at most 168, at least or exactly or at most 169, at least or exactly or at most 170, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, at least or exactly or at most 199, at least or exactly or at most 200, at least or exactly or at most 201, or at least or exactly or at most 202 amino acid residues in SEQ ID NO: 2 or SEQ ID NO: 7, or wherein the at least or exactly 35 contiguous amino acid residues present in SEQ ID NO: 7 in the definition of $A^1$ are at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most-224, at least or exactly or at most 225, at least or exactly or at most 226, at least or exactly or at most 227, at least or exactly or at most 228, at least or exactly or at most 229, at least or exactly or at most 230, at least or exactly or at most 231, at least or exactly or at most 232, at least or exactly or at most 233, at least or exactly or at most 234, at least or exactly or at most 235, at least or exactly or at most 236, at least or exactly or at most 237, at least or exactly or at most 238, at least or exactly or at most 239, at least or exactly or at most 240, at least or exactly or at most 241, at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253, at least or exactly or at most 254, at least or exactly or at most 255, at least or exactly or at most 256, at least or exactly or at most 257, at least or exactly or at most 258, at least or exactly or at most 259, at least or exactly or at most 260, at least or exactly or at most 261, at least or exactly or at most 262, at least or exactly or at most 263, at least or exactly or at most 264, at least or exactly or at most 265, at least or exactly or at most 266, at least or exactly or at most 267, at least or exactly or at most 268, at least or exactly or at most 269, at least or exactly or at most 270, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 286, at least or exactly or at most 287, at least or exactly or at most 288, at least or exactly or at most 289, at least or exactly or at most 290, at least or exactly or at most 291, at least or exactly or at most 292, at least or exactly or at most 293, at least or exactly or at most 294, at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, at least or exactly or at most 303, at least or exactly or at most 304, at least or exactly or at most 305, at least or exactly or at most 306, at least or exactly or at most 307, at least or exactly or at most 308, at least or exactly or at most 309, at least or exactly or at most 310, at least or exactly or at most 311, at least or exactly or at most 312, at least or exactly or at most 313, at least or exactly or at most 314, at least or exactly or at most 315, at least or exactly or at most 316, at least or exactly or at most 317, at least or exactly or at most 318, at least or exactly or at most 319, at least or exactly or at most 320, at least or exactly or at most 321, at least or exactly or at most 322, at least or exactly or at most 323, at least or exactly or at most 324, at least or exactly or at most 325, at least or exactly or at most 326, at least or exactly or at most 327, at least or exactly or at most 328, at least or exactly or at most 329, at least or exactly or at most 330, at least or exactly or at most 331, at least or exactly or at most 332, at least or exactly or at most 333, at least or exactly or at most 334, at least or exactly or at most 335, at least or exactly or at most 336, at least or exactly or at most 337, at least or exactly or at most 338, at least or exactly or at most 339, at least or exactly or at most 340, at least or exactly or at most 341, at least or exactly or at most 342, at least or exactly or at most 343, at least or exactly or at most 344, at least or exactly or at most 345, at least or exactly or at most 346, at least or exactly or at most 347, at least or exactly or at most 348, at least or exactly or at most 349, at least or exactly or at most 350, at least or exactly or at most 351, at least or exactly or at most 352, at least or exactly or at most 353, at least or exactly or at most 354, at least or exactly or at most 355, at least or exactly or at most 356, at least or exactly or at most 357, at least or exactly or at most 358, at least or exactly or at most 359, at least or exactly or at most 360, at least or exactly or at most 361, at least or exactly or at most 362, at least or exactly or at most 363, at least or exactly or at most 364, at least or exactly or at most 365, at least or exactly or at most 366, at least or exactly or at most 367, at least or exactly or at most 368, at least or exactly or at most 369, at least or exactly or at most 370, at least or exactly or at most 371, at least or exactly or at most 372, at least or exactly or at most 373, at least or exactly or at most 374, at least or exactly or at most 375, at least or exactly or at most 376, at least or exactly or at most 377, at least or exactly or at most 378, at least or exactly or at most 379, at least or exactly or at most 380, at least or exactly or at most 381, at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, at least or exactly or at most 390, at least or exactly or at most 391, at least or exactly or at most 392, at least or exactly or at most 393, at least or exactly or at most 394, at least or exactly or at most 395, at least or exactly or at most 396, at least or exactly or at most 397, at least or exactly or at most 398, at least or exactly or at most 399, at least or exactly or at most 400, at least or exactly or at most 401, at least or exactly or at most 402, at least or exactly or at most 403, or at least or exactly or at most 404, at least or exactly or at most 405, at least or exactly or at most 406, at least or exactly or at most 407, at least or exactly or at most 408, or at least or exactly or at most 409 amino acid residues in SEQ ID NO: 7.

4. The chimeric polypeptide according to claim 1, wherein the at least or exactly 35 contiguous amino acid residues present in SEQ ID NO: 2 or SEQ ID NO: 7 in the definition of $A^1$ and/or $A^2$ commences at amino acid residue 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, or 168 in SEQ ID NO: 2 and/or SEQ ID NO: 7, or wherein the at least or exactly 35 amino acid residues present in SEQ ID NO: 7 in the definition of $A^1$ commences at amino acid residue 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, or 375 in SEQ ID NO: 7, with the proviso that the number of the selected commencing amino acid residue satisfies the formula $N \leq L-n+1$, where N is the number of the selected residue in SEQ ID NO: 2 and/or SEQ ID NO: 7, L is the number of amino acid residues in the sequence selected from SEQ ID NOs: 6-9, and n is the number of contiguous amino acid residues.

5. The chimeric polypeptide according to claim 1, wherein the $a^1$ is selected from the group consisting of
1) a methionine residue,
2) An amino acid sequence located, or directly linked, N-terminally to the $A^1$ amino acid sequence,
3) An amino acid sequence that comprises or constitutes a purification tag,
4) an amino acid sequence that comprises or constitutes an immunogenic carrier molecule, 5) An amino acid sequence that exerts adjuvant activity, and 6) any combination of 1) to 5).

6. The chimeric polypeptide according to claim 5, wherein, when $a^1$ is an amino acid sequence then $a^1$ has an N-terminal methionine residue.

7. The chimeric polypeptide according to claim 1, wherein the $a^2$ is selected from the group consisting of
   i) an amino acid sequence located, or directly linked, N-terminally to the $A^2$ amino acid sequence,
   ii) an amino acid sequence that comprises or constitutes a purification tag,
   iii) an amino acid sequence that comprises or constitutes an immunogenic carrier molecule,
   iv) an amino acid sequence that exerts adjuvant activity, and
   v) any combination of i) to iv).

8. The chimeric polypeptide according to claim 1, wherein L is a linker.

9. The chimeric polypeptide according to claim 8, wherein the linker comprises glycine and/or serine residues.

10. The chimeric polypeptide according to claim 9, wherein the linker comprises or consists of the amino acid sequence GSGGGA (SEQ ID NO: 10) or GSGG-GAGSGGGA (SEQ ID NO: 11).

11. The chimeric polypeptide according to claim 1, which comprises or consists of the amino acid sequence of SEQ ID NO: 12, or SEQ ID NO: 61.

12. The chimeric polypeptide according to claim 1, which is further covalently linked to an immunogenic carrier molecule.

13. The chimeric polypeptide according to claim 12, wherein the immunogenic carrier molecule is a polypeptide that induces T-helper lymphocyte responses in a majority of humans.

14. A pharmaceutical composition comprising an immunogenically effective amount of the chimeric polypeptide according to claim 11 and a pharmaceutically acceptable carrier, vehicle or diluent.

15. The pharmaceutical composition according to claim 14, which further comprises an immunological adjuvant.

16. The pharmaceutical composition according to claim 15, wherein the adjuvant is an aluminium based adjuvant.

17. A chimeric polypeptide comprising two non-identical amino acid sequences, wherein one of the amino acid sequences is constituted by at least or exactly 35 contiguous amino acid residues present in SEQ ID NO: 7 or an amino acid sequence with at least 80% sequence identity with an amino acid sequence constituted by at least or exactly 35 contiguous amino acid residues present in SEQ ID NO: 7, and the other amino acid sequence is constituted by at least or exactly 35 contiguous amino acid residues present in SEQ ID NO: 2 or an amino acid sequence with at least 80% sequence identity with an amino acid sequence constituted by at least or exactly 35 contiguous amino acid residues present in SEQ ID NO: 2.

18. A method of inducing a protective adaptive immune response against *Staphylococcus aureus* in an animal by administering at least once an immunogenically effective amount of the chimeric polypeptide according to claim 11.

19. A method of inducing an immune response in an animal by administering at least once the pharmaceutical composition according to claim 18.

20. The method of claim 19, wherein the animal receives between 0.5 and 5,000 micrograms of the chimeric polypeptide per administration.

21. The method of claim 19, wherein the animal receives a first priming administration of the chimeric polypeptide and one or more booster administrations of the chimeric polypeptide.

22. The method of claim 19, wherein the animal is a human being.

23. The method of claim 19, wherein the administration is for the purpose of inducing antibodies specific to the chimeric polypeptide.

24. A pharmaceutical composition comprising an immunogenically effective amount of the chimeric polypeptide according to claim 1 and a pharmaceutically acceptable carrier, vehicle or diluent.

* * * * *

SEQUENCE LISTING

```
Sequence total quantity: 146
SEQ ID NO: 1             moltype = AA  length = 199
FEATURE                  Location/Qualifiers
source                   1..199
                         mol_type = protein
                         organism = Staphylococcus aureus
SEQUENCE: 1
```

```
MTEKEKMLAE KWYDANFDQD LINERARAKD ICFELNHTKP SDKNKRKELI DELFQTTTDN    60
VSISIPFDTD YGWNVKLGKN VYVNTNCYFM DGGQITIGDN VFIGPNCGFY TATHPLNFHH   120
RNEGFEKAGP INIGSNTWFG GHVAVLPGVT IGEGSVIGAG SVVTKDIPPH SLAVGNPCKV   180
VRKIDNEVPS EALNDETLN                                               199

SEQ ID NO: 2              moltype = AA   length = 202
FEATURE                   Location/Qualifiers
source                    1..202
                          mol_type = protein
                          organism = Staphylococcus aureus
SEQUENCE: 2
KRIKQHPDVQ KVTDATSKVA SKTSAAISNT ASDVKEYVGD KKQDFENKRE LKKFAREHDP    60
AYIEKKGEKL AKQNRKDADK MNKILQKNIE KRHKEEQKAR EKNEIQRIKD MKKSQKYEVK   120
AGLTPNKLDE KTEKKGDKLA EKNRKEIAKM NKKLQKNIEK RHKEEQKRQQ EADKARIKSF   180
KKYKDYVAKS ASQQNKENNT EA                                           202

SEQ ID NO: 3              moltype = AA   length = 293
FEATURE                   Location/Qualifiers
source                    1..293
                          mol_type = protein
                          organism = Staphylococcus aureus
SEQUENCE: 3
ADSDINIKTG TTDIGSNTTV KTGDLVTYDK ENGMLKKVFY SFIDDKNHNK KLLVIRTKGT    60
IAGQYRVYSE EGANKSGLAW PSAFKVQLQL PDNEVAQISD YYPRNSIDTK EYMSTLTYGF   120
NGNVTGDDTG KIGGLIGANV SIGHTLKYVQ PDFKTILESP TDKKVGWKVI FNNMVNQNWG   180
PYDRDSWNPV YGNQLFMKTR NGSMKAADNF LDPNKASSLL SSGFSPDFAT VITMDRKASK   240
QQTNIDVIYE RVRDDYQLHW TSTNWKGTNT KDKWIDRSSE RYKIDWEKEE MTN          293

SEQ ID NO: 4              moltype = AA   length = 351
FEATURE                   Location/Qualifiers
source                    1..351
                          mol_type = protein
                          organism = Staphylococcus aureus
SEQUENCE: 4
AKDNLNGEKP TTNLNHNVTS PSVNSEMNNN ETGTPHESNQ AGNEGTGSNS RDANPDSNNV    60
KPDSNNQNPS PDSKPDPNNP NPGPNPKPDP DKPKPNPEPK PDDKPDPDKP KPNPDPKPDP   120
DKPKPNPDPK PDPDKPKPNP DPKPDPNPNP KPDPNKPNPN PSPNPNPQPG D SNQSGGSKNG   180
GTWNPNASDG SNQGQWQPNG NQGNSQNPTG NDFVSQRFLA LANGAYKYNP YILNQINQLG   240
KEYGEVTDED IYNIIRKQNF SGNAYLNGLQ QQSNYFRFQY FNPLKSERYY RNLDEQVLAL   300
ITGEIGSMPD LKKPEDKPDS KQRSFEPHEK DDFTVVKKQE DNKKSASTAY S            351

SEQ ID NO: 5              moltype = AA   length = 365
FEATURE                   Location/Qualifiers
source                    1..365
                          mol_type = protein
                          organism = Staphylococcus aureus
SEQUENCE: 5
GFLNKSKNEQ AALKAQQAAI KEEASANNLS DTSQEAQEIQ EAKREAQAEA DKSVAVSNKE    60
SKAVALKAQQ AAIKEEASAN NLSDTSQEAQ EIQEAKKEAQ AETDKSAAVS NEEPKAVALK   120
AQQAAIKEEA SANNLSDISQ EAQEVQEAKK EAQAEKDSDT LTKDASAAKV EVSKPESQAE   180
RLANAAKQKQ AKLTPGSKES QLTEALFAEK PVAKNDLKEI PQLVTKKNDV SETETVNIDN   240
KDTVKQKEAK FENGVITRKA DEKTTNNTAV DKKSGKQSKK TTPSNKRNAS KASTNKTSGQ   300
KKQHNKKSSQ GAKKQSSSSK STQKNNQTSN KNSKTTNAKS SNASKTPNAK VEKAKSIEK   360
RTFND                                                              365

SEQ ID NO: 6              moltype = AA   length = 390
FEATURE                   Location/Qualifiers
source                    1..390
                          mol_type = protein
                          organism = Staphylococcus aureus
SEQUENCE: 6
KVAKQGQYKN QDPIVLVHGF NGFTDDINPS VLAHYWGGNK MNIRQDLEEN GYKAYEASIS    60
AFGSNYDRAV ELYYYIKGGR VDYGAAHAAK YGHERYGKTY EGIYKDWKPG QKVHLVGHSM   120
GGQTIRQLEE LLRNGSREEI EYQKKHGGEI SPLFKGNNDN MISSITTLGT PHNGTHASDL   180
AGNEALVRQI VFDIGKMFGN KNSRVDFGLA QWGLKQKPNE SYIDYVKRVK QSNLWKSKDN   240
GFYDLTREGA TDLNRKTSLN PNIVYKTYTG EATHKALNSD RQKADLNMFF PPVITGNLIG   300
KATEKEWREN DGLVSVISSQ HPFNQAYTNA TDKIQKGIWQ VTPTKHDWDH VDFVGQDSSD   360
TVRTREELQD FWHHLADDLV KTEKVTDTKQ                                   390

SEQ ID NO: 7              moltype = AA   length = 409
FEATURE                   Location/Qualifiers
source                    1..409
                          mol_type = protein
                          organism = Staphylococcus aureus
SEQUENCE: 7
MDIGKKHVIP KSQYRRKRRE FFHNEDREEN LNQHQDKQNI DNTTSKKADK QIHKDSIDKH    60
ERFKNSLSSH LEQRNRDVNE NKAEESKSNQ DSKSAYNRDH YLTDDVSKKQ NSLDSVDQDT   120
EKSKYYEQNS EATLSTKSTD KVESTMRKL SSDKNKVGHE EQHVLSKPSE HDKETRIDSE   180
SSRTDSDSSM QTEKIKKDSS DGNKSSNLKS EVISDKSNTV PKLSESDDEV NNQKPLTLPE   240
```

```
EQKLKRQQSQ NEQTKTYTYG DSEQNDKSNH ENDLSHHIPS ISDDKDNVMR ENHIVDDNPD    300
NDINTPSLSK TDDDRKLDEK IHVEDKHKQN ADSSETVGYQ SQSTASHRST EKRNISINDH    360
DKLNGQKTNT KTSANNNQKK ATSKLNKGRA TNNNYSDILK KFWMMYWPK                409

SEQ ID NO: 8            moltype = AA   length = 412
FEATURE                 Location/Qualifiers
source                  1..412
                        mol_type = protein
                        organism = Staphylococcus aureus
SEQUENCE: 8
IDSKNKPANS DIKFEVTQKS DAVKALKELP KSENVKNIYQ DYAVTDVKTD KKGFTHYTLQ    60
PSVDGVHAPD KEVKVHADKS GKVVLINGDT DAKKVKPTNK VTLSKDDAAD KAFKAVKIDK    120
NKAKNLKDKV IKENKVEIDG DSNKYVYNVE LITVTPEISH WKVKIDAQTG EILEKMNLVK    180
EAAETGKGKG VLGDTKDINI NSIDGGFSLE DLTHQGKLSA FSFNDQTGQA TLITNEDENF    240
VKDEQRAGVD ANYYAKQTYD YYKDTFGRES YDNQGSPIVS LTHVNNYGGQ DNRNNAAWIG    300
DKMIYGDGDG RTFTSLSGAN DVVAHELTHG VTQETANLEY KDQSGALNES FSDVFGYFVD    360
DEDFLMGEDV YTPGKEGDAL RSMSNPEQFG QPAHMKDYVF TEKDNGGVHT NS            412

SEQ ID NO: 9            moltype = AA   length = 592
FEATURE                 Location/Qualifiers
source                  1..592
                        mol_type = protein
                        organism = Staphylococcus aureus
SEQUENCE: 9
DTPQKDTTAK TTSHDSKKSN DDETSKDTTS KDIDKADNNN TSNQDNNDKK FKTIDDSTSD    60
SNNIIDPIYK NLPQTNINQL LTKNKYDDNY SLTTLIQNLF NLNSDISDYE QPRNGEKSTN    120
DSNKNSDNSI KNDTDTQSSK QDKADNQKAP KSNNTKPSTS NKQPNSPKPT QPNQSNSQPA    180
SDDKANQKSS SKDNQSMSDS ALDSILDQYS EDAKKTQKDY ASQSKKDKNE KSNTKNPQLP    240
TQDELKHKSS PAQSFNNDVN QKDTRATSLF ETDPSISNND DSGQFNVVDS KDTRQFVKSI    300
AKDAHRIGQD NDIYASVMIA QAILESDSGR SALAKSPNHN LFGIKGAFEG NSVPFNTLEA    360
DGNKLYSINA GFRKYPSTKE SLKDYSDLIK NGIDGNRTIY KPTWKSEADS YKDATSHLSK    420
TYATDPNYAK KLNSIIKHYQ LTQFDDERMP DLDKYERSIK DYDDSSDEFK PFREVSDSMP    480
YPHGQCTWYV YNRMKQFGTS ISGDLGDAHN WNNRAQYRDY QVSHTPKRHA AVVFEAGQFG    540
ADQHYGHVAF VEKVNSDGSI VISESNVKGL GIISHRTINA AAAEELSYIT GK            592

SEQ ID NO: 10           moltype = AA   length = 6
FEATURE                 Location/Qualifiers
REGION                  1..6
                        note = Peptide linker
source                  1..6
                        mol_type = protein
                        organism = synthetic construct
SEQUENCE: 10
GSGGGA                                                                6

SEQ ID NO: 11           moltype = AA   length = 12
FEATURE                 Location/Qualifiers
REGION                  1..12
                        note = Peptide linker
source                  1..12
                        mol_type = protein
                        organism = synthetic construct
SEQUENCE: 11
GSGGGAGSGG GA                                                         12

SEQ ID NO: 12           moltype = AA   length = 617
FEATURE                 Location/Qualifiers
REGION                  1..617
                        note = Chimeric polypeptide
REGION                  1..409
                        note = MISC_FEATURE - SEQ ID NO: 9
REGION                  410..415
                        note = MISC_FEATURE - GSGGGA linker
REGION                  416..617
                        note = MISC_FEATURE - SEQ ID NO: 2
source                  1..617
                        mol_type = protein
                        organism = synthetic construct
SEQUENCE: 12
MDIGKKHVIP KSQYRRKRRE FFHNEDREEN LNQHQDKQNI DNTTSKKADK QIHKDSIDKH    60
ERFKNSLSSH LEQRNRDVNE NKAEESKSNQ DSKSAYNRDH YLTDDVSKKQ NSLDSVDQDT    120
EKSKYYEQNS EATLSTKSTD KVESTEMRKL SSDDKNKVGH EQHVLSKPSE HDKETRIDSE    180
SSRTDSDSSM QTEKIKKDSS DGNKSSNLKS EVISDKSNTV PKLSESDDEV NNQKPLTLPE    240
EQKLKRQQSQ NEQTKTYTYG DSEQNDKSNH ENDLSHHIPS ISDDKDNVMR ENHIVDDNPD    300
NDINTPSLSK TDDDRKLDEK IHVEDKHKQN ADSSETVGYQ SQSTASHRST EKRNISINDH    360
DKLNGQKTNT KTSANNNQKK ATSKLNKGRA TNNNYSDILK KFWMMYWPKG SGGGAKRIKQ    420
HPDVQKVTDA TSKVASKTSA AISNTASDVK EYVGDKKQDF ENKRELKKFA REHDPAYIEK    480
KGEEKLAKQNR KDADKMNKIL QKNIEKRHKE EQKAREKNEI QRIKDMKKSQ KYEVKAGLTP    540
NKLDEKTEKK GDKLAEKNRK EIAKMNKKLQ KNIEKRHKEE QKRQQEADKA RIKSFKKYKD    600
```

-continued

```
YVAKSASQQN KENNTEA                                                617

SEQ ID NO: 13           moltype = AA  length = 797
FEATURE                 Location/Qualifiers
REGION                  1..797
                        note = Chimeric polypeptide
REGION                  1..199
                        note = MISC_FEATURE - SEQ ID NO: 1
REGION                  200..205
                        note = MISC_FEATURE - GSGGGA linker
REGION                  206..797
                        note = MISC_FEATURE - SEQ ID NO: 7
source                  1..797
                        mol_type = protein
                        organism = synthetic construct
SEQUENCE: 13
MTEKEKMLAE KWYDANFDQD LINERARAKD ICFELNHTKP SDKNKRKELI DELFQTTTDN  60
VSISIPFDTD YGWNVKLGKN VYVNTNCYFM DGGQITIGDN VFIGPNCGFY TATHPLNFHH  120
RNEGFEKAGP INIGSNTWFG GHVAVLPGVT IGEGSVIGAG SVVTKDIPPH SLAVGNPCKV  180
VRKIDNEVPS EALNDETLNG SGGGADTPQK DTTAKTTSHD SKKSNDDETS KDTTSKDIDK  240
ADNNNTSNQD NNDKKFKTID DSTSDSNNII DFIYKNLPQT NINQLLTKNK YDDNYSLTTL  300
IQNLFNLNSD ISDYEQPRNG EKSTNDSNKN SDNSIKNDTD TQSSKQDKAD NQKAPKSNNT  360
KPSTSNKQPN SPKPTQPNQS NSQPASDDKA NQKSSSKDNQ SMSDSALDSI LDQYSEDAKK  420
TQKDYASQSK KDKNEKSNTK NPQLPTQDEL KHKSKPAQSF NNDVNQKDTR ATSLFETDPS  480
ISNNDDSGQF NVVDSKDTRQ FVKSIAKDAH RIGQDNDIYA SVMIAQAILE SDSGRSALAK  540
SPNHNLFGIK GAFEGNSVPF NTLEADGNKL YSINAGFRKY PSTKESLKDY SDLIKNGIDG  600
NRTIYKPTWK SEADSYKDAT SHLSKTYATD PNYAKKLNSI IKHYQLTQFD DERMPDLDKY  660
ERSIKDYDDS SDEFKPFREV SDSMPYPHGQ CTWYVYNRMK QFGTSISGDL GDAHNWNNRA  720
QYRDYQVSHT PKRHAAVFPE AGQFGADQHY GHVAFVEKVN SDGSIVISES NVKGLGIISH  780
RTINAAAAEE LSYITGK                                                797

SEQ ID NO: 14           moltype = AA  length = 814
FEATURE                 Location/Qualifiers
REGION                  1..814
                        note = Chimeric polypeptide
REGION                  1..412
                        note = MISC_FEATURE - SEQ ID NO: 6
REGION                  413..424
                        note = MISC_FEATURE - GSGGGAGSGGGA linker
REGION                  425..814
                        note = MISC_FEATURE - SEQ ID NO: 8
source                  1..814
                        mol_type = protein
                        organism = synthetic construct
SEQUENCE: 14
IDSKNKPANS DIKFEVTQKS DAVKALKELP KSENVKNIYQ DYAVTDVKTD KKGFTHYTLQ  60
PSVDGVHAPD KEVKVHADKS GKVVLINGDT DAKKVKPTNK VTLSKDDAAD KAFKAVKIDK  120
NKAKNLKDKV IKENKVEIDG DSNKYVNVE LITVTPEISH WKVKIDAQTG EILEKMNLVK  180
EAAETGKGKG VLGDTKDINI NSIDGGFSLE DLTHQGKLSA FSFNDQTGQA TLITNEDENF  240
VKDEQRAGVD ANYYAKQTYD YYKDTFGRES YDNQGSPIVS LTHVNNYGGQ DNRNNAAWIG  300
DKMIYGDGDG RTFTSLSGAN DVVAHELTHG VTQETANLEY KDQSGALNES FSDVFGYFVD  360
DEDFLMGEDV YTPGKEGDAL RSMSNPEQFG QPAHMKDYVF TEKDNGGVHT NSGSGGGAGS  420
GGGAKVAKQG QYKNQDPIVL VHGFNGFTDD INPSVLAHYW GGNKMNIRQD LEENGYKAYE  480
ASISAFGSNY DRAVELYYYI KGGRVDYGAA HAAKYGHERY GKTYEGIYKD WKPGQKVHLV  540
GHSMGGQTIR QLEELLRNGS REEIEYQKKH GGEISPLFKG NNDNMISSIT TLGTPHNGTH  600
ASDLAGNEAL VRQIVFDIGK MFGNKNSRVD FGLAQWGLKQ KPNESYIDYV KRVKQSNLWK  660
SKDNGFYDLT REGATDLNRK TSLNPNIVYK TYTGEATHKA LNSDRQKADL NMFFPFVITG  720
NLIGKATEKE WRENDGLVSV ISSQHPFNQA YTNATDKIQK GIWQVTPTKH DWDHVDFVGQ  780
DSSDTVRTRE ELQDFWHHLA DDLVKTEKVT DTKQ                             814

SEQ ID NO: 15           moltype = AA  length = 988
FEATURE                 Location/Qualifiers
REGION                  1..988
                        note = Chimeric polypeptide
REGION                  1..592
                        note = MISC_FEATURE - SEQ ID NO: 7
REGION                  593..598
                        note = MISC_FEATURE - GSGGGA linker
REGION                  599..988
                        note = MISC_FEATURE - SEQ ID NO: 8
source                  1..988
                        mol_type = protein
                        organism = synthetic construct
SEQUENCE: 15
DTPQKDTTAK TTSHDSKKSN DDETSKDTTS KDIDKADNNN TSNQDNNDKK FKTIDDSTSD  60
SNNIIDFIYK NLPQTNINQL LTKNKYDDNY SLTTLIQNLF NLNSDISDYE QPRNGEKSTN  120
DSNKNSDNSI KNDTDTQSSK QDKADNQKAP KSNNTKPSTS NKQPNSPKPT QPNQSNSQPA  180
SDDKANQKSS SKDNQSMSDS ALDSILDQYS EDAKKTQKDY ASQSKKDKNE KSNTKNPQLP  240
TQDELKHKSK PAQSFNNDVN QKDTRATSLF ETDPSISNND DSGQFNVVDS KDTRQFVKSI  300
```

```
AKDAHRIGQD NDIYASVMIA QAILESDSGR SALAKSPNHN LFGIKGAFEG NSVPFNTLEA    360
DGNKLYSINA GFRKYPSTKE SLKDYSDLIK NGIDGNRTIY KPTWKSEADS YKDATSHLSK    420
TYATDPNYAK KLNSIIKHYQ LTQFDDERMP DLDKYERSIK DYDDSSDEFK PFREVSDSMP    480
YPHGQCTWYV YNRMKQFGTS ISGDLGDAHN WNNRAQYRDY QVSHTPKRHA AVVFEAGQFG    540
ADQHYGHVAF VEKVNSDGSI VISESNVKGL GIISHRTINA AAAEELSYIT GKGSGGGAKV    600
AKQGQYKNQD PIVLVHGFNG FTDDINPSVL AHYWGGNKMN IRQDLEENGY KAYEASISAF    660
GSNYDRAVEL YYYIKGGRVD YGAAHAAKYG HERYGKTYEG IYKDWKPGQK VHLVGHSMGG    720
QTIRQLEELL RNGSREEIEY QKKHGGEISP LFKGNNDNMI SSITTLGTPH NGTHASDLAG    780
NEALVRQIVF DIGKMFGNKN SRVDFGLAQW GLKQKPNESY IDYVKRVKQS NLWKSKDNGF    840
YDLTREGATD LNRKTSLNPN IVYKTYGEA  THKALNSDRQ KADLNMFFPF VITGNLIGKA    900
TEKEWRENDG LVSVISSQHP FNQAYTNATD KIQKGIWQVT PTKHDWDHVD FVGQDSSDTV    960
RTREELQDFW HHLADDLVKT EKVTDTKQ                                       988

SEQ ID NO: 16           moltype = AA   length = 722
FEATURE                 Location/Qualifiers
REGION                  1..722
                        note = Chimeric polypeptide
REGION                  1..351
                        note = MISC_FEATURE - SEQ ID NO: 5
REGION                  352..357
                        note = MISC_FEATURE - GSGGGA linker
REGION                  358..722
                        note = MISC_FEATURE - SEQ ID NO: 4
source                  1..722
                        mol_type = protein
                        organism = synthetic construct
SEQUENCE: 16
AKDNLNGEKP TTNLNHNVTS PSVNSEMNNN ETGTPHESNQ AGNEGTGSNS RDANPDSNNV     60
KPDSNNQNPS PDSKPDPNNP NPGPNPKPDP DKPKPNPEPK PDPKPDPDKP KPNPDPKPDP    120
DKPKPNPDPK PDPDKPKPNP DPKPKPNPNP KPDPNKPNPN PSPNPNQPGD SNQSGGSKNG    180
GTWNPNASDG SNQGQWQPNG NQGNSQNPTG NDFVSQRFLA LANGAYKYNP YILNQINQLG    240
KEYGEVTDED IYNIIRKQNF SGNAYLNGLQ QQSNYFRFQY FNPLKSERYY RNLDEQVLAL    300
ITGEIGSMPD LKKPEDKPDS KQRSFEPHEK DDFTVVKKQE DNKKSASTAY SGSGGGAGFL    360
NKSKNEQAAL KAQQQAAIKEE ASANNLSDTS QEAQEIQEAK REAQAEADKS VAVSNKESKA    420
VALKAQQAAI KEEASANNLS DTSQEAQEIQ EAKKEAQAET DKSAAVSNEE PKAVALKAQQ    480
AAIKEEASAN NLSDISQEAQ EVQEAKKEAQ AEKDSDTLTK DASAAKVEVS KPESQAERLA    540
NAAKQKQAKL TPGSKESQLT EALFAEKPVA KNDLKEIPQL VTKKNDVSET ETVNIDNKDT    600
VKQKEAKFEN GVITRKADEK TTNNTAVDKK SGKQSKKTTP SNKRNASKAS TNKTSGQKKQ    660
HNKKSSOGAK KQSSSSKSTQ KNNQTSNKNS KTTNAKSSNA SKTPNAKVEK AKSKIEKRTF    720
ND                                                                   722

SEQ ID NO: 17           moltype = AA   length = 620
FEATURE                 Location/Qualifiers
REGION                  1..620
                        note = Chimeric polypeptide
REGION                  1..409
                        note = MISC_FEATURE - SEQ ID NO: 9
REGION                  410..421
                        note = MISC_FEATURE - GSGGGAGSGGGA linker
REGION                  422..620
                        note = MISC_FEATURE - SAR35 (SEQ ID NO: 1)
REGION                  422..620
                        note = MISC_FEATURE - SEQ ID NO: 1
source                  1..620
                        mol_type = protein
                        organism = synthetic construct
SEQUENCE: 17
MDIGKKHVIP KSQYRRKRRE FFHNEDREEN LNQHQDKQNI DNTTSKKADK QIHKDSIDKH     60
ERFKNSLSSH LEQRNRDVNE NKAEEESKSNQ DSKSAYNRDH YLTDDVSKKQ NSLDSVDQDT   120
EKSKYYEQNS EATLSTKSTD KVESTEMRKL SSDKNKVGHE EQHVLSKPSE HDKETRIDSE    180
SSRTDSDSSM QTEKIKKDSS DGNKSSNLKS EVISDKSNTV PKLSESDDEV NNQKPLTLPE    240
EQKLKRQQSQ NEQTKTYTYG DSEQNDKSNH ENDLSHHIPS ISDDKDNVMR ENHIVDDNPD    300
NDINTPSLSK TDDDRKLDEK IHVEDKHKQN ADSSETVGYQ SQSTASHRST EKRNISINDH    360
DKLNGQKTNT KTSANNNQKK ATSKLNKGRA TNNNYSDILK KFWMMYWPKG SGGGAGSGGG    420
AMTEKEKMLA EKWYDANFDQ DLINERARAK DICFELNHTK PSDKNKRKEL IDELFQTTTD    480
NVSISIPFDT DYGWNVKLGK NVYVNTNCYF MDGGQITIGD NVFIGPNCGF YTATHPLNFH    540
HRNEGFEKAG PINIGSNTWF GGHVAVLPGV TIGEGSVIGA GSVVTKDIPP HSLAVGNPCK    600
VVRKIDNEVP SEALNDETLN                                                620

SEQ ID NO: 18           moltype = AA   length = 498
FEATURE                 Location/Qualifiers
REGION                  1..498
                        note = Chimeric polypeptide
REGION                  1..293
                        note = MISC_FEATURE - Residues 27-319 of S. aureus alpha
                         hemolysin (residues 27-319 ofSEQ ID NO: 2)
REGION                  294..299
                        note = MISC_FEATURE - GSGGGA linker
REGION                  300..498
```

```
                        note     = MISC_FEATURE - SEQ ID NO: 1
source                  1..498
                        mol_type = protein
                        organism = synthetic construct
SEQUENCE: 18
ADSDINIKTG TTDIGSNTTV KTGDLVTYDK ENGMLKKVFY SFIDDKNHNK KLLVIRTKGT     60
IAGQYRVYSE EGANKSGLAW PSAFKVQLQL PDNEVAQISD YYPRNSIDTK EYMSTLTYGF    120
NGNVTGDDTG KIGGLIGANV SIGHTLKYVQ PDFKTILESP TDKKVGWKVI FNNMVNQNWG    180
PYDRDSWNPV YGNQLFMKTR NGSMKAADNF LDPNKASSLL SSGFSPDFAT VITMDRKASK    240
QQTNIDVIYE RVRDDYQLHW TSTNWKGTNT KDKWIDRSSE RYKIDWEKEE MTNGSGGGAM    300
TEKEKMLAEK WYDANFDQDL INERARAKDI CFELNHTKPS DKNKRKELID ELFQTTTDNV    360
SISIPFDTDY GWNVKLGKNV YVNTNCYFMD GGQITIGDNV FIGPNCGFYT ATHPLNFHHR    420
NEGFEKAGPI NIGSNTWFGG HVAVLPGVTI GEGSVIGAGS VVTKDIPPHS LAVGNPCKVV    480
RKIDNEVPSE ALNDETLN                                                 498

SEQ ID NO: 19           moltype = AA   length = 689
FEATURE                 Location/Qualifiers
REGION                  1..689
                        note = Chimeric polypeptide
REGION                  1..293
                        note = MISC_FEATURE - Residues 27-319 of S. aureus alpha
                         hemolysin (residues 27-319 ofSEQ ID NO: 2)
REGION                  294..299
                        note = MISC_FEATURE - GSGGGA linker
REGION                  300..689
                        note = MISC_FEATURE - SEQ ID NO: 8
source                  1..689
                        mol_type = protein
                        organism = synthetic construct
SEQUENCE: 19
ADSDINIKTG TTDIGSNTTV KTGDLVTYDK ENGMLKKVFY SFIDDKNHNK KLLVIRTKGT     60
IAGQYRVYSE EGANKSGLAW PSAFKVQLQL PDNEVAQISD YYPRNSIDTK EYMSTLTYGF    120
NGNVTGDDTG KIGGLIGANV SIGHTLKYVQ PDFKTILESP TDKKVGWKVI FNNMVNQNWG    180
PYDRDSWNPV YGNQLFMKTR NGSMKAADNF LDPNKASSLL SSGFSPDFAT VITMDRKASK    240
QQTNIDVIYE RVRDDYQLHW TSTNWKGTNT KDKWIDRSSE RYKIDWEKEE MTNGSGGGAK    300
VAKQGQYKNQ DPIVLVHGFN GFTDDINPSV LAHYWGGNKM NIRQDLEENG YKAYEASISA    360
FGSNYDRAVE LYYYIKGGRV DYGAAHAAKY GHERYGKTYE GIYKDWKPGQ KVHLVGHSMG    420
GQTIRQLEEL LRNGSREEIE YQKKHGGEIS PLFKGNNDNM ISSITTLGTP HNGTHASDLA    480
GNEALVRQIV FDIGKMFGNK NSRVDFGLAQ WGLKQKPNES YIDYVKRVKQ SNLWKSKDNG    540
FYDLTREGAT DLNRKTSLNP NIVYKTYTGE ATHKALNSDR QKADLNMFFP FVITGNLIGK    600
ATEKEWREND GLVSVISSQH PFNQAYTNAT DKIQKGIWQV TPTKHDWDHV DFVGQDSSDT    660
VRTREELQDF WHHLADDLVK TEKVTDTKQ                                     689

SEQ ID NO: 20           moltype = AA   length = 501
FEATURE                 Location/Qualifiers
REGION                  1..501
                        note = Chimeric polypeptide
REGION                  1..293
                        note = MISC_FEATURE - Residues 27-319 of S. aureus alpha
                         hemolysin (residues 27-319 ofSEQ ID NO: 2)
REGION                  294..299
                        note = MISC_FEATURE - GSGGGA linker
REGION                  300..501
                        note = MISC_FEATURE - (SEQ ID NO: 2
source                  1..501
                        mol_type = protein
                        organism = synthetic construct
SEQUENCE: 20
ADSDINIKTG TTDIGSNTTV KTGDLVTYDK ENGMLKKVFY SFIDDKNHNK KLLVIRTKGT     60
IAGQYRVYSE EGANKSGLAW PSAFKVQLQL PDNEVAQISD YYPRNSIDTK EYMSTLTYGF    120
NGNVTGDDTG KIGGLIGANV SIGHTLKYVQ PDFKTILESP TDKKVGWKVI FNNMVNQNWG    180
PYDRDSWNPV YGNQLFMKTR NGSMKAADNF LDPNKASSLL SSGFSPDFAT VITMDRKASK    240
QQTNIDVIYE RVRDDYQLHW TSTNWKGTNT KDKWIDRSSE RYKIDWEKEE MTNGSGGGGS    300
RIKQHPDVQK VTDATSKVAS KTSAAISNTA SDVKEYVGDK KQDFENKREL KKFAREHDPA    360
YIEKKGEKLA KQNRKDADKM NKILQKNIEK RHKEEQKARE KNEIQRIKDM KKSQKYEVKA    420
GLTPNKLDEK TEKKGDKLAE KNRKEIAKMN KKLQKNIEKR HKEEQKRQQE ADKARIKSFK    480
KYKDYVAKSA SQQNKENNTE A                                             501

SEQ ID NO: 21           moltype = AA   length = 15
FEATURE                 Location/Qualifiers
source                  1..15
                        mol_type = protein
                        organism = Staphylococcus aureus
SEQUENCE: 21
EPINFILKSS TKLKA                                                     15

SEQ ID NO: 22           moltype = AA   length = 15
FEATURE                 Location/Qualifiers
source                  1..15
```

```
                        mol_type = protein
                        organism = Staphylococcus aureus
SEQUENCE: 22
FLKLFRITNP IARGL                                               15

SEQ ID NO: 23           moltype = AA   length = 15
FEATURE                 Location/Qualifiers
source                  1..15
                        mol_type = protein
                        organism = Staphylococcus aureus
SEQUENCE: 23
GLYFVAMNNL KAAGQ                                               15

SEQ ID NO: 24           moltype = AA   length = 15
FEATURE                 Location/Qualifiers
source                  1..15
                        mol_type = protein
                        organism = Staphylococcus aureus
SEQUENCE: 24
IIKKLFRLPA IKRFE                                               15

SEQ ID NO: 25           moltype = AA   length = 15
FEATURE                 Location/Qualifiers
source                  1..15
                        mol_type = protein
                        organism = Staphylococcus aureus
SEQUENCE: 25
ILLGYFVAQR ALVKA                                               15

SEQ ID NO: 26           moltype = AA   length = 15
FEATURE                 Location/Qualifiers
source                  1..15
                        mol_type = protein
                        organism = Staphylococcus aureus
SEQUENCE: 26
KADALKAITA LKLQM                                               15

SEQ ID NO: 27           moltype = AA   length = 15
FEATURE                 Location/Qualifiers
source                  1..15
                        mol_type = protein
                        organism = Staphylococcus aureus
SEQUENCE: 27
KHQIRMLSIP RDTIS                                               15

SEQ ID NO: 28           moltype = AA   length = 15
FEATURE                 Location/Qualifiers
source                  1..15
                        mol_type = protein
                        organism = Staphylococcus aureus
SEQUENCE: 28
KRIFKMSPIH HHFEL                                               15

SEQ ID NO: 29           moltype = AA   length = 15
FEATURE                 Location/Qualifiers
source                  1..15
                        mol_type = protein
                        organism = Staphylococcus aureus
SEQUENCE: 29
KTLFVALNNK ARIPE                                               15

SEQ ID NO: 30           moltype = AA   length = 15
FEATURE                 Location/Qualifiers
source                  1..15
                        mol_type = protein
                        organism = Staphylococcus aureus
SEQUENCE: 30
LDQIIAQANL RLATM                                               15

SEQ ID NO: 31           moltype = AA   length = 15
FEATURE                 Location/Qualifiers
source                  1..15
                        mol_type = protein
                        organism = Staphylococcus aureus
SEQUENCE: 31
LMGIRAFRKL LPNIP                                               15

SEQ ID NO: 32           moltype = AA   length = 15
FEATURE                 Location/Qualifiers
```

```
source                         1..15
                               mol_type = protein
                               organism = Staphylococcus aureus
SEQUENCE: 32
MHFIAISINH RTADV                                                          15

SEQ ID NO: 33                  moltype = AA  length = 15
FEATURE                        Location/Qualifiers
source                         1..15
                               mol_type = protein
                               organism = Staphylococcus aureus
SEQUENCE: 33
QRHFQIGYNR AARII                                                          15

SEQ ID NO: 34                  moltype = AA  length = 15
FEATURE                        Location/Qualifiers
source                         1..15
                               mol_type = protein
                               organism = Staphylococcus aureus
SEQUENCE: 34
SSNVYMFKTA LKLAG                                                          15

SEQ ID NO: 35                  moltype = AA  length = 15
FEATURE                        Location/Qualifiers
source                         1..15
                               mol_type = protein
                               organism = Staphylococcus aureus
SEQUENCE: 35
STFIYKIANE RLFSR                                                          15

SEQ ID NO: 36                  moltype = AA  length = 15
FEATURE                        Location/Qualifiers
source                         1..15
                               mol_type = protein
                               organism = Staphylococcus aureus
SEQUENCE: 36
SVTIIKSLQA IRVPF                                                          15

SEQ ID NO: 37                  moltype = AA  length = 15
FEATURE                        Location/Qualifiers
source                         1..15
                               mol_type = protein
                               organism = Staphylococcus aureus
SEQUENCE: 37
TSQFHVLRAL RLAQK                                                          15

SEQ ID NO: 38                  moltype = AA  length = 15
FEATURE                        Location/Qualifiers
source                         1..15
                               mol_type = protein
                               organism = Staphylococcus aureus
SEQUENCE: 38
VLFYLRSNKR QIIEK                                                          15

SEQ ID NO: 39                  moltype = AA  length = 15
FEATURE                        Location/Qualifiers
source                         1..15
                               mol_type = protein
                               organism = Staphylococcus aureus
SEQUENCE: 39
WKRIGRLKSI PIFMY                                                          15

SEQ ID NO: 40                  moltype = AA  length = 15
FEATURE                        Location/Qualifiers
source                         1..15
                               mol_type = protein
                               organism = Staphylococcus aureus
SEQUENCE: 40
YFRFQYFNPL KSERY                                                          15

SEQ ID NO: 41                  moltype = AA  length = 175
FEATURE                        Location/Qualifiers
REGION                         1..175
                               note = Multiple linked epitopes
source                         1..175
                               mol_type = protein
                               organism = synthetic construct
SEQUENCE: 41
VLFYLRSNKR QIIEKGPGPG EPINFILKSS TKLKAGPGPG GLYFVAMNNL KAAGQGPGPG         60
```

```
KADALKAITA LKLQMGPGPG KHQIRMLSIP RDTISGPGPG LDQIIAQANL RLATMGPGPG   120
QRHFQIGYNR AARIIGPGPG SSNVYMFKTA LKLAGGPGPG YFRFQYFNPL KSERY       175

SEQ ID NO: 42           moltype = AA  length = 215
FEATURE                 Location/Qualifiers
REGION                  1..215
                        note = Multiple linked epitopes
source                  1..215
                        mol_type = protein
                        organism = synthetic construct
SEQUENCE: 42
TSQFHVLRAL RLAQKGPGPG FLKLFRITNP IARGLGPGPG IIKKLFRLPA IKRFEGPGPG   60
ILLGYFVAQR ALVKAGPGPG KRIFKMSPIH HHFELGPGPG KTLFVALNNK ARIPEGPGPG  120
LMGIRAFRKL LPNIPGPGPG MHFIAISINH RTADVGPGPG STFIYKIANE RLFSRGPGPG  180
SVTIIKSLQA IRVPFGPGPG WKRIGRLKSI PIFMY                            215

SEQ ID NO: 43           moltype = AA  length = 453
FEATURE                 Location/Qualifiers
REGION                  1..453
                        note = Scaffold protein with multiple inserted epitopes
source                  1..453
                        mol_type = protein
                        organism = synthetic construct
SEQUENCE: 43
MSSLPVGPVA WSDGMLIETQ HFQQLKRIFK MSPIHHHFEL SNHGWGFTLL DLDQDGLGLG   60
RLMGIRAFRK LLPNIPFSLP SDDPLPPPLE TELAQAGDIA CLALQAARTG GPEMAFGDVE  120
LASRYRAVST EVPDLAVGLD APGTPFLKLF RITNPIARGL WKRIGRLKSI PIFMYRVAGR  180
NASRTVSLDP RFIPPKTLFV ALNNKARIPE ELQSTSVTII KSLQAIRVPF TGGGVADLIE  240
ILLGYFVAQR ALVKANLDAF DPLPPMHFIA ISINHRTADV VLPGVDEELA DRELGYDHDD  300
LQTSFTSQFH VLRALRLAQK ETPVLPLRFE DRGDQVHICI VDKQWNLKKL IFAFSIIKKL  360
FRLPAIKRFE TKLGAVEQIQ KLVDLQLPGA RLNALPNPPR QIPYYAQSTY FEVESTDPFW  420
KQTLAGSAMA LRIVGDFPST FIYKIANERL FSR                              453

SEQ ID NO: 44           moltype = AA  length = 453
FEATURE                 Location/Qualifiers
REGION                  1..453
                        note = Scaffold protein with multiple inserted epitopes
source                  1..453
                        mol_type = protein
                        organism = synthetic construct
SEQUENCE: 44
MSSLPVGPVA WSDGMLIETQ HFQQLERHLA HQASLRLGQT SNHGWGFTLL DLDQDGLGLG   60
RLGLRSSNVY MFKTALKLAG SDDPLPPPLE TELAQAGDIA CLALQAARTG GPEMAFGDVE  120
LASRYRAVST EVPDLAVGLD APGTPRRLTI ETGQLVTRLC WKSQVLFYLR SNKRQIIEKR  180
NASRTVSLDP RFIPPEPINF ILKSSTKLKA ELQSTQRHFQ IGYNRAARII TGGGVADLIE  240
LLLRQLDQII AQANLRLATM DPLPPGLYFV AMNNLKAAGQ VLPGVDEELA DRELGYDHDD  300
LQTSFEPLAM MLRQALARVI ETPVLPLRFE DRGDQVHICI VDKQWNLKKL IFAFSKADAL  360
KAITALKLQM TKLGAVEQIQ KLVDLQLPGA RLNALPNPPR QIPYYAQSTY FEVESKHQIR  420
MLSIPRDTIS LRIVGDYFRF QYFNPLKSER YVA                              453

SEQ ID NO: 45           moltype = AA  length = 5
FEATURE                 Location/Qualifiers
REGION                  1..5
                        note = Peptide linker
source                  1..5
                        mol_type = protein
                        organism = synthetic construct
SEQUENCE: 45
GPGPG                                                               5

SEQ ID NO: 46           moltype = DNA  length = 1854
FEATURE                 Location/Qualifiers
misc_feature            1..1854
                        note = Recombinant DNA encoding chimeric protein
source                  1..1854
                        mol_type = other DNA
                        organism = synthetic construct
SEQUENCE: 46
atggatattg gtaaaaaaca tgtaattcct aaaagtcagt accgacgtaa gcgtcgtgaa   60
ttcttccaca acgaagacag agaagaaaat ttaaatcaac atcaagataa acaaatatat  120
gataatacaa catcaaaaaa agcagataag caaatacata aagattcaat tgataagcac  180
gaacgtttta aaaatagttt atcatcgcat ttagaacaga gaaaccgtga tgttaatgag  240
aataaagctg agaaaagtaa aagtaatcag gatagtaagt cagcatataa cagagatcat  300
tatttaacag acgatgtatc taaaaaacaa aattcattag attcagtgga ccaagataca  360
gagaaatcaa aatattatga gcaaaattct gaagcgactt tatcaactaa atcaaccgat  420
aaagtagaat caactgaaat gagaaagcta agttcagata aaaacaaagt tggtcatgaa  480
gagcaacatg tactttctaa accttcagaa catgataaag agactagaat tgattctgag  540
tcttcaagaa ctgattcaga cagctcgatg cagacagaga aaataaaaaa agacagttca  600
gatggaaata aaagtagtaa tctgaaatct gaagtaatat cagacaaatc aaatacagta  660
```

```
ccaaaattgt cggaatctga tgatgaagta aataatcaga agccattaac tttaccggaa    720
gaacagaaat tgaaaagaca gcaaagtcaa aatgagcaaa caaaaaccta tacatatggt    780
gatagcgaac aaaatgacaa gtctaatcat gaaaatgatt taagtcatca tataccatcg    840
ataagtgatg ataaagataa cgtcatgaga gaaaatcata ttgttgacga taatcctgat    900
aatgatatca atacaccatc attatcaaaa acagatgacg atcgaaaact tgatgaaaaa    960
attcatgttg aagataaaca taaacaaaat gcagactcgt ctgaaacggt gggatatcaa   1020
agtcagtcaa ctgcatctca tcgtagcact gaaaaaagaa atatttctat taatgaccat   1080
gataaattaa acggtcaaaa aacaaataca aagacatcgg caaataataa tcaaaaaaag   1140
gctacatcaa aattgaacaa agggcgcgct acgaataata attatagtga cattttgaaa   1200
aagttttgga tgatgtattg gcctaaaggt tctggcggag gggctaaacg tatcaaacaa   1260
catccggacg tacaaaaagt tacagatgct acaagtaaag ttgcttcaaa acatctgca    1320
gcaatcagta acacagcgag tgatgttaaa gaatatgtcg gcgataaaaa acaagatttt   1380
gaaaataagc gtgaacttaa aaagtttgct agagaacatg atcctgccta tattgagaaa   1440
aaaggcgaaa aattagctaa acaaaatcgt aaagacgctg ataaaatgaa taaaatactt   1500
caaaaaaata tcgaaaagcg tcataaagaa gagcaaaaag cccgcgaaaa gaatgaaata   1560
caacgtatta aagatatgaa aaagtcacaa aaatacgaag taaagcagg cttaacacct   1620
aataaattag atgagaaaac tgagaaaaaa ggcgataaac tagctgaaaa aaatcgcaaa   1680
gaaatcgcta aaatgaataa aaagttcaa aaaaatattg aaaaacgaca caagaagaa   1740
caaaaacgcc aacaagaagc tgataaagca cgcatcaagt catttaaaaa atataaagat   1800
tatgttgcca aaagcgcctc tcaacaaaat aaagaaaaca atacagaggc ataa         1854

SEQ ID NO: 47           moltype = DNA  length = 2394
FEATURE                 Location/Qualifiers
misc_feature            1..2394
                        note = Recombinant DNA encoding chimeric protein
source                  1..2394
                        mol_type = other DNA
                        organism = synthetic construct
SEQUENCE: 47
atgactgaaa aagaaaaaat gttagcagaa aaatggtacg atgcaaactt tgatcaagac     60
ttaatcaatg aacgtgcacg agcgaaagat atttgctttg aattaaatca tacaaagccg    120
agtgacaaaa ataaaagaaa ggaattaatc gatgaattat ttcaaacaac aacagacaat    180
gtaagtattt cgattccttt tgatacagat tatggttgga acgttaaact aggaaaaaat    240
gtctatgtaa acaccaattg ttattttatg gatggtggac agattacaat tggcgataat    300
gttttatag gacctaattg tggattctac acagcaacac atccacttaa ttttcatcat    360
agaaatgaag gatttgaaaa agcaggacca attaatattg gcagtaatac ttggttttggc   420
ggacatgtag ccgtgcttcc gggagtgacg attggagaag gcagtgtgat tggtgctggt    480
agtgttgtca ccaaagatat tccgccacac agtttagcgg ttggaaaccc ttgtaaagtc    540
gttcgtaaaa ttgataatga ggtaccatca gaagcattga acgatgaaac actaaatggt    600
tctggcggag gggctgatac acctcaaaaa gatactacag ctaagacaac atctcatgat    660
tcaaaaaaat ctaatgacga tgaaacttct aaggatacta caagtaaaga tattgataaa    720
gcagacaaca ataatacaag taccaagac aataacgaca aaaaatttaa aactatagac    780
gacagcactt cagactctaa caatatcatt gattttattt ataagaattt accacaaacc    840
aatataaaacc aattgctaac caaaaataaa tacgataaa attactcatt aacaacttta   900
atccaaaaccc tattcaattt aaaattcggat atttctgatt acgaacaacc tcgtaatggc    960
gaaaagtcaa caaatgattc gaataaaaac agtgacaata gcatcaaaaa tgacactgat  1020
acgcaatcat ctaaacaaga taagcagac aatcaaaaag caccttaaaatc aaacaataca  1080
aaaccaagta catctaataa gcaaccaaat tcgccaaagc caacacaacc taatcaatca   1140
aatagtcaac cagcaagtga cgataaagca aatcaaaaat cttcatcgaa agataatcaa  1200
tcaatgtcag attcggcttt agactctatt ttggatcaat acagtgaaga tgcaaagaaa   1260
acacaaaag attatgcatc tcaatctaaa aaagacaaaa atgaaaaatc taatacaaag  1320
aatccacagt taccaacaca agatgaattg aaacataaat ctaaacctgc tcaatcattc   1380
aataacgatg ttaatcaaaa ggatacacgt gcaacatcat tattcgaaac agatcctagt   1440
atatctaaca atgatgatag cggacaattt aacgttgttg actcaaaaga tacacgtcaa   1500
tttgtcaaat caattgctaa agatgcacat acgcattgtc aagataacga tatttatgcg   1560
tctgtcatga ttgcccaagc aatcttagaa tctgactcag gtcgtagtgc tttagctaag   1620
tcaccaaacc ataatttatt cggtatcaaa ggtgcttttg aagggaattc tgttccttt    1680
aacacattag aagctgatgg taataaattg tatagtatta atgctggatt ccgaaaatat   1740
ccaagcacga aagaatcact aaaagattac tctgaccttta ttaaaaatgg tattgatgc    1800
aatcgaacaa tttataaacc aacatggaaa tcggaagccg attcttataa agatgcaaca   1860
tcacacttat ctaaaacata tgctacagat ccaaactatg ctaagaaatt aaacagtatt   1920
attaaacact atcaattaac tcagtttgac gatgaacgca tgccagattt agataaatat   1980
gaacgttcta tcaaggatta tgatgattca tcagatgaat tcaaaccttt ccgtgaggta   2040
tctgatagta tgccatatcc acatgtgtcaa tgtacttggt acgtatataa ccgtatgaaa   2100
caatttggta catctatctc aggtgattta ggtgatgcac ataattggaa taatcgagct   2160
caataccgtg atactcaagt aagtcataca ccaaaacgtc atgctgctgt tgtatttgag   2220
gctggacaat tggtgcaga tcaacattac ggtcatgtag catttgttga aaaagttaac   2280
agtgatggtt ctatcgttat ttcagaatcc aatgttaaag gattaggtat catttctcat   2340
agaactatca atgcagctgc cgctgaagaa ttatcatata ttacaggtaa ataa         2394

SEQ ID NO: 48           moltype = DNA  length = 2445
FEATURE                 Location/Qualifiers
misc_feature            1..2445
                        note = Recombinant DNA encoding chimeric protein
source                  1..2445
                        mol_type = other DNA
                        organism = synthetic construct
SEQUENCE: 48
attgattcaa aaaataaacc agctaattct gatattaaat ttgaggtgac tcaaaagagt     60
```

```
gatgcggtca aagcattaaa agaattgcct aaatccgaaa atgtaaaaaa tatttatcaa    120
gattacgctg ttactgatgt aaaaactgat aaaaaaggat ttacgcatta tacattgcaa    180
ccgagtgttg atggtgttca tgcacctgac aaagaagtga agtcacacgc agacaaatca    240
ggaaaagtcg ttttaatcaa tggggatact gatgcgaaga agtaaagcc aacgaataaa     300
gtgacattaa gtaaagatga cgcagccgac aaagcattta aagcagttaa gattgataag    360
aataaagcga aaaatcttaa agataaagtc attaaagaaa acaaagttga aatcgatggt    420
gacagtaata aatacgttta taatgttgag ttaattacag tgacaccaga aatttcacat    480
tggaaagtta aaattgatgc tcaaactggc gaaattttag aaaaaatgaa cttagttaaa    540
gaagctgcag aaactggtaa aggaaaaggt gtacttggcg atacaaaaga tatcaatatc    600
aatagtattg acggtggatt tagcctagaa gatttaacgc atcaaggtaa attatcagca    660
tttagctta atgatcaaac aggtcaagca acattgatta ctaatgaaga tgaaaacttc    720
gtaaaagatg agcaacgtgc tggcgtagat gcaaattatt acgctaaaca aacatatgat    780
tattcaaaag acacatttgg tcgtgaatca tatgacaacc aaggtagtcc aattgtttca    840
ttaacgcatg ttaataacta cggtggtcaa gataacagaa ataatgccgc atggatcggt    900
gacaaaatga tctatggtga tggtgatggt cgcacattca caagtttatc gggtgcaaat    960
gacgtagtag cacacgaatt aacacacggt gtgacacaag agacagcgaa cttagaaatt    1020
aaggaccagt caggcgctct aaatgaaagc ttttcagatt tttttggata ctttgtagat    1080
gacgaggatt tcttaatggg tgaagatgtc tacacacctg gaaaagaggg agacgcttta    1140
cgcagcatgt caaacccaga acaatttggt caaccagctc atatgaaaga ctatgtattc    1200
actgaaaaag ataatggtgg cgtacatacg aattctggtt ctggcggagg ggctggaagt    1260
ggtgggggcg ccaaagttgc caaacaaggg cagtataaaa atcaagaccc tatcgtgtta    1320
gtgcatggtt tcaatggatt tacagtatgat attaatcctt cagtgttagc tcattattgg    1380
ggcggtaata aaatgaacat tcgccaagat ttagaagaaa atggttacaa agcttatgaa    1440
gcaagtataa gtgcttttgg aagtaactat gaccgcgcag ttgaacttta ttattataatc    1500
aaaggcggtc gtgtagatta tggtgcagca catgcagcaa aatatggaca tgaacgttat    1560
ggaaaaacat acgaaggaat ttacaaagac tggaaaccaa gacgaaaggt acacctagtt    1620
ggacatagta tgggtggtca aacgatacgt caactagaag aattactgcg taatggtagt    1680
cgtgaagaaa tagagtatca aaagaaacat ggtggcgaaa tttctccact attcaaaggt    1740
aataatgaca atatgatttc atcaattact actttaggaa cgccacataa tggaacgcat    1800
gcttcagatt tagctggtaa tgaagcttta gtgagacaaa ttgtatttga tatcggtaaa    1860
atgtttggta ataaaaactc tagagtagac ttcgggttgg ctcaatgggg tctaaaacag    1920
aagccaaatg aatcatacat tgattatgtc aaacgcgtta aacactcaa tttatggaaa    1980
tcaaaagata atggatttta cgatctgacg cgtgagggtg caacgatttt aaatcgtaaa    2040
acgtcgttga accctaacat tgtgtataaa acatacgtg gtgaagcaac gcacaaagca    2100
ttaaatagcg atagacaaaa agcagactta aatatgtttt tcccatttgt gattactggt    2160
aacttaatcg gtaaagctac tgaaaaagaa tggcgagaaa acgatggttt agtatccgtt    2220
atttcttctc agcatccatt taatcaagct tatacaaatg cgacggataa aattcaaaaa    2280
ggcatttggc aagtaacgcc tacaaaacat gattgggatc atgttgattt tgtcggacaa    2340
gatagttctg atacagtgcg cacaagagaa gaattacaag attttttggca tcatttagca    2400
gacgatttag tgaaaactga aaaggtgact gatactaagc aataa                    2445
SEQ ID NO: 49      moltype = DNA  length = 2967
FEATURE            Location/Qualifiers
misc_feature       1..2967
                   note = Recombinant DNA encoding chimeric protein
source             1..2967
                   mol_type = other DNA
                   organism = synthetic construct
SEQUENCE: 49
gatacacctc aaaaagatac tacagctaag acaaacatctc atgattcaaa aaaatctaat    60
gacgatgaaa cttctaagga tactacaagt aaagatattg ataagcgaca caacaataat    120
acaagtaacc aagacaataa cgacaaaaaa tttaaaacta tagacgacag cacttcagac    180
tctaacaata tcattgattt tatttataag aatttaccac aaaccaatat aaaccaattg    240
ctaaccaaaa ataaatacga tgataattac tcattaacaa ctttaatcca aaacctattc    300
aatttaaatt cggatatttc tgattacgaa caacctcgta atggcgaaaa gtcaacaaat    360
gattcgaata aaaacagtga caatagcatc aaaaatgaca ctgatacgca atcatctaaa    420
caagataaag cagacaatca aaaagcaccct aaatcaaaca atacaaaacc aagtacatct    480
aataagcaac caaattcgcc aaagccaaca caacctaatc aatcaaatag tcaaccagca    540
agtgacgatta aagcaaatca aaaatcttca tcgaaagata atcaatcaat gtcagattcg    600
gctttagact ctatttttgga tcaatacagt gaagatgcaa agaaaacaca aaaagattat    660
gcatctcaat ctaaaaaaga caaaaatgaa aaatctaata caagaatccc acagttacca    720
acacaagatg aattgaaaca taaatctaaa cctgctcaat cattcaataa cgatgttaat    780
caaaaggata cacgtgcaac atcattattc gaaacagatc ctagtatatc taacaatgat    840
gatagcggac aatttaacgt tgttgactca aagtaccgct caatttgt caaatcaatt    900
gctaaagatg cacatcgcat tggtcaagat aacgatattt atgcgtctgt catgattgcc    960
caagcaatct tagaatctga ctcaggtcgt agtgctttag ctaagtcacc aaaccataat    1020
ttattcggta tcaaggtgtg ttttgaaggg aattctgttc cttttaacac attagaagct    1080
gatggtaata aattgtatag tattaatgct ggattccgaa aatatccaag cacgaaagaa    1140
tcactaaaag attactctga ccttattaaa aatggtattg atggcaatcg aacaatttat    1200
aaaccaacat ggaaatcgga agccgattct tataaagatg caacatcaca cttatctaaa    1260
acatatgcta cagatccaaa ctatgctaag aaattaaaca gtattattaa acactatcaa    1320
ttaactcagt ttgacgatga acgcatgcca gatttagata aatatgaacg ttctatcaag    1380
gattatgatg attcatcaga tgaattcaaa cctttccgtt aggtatctga tagtatgcca    1440
tatccacatg gtcaagtgta ttggtacgta taaccgtata gaaacaatt tggtacatct    1500
atctcaggtc atttaggtga tgcacataat tggaataatc gagctcaata ccgtgattat    1560
caagtaagtc atacaccaaa acgtcatgct gctgttgtat ttgaggctgg acaatttggt    1620
gcagatcaac attacggtca tgtagcattt gttgaaaaag ttaacagtga tggttctatc    1680
gttatttcag aatccaatgt taaaggatta ggtatcattt tcatagaac tatcaatgca    1740
gctgccgctg aagaattatc atatattaca ggtaaaggtt ctggcggagg ggctaaagtt    1800
```

-continued

```
gccaaacaag ggcagtataa aaatcaagac cctatcgtgt tagtgcatgg tttcaatgga    1860
tttacagatg atattaatcc ttcagtgtta gctcattatt ggggcggtaa taaaatgaac    1920
attcgccaag atttagaaga aaatggttac aaagcttatg aagcaagtat aagtgctttt    1980
ggaagtaact atgaccgcgc agttgaactt tattattata tcaaaggcgg tcgtgtagat    2040
tatgtgtgcag cacatgcagc aaaaatatgga catgaacgt atggaaaaac atacgaagga    2100
atttacaaag actggaaacc aggacagaag gtacacctag ttggacatag tatgggtggt    2160
caaacgatac gtcaactaga agaattactg cgtaatggta gtcgtgaaga aatagagtat    2220
caaaagaaac atggtggcga aatttctcca ctattcaaag gtaataatga caatatgatt    2280
tcatcaatta ctactttagg aacgccacat aatggaacgc atgcttcaga tttagctggt    2340
aatgaagctt tagtgagaca aattgtattt gatatcggta aaatgtttgg taataaaaac    2400
tctagagtag acttcgggtt ggctcaatgg ggtctaaaac agaagccaaa tgaatcatac    2460
attgattatg tcaaacgcgt taaacaatct aatttatgga aatcaaaaga taatggatt     2520
tacgatctga cgcgtgaggg tgcaacagat ttaaatcgta aaacgtcgtt gaaccctaac    2580
attgtgtata aaacatacac tggtgaagca acgcacaaag cattaaatag cgatagacaa    2640
aaagcagact taaatatgtt tttcccattt gtgattactg gtaacttaat cggtaaagct    2700
actgaaaaag aatggcgaga aacgatggt ttagtatccg ttatttcttc tcagcatcca     2760
tttaatcaag cttatacaaa tgcgacggat aaaattcaaa aaggcatttg gcaagtaacg    2820
cctacaaaac atgattggga tcatgttgat tttgtcggac aagatagttc tgatacagtg    2880
cgcacaagag aagaattaca agatttttgg catcatttag cagacgattt agtgaaaact    2940
gaaaaggtga ctgatactaa gcaataa                                        2967

SEQ ID NO: 50        moltype = DNA  length = 2169
FEATURE              Location/Qualifiers
misc_feature         1..2169
                     note = Recombinant DNA encoding chimeric protein
source               1..2169
                     mol_type = other DNA
                     organism = synthetic construct
SEQUENCE: 50
gcaaaggata acttaaatgg agaaaagcca acgactaatt tgaatcataa tgtaacttca    60
ccatcagtaa atagtgaaat gaataataat gagactggga caccctcacga atcaaatcaa   120
gctggtaatg aaggaactgg ttcgaatagt cgtgatgcta atcctgattc gaataatgtg    180
aagccagact caaacaacca aaacccaagt ccagattcaa aacctgaccc aaataaccca    240
aacccaggtc cgaatccgaa gccagaccca gataagccga aaccaaatcc ggaaccaaag    300
ccagacccaa agccagaccc agataaacca aagccaaatc cggatccaaa gccagaccca    360
gataagccga aaccaaatcc ggatccaaaa ccagatccag acaaaccgaa gccaaatccg    420
gatccaaaac cagatccaaa tccgaatcca aaaccagacc ctaataagcc aaatccaaat    480
ccgtctccaa atcccaatca acctggggat tccaatcaat ctggtggctc gaaaaatggg    540
gggacatgga acccaaatgc ttcagatgga tctaatcaag gtcaatggca accaagtgga    600
aatcaaggaa actcacaaaa tcctactggt aatgattttg tatcccaacg atttttagcc    660
ttggcgaatg gggcttacaa gtataatccg tatattttaa atcaaattaa tcaattgggg    720
aaagaatatg gtgaggtaac tgatgaagat atctacaata tcatccgtaa acaaaacttc    780
agcggaaaatg catatttaaa tggattacaa cagcaatcga attactttag attccaatat    840
ttcaatccat tgaaatcaga aaggtactat cgtaatttag atgaacaagt actcgcatta    900
attactggcg aaattggatc aatgccagat ttgaaaaagc ccgaagataa gccggattca    960
aaacaacgtt catttgagcc tcatgaaaaa gatgatttta cagttgtaaa aaacaagaa    1020
gataataaga aagtgcgtc aactgcatat agtggtctg gcggagggg tggattttta     1080
aacaaatcta aaaatgagca agcggcatta aaggcacaac aagcagcgat aaaagaagaa   1140
gcaagtgcaa ataatttaag tgatacatca caagaagcac aagagattca agaagctaaa   1200
agagaagcac aagcagaagc ggataaaagt gtggctgtat caaataaaga atcaaaagca   1260
gtggcattga aagcacaaca agcagcgata aaagaagaa caagtgcaaa taatttgat    1320
gatacatcac aagaggcaca agagattcaa gaagctaaaa agaagcaca agcagaaaca    1380
gataaaagtg cagctgtatc aaatgaagaa ccaaaagcag tggcattgaa agcacaacaa   1440
gcagcgataa agaagaagc aagtgcaaat aatttaagtg atatatcaca agaggcacaa   1500
gaggttcaag aagctaaaaa gaagcacaa gcagagaaaa acagtgacac attaactaaa    1560
gatgcaagtg cagcaaaggt agaagtatca aaaccagagt cacaagctga aagattagca   1620
aacgctgcaa aacagaagca agctaaatta acaccaggtt caaaagagag tcaattaact   1680
gaagcgttat ttgcagaaaa accagttgct aaaaatgact tgaaagaaat tcctcaatta   1740
gttactaaaa agaatgatgt atcagagaca gagacgttta atatagataa taaagacact   1800
gttaaacaaa aagaagctaa atttgaaaat ggtgttatta cacgtaaagc tgatgaaaaa   1860
acaactaata atacagctgt tgacaagaaa tcaggtaaac aatctaaaaa acaacacct    1920
tcaaataaac gaaatgcatc aaaagcatct acaaataaaa cttcaggtca gaaaagcaa    1980
cataataaga aatcatcaca aggtgcaaag aaacaaagta gttcaagtaa gtcaactcaa   2040
aagaataatc aaactagtaa taagaattca aaaacaacaa atgctaaatc atccaatgca   2100
tcaaaaacgc caaatgctaa agttgagaaa gctaaaagta aaatagagaa acgtacattc   2160
aatgactaa                                                            2169

SEQ ID NO: 51        moltype = DNA  length = 1863
FEATURE              Location/Qualifiers
misc_feature         1..1863
                     note = Recombinant DNA encoding chimeric protein
source               1..1863
                     mol_type = other DNA
                     organism = synthetic construct
SEQUENCE: 51
atggatattg gtaaaaaaca tgtaattcct aaaagtcagt accgacgtaa gcgtcgtgaa    60
ttcttccaca acgaagacag agaagaaaat ttaaatcaac atcaagataa acaaaatata    120
gataatacaa catcaaaaaa agcagataag caaaatacata aagattcaat tgataagcac    180
gaacgtttta aaaatagttt atcatcgcat ttagaacaga gaaaccgtga tgttaatgag    240
```

```
aataaagctg aagaaagtaa aagtaatcag gatagtaagt cagcatataa cagagatcat   300
tatttaacag acgatgtatc taaaaaacaa aattcattag attcagtgga ccaagataca   360
gagaaatcaa aatattatga gcaaaattct gaagcgactt tatcaactaa atcaaccgat   420
aaagtagaat caactgaaat gagaaagcta agttcagata aaaacaaagt tggtcatgaa   480
gagcaacatg tactttctaa accttcagaa catgataaag agactagaat tgattctgag   540
tcttcaagaa ctgattcaga cagctcgatg cagacagaga aaataaaaaa agacagttca   600
gatgggaaata aaagtagtaa tctgaaatct gaagtaatat cagacaaatc aaatacagta   660
ccaaaattgt cggaatctga tgatgaagta aataatcaga agccattaac tttaccggaa   720
gaacagaaat tgaaaagaca gcaaagtcaa aatgagcaaa caaaaaccta tacatatggt   780
gatagcgaac aaaatgacaa gtctaatcat gaaaatgatt taagtcatca tataccatgg   840
ataagtgatg ataaagataa cgtcatgaga gaaaatcata ttgttgacga taatcctgat   900
aatgatatca atacaccatc attatcaaaa acagatgacg atcgaaaact tgatgaaaaa   960
attcatgttg aagataaaca taaacaaaat gcagactcgt ctgaaacggt gggatatcca  1020
agtcagtcaa ctgcatctca tcgtagcact gaaaaaagaa atattctat taatgaccat  1080
gataaattaa acggtcaaaa aacaaataca aagacatcgg caaataataa tcaaaaaaag  1140
gctacatcaa aattgaacaa agggcgcgct acgaataata attatagtga catttttgaaa  1200
aagttttgga tgatgtattg gcctaaaggt tctggcggag gggctggaag tggtgggggc  1260
gccatgactg aaaaagaaaa aatgttagca gaaaaatggt acgatgcaaa ctttgatcaa  1320
gacttaatca atgaacgtgc acgagcgaaa gatatttgct ttgaattaaa tcatacaaag  1380
ccgagtgaca aaaataaaag aaaggaatta atcgatgaat tatttcaaac aacaacagac  1440
aatgtaagta tttcgattcc ttttgataca gattatggtt ggaacgttaa actaggaaaa  1500
aatgtctatg taaacaccaa ttgttatttt atggatggtg gacagattac aattggcgat  1560
aatgtttta taggacctaa ttgtggattc tacacagcaa cacatccact taattttcat  1620
catagaaatg aaggatttga aaaagcagga ccaattaata ttggcagtaa tacttggttt  1680
ggcggacatg tagccgtgct tccgggagtg acgattgagg aaggcagtgt gattggtgct  1740
ggtagtgttg tcaccaaaga tattccgcca cacagtttag cggttggaaa cccttgtaaa  1800
gtcgttcgta aaattgataa tgaggtacca tcagaagcat tgaacgatga aacactaaat  1860
tag                                                                1863

SEQ ID NO: 52         moltype = DNA  length = 1497
FEATURE               Location/Qualifiers
misc_feature          1..1497
                      note = Recombinant DNA encoding chimeric protein
source                1..1497
                      mol_type = other DNA
                      organism = synthetic construct
SEQUENCE: 52
gcagattctg atattaatat taaaaccggt actacagata ttggaagcaa tactacagta    60
aaaacaggtg atttagtcac ttatgataaa gaaaatggca tgttaaaaaa agtatttat   120
agttttatcg atgataaaaa tcataataaa aaactgctag ttattagaac gaaaggtacc   180
attgctggtc aatatagagt ttatagcgaa gaaggtgcta acaaaagtgg tttagcctgg   240
ccttcagcct ttaaggtaca gttgcaacta cctgataatg aagtagctca aatatctgat   300
tactatccaa gaaattcgat tgataaaaa gagtatatga gtactttaac ttatggattc   360
aacggtaatg ttactggtga tgatacagga aaaattggcg gccttattgg tgcaaatgtt   420
tcgattggtc atacactgaa atatgttcaa cctgatttca aaacaatttt agagagccca   480
actgataaaa aagtaggctg gaaagtgata tttaacaata tggtgaatca aaattgggga   540
ccatatgata gagattcttg gaacccggta tatggcaatc aacttttcat gaaaactaga   600
aatggctcta tgaaagcagc agataacttc cttgatccta caaagcaag ttctctatta   660
tcttcagggt tttcaccaga cttcgctaca gttattacta tggatagaaa agcatccaaa   720
caacaaacaa atatagatgt aatatacgaa cgagttcgtg atgactacca attgcactgg   780
acttcaacaa attggaaagg taccaatact aaagataaat ggatagatcg ttcttcagaa   840
agatataaaa tcgattggga aaagaagaa atgacaaatg ttctggcgg aggggctatg   900
actgaaaaag aaaaaaatgtt agcagaaaaa tggtacgatg caaactttga tcaagactta   960
atcaatgaac gtgcacgagc gaaagatatt tgctttgaat aaatcatac aaagccgagt  1020
gacaaaaata aagaaagga attaatcgat gaattatttc aaacaacaac agacaatgta  1080
agtatttcga ttccttttga tacagattat ggttgaacg ttaaactagg aaaaaatgtt  1140
tatgtaaaca ccaattgtta ttttatggat ggtggacaga ttacaattgg cgataatgtt  1200
tttataggac taattgtgg attctacaca gcaacacatc cacttaatt tcatcataga  1260
aatgaaggat ttgaaaaagc aggaccaatt aatattggca gtaatacttg gtttggcgga  1320
catgtagccg tgcttccggg agtgacgatt ggagaaggca gtgtgattgg tgctggtagt  1380
gttgtcacca aagatattcc gccacacagt ttagcggttg gaaacccttg taagtcgtt  1440
cgtaaaattg ataatgaggt accatcagaa gcattgaacg atgaaacact aaattag     1497

SEQ ID NO: 53         moltype = DNA  length = 2070
FEATURE               Location/Qualifiers
misc_feature          1..2070
                      note = Recombinant DNA encoding chimeric protein
source                1..2070
                      mol_type = other DNA
                      organism = synthetic construct
SEQUENCE: 53
gcagattctg atattaatat taaaaccggt actacagata ttggaagcaa tactacagta    60
aaaacaggtg atttagtcac ttatgataaa gaaaatggca tgttaaaaaa agtatttat   120
agttttatcg atgataaaaa tcataataaa aaactgctag ttattagaac gaaaggtacc   180
attgctggtc aatatagagt ttatagcgaa gaaggtgcta acaaaagtgg tttagcctgg   240
ccttcagcct ttaaggtaca gttgcaacta cctgataatg aagtagctca aatatctgat   300
tactatccaa gaaattcgat tgataaaaa gagtatatga gtactttaac ttatggattc   360
aacggtaatg ttactggtga tgatacagga aaaattggcg gccttattgg tgcaaatgtt   420
tcgattggtc atacactgaa atatgttcaa cctgatttca aaacaatttt agagagccca   480
```

-continued

```
actgataaaa aagtaggctg gaaagtgata tttaacaata tggtgaatca aaattgggga    540
ccatatgata gagattcttg gaacccggta tatggcaatc aacttttcat gaaaactaga    600
aatggctcta tgaaagcagc agataacttc cttgatccta acaaagcaag ttctctatta    660
tcttcagggt tttcaccaga cttcgctaca gttattacta tggatagaaa agcatccaaa    720
caacaaacaa atatagatgt aatatacgaa cgagttcgtg atgactacca attgcactgg    780
acttcaacaa attggaaagg taccaatact aaagataaat ggatagatcg ttcttcagaa    840
agatataaaa tcgattggga aaagaagaaa atgacaaatg ttctggcgg aggggctaaa     900
gttgccaaac aagggcagta taaaaatcaa gaccctatcg tgttagtgca tggtttcaat    960
ggatttacag atgatattaa tccttcagtg ttagctcatt attggggcgg taataaaatg   1020
aacattcgcc aagatttaga agaaaatggt tacaaagctt atgaagcaag tataagtgct   1080
tttggaagta actatgaccg cgcagttgaa ctttattatt atatcaaagg cggtcgtgta   1140
gattatggtg cagcacatgc agcaaaatat ggacatgaac gttatggaaa aacatacgaa   1200
ggaatttaca aagactggaa accaggacag aaggtacacc tagttggaca tagtatgggt   1260
ggtcaaacga tacgtcaact agaagaatta ctgcgtaatg gtagtcgtga agaataggaa   1320
tatcaaaaga aacatggtgg cgaaattct ccactattca aaggtaataa tgacaatatg    1380
atttcatcaa ttactacttt aggaacgcca cataatggaa cgcatgcttc agatttagct   1440
ggtaatgaag ctttagtgag acaaattgta tttgatatcg taaaatgtt tggtaataaa    1500
aactctagag tagacttcgg gttggctcaa tggggtctaa aacagaagcc aaatgaatca   1560
tacattgatt atgtcaaacg cgttaaacaa tctaatttat ggaaatcaaa agataatgga   1620
ttttacgatc tgacgcgtga gggtgcaaca gatttaaatc gtaaacgtc gttgaaccct    1680
aacattgtgt ataaaacata cactggtgaa gcaacgcaca aagcattaaa tagcgataga   1740
caaaaagcag acttaaatat gttttctcca tttgtgatta ctgttaactt aatcggtaaa   1800
gctactgaaa aagaatggcg agaaaacgat ggtttagtat ccgttatttc ttctcagcat   1860
ccatttaatc aagcttatac aaatgcgacg gataaaattc aaaaaggcat ttggcaagta   1920
acgcctacaa aacatgattg ggatcatgtt gattttgtcg acaagatag ttctgataca    1980
gtgcgcacaa gagaagaatt acaagatttt tggcatcatt agcagacga tttagtgaaa    2040
actgaaaagg tgactgatac taagcaataa                                    2070
```

```
SEQ ID NO: 54           moltype = DNA  length = 1506
FEATURE                 Location/Qualifiers
misc_feature            1..1506
                        note = Recombinant DNA encoding chimeric protein
source                  1..1506
                        mol_type = other DNA
                        organism = synthetic construct
SEQUENCE: 54
gcagattctg atattaatat taaaaccggt actacagata ttggaagcaa tactacagta     60
aaaacaggtg atttagtcac ttatgataaa gaaaatggca tgttaaaaaa agtattttat   120
agttttatcg atgataaaaa tcataataaa aaactgctag ttattagaac gaaaggtacc    180
attgctggtc aatatagagt ttatagcgaa gaaggtgcta caaaagtgg tttagcctgg    240
ccttcagcct ttaaggtaca gttgcaacta cctgataatg aagtagctca aatatctgat    300
tactatccaa gaaattcgat tgatacaaaa gagtatatga gtactttaac ttatggattc    360
aacggtaatg ttactggtga tgatacagga aaaattgcg gccttattgg tgcaaatgtt    420
tcgattggtc atacactgaa atatgttcaa cctgatttca aaacaatttt agagagccca    480
actgataaaa aagtaggctg gaaagtgata tttaacaata tggtgaatca aaattgggga    540
ccatatgata gagattcttg gaacccggta tatggcaatc aacttttcat gaaaactaga    600
aatggctcta tgaaagcagc agataacttc cttgatccta acaaagcaag ttctctatta    660
tcttcagggt tttcaccaga cttcgctaca gttattacta tggatagaaa agcatccaaa    720
caacaaacaa atatagatgt aatatacgaa cgagttcgtg atgactacca attgcactgg    780
acttcaacaa attggaaagg taccaatact aaagataaat ggatagatcg ttcttcagaa    840
agatataaaa tcgattggga aaagaagaaa atgacaaatg ttctggcgg aggggctaaa     900
cgtatcaaac aacatccgga cgtacaaaaa gttacagatg ctacaagtaa agttgcttca    960
aaaacatctg cagcaatcag taacacacg agtgatgtta agaatatgt cggcgataaa    1020
aaacaagatt ttgaaaataa gcgtgaactt aaaaagtttg ctagagaaca tgatcctgcc   1080
tatattgaga aaaaaggcga aaaattagct aaacaaaatc gtaaagacg tgataaaatg    1140
aataaaaatac ttcaaaaaaa tatcgaaaag cgtcataaag aagagcaaaa agcccgcgaa   1200
aagaatgaaa tacaacgtat aaagatatg aaaaagtcac aaaaatacga agtaaaagca    1260
ggcttaacac ctaataaatt agatgagaaa actgagaaaa aaggcgataa actagctgaa   1320
aaaatcgca aagaaatcgc taaaatgaat aaaaagttac aaaaaaatat tgaaaaacga    1380
cacaaagaag aacaaaaacg ccaacaagaa gctgataaag cacgcatcaa gtcatttaaa   1440
aaatataaag attatgttgc caaagcgcc tctcaacaaa ataaagaaaa caatacagag    1500
gcataa                                                              1506
```

```
SEQ ID NO: 55           moltype = DNA  length = 528
FEATURE                 Location/Qualifiers
misc_feature            1..528
                        note = Recombinant DNA encoding chimeric protein
source                  1..528
                        mol_type = other DNA
                        organism = synthetic construct
SEQUENCE: 55
gtgctgtttt atctgcgcag caacaaacgc cagattattg aaaaaggccc gggcccgggc     60
gaaccgatta actttattct gaaaagcagc accaaactga agcgggccc gggcccgggc    120
ggcctgtatt ttgtggcgat gaacaacctg aaagcggcgg gccaggcccc gggcccgggc    180
aaagcggatg cgctgaaagc gattaccgcg ctgaaactgc agatgggccc gggcccgggc    240
aaacatcaga ttcgcatgct gagcattccg cgcgatacca ttagcggccc gggcccgggc    300
ctggatcaga ttattgcgca ggcgaacctg cgcctggcga ccatgggccc gggcccgggc    360
cagcgccatt ttcagattgg ctataaccgc gcggcgcgca ttattggccc gggcccgggc    420
agcagcaacg tgtatatgtt taaaccgcg ctgaaactgg cggcggccc gggcccgggc     480
```

```
tattttcgct tcagtattt aacccgctg aaaagcgaac gctattaa              528

SEQ ID NO: 56           moltype = DNA   length = 648
FEATURE                 Location/Qualifiers
misc_feature            1..648
                        note = Recombinant DNA encoding chimeric protein
source                  1..648
                        mol_type = other DNA
                        organism = synthetic construct
SEQUENCE: 56
accagccagt tcatgtgct gcgcgcgctg cgcctggcgc agaaaggccc gggcccgggc    60
tttctgaaac tgtttcgcat taccaacccg attgcgcgcg gcctgggccc gggcccgggc   120
attattaaaa aactgtttcg cctgccggcg attaaacgct ttgaaggccc gggcccgggc   180
attctgctgg gctattttgt ggcgcagcgc gcgctggtga agcgggccc gggcccgggc    240
aaacgcattt ttaaaatgag cccgattcat catcattttg aactgggccc gggcccgggc   300
aaaaccctgt tgtggcgct gaacaacaaa gcgcgcattc cggaaggccc gggcccgggc    360
ctgatgggca ttcgcgcgtt tcgcaaactg ctgccgaaca ttccgggccc gggcccgggc   420
atgcatttta ttgcgattag cattaaccat cgcaccgcgc atgtggccc gggcccgggc    480
agcacccttta tttataaaat tgcgaacgaa cgcctgttta gccgcggccc gggcccgggc   540
agcgtgacca ttattaaaag cctgcaggcg attcgcgtgc cgtttggccc gggcccgggc   600
tggaaacgca ttggccgcct gaaaagcatt ccgatttta tgtattaa               648

SEQ ID NO: 57           moltype = DNA   length = 1362
FEATURE                 Location/Qualifiers
misc_feature            1..1362
                        note = Recombinant DNA encoding chimeric protein
source                  1..1362
                        mol_type = other DNA
                        organism = synthetic construct
SEQUENCE: 57
atgagcagcc tgccggtggg cccggtggcg tggagcgatg gcatgctgat tgaaacccag    60
cattttcagc agctgaaacg cattttaaaa atgagcccga ttcatcatca ttttgaactg   120
agcaaccatg gctggggctt taccctgctg gatctggatc aggatggcct gggcctgggc   180
cgcctgatgg gcattcgcgc gtttcgcaaa ctgctgccga acattccgtt tagcctgccg   240
agcgatgatc cgctgccgcc gcgctggaa accgaactgg cgcaggcggg cgatattgcg   300
tgcctggcgc tgcaggcggc gcgcaccggc ggcccggaaa tggcgtttgg cgatgtggaa   360
ctggcgagcc gctatcgcgc ggtgagcacc gaagtgccgg atctggcggt gggcctggat   420
gcgccgggca ccccgtttct gaaactgttt cgcattacca acccgattgc gcgcggcctg   480
tggaaacgca ttggccgcct gaaaagcatt ccgatttta tgtatcgcgt gcggggccg    540
aacgcgagcc gcaccgtgag cctggatccg cgctttattc cgccgaaaac cctgtttgtg   600
gcgctgaaca caaagcgcg cattccggaa gaactgcaga gcaccagcgt gaccattatt    660
aaaagcctgc aggcgattcg cgtgccgttt accggcggcg cgtggcgga tctgattgaa   720
attctgctgg gctattttgt ggcgcagcgc gcgctggtga agcgaacct ggatgcgttt    780
gatccgctgc cgccgatgca ttttattgcg attagcatta accatcgcac cgcggatgtg   840
gtgctgccgg gcgtggatga agaactggcg gatcgcgaac tgggctatga tcatgatgat   900
ctgcagacca gctttaccag ccagtttcat gtgctgcgcg cgctgcgcct ggcgcagaaa   960
gaaccccggg tgctgccgct gcgctttgaa gatcgcggcg atcaggtgca tatttgcatt  1020
gtggataaac agtggaacct gaaaaactg atttttgcgt ttagcattat taaaaaactg  1080
tttcgcctgc cggcgattaa acgctttgaa accaaactgg cgcggtgga acagattcag   1140
aaactggtgg atctgcagct gccgggcgcg cgcctgaacg cgctgccgaa cccgccgcgc  1200
cagattccgt attatgcgca gagcacctat tttgaagtgg aaagcaccga tccgttttgg  1260
aaacagaccc tggcgggcag cgcgatggcg ctgcgcattg tgggcgattt tccgagcacc  1320
tttatttata aaattgcgaa cgaacgcctg tttagccgct aa                    1362

SEQ ID NO: 58           moltype = DNA   length = 1362
FEATURE                 Location/Qualifiers
misc_feature            1..1362
                        note = Recombinant DNA encoding chimeric protein
source                  1..1362
                        mol_type = other DNA
                        organism = synthetic construct
SEQUENCE: 58
atgagcagcc tgccggtggg cccggtggcg tggagcgatg gcatgctgat tgaaaccag    60
cattttcagc agctggaacg ccatctggcg catcaggcg gcctgcgcc gggccagacc    120
agcaaccatg gctggggctt taccctgctg gatctggatc aggatggcct gggcctgggc   180
cgcctgggcc tgcgcagcag caacgtgtat atgtttaaaa ccgcgctgaa actggcgggc   240
agcgatgatc cgctgccgcc gcgctggaa ccgaactggc gcaggcggg cgatattgcg   300
tgcctggcgc tgcaggcggc gcgcaccggc ggcccggaaa tggcgtttgg cgatgtggaa   360
ctggcgagcc gctatcgcgc ggtgagcacc gaagtgccgg atctggcggt gggcctggat   420
gcgccgggca ccccgcgccg cctgaccatt gaaaccggcc agctggtgac cgcctgtgtg   480
tggaaaagcc aggtgctgtt ttatctgcgc agcaacaaac gccagattat tgaaaaacgc   540
aacgcgagcc gcaccgtgag cctggatccg cgctttattc gccgaacc gattaacttt    600
attctgaaaa gcagcaccaa actgaaagcg gaactgcaga gcacccagcg ccattttcag  660
attggctata accgcgcgcg gcattaccgg ccggggtga tctgattgaa               720
ctgctgctgc gccagctgga tcagattatt gcgcaggcga acctgcgcct ggcgaccatg   780
gatccgctgc cgccgggcct gtattttgtg gcgatgaaca acctgaaagc ggcgggccag   840
gtgctgccgg gcgtggatga agaactggcg gatcgcgaac tgggctatga tcatgatgat   900
ctgcagacca gctttgaacc gctggcgatg atgctgcgcc aggcgctggc gcgcgtgatt   960
gaaccccggg tgctgccgct gcgctttgaa gatcgcggcg atcaggtgca tatttgcatt  1020
```

```
gtggataaac agtggaacct gaaaaaactg attttttgcgt ttagcaaagc ggatgcgctg    1080
aaagcgatta ccgcgctgaa actgcagatg accaaactgg gcgcggtgga acagattcag    1140
aaactggtgg atctgcagct gccgggcgcg cgcctgaacg cgctgccgaa cccgccgcgc    1200
cagattccgt attatgcgca gagcacctat tttgaagtgg aaagcaaaca tcagattcgc    1260
atgctgagca ttccgcgcga taccattagc ctgcgcattg tgggcgatta ttttcgcttt    1320
cagtattta   acccgctgaa aagcgaacgc tatgtggcgt aa                      1362

SEQ ID NO: 59           moltype = AA   length = 623
FEATURE                 Location/Qualifiers
REGION                  1..623
                        note = Chimeric polypeptide
source                  1..623
                        mol_type = protein
                        organism = synthetic construct
SEQUENCE: 59
KRIKQHPDVQ KVTDATSKVA SKTSAAISNT ASDVKEYVGD KKQDFENKRE LKKFAREHDP     60
AYIEKKGEKL AKQNRKDADK MNKILQKNIE KRHKEEQKAR EKNEIQRIKD MKKSQKYEVK    120
AGLTPNKLDE KTEKKGDKLA EKNRKEIAKM NKKLQKNIEK RHKEEQKRQQ EADKARIKSF    180
KKYKDYVAKS ASQQNKENNT EAGSGGGAGS GGGAMDIGKK HVIPKSQYRR KRREFFHNED    240
REENLNQHQD KQNIDNTTSK KADKQIHKDS IDKHERFKNS LSSHLEQRNR DVNENKAEES    300
KSNQDSKSAY NRDHYLTDDV SKKQNSLDSV DQDTEKSKYY EQNSEATLST KSTDKVESTE    360
MRKLSSDKNK VGHEEQHVLS KPSEHDKETR IDSESSRTDS DSSMQTEKIK KDSSDGNKSS    420
NLKSEVISDK SNTVPKLSES DDEVNNQKPL TLPEEQKLKR QQSQNEQTKT YTYGDSEQND    480
KSNHENDLSH HIPSISDDKD NVMRENHIVD DNPDNDINTP SLSKTDDDRK LDEKIHVEDK    540
HKQNADSSET VGYQSQSTAS HRSTEKRNIS INDHDKLNGQ KTNTKTSANN NQKKATSKLN    600
KGRATNNNYS DILKKFWMMY WPK                                            623

SEQ ID NO: 60           moltype = AA   length = 623
FEATURE                 Location/Qualifiers
REGION                  1..623
                        note = Chimeric polypeptide
source                  1..623
                        mol_type = protein
                        organism = synthetic construct
SEQUENCE: 60
MDIGKKHVIP KSQYRRKRRE FFHNEDREEN LNQHQDKQNI DNTTSKKADK QIHKDSIDKH     60
ERFKNSLSSH LEQRNRDVNE NKAEESKSNQ DSKSAYNRDH YLTDDVSKKQ NSLDSVDQDT    120
EKSKYYEQNS EATLSTKSTD KVESTEMRKL SSDKNKVGHE EQHVLSKPSE HDKETRIDSE    180
SSRTDSDSSM QTEKIKKDSS DGNKSSNLKS EVISDKSNTV PKLSESDDEV NNQKPLTLPE    240
EQKLKRQQSQ NEQTKTYTYG DSEQNDKSNH ENDLSHHIPS ISDDKDNVMR ENHIVDDNPD    300
NDINTPSLSK TDDDRKLDEK IHVEDKHKQN ADSSETVGYQ SQSTASHRST EKRNISINDH    360
DKLNGQKTNT KTSANNNQKK ATSKLNKGRA TNNNYSDILK KFWMMYWPKG SGGGAGSGGG    420
AKRIKQHPDV QKVTDATSKV ASKTSAAISN TASDVKEYVG DKKQDFENKR ELKKFAREHD    480
PAYIEKKGEK LAKQNRKDAD KMNKILQKNI EKRHKEEQKA REKNEIQRIK DMKKSQKYEV    540
KAGLTPNKLD EKTEKKGDKL AEKNRKEIAK MNKKLQKNIE KRHKEEQKRQ QEADKARIKS    600
FKKYKDYVAK SASQQNKENN TEA                                            623

SEQ ID NO: 61           moltype = AA   length = 617
FEATURE                 Location/Qualifiers
REGION                  1..617
                        note = Chimeric polypeptide
source                  1..617
                        mol_type = protein
                        organism = synthetic construct
SEQUENCE: 61
MDIGKKHVIP KSQYRRKRRE FFHNEDREEN LNQHQDKQNI DNTTSKKADK QIHKDSIDKH     60
ERFKNSLSSH LEQRNRDVNE NKAEESKSNQ DSKSAYNRDH YLTDDVSKKQ NSLDSVDQDT    120
EKSKYYEQNS EATLSTKSTD KVESTEMRKL SSDKNKVGHE EQHVLSKPSE HDKETRIDSE    180
SSRTDSDSSM QTEKIKKDSS DGNKSSNLKS EVISDKSNTV PKLSESDDEV NNQKPLTLPE    240
EQKLKRQQSQ NEQTKTYTYG DSEQNDKSNH ENDLSHHIPS ISDDKDNVMR ENHIVDDNPD    300
NDINTPSLSK TDDDRKLDEK IHVEDKHKQN ADSSETVGYQ SQSTASHRST EKRNISINDH    360
DKLNGQKTNT KTSANNNQKK ATSKLNKGRA TNNNYSDILK KFWMMYWPKG SGGGAKRIKQ    420
HPDVQKVTDA TSKVASKTSA AISNTASDVK EYVGDKKQDF ENKRELKKFA REHDPAYIEK    480
KGEKLAKQNR KDADKMNKIL QKNIEKRHKE EQKAREKNEI QRIKDMKKSQ KYEVKAGLTP    540
NKLDEKTEKK GDKLAEKNRK EIAKMNKKLQ KNIEKRHKEE QKRQQEADKA RIKSFKKYKD    600
YVAKSASQQN KENNTEA                                                   617

SEQ ID NO: 62           moltype = AA   length = 620
FEATURE                 Location/Qualifiers
REGION                  1..620
                        note = Chimeric polypeptide
source                  1..620
                        mol_type = protein
                        organism = synthetic construct
SEQUENCE: 62
MDIGKKHVIP KSQYRRKRRE FFHNEDREEN LNQHQDKQNI DNTTSKKADK QIHKDSIDKH     60
ERFKNSLSSH LEQRNRDVNE NKAEESKSNQ DSKSAYNRDH YLTDDVSKKQ NSLDSVDQDT    120
EKSKYYEQNS EATLSTKSTD KVESTEMRKL SSDKNKVGHE EQHVLSKPSE HDKETRIDSE    180
SSRTDSDSSM QTEKIKKDSS DGNKSSNLKS EVISDKSNTV PKLSESDDEV NNQKPLTLPE    240
```

```
EQKLKRQQSQ NEQTKTYTYG DSEQNDKSNH ENDLSHHIPS ISDDKDNVMR ENHIVDDNPD    300
NDINTPSLSK TDDDRKLDEK IHVEDKHKQN ADSSETVGYQ SQSTASHRST EKRNISINDH    360
DKLNGQKTNT KTSANNNQKK ATSKLNKGRA TNNNYSDILK KFWMMYWPKG SGGGAGSGGG    420
AMTEKEKMLA EKWYDANFDQ DLINERARAK DICFELNHTK PSDKNKRKEL IDELFQTTTD    480
NVSISIPFDT DYGWNVKLGK NVYVNTNCYF MDGGQITIGD NVFIGPNCGF YTATHPLNFH    540
HRNEGFEKAG PINIGSNTWF GGHVAVLPGV TIGEGSVIGA GSVVTKDIPP HSLAVGNPCK    600
VVRKIDNEVP SEALNDETLN                                               620

SEQ ID NO: 63           moltype = AA  length = 614
FEATURE                 Location/Qualifiers
REGION                  1..614
                        note = Chimeric polypeptide
source                  1..614
                        mol_type = protein
                        organism = synthetic construct
SEQUENCE: 63
MDIGKKHVIP KSQYRRKRRE FFHNEDREEN LNQHQDKQNI DNTTSKKADK QIHKDSIDKH     60
ERFKNSLSSH LEQRNRDVNE NKAEESKSNQ DSKSAYNRDH YLTDDVSKKQ NSLDSVDQDT    120
EKSKYYEQNS EATLSTKSTD KVESTEMRKL SSDKNKVGHE EQHVLSKPSE HDKETRIDSE    180
SSRTDSDSSM QTEKIKKDSS DGNKSSNLKS EVISDKSNTV PKLSESDDEV NNQKPLTLPE    240
EQKLKRQQSQ NEQTKTYTYG DSEQNDKSNH ENDLSHHIPS ISDDKDNVMR ENHIVDDNPD    300
NDINTPSLSK TDDDRKLDEK IHVEDKHKQN ADSSETVGYQ SQSTASHRST EKRNISINDH    360
DKLNGQKTNT KTSANNNQKK ATSKLNKGRA TNNNYSDILK KFWMMYWPKG SGGGAMTEKE    420
KMLAEKWYDA NFDQDLINER ARAKDICFEL NHTKPSDKNK RKELIDELFQ TTTDNVSISI    480
PFDTDYGWNV KLGKNVYVNT NCYFMDGGQI TIGDNVFIGP NCGFYTATHP LNFHHRNEGF    540
EKAGPINIGS NTWFGGHVAV LPGVTIGEGS VIGAGSVVTK DIPPHSLAVG NPCKVVRKID    600
NEVPSEALND ETLN                                                     614

SEQ ID NO: 64           moltype = AA  length = 805
FEATURE                 Location/Qualifiers
REGION                  1..805
                        note = Chimeric polypeptide
source                  1..805
                        mol_type = protein
                        organism = synthetic construct
SEQUENCE: 64
MDIGKKHVIP KSQYRRKRRE FFHNEDREEN LNQHQDKQNI DNTTSKKADK QIHKDSIDKH     60
ERFKNSLSSH LEQRNRDVNE NKAEESKSNQ DSKSAYNRDH YLTDDVSKKQ NSLDSVDQDT    120
EKSKYYEQNS EATLSTKSTD KVESTEMRKL SSDKNKVGHE EQHVLSKPSE HDKETRIDSE    180
SSRTDSDSSM QTEKIKKDSS DGNKSSNLKS EVISDKSNTV PKLSESDDEV NNQKPLTLPE    240
EQKLKRQQSQ NEQTKTYTYG DSEQNDKSNH ENDLSHHIPS ISDDKDNVMR ENHIVDDNPD    300
NDINTPSLSK TDDDRKLDEK IHVEDKHKQN ADSSETVGYQ SQSTASHRST EKRNISINDH    360
DKLNGQKTNT KTSANNNQKK ATSKLNKGRA TNNNYSDILK KFWMMYWPKG SGGGAKVAKQ    420
GQYKNQDPIV LVHGFNGFTD DINPSVLAHY WGGNKMNIRQ DLEENGYKAY EASISAFGSN    480
YDRAVELYYY IKGGRVDYGA AHAAKYGHER YGKTYEGIYK DWKPGQKVHL VGHSMGGQTI    540
RQLEELLRNG SREEIEYQKK HGGEISPLFK GNNDNMISSI TTLGTPHNGT HASDLAGNEA    600
LVRQIVFDIG KMFGNKNSRV DFGLAQWGLK QKPNESYIDY VKRVKQSNLW KSKDNGFYDL    660
TREGATDLNR KTSLNPNIVY KTYTGEATHK ALNSDRQKAD LNMFFPPVIT GNLIGKATEK    720
EWRENDGLVS VISSQHPFNQ AYTNATDKIQ KGIWQVTPTK HDWDHVDFVG QDSSDTVRTR    780
EELQDFWHHL ADDLVKTEKV TDTKQ                                         805

SEQ ID NO: 65           moltype = AA  length = 1003
FEATURE                 Location/Qualifiers
REGION                  1..1003
                        note = Chimeric polypeptide
source                  1..1003
                        mol_type = protein
                        organism = synthetic construct
SEQUENCE: 65
RNLLLQKSQ ARQTAEDIVN QAHKEADNIK KEKLLEAKEE NQILREQTEA ELRERRSELQ      60
RQETRLLQKE ENLERKSDLL DKKDEILEQK ESKIEEKQQQ VDAKESSVQT LIMKHEQELE    120
RISGLTQEEA INEQLQRVEE ELSQDIAVLV KEKEKEAKEK VDKTAKELLA TAVQRLAADH    180
TSESTVSVVN LPNDEMKGRI IGREGRNIRT LETLTGIDLI IDDTPEAVIL SGFDPIRREI    240
ARTALVNLVS DGRIHPGRIE DMVEKARKEV DDIIREAGEQ ATFEVNAHNM HPDLVKIVGR    300
LNYRTSYGQN VLKHSIEVAH LASMLAAELG EDETLAKRAG LLHDVGKAID HEVEGSHVEI    360
GVELAKKYGE NETVINAIHS HHGDVEPTSI ISILVAAADA LSAARPGARK ETLENYIRRL    420
ERLETLSESY DGVEKAFAIQ AGREIRVIVS PEEIDDLKSY RLARDIKNQI EDELQYPGHI    480
KVTVVRETRA VEYAKKPEPK PAPAPKPACG NDDGKDKDGK VTIKTTVYPL QSFAEQIGGK    540
HVKVSSIYPA GTDLHSYEPT QKDILSASKS DLFMYTGDNL DPVAKKVAST IKDKDKKLSL    600
EDKLDKAKLL TDQHEHGEEH EHEGHDHEKE EHHHHGGYDP HVWLDPKINQ TFAKEIKDEL    660
VKKDPKHKDD YEKNYKKLND DLKKIDNDMK QVTKDKQGNA VFISHESIGY LADRYGFVQK    720
GIQNMNAEDP SQKELTKIVK EIRDSNAKYI LYEDNVANKV TETIRKETDA KPLKFYNMES    780
LNKEQQKKDN ITYQSLMKSN IENIGKALDS GVKVKDDKAE SKHDKAISDG YFKDEQVKDR    840
ELSDYAGEWQ SVYPLYKDGT LDEVMEHKAE NDPKKSAKDL KAYYDKGYKT DITNIDIKGN    900
EITFTKDGKK HTGKYEYNGK KTLKYPKGNR GVRFMFKLVD GNDKDLPKFI QFSDHNIAPK    960
KAEHFHIFMG NDNDALLKEM DNWPTYYPSK LNKDQIKEEM LAH                     1003

SEQ ID NO: 66           moltype = AA  length = 1009
FEATURE                 Location/Qualifiers
```

| | | |
|---|---|---|
| REGION | 1..1009 | |
| | note = Chimeric polypeptide | |
| source | 1..1009 | |
| | mol_type = protein | |
| | organism = synthetic construct | |

SEQUENCE: 66

```
MNEKVEGMTL ELKLDHLGVQ EGMKGLKRQL GVVNSEMKAN LSAFDKSEKS MEKYQARIKG    60
LNDRLKVQKK MYSQVEDELK QVNANYQKAK SSVKDVEKAY LKLVEANKKE KLALDKSKEA   120
LKSSNTELKK AENQYKRTNQ RKQDAYQKLK QLRDAEQKLK NSNQATTAQL KRASDAVQKQ   180
SAKHKALVEQ YKQEGNQVQK LKVQNDNLSK SNDKIESSYA KTNTKLKQTE KEFNDLNNTI   240
KNHSANVAKA ETAVNKEKAA LNNLERSIDK ASSEMKTFNK EQMIAQSHFG KLASQADVMS   300
KKFSSIGDKM TSLGRTMTMG VSTPITLGLG AALKTSADFE GQMSRVGAIA QASSKDLKSM   360
SNQAVDLGAK TSKSANEVAK GMEELAALGF NAKQTMEAMP GVISAAEASG AEMATTATVM   420
ASAINSFGLK ASDANHVADL LARSANDSAA DIQYMGDALK YAGTPAKALG VSIEDTSAAI   480
EVLSNSGLEG SQAGTALRAS FIRLANPSKN TAKEMKKLGI HLSDAKGQFV GMGELIRQFQ   540
DNMKGMTREQ KLATVATIVG TEAASGFLAL IEAGPDKINS YSKSLKNSNG ESKKAADLMK   600
DNLKGALEQL GGAFESLAIE VGKDLTPMIR AGAEGLTKLV DGFTHLPGWV RKGSGGGAAK   660
DNLNGEKPTT NLNHNVTSPS VNSEMNNNET GTPHESNQAG NEGTGSNSRD ANPDSNNVKP   720
DSNNQNPSPD SKPDPNNPNP GPNPKPDPDK PKPNPEPKPD PKPDPDKPKP NPDPKPDPDK   780
PKPNPDDPKPD PDKPKPNPDP KPDPNPNPKP DPNKPNPNPS PNPNQPGDSN QSGGSKNGGT   840
WNPNASDGSN QGQWQPNGNQ GNSQNPTGND FVSQRFLALA NGAYKYNPYI LNQINQLGKE   900
YGEVTDEDIY NIIRKQNFSG NAYLNGLQQQ SNYFRFQYFN PLKSERYYRN LDEQVLALIT   960
GEIGSMPDLK KPEDKPDSKQ RSFEPHEKDD FTVVKKQEDN KKSASTAYS              1009
```

| | | |
|---|---|---|
| SEQ ID NO: 67 | moltype = AA length = 728 | |
| FEATURE | Location/Qualifiers | |
| REGION | 1..728 | |
| | note = Chimeric polypeptide | |
| source | 1..728 | |
| | mol_type = protein | |
| | organism = synthetic construct | |

SEQUENCE: 67

```
GFLNKSKNEQ AALKAQQAAI KEEASANNLS DTSQEAQEIQ EAKREAQAEA DKSVAVSNKE    60
SKAVALKAQQ AAIKEEASAN NLSDTSQEAQ EIQEAKREAQ AETDKSAAVS NEEPKAVALK   120
AQQAAIKEEA SANNLSDISQ EAQEVQEAKK EAQAEKDSDT LTKDASAAKV EVSKPESQAE   180
RLANAAKQKQ AKLTPGSKES QLTEALFAEK PVAKNDLKEI PQLVTKKNDV SETETVNIDN   240
KDTVKQKEAK FENGVITRKA DEKTTNNTAV DKKSGKQSKK TTPSNKRNAS KASTNKTSGQ   300
KKQHNKKSSQ GAKKQSSSSK STQKNNQTSN KNSKTTNAKS SNASKTPNAK VEKAKSKIEK   360
RTFNDGSGGG AGSGGGAAKD NLNGEKPTTN LNHNVTSPSV NSEMNNNETG TPHESNQAGN   420
EGTGSNSRDA NPDSNNVKPD SNNQNPSPDS KPDPNNPNPG PNPKPDPDKP KPNPEPKPDP   480
KPDPDKPKPN PDPKPDPDKP KPNPDPKPDP DKPKPNPDPK PDPNPNPKPD PNKPNPNPSP   540
NPNQPGDSNQ SGGSKNGGTW NPNASDGSNQ GQWQPNGNQG NSQNPTGNDF VSQRFLALAN   600
GAYKYNPYIL NQINQLGKEY GEVTDEDIYN IIRKQNFSGN AYLNGLQQQS NYFRFQYFNP   660
LKSERYYRNL DEQVLALITG EIGSMPDLKK PEDKPDSKQR SFEPHEKDDF TVVKKQEDNK   720
KSASTAYS                                                           728
```

| | | |
|---|---|---|
| SEQ ID NO: 68 | moltype = AA length = 722 | |
| FEATURE | Location/Qualifiers | |
| REGION | 1..722 | |
| | note = Chimeric polypeptide | |
| source | 1..722 | |
| | mol_type = protein | |
| | organism = synthetic construct | |

SEQUENCE: 68

```
AKDNLNGEKP TTNLNHNVTS PSVNSEMNNN ETGTPHESNQ AGNEGTGSNS RDANPDSNNV    60
KPDSNNQNPS PDSKPDPNNP NPGPNPKPDP DKPKPNPEPK PDPKPDPDKP KPNPDPKPDP   120
DKPKPNPDPK PDPDKPKPNP DPKPDPNPNP KPDPNKPNPN PSPNPNQPGD SNQSGGSKNG   180
GTWNPNASDG SNQGQWQPNG NQGNSQNPTG NDFVSQRFLA LANGAYKYNP YILNQINQLG   240
KEYGEVTDED IYNIIRKQNF SGNAYLNGLQ QQSNYFRFQY FNPLKSERYY RNLDEQVLAL   300
ITGEIGSMPD LKKPEDKPDS KQRSFEPHEK DDFTVVKKQE DNKKSASTAY SGSGGGAGFL   360
NKSKNEQAAL KAQQAAIKEE ASANNLSDTS QEAQEIQEAK REAQAEADKS VAVSNKESKA   420
VALKAQQAAI KEEASANNLS DTSQEAQEIQ EAKKEAQAET DKSAAVSNEE PKAVALKAQQ   480
AAIKEEASAN NLSDISQEAQ EVQEAKKEAQ AEKDSDTLTK DASAAKVEVS KPESQAERLA   540
NAAKQKQAKL TPGSKESQLT EALFAEKPVA KNDLKEIPQL VTKKNDVSET ETVNIDNKDT   600
VKQKEAKFEN GVITRKADEK TTNNTAVDKK SGKQSKKTTP SNKRNASKAS TNKTSGQKKQ   660
HNKKSSQGAK KQSSSSKSTQ KNNQTSNKNS KTTNAKSSNA SKTPNAKVEK AKSKIEKRTF   720
ND                                                                 722
```

| | | |
|---|---|---|
| SEQ ID NO: 69 | moltype = AA length = 867 | |
| FEATURE | Location/Qualifiers | |
| REGION | 1..867 | |
| | note = Chimeric polypeptide | |
| source | 1..867 | |
| | mol_type = protein | |
| | organism = synthetic construct | |

SEQUENCE: 69

```
ACGNDDGKDK DGKVTIKTTV YPLQSFAEQI GGKHVKVSSI YPAGTDLHSY EPTQKDILSA    60
SKSDLFMYTG DNLDPVAKKV ASTIKDKDKK LSLEDKLDKA KLLTDQHEHG EEHEHEGHDH   120
EKEEHHHHGG YDPHVWLDPK INQTFAKEIK DELVKKDPKH KDDYEKNYKK LNDDLKKIDN   180
```

```
DMKQVTKDKQ GNAVFISHES IGYLADRYGF VQKGIQNMNA EDPSQKELTK IVKEIRDSNA   240
KYILYEDNVA NKVTETIRKE TDAKPLKFYN MESLNKEQQK KDNITYQSLM KSNIENIGKA   300
LDSGVKVKDD KAESKHDKAI SDGYFKDEQV KDRELSDYAG EWQSVYPYLK DGTLDEVMEH   360
KAENDPKKSA KDLKAYYDKG YKTDITNIDI KGNEITFTKD GKKHTGKYEY NGKKTLKYPK   420
GNRGVRFMFK LVDGNDKDLP KFIQFSDHNI APKKAEHFHI FMGNDNDALL KEMDNWPTYY   480
PSKLNKDQIK EEMLAHGSGG GAGFLNKSKN EQAALKAQQA AIKEEASANN LSDTSQEAQE   540
IQEAKREAQA EADKSVAVSN KESKAVALKA QQAAIKEEAS ANNLSDTSQE AQEIQEAKKE   600
AQAETDKSAA VSNEEPKAVA LKAQQAAIKE EASANNLSDI SQEAQEVQEA KKEAQAEKDS   660
DTLTKDASAA KVEVSKPESQ AERLANAAKQ KQAKLTPGSK ESQLTEALFA EKPVAKNDLK   720
EIPQLVTKKN DVSETETVNI DNKDTVKQKE AKFENGVITR KADEKTTNNT AVDKKSGKQS   780
KKTTPSNKRN ASKASTNKTS GQKKQHNKKS SQGAKKQSSS SKSTQKNNQT SNKNSKTTNA   840
KSSNASKTPN AKVEKAKSKI EKRTFND                                      867

SEQ ID NO: 70          moltype = AA   length = 797
FEATURE                Location/Qualifiers
REGION                 1..797
                       note = Chimeric polypeptide
source                 1..797
                       mol_type = protein
                       organism = synthetic construct
SEQUENCE: 70
MTEKEKMLAE KWYDANFDQD LINERARAKD ICFELNHTKP SDKNKRKELI DELFQTTTDN    60
VSISIPFDTD YGWNVKLGKN VYVNTNCYFM DGGQITIGDN VFIGPNCGFY TATHPLNFHH   120
RNEGFEKAGP INIGSNTWFG GHVAVLPGVT IGEGSVIGAG SVVTKDIPPH SLAVGNPCKV   180
VRKIDNEVPS EALNDETLNG SGGGADTPQK DTTAKTTSHD SKKSNDDETS KDTTSKDIDK   240
ADNNNTSNQD NNDKKFPKTID DSTSDSNNII DFIYKNLPQT NINQLLTKNK YDDNYSLTTL   300
IQNLFNLNSD ISDYEQPRNG EKSTNDSNKN SDNSIKNDTD TQSSKQDKAD NQKAPKSNNT   360
KPSTSNKQPN SPKPTQPNQS NSQPASDDKA NQKSSSKDNQ SMSDSALDSI LDQYSEDAKK   420
TQKDYASQSK KDKNEKSNTK NPQLPTQDEL KHKSKPAQSF NNDVNQKDTR ATSLFETDPS   480
ISNNDDSGQF NVVDSKDTRQ FVKSIAKDAH RIGQDNDIYA SVMIAQAILE SDSGRSALAK   540
SPNHNLFGIK GAFEGNSVPF NTLEADGNKL YSINAGFRKY PSTKESLKDY SDLIKNGIDG   600
NRTIYKPTWK SEADSYKDAT SHLSKTYATD PNYAKKLNSI IKHYQLTQFD DERMPDLDKY   660
ERSIKDYDDS SDEFKPFREV SDSMPYPHGQ CTWYVYNRMK QFGTSISGDL GDAHNWNNRA   720
QYRDYQVSHT PKRHAAVVFE AGQFGADQHY GHVAFVEKVN SDGSIVISES NVKGLGIIISH   780
RTINAAAAEE LSYITGK                                                 797

SEQ ID NO: 71          moltype = AA   length = 783
FEATURE                Location/Qualifiers
REGION                 1..783
                       note = Chimeric polypeptide
source                 1..783
                       mol_type = protein
                       organism = synthetic construct
SEQUENCE: 71
IDSKNKPANS DIKFEVTQKS DAVKALKELP KSENVKNIYQ DYAVTDVKTD KKGFTHYTLQ    60
PSVDGVHAPD KEVKVHADKS GKVVLINGDT DAKKVKPTNK VTLSKDDAAD KAFKAVKIDK   120
NKAKNLKDKV IKENKVEIDG DSNKYVYNVE LITVTPEISH WKVKIDAQTG EILEKMNLVK   180
EAAETGKGKG VLGDTKDINI NSIDGGFSLE DLTHQGKLSA FSFNDQTGQA TLITNEDENF   240
VKDEQRAGVD ANYYAKQTYD YYKDTFGRES YDNQGSPIVS LTHVNNYGGQ DNRNNAAWIG   300
DKMIYGDGDG RTFTSLSGAN DVVAHELTHG VTQETANLEY KDQSGALNES FSDVFGYFVD   360
DEDFLMGEDV YTPGKEGDAL RSMSNPEQFG QPAHMKDYVF TEKDNGGVHT NSGSGGGAGF   420
LNKSKNEQAA LKAQQAAIKE EASANNLSDT SQEAQEIQEA KREAQAEADK SVAVSNKESK   480
AVALKAQQAA IKEEASANNL SDTSQEAQEI QEAKKEAQAE TDKSAAVSNE EPKAVALKAQ   540
QAAIKEEASA NNLSDISQEA QEVQEAKKEA QAEKDSDTLT KDASAAKVEV SKPESQAERL   600
ANAAKQKQAK LTPGSKESQL TEALFAEKPV AKNDLKEIPQ LVTKKNDVSE TETVNIDNKD   660
TVKQKEAKFE NGVITRKADE KTTNNTAVDK KSGKQSKKTT PSNKRNASKA STNKTSGQKK   720
QHNKKSSQGA KKQSSSSKST QKNNQTSNKN SKTTNAKSSN ASKTPNAKVE KAKSKIEKRT   780
FND                                                                 783

SEQ ID NO: 72          moltype = AA   length = 769
FEATURE                Location/Qualifiers
REGION                 1..769
                       note = Chimeric polypeptide
source                 1..769
                       mol_type = protein
                       organism = synthetic construct
SEQUENCE: 72
IDSKNKPANS DIKFEVTQKS DAVKALKELP KSENVKNIYQ DYAVTDVKTD KKGFTHYTLQ    60
PSVDGVHAPD KEVKVHADKS GKVVLINGDT DAKKVKPTNK VTLSKDDAAD KAFKAVKIDK   120
NKAKNLKDKV IKENKVEIDG DSNKYVYNVE LITVTPEISH WKVKIDAQTG EILEKMNLVK   180
EAAETGKGKG VLGDTKDINI NSIDGGFSLE DLTHQGKLSA FSFNDQTGQA TLITNEDENF   240
VKDEQRAGVD ANYYAKQTYD YYKDTFGRES YDNQGSPIVS LTHVNNYGGQ DNRNNAAWIG   300
DKMIYGDGDG RTFTSLSGAN DVVAHELTHG VTQETANLEY KDQSGALNES FSDVFGYFVD   360
DEDFLMGEDV YTPGKEGDAL RSMSNPEQFG QPAHMKDYVF TEKDNGGVHT NSGSGGGAAK   420
DNLNGEKPTT NLNHNVTSPS VNSEMNNNET GTPHESNQAG NEGTGSNSRD ANPDSNNVKP   480
DSNNQNPSPD SKPDPNNPNP GPNPKPDPDK PKPNPEPKPD PKPDPDKPKP NPDPKPDPDK   540
PKPNPDPKPD PDKPKPNPDP KPDPNPNPKP DPNKPNPNPS PNPNQPGDSN QSGGSKNGGT   600
WNPNASDGSN QGQWQPNGNQ GNSQNPTGND FVSQRFLALA NGAYKYNPYI LNQINQLGKE   660
YGEVTDEDIY NIIRKQNFSG NAYLNGLQQQ SNYFRFQYFN PLKSERYYRN LDEQVLALIT   720
```

```
GEIGSMPDLK KPEDKPDSKQ RSFEPHEKDD FTVVKKQEDN KKSASTAYS           769

SEQ ID NO: 73              moltype = AA  length = 814
FEATURE                    Location/Qualifiers
REGION                     1..814
                           note = Chimeric polypeptide
source                     1..814
                           mol_type = protein
                           organism = synthetic construct
SEQUENCE: 73
IDSKNKPANS DIKFEVTQKS DAVKALKELP KSENVKNIYQ DYAVTDVKTD KKGFTHYTLQ  60
PSVDGVHAPD KEVKVHADKS GKVVLINGDT DAKKVKPTNK VTLSKDDAAD KAFKAVKIDK 120
NKAKNLKDKV IKENKVEIDG DSNKYVYNVE LITVTPEISH WKVKIDAQTG EILEKMNLVK 180
EAAETGKGKG VLGDTKDINI NSIDGGFSLE DLTHQGKLSA FSFNDQTGQA TLITNEDENF 240
VKDEQRAGVD ANYYAKQTYD YYKDTFGRES YDNQGSPIVS LTHVNNYGGQ DNRNNAAWIG 300
DKMIYGDGDG RTFTSLSGAN DVVAHELTHG VTQETANLEY KDQSGALNES FSDVFGYFVD 360
DEDFLMGEDV YTPGKEGDAL RSMSNPEQFG QPAHMKDYVF TEKDNGGVHT NSGSGGGAGS 420
GGGAKVAKQG QYKNQDPIVL VHGFNGFTDD INPSVLAHYW GGNKMNIRQD LEENGYKAYE 480
ASISAFGSNY DRAVELYYYI KGGRVDYGAA HAAKYGHERY GKTYEGIYKD WKPGQKVHLV 540
GHSMGGQTIR QLEELLRNGS REEIEYQKKH GGEISPLFKG NNDNMISSIT TLGTPHNGTH 600
ASDLAGNEAL VRQIVFDIGK MFGNKNSRVD FGLAQWGLKQ KPNESYIDYV KRVKQSNLWK 660
SKDNGFYDLT REGATDLNRK TSLNPNIVYK TYTGEATHKA LNSDRQKADL NMFFPFVITG 720
NLIGKATEKE WRENDGLVSV ISSQHPFNQA YTNATDKIQK GIWQVTPTKH DWDHVDFVGQ 780
DSSDTVRTRE ELQDFWHHLA DDLVKTEKVT DTKQ                           814

SEQ ID NO: 74              moltype = AA  length = 797
FEATURE                    Location/Qualifiers
REGION                     1..797
                           note = Chimeric polypeptide
source                     1..797
                           mol_type = protein
                           organism = synthetic construct
SEQUENCE: 74
DTPQKDTTAK TTSHDSKKSN DDETSKDTTS KDIDKADNNN TSNQDNNDKK FKTIDDSTSD  60
SNNIIDFIYK NLPQTNINQL LTKNKYDDNY SLTTLIQNLF NLNSDISDYE QPRNGEKSTN 120
DSNKNSDNSI KNDTDTQSSK QDKADNQKAP KSNNTKPSTS NKQPNSPKPT QPNQSNSQPA 180
SDDKANQKSS SKDNQSMSDS ALDSILDQYS EDAKKTQKDY ASQSKKDKNE KSNTKNPQLP 240
TQDELKHKSK PAQSFNNDVN QKDTRATSLF ETDPSISNND DSGQFNVVDS KDTRQFVKSI 300
AKDAHRIGQD NDIYASVMIA QAILESDSGR SALAKSPNHN LFGIKGAFEG NSVPFNTLEA 360
DGNKLYSINA GFRKYPSTKE SLKDYSDLIK NGIDGNRTIY KPTWKSEADS YKDATSHLSK 420
TYATDPNYAK KLNSIIKHYQ LTQFDDERMP DLDKYERSIK DYDDSSDEFK PFREVSDSMP 480
YPHGQCTWYV YNRMKQFGTS ISGDLGDAHN WNNRAQYRDY QVSHTPKRHA AVVFEAGQFG 540
ADQHYGHVAF VEKVNSDGSI VISESNVKGL GIISHRTINA AAAEELSYIT GKGSGGGAMT 600
EKEKMLAEKW YDANFDQDLI NERARAKDIC FELNHTKPSD KNKRKELIDE LFQTTDNVS 660
ISIPFDTDYG WNVKLGKNVY VNTNCYFMDG GQITIGDNVF IGPNCGFYTA THPLNFHHRN 720
EGFEKAGPIN IGSNTWFGGH VAVLPGVTIG EGSVIGAGSV VTKDIPPHSL AVGNPCKVVR 780
KIDNEVPSEA LNDETLN                                             797

SEQ ID NO: 75              moltype = AA  length = 803
FEATURE                    Location/Qualifiers
REGION                     1..803
                           note = Chimeric polypeptide
source                     1..803
                           mol_type = protein
                           organism = synthetic construct
SEQUENCE: 75
DTPQKDTTAK TTSHDSKKSN DDETSKDTTS KDIDKADNNN TSNQDNNDKK FKTIDDSTSD  60
SNNIIDFIYK NLPQTNINQL LTKNKYDDNY SLTTLIQNLF NLNSDISDYE QPRNGEKSTN 120
DSNKNSDNSI KNDTDTQSSK QDKADNQKAP KSNNTKPSTS NKQPNSPKPT QPNQSNSQPA 180
SDDKANQKSS SKDNQSMSDS ALDSILDQYS EDAKKTQKDY ASQSKKDKNE KSNTKNPQLP 240
TQDELKHKSK PAQSFNNDVN QKDTRATSLF ETDPSISNND DSGQFNVVDS KDTRQFVKSI 300
AKDAHRIGQD NDIYASVMIA QAILESDSGR SALAKSPNHN LFGIKGAFEG NSVPFNTLEA 360
DGNKLYSINA GFRKYPSTKE SLKDYSDLIK NGIDGNRTIY KPTWKSEADS YKDATSHLSK 420
TYATDPNYAK KLNSIIKHYQ LTQFDDERMP DLDKYERSIK DYDDSSDEFK PFREVSDSMP 480
YPHGQCTWYV YNRMKQFGTS ISGDLGDAHN WNNRAQYRDY QVSHTPKRHA AVVFEAGQFG 540
ADQHYGHVAF VEKVNSDGSI VISESNVKGL GIISHRTINA AAAEELSYIT GKKPEPKPAP 600
APKPMTEKEK MLAEKWYDAN FDQDLINERA RAKDICFELN HTKPSDKNKR KELIDELFQT 660
TDNVSISIP FDTDYGWNVK LGKNVYVNTN CYFMDGGQIT IGDNVFIGPN CGFYTATHPL 720
NFHHRNEGFE KAGPINIGSN TWFGGHVAVL PGVTIGEGSV IGAGSVVTKD IPPHSLAVGN 780
PCKVVRKIDN EVPSEALNDE TLN                                      803

SEQ ID NO: 76              moltype = AA  length = 988
FEATURE                    Location/Qualifiers
REGION                     1..988
                           note = Chimeric polypeptide
source                     1..988
                           mol_type = protein
                           organism = synthetic construct
SEQUENCE: 76
```

```
DTPQKDTTAK TTSHDSKKSN DDETSKDTTS KDIDKADNNN TSNQDNNDKK FKTIDDSTSD    60
SNNIIDFIYK NLPQTNINQL LTKNKYDDNY SLTTLIQNLF NLNSDISDYE QPRNGEKSTN   120
DSNKNSDNSI KNDTDTQSSK QDKADNQKAP KSNNTKPSTS NKQPNSPKPT QPNQSNSQPA   180
SDDKANQKSS SKDNQSMSDS ALDSILDQYS EDAKKTQKDY ASQSKKDKNE KSNTKNPQLP   240
TQDELKHKSK PAQSFNNDVN QKDTRATSLF ETDPSISNND DSGQFNVVDS KDTRQFVKSI   300
AKDAHRIGQD NDIYASVMIA QAILESDSGR SALAKSPNHN LFGIKGAFEG NSVPFNTLEA   360
DGNKLYSINA GFRKYPSTKE SLKDYSDLIK NGIDGNRTIY KPTWKSEADS YKDATSHLSK   420
TYATDPNYAK KLNSIIKHYQ LTQFDDERMP DLDKYERSIK DYDDSSDEFK PFREVSDSMP   480
YPHGQCTWYV YNRMKQFGTS ISGDLGDAHN WNNRAQYRDY QVSHTPKRHA AVVFEAGQFG   540
ADQHYGHVAF VEKVNSDGSI VISESNVKGL GIISHRTINA AAAEELSYIT GKGSGGGAKV   600
AKQGQYKNQD PIVLVHGFNG FTDDINPSVL AHYWGGNKMN IRQDLEENGY KAYEASISAF   660
GSNYDRAVEL YYYIKGGRVD YGAAHAAKYG HERYGKTYEG IYKDWKPGQK VHLVGHSMGG   720
QTIRQLEELL RNGSREEIEY QKKHGGEISP LFKGNNDNMI SSITTLGTPH NGTHASDLAG   780
NEALVRQIVF DIGKMFGNKN SRVDFGLAQW GLKQKPNESY IDYVKRVKQS NLWKSKDNGF   840
YDLTREGATD LNRKTSLNPN IVYKTYTGEA THKALNSDRQ KADLNMFFPF VITGNLIGKA   900
TEKEWRENDG LVSVISSQHP FNQAYTNATD KIQKGIWQVT PTKHDWDHVD FVGQDSSDTV   960
RTREELQDFW HHLADDLVKT EKVTDTKQ                                     988

SEQ ID NO: 77           moltype = AA  length = 784
FEATURE                 Location/Qualifiers
REGION                  1..784
                        note = Chimeric polypeptide
source                  1..784
                        mol_type = protein
                        organism = synthetic construct
SEQUENCE: 77
DTPQKDTTAK TTSHDSKKSN DDETSKDTTS KDIDKADNNN TSNQDNNDKK FKTIDDSTSD    60
SNNIIDFIYK NLPQTNINQL LTKNKYDDNY SLTTLIQNLF NLNSDISDYE QPRNGEKSTN   120
DSNKNSDNSI KNDTDTQSSK QDKADNQKAP KSNNTKPSTS NKQPNSPKPT QPNQSNSQPA   180
SDDKANQKSS SKDNQSMSDS ALDSILDQYS EDAKKTQKDY ASQSKKDKNE KSNTKNPQLP   240
TQDELKHKSK PAQSFNNDVN QKDTRATSLF ETDPSISNND DSGQFNVVDS KDTRQFVKSI   300
AKDAHRIGQD NDIYASVMIA QAILESDSGR SALAKSPNHN LFGIKGAFEG NSVPFNTLEA   360
DGNKLYSINA GFRKYPSTKE SLKDYSDLIK NGIDGNRTIY KPTWKSEADS YKDATSHLSK   420
TYATDPNYAK KLNSIIKHYQ LTQFDDERMP DLDKYERSIK DYDDSSDEFK PFREVSDSMP   480
YPHGQCTWYV YNRMKQFGTS ISGDLGDAHN WNNRAQYRDY QVSHTPKRHA AVVFEAGQFG   540
ADQHYGHVAF VEKVNSDGSI VISESNVKGL GIISHRTINA AAAEELSYIT GKGSGGGAKV   600
AKQGQYKNQD PIVLVHGFNG FTDDINPSVL AHYWGGNKMN IRQDLEENGY KAYEASISAF   660
GSNYDRAVEL YYYIKGGRVD YGAAHAAKYG HERYGKTYEG IYKDWKPGQK VHLVGHSMGG   720
QTIRQLEELL RNGSREEIEY QKKHGGEISP LFKGNNDNMI SSITTLGTPH NGTHASDLAG   780
NEAL                                                               784

SEQ ID NO: 78           moltype = AA  length = 501
FEATURE                 Location/Qualifiers
REGION                  1..501
                        note = Chimeric polypeptide
source                  1..501
                        mol_type = protein
                        organism = synthetic construct
SEQUENCE: 78
ADSDINIKTG TTDIGSNTTV KTGDLVTYDK ENGMLKKVFY SFIDDKNHNK KLLVIRTKGT    60
IAGQYRVYSE EGANKSGLAW PSAFKVQLQL PDNEVAQISD YYPRNSIDTK EYMSTLTYGF   120
NGNVTGDDTG KIGGLIGANV SIGHTLKYVQ PDFKTILESP TDKKVGWKVI FNNMVNQNWG   180
PYDRDSWNPV YGNQLFMKTR NGSMKAADNF LDPNKASSLL SSGFSPDFAT VITMDRKASK   240
QQTNIDVIYE RVRDDYQLHW TSTNWKGTNT KDKWIDRSSE RYKIDWEKEE MTNGSGGGAK   300
RIKQHPDVQK VTDATSKVAS KTSAAISNTA SDVKEYVGDK KQDFENKREL KKFAREHDPA   360
YIEKKGEKLA KQNRKADKM NKILQKNIEK RHKEEQKARE KNEIQRIKDM KKSQKYEVKA   420
GLTPNKLDEK TEKKGDKLAE KNRKEIAKMN KKLQKNIEKR HKEEQKRQQE ADKARIKSFK   480
KYKDYVAKSA SQQNKENNTE A                                            501

SEQ ID NO: 79           moltype = AA  length = 498
FEATURE                 Location/Qualifiers
REGION                  1..498
                        note = Chimeric polypeptide
source                  1..498
                        mol_type = protein
                        organism = synthetic construct
SEQUENCE: 79
ADSDINIKTG TTDIGSNTTV KTGDLVTYDK ENGMLKKVFY SFIDDKNHNK KLLVIRTKGT    60
IAGQYRVYSE EGANKSGLAW PSAFKVQLQL PDNEVAQISD YYPRNSIDTK EYMSTLTYGF   120
NGNVTGDDTG KIGGLIGANV SIGHTLKYVQ PDFKTILESP TDKKVGWKVI FNNMVNQNWG   180
PYDRDSWNPV YGNQLFMKTR NGSMKAADNF LDPNKASSLL SSGFSPDFAT VITMDRKASK   240
QQTNIDVIYE RVRDDYQLHW TSTNWKGTNT KDKWIDRSSE RYKIDWEKEE MTNGSGGGAM   300
TEKEKMLAEK WYDANFDQDL INERARAKDI CFELNHTKPS DKNKRKELID ELFQTTTDNV   360
SISIPFDTDY GWNVKLGKNV YVNTNCYFMD GGQITIGDNV FIGPNCGFYT ATHPLNPHHR   420
NEGFEKAGPI NIGSNTWFGG HVAVLPGVTI GEGSVIGAGS VVTKDIPPHS LAVGNPCKVV   480
RKIDNEVPSE ALNDETLN                                                498

SEQ ID NO: 80           moltype = AA  length = 689
FEATURE                 Location/Qualifiers
```

```
REGION                          1..689
                                note = Chimeric polypeptide
source                          1..689
                                mol_type = protein
                                organism = synthetic construct
SEQUENCE: 80
ADSDINIKTG TTDIGSNTTV KTGDLVTYDK ENGMLKKVFY SFIDDKNHNK KLLVIRTKGT    60
IAGQYRVYSE EGANKSGLAW PSAFKVQLQL PDNEVAQISD YYPRNSIDTK EYMSTLTYGF   120
NGNVTGDDTG KIGGLIGANV SIGHTLKYVQ PDFKTILESP TDKKVGWKVI FNNMVNQNWG   180
PYDRDSWNPV YGNQLFMKTR NGSMKAADNF LDPNKASSLL SSGFSPDFAT VITMDRKASK   240
QQTNIDVIYE RVRDDYQLHW TSTNWKGTNT KDKWIDRSSE RYKIDWEKEE MTNGSGGGAK   300
VAKQGQYKNQ DPIVLVHGFN GFTDDINPSV LAHYWGGNKM NIRQDLEENG YKAYEASISA   360
FGSNYDRAVE LYYYIKGGRV DYGAAHAAKY GHERYGKTYE GIYKDWKPGQ KVHLVGHSMG   420
GQTIRQLEEL LRNGSREEIE YQKKHGGEIS PLFKGNNDNM ISSITTLGTP HNGTHASDLA   480
GNEALVRQIV FDIGKMFGNK NSRVDFGLAQ WGLKQKPNES YIDYVKRVKQ SNLWKSKDNG   540
FYDLTREGAT DLNRKTSLNP NIVYKTYTGE ATHKALNSDR QKADLNMFFP FVITGNLIGK   600
ATEKEWREND GLVSVISSQH PFNQAYTNAT DKIQKGIWQV TPTKHDWDHV DFVGQDSSDT   660
VRTREELQDF WHHLADDLVK TEKVTDTKQ                                    689

SEQ ID NO: 81                   moltype = AA   length = 390
FEATURE                         Location/Qualifiers
REGION                          1..390
                                note = Chimeric polypeptide
source                          1..390
                                mol_type = protein
                                organism = synthetic construct
SEQUENCE: 81
KVAKQGQYKN QDPIVLVHGF NGFTDDINPS VLAHYWGGNK MNIRQDLEEN GYKAYEASIS    60
AFGSNYDRAV ELYYYIKGGR VDYGAAHAAK YGHERYGKTY EGIYKDWKPG QKVHLVGHSM   120
GGQTIRQLEE LLRNGSREEI EYQKKHGGEI SPLFKGNNDN MISSITTLGT PHNGTHASDL   180
AGNEALVRQI VFDIGKMFGN KNSRVDFGLA QWGLKQKPNE SYIDYVKRVK QSNLWKSKDN   240
GFYDLTREGA TDLNRKTSLN PNIVYKTYTG EATHKALNSD RQKADLNMFF PFVITGNLIG   300
KATEKEWREN DGLVSVISSQ HPFNQAYTNA TDKIQKGIWQ VTPTKHDWDH VDFVGQDSSD   360
TVRTREELQD FWHHLADDLV KTEKVTDTKQ                                   390

SEQ ID NO: 82                   moltype = AA   length = 186
FEATURE                         Location/Qualifiers
REGION                          1..186
                                note = Chimeric polypeptide
source                          1..186
                                mol_type = protein
                                organism = synthetic construct
SEQUENCE: 82
KVAKQGQYKN QDPIVLVHGF NGFTDDINPS VLAHYWGGNK MNIRQDLEEN GYKAYEASIS    60
AFGSNYDRAV ELYYYIKGGR VDYGAAHAAK YGHERYGKTY EGIYKDWKPG QKVHLVGHSM   120
GGQTIRQLEE LLRNGSREEI EYQKKHGGEI SPLFKGNNDN MISSITTLGT PHNGTHASDL   180
AGNEAL                                                             186

SEQ ID NO: 83                   moltype = AA   length = 293
FEATURE                         Location/Qualifiers
REGION                          1..293
                                note = Chimeric polypeptide
source                          1..293
                                mol_type = protein
                                organism = synthetic construct
SEQUENCE: 83
ADSDINIKTG TTDIGSNTTV KTGDLVTYDK ENGMLKKVFY SFIDDKNHNK KLLVIRTKGT    60
IAGQYRVYSE EGANKSGLAW PSAFKVQLQL PDNEVAQISD YYPRNSIDTK EYMSTLTYGF   120
NGNVTGDDTG KIGGLIGANV SIGHTLKYVQ PDFKTILESP TDKKVGWKVI FNNMVNQNWG   180
PYDRDSWNPV YGNQLFMKTR NGSMKAADNF LDPNKASSLL SSGFSPDFAT VITMDRKASK   240
QQTNIDVIYE RVRDDYQLHW TSTNWKGTNT KDKWIDRSSE RYKIDWEKEE MTN          293

SEQ ID NO: 84                   moltype = AA   length = 573
FEATURE                         Location/Qualifiers
REGION                          1..573
                                note = Chimeric polypeptide
source                          1..573
                                mol_type = protein
                                organism = synthetic construct
SEQUENCE: 84
AAEETGGTNT EAQPKTEAVA SPTTTSEKAP ETKPVANAVS VSNKEVEAPT SETKEAKEVK    60
EVKAPKETKE VKPAAKATNN TYPILNQELR EAIKNPAIKD KDHSAPNSRP IDFEMKKKDG   120
TQQFYHYASS VKPARVIFTD SKPEIELGLQ SGQFWRKFEV YEGDKKLPIK LVSYDTVKDY   180
AYIRFSVSNG TKAVKIVSST HFNNKEEKYD YTLMEFAQPI YNSADKFKTE EDYKAEKLLA   240
PYKKAKTLER QVYELNKIQD KLPEKLKAEY KKKLEDTKKA LDEQVKSAIT EFQNVQPTNE   300
KMTDLQDTKY VVYESVENNE SMMDTFVKHP IKTGMLNGKK YMVMETTNDD YWKDFMVEGQ   360
RVRTISKDAK NNTRTIIFPY VEGKTLYDAI VKVHVKTIDY DGQYHVRIVD KEAFTKANTD   420
KSNKKEQQDN SAKKEATPAT PSKPTPSPVE KESQKQDSQK DDNKQLPSVE KENDASSESG   480
KDKTPATKPT KGEVESSSTT PTKVVSTTQN VAKPTTASSK TTKDVVQTSA GSSEAKDSAP   540
```

```
LQKANIKNTN DGHTQSQNNK NTQENKAKSL PQT                                        573

SEQ ID NO: 85            moltype = AA   length = 409
FEATURE                  Location/Qualifiers
REGION                   1..409
                         note = Chimeric polypeptide
source                   1..409
                         mol_type = protein
                         organism = synthetic construct
SEQUENCE: 85
MDIGKKHVIP KSQYRRKRRE FFHNEDREEN LNQHQDKQNI DNTTSKKADK QIHKDSIDKH   60
ERFKNSLSSH LEQRNRDVNE NKAEESKSNQ DSKSAYNRDH YLTDDVSKKQ NSLDSVDQDT  120
EKSKYYEQNS EATLSTKSTD KVESTEMRKL SSDKNKVGHE EQHVLSKPSE HDKETRIDSE  180
SSRTDSDSSM QTEKIKKDSS DGNKSSNLKS EVISDKSNTV PKLSESDDEV NNQKPLTLPE  240
EQKLKRQQSQ NEQTKTYTYG DSEQNDKSNH ENDLSHHIPS ISDDKDNVMR ENHIVDDNPD  300
NDINTPSLSK TDDDRKLDEK IHVEDKHKQN ADSSETVGYQ SQSTASHRST EKRNISINDH  360
DKLNGQKTNT KTSANNNQKK ATSKLNKGRA TNNNYSDILK KFWMMYWPK             409

SEQ ID NO: 86            moltype = AA   length = 592
FEATURE                  Location/Qualifiers
REGION                   1..592
                         note = Chimeric polypeptide
source                   1..592
                         mol_type = protein
                         organism = synthetic construct
SEQUENCE: 86
DTPQKDTTAK TTSHDSKKSN DDETSKDTTS KDIDKADNNN TSNQDNNDKK FKTIDDSTSD   60
SNNIIDFIYK NLPQTNINQL LTKNKYDDNY SLTTLIQNLF NLNSDISDYE QPRNGEKSTN  120
DSNKNSDNSI KNDTDTQSSK QDKADNQKAP KSNNTKPSTS NKQPNSPKPT QPNQSNSQPA  180
SDDKANQKSS SKDNQSMSDS ALDSILDQYS EDAKKTQKDY ASQKSKKDNE KSNTKNPQLP  240
TQDELKHKSK PAQSFNNDVN QKDTRATSLF ETDPSISNND DSGQFNVVDS KDTRQFVKSI  300
AKDAHRIGQD NDIYASVMIA QAILESDSGR SALAKSPNHN LFGIKGAFEG NSVPFNTLEA  360
DGNKLYSINA GFRKYPSTKE SLKDYSDLIK NGIDGNRTIY KPTWKSEADS YKDATSHLSK  420
TYATDPNYAK KLNSIIKHYQ LTQFDDERMP DLDKYERSLK DYDDSSDEFK PPREVSDSMP  480
YPHGQCTWYV YNRMQFGTS ISGDLGDAHN WNNRAQYRDY QVSHTPKRHA AVVFEAGQFG  540
ADQHYGHVAF VEKVNSDGSI VISESNVKGL GIISHRTINA AAAEELSYIT GK         592

SEQ ID NO: 87            moltype = AA   length = 793
FEATURE                  Location/Qualifiers
source                   1..793
                         mol_type = protein
                         organism = Staphylococcus aureus
SEQUENCE: 87
QTKYGDQSEK GSQSVSNKNN KIHIAIVNED QPTTYNGKKV ELGQAFIKRL ANEKNYKFET   60
VTRNVAESGL KNGGYQVMIV IPENFSKLAM QLDAKTPSKI SLQYKTAVGQ KEEVAKNTEK  120
VVSNVLNDFN KNLVEIYLTS IIDNLHNAQK NVGAIMTREH GVNSKFSNYL LNPINDFPEL  180
FTDTLVNSIS ANKDITKWFQ TYNKSLLSAN SDTFRVNTDY NVSTLIEKQN SLFDEHNTAM  240
DKMLQDYKSQ KDSVELDNYI NALKQMDSQI DQQSSMQDTG KEEYKQTVKE NLDKLREIIQ  300
SQESPFSKGM IEDYRKQLTE SLQDELANNK DLQDALNSIK MNNAQFAENL EKQLHDDIVK  360
EPDSDTTFIY NMSKQDFIAA GLNEDEANKY EAIVKEAKRY KNEYNLKKPL AEHINLTDYD  420
NQVAQDTSSL INDGVKVQRT ETIKSNDINQ LTVATDPHFN FEGDIKINGK KYDIKDQSVQ  480
LDTSNKEYKV EVNGVAKLKK DAEKDFLKDK TMHLQLLFGQ ANRQDEPNDK KATSVVDVTL  540
NHNLDGRLSK DALSQQLSAL SRFDAHYKMY TDTKGREDKP FDNKRLIDMM VDQVINDMES  600
FKDDKVAVLH QIDSMEENSD KLIDDILNNK KNTTKNEDI SKLIDQLENV KKTFAEEPQE  660
PKIDKGKNDE FNTMSSNLDK EISRISEKST QLLSDTQESK TIADSVSGQL NQLDNNVNKL  720
HATGRALGVR ANDLRMQMAK NDKDNELFAK EFKKVLQNSK DGDRQNQALK AFMSNPVQKK  780
NLENVLANNG NTD                                                    793

SEQ ID NO: 88            moltype = AA   length = 202
FEATURE                  Location/Qualifiers
source                   1..202
                         mol_type = protein
                         organism = Staphylococcus aureus
SEQUENCE: 88
KRIKQHPDVQ KVTDATSKVA SKTSAAISNT ASDVKEYVGD KKQDFENKRE LKKFAREHDP   60
AYIEKKGEKL AKQNRKDADK MNKILQKNIE KRHEEQKAR EKNEIQRIKD MKKSQKYEVK  120
AGLTPNKLDE KTEKKGDKLA EKNRKEIAKM NKKLQKNIEK RHEEQKRQQ EADKARIKSF  180
KKYKDYVAKS ASQQNKENNT EA                                          202

SEQ ID NO: 89            moltype = AA   length = 409
FEATURE                  Location/Qualifiers
source                   1..409
                         mol_type = protein
                         organism = Staphylococcus aureus
SEQUENCE: 89
MDIGKKHVIP KSQYRRKRRE FFHNEDREEN LNQHQDKQNI DNTTSKKADK QIHKDSIDKH   60
ERFKNSLSSH LEQRNRDVNE NKAEESKSNQ GSKSAYNKDH YLTDDVSKKQ NSLDSVDQDT  120
EKSKYYEQNT EATLSTNSTD KVESTDMRKL SSDKNKVGHE EQHVLSKPSE HDKETRIDFE  180
SSRTDSDSSM QTEKIKKDSS DGNKSSNLKS EVISDKSNSV PILSESDDEV NNQKPLTLPE  240
```

```
EQKLKRQQSQ NEQTKTYTYG DSEQNDKSNH ENDLSHHTPS ISDDKDYVMR EDHIVDDNPD   300
NDINTPSLSK IDDDRKLDEK IHVEDKHKQN ADSSETVGYQ SQSSASHRST EKRNMAINDH   360
DKLNGQKPNT KTSANNNQKK ATSKLNKGRA TNNNYSAILK KFWMMYWPK              409

SEQ ID NO: 90            moltype = AA   length = 495
FEATURE                  Location/Qualifiers
source                   1..495
                         mol_type = protein
                         organism = Staphylococcus aureus
SEQUENCE: 90
RNLLLQKQSQ ARQTAEDIVN QAHKEADNIK KEKLLEAKEE NQILREQTEA ELRERRSELQ    60
RQETRLLQKE ENLERKSDLL DKKDEILEQK ESKIEEKQQQ VDAKESSVQT LIMKHEQELE   120
RISGLTQEEA INEQLQRVEE ELSQDIAVLV KEKEKEAKEK VDKTAKELLA TAVQRLAADH   180
TSESTVSVVN LPNDEMKGRI IGREGRNIRT LETLTGIDLI IDDTPEAVIL SGFDPIRREI   240
ARTALVNLVS DGRIHPGRIE DMVEKARKEV DDIIREAGEQ ATFEVNAHNM HPDLVKIVGR   300
LNYRTSYGQN VLKHSIEVAH LASMLAAELG EDETLAKRAG LLHDVGKAID HEVEGSHVEI   360
GVELAKKYGE NETVINAIHS HHGDVEPTSI ISILVAAADA LSAARPGARK ETLENYIRRL   420
ERLETLSESY DGVEKAFAIQ AGREIRVIVS PEEIDDLKSY RLARDIKNQI EDELQYPGHI   480
KVTVVRETRA VEYAK                                                   495

SEQ ID NO: 91            moltype = AA   length = 144
FEATURE                  Location/Qualifiers
source                   1..144
                         mol_type = protein
                         organism = Staphylococcus aureus
SEQUENCE: 91
NNHNNGTKEN KIANTNKNNA DESKDKDTSK DASKDKSKST DSDKSKDDQD KATKDESDND    60
QNNANQANNQ AQNNQNQQQA NQNQQQQQQR QGGGQRHTVN GQENLYRIAI QYYGSGSPEN   120
VEKIRRANGL SGNNIRNGQQ IVIP                                         144

SEQ ID NO: 92            moltype = AA   length = 652
FEATURE                  Location/Qualifiers
source                   1..652
                         mol_type = protein
                         organism = Staphylococcus aureus
SEQUENCE: 92
MNEKVEGMTL ELKLDHLGVQ EGMKGLKRQL GVVNSEMKAN LSAFDKSEKS MEKYQARIKG    60
LNDRLKVQKK MYSQVEDELK QVNANYQKAK SSVKDVEKAY LKLVEANKKE KLALDKSKEA   120
LKSSNTELKK AENQYKRTNQ RKQDAYQKLK QLRDAEQKLK NSNQATTAQL KRASDAVQKQ   180
SAKHKALVEQ YKQEGNQVQK LKVQNDNLSK SNDKIESSYA KTNTKLKQTE KEFNDLNNTI   240
KNHSANVAKA ETAVNKEKAA LNNLERSIDK ASSEMKTFNK EQMIAQSHFG KLASQADVMS   300
KKFSSIGDKM TSLGRTMTMG VSTPITLGLG AALKTSADFE GQMSRVGAIA QASSKDLKSM   360
SNQAVDLGAK TSKSANEVAK GMEELAALGF NAKQTMEAMP GVISAAEASG AEMATTATVM   420
ASAINSFGLK ASDANHVADL LARSANDSAA DIQYMGDALK YAGTPAKALG VSIEDTSAAI   480
EVLSNSGLEG SQAGTALRAS FIRLANPSKN TAKEMKKLGI HLSDAKGQFV GMGELIRQFQ   540
DNMKGMTREQ KLATVATIVG TEAASGFLAL IEAGPDKINS YSKSLKNSNG ESKKAADLMK   600
DNLKGALEQL GGAFESLAIE VGKDLTPMIR AGAEGLTKLV DGFTHLPGWV RK           652

SEQ ID NO: 93            moltype = AA   length = 199
FEATURE                  Location/Qualifiers
source                   1..199
                         mol_type = protein
                         organism = Staphylococcus aureus
SEQUENCE: 93
MTEKEKMLAE KWYDANFDQD LINERARAKD ICFELNHTKP SDKNKRKELI DELFQTTTDN    60
VSISIPFDTD YGWNVKLGKN VYVNTNCYFM DGGQITIGDN VFIGPNCGFY TATHPLNFHH   120
RNEGFEKAGP INIGSNTWFG GHVAVLPGVT IGEGSVIGAG SVVTKDIPPH SLAVGNPCKV   180
VRKIDNEVPS EALNDETLN                                               199

SEQ ID NO: 94            moltype = AA   length = 592
FEATURE                  Location/Qualifiers
source                   1..592
                         mol_type = protein
                         organism = Staphylococcus aureus
SEQUENCE: 94
DTPQKDTTAK TTSHDSKKST DDETSKDTTS KDIDKADNNN TSNQDNNDKK VKTIDDSTSD    60
SNNIIDFIYK NLPQTNINQL LTKNKYDDNY SLTTLIQNLF NLNSDISDYE QPRNGEKSTN   120
DSNKNSDNSI KNDTDTQSSK QDKADNQKAP KSNNTKPSTS NKQPNSPKPT QPNQSNSQPA   180
SDDKVNQKSS SKDNQSMSDS ALDSILDQYS EDAKKTQKDY ASQSKKDKNE KSNTKNPQLP   240
TQDELKHKSK PAQSFNNDVN QKDTRATSLF ETDPSISNND DSGQFNVVDS KDTRQFVKSI   300
AKDAHRIGQD NDIYASVMIA QAILESDSGR SALAKSPNHN LFGIKGAFEG NSVPFNTLEA   360
DGNQLYSINA GFRKYPSTKE SLKDYSDLIK NGIDGNRTIY KPTWKSEADS YKDATSHLSK   420
TYATDPNYAK KLNSIIKHYQ LTQFDDERMP DLDKYERSIK DYDDSSDEFK PPREVSDNMP   480
YPHGQCTWYV YNRMQFGTS ISGDLGDAHN WNNRAQYRDY QVSHTPKRHA AVVFEAGQFG   540
ADQHYGHVAF VEKVNSDGSI VISESNVKGL GIISHRTINA AAAEELSYIT GK           592

SEQ ID NO: 95            moltype = AA   length = 441
FEATURE                  Location/Qualifiers
source                   1..441
```

```
                            mol_type = protein
                            organism = Staphylococcus aureus
SEQUENCE: 95
AEKQVNMGNS QEDTVTAQSI GDQQTRENAN YQRENGVDEQ QHTENLTKNL HNDKTISEEN    60
HRKTDDLNKD QLKDDKKSSL NNKNIQRDTT KNNNANPRDV NQGLEQAIND GKQSKVASQQ   120
QSKEADNSQD LNANNNLPSQ SRTKVSPSLN KSDQTSQREI VNETEIEKVQ PQQKNQANDK   180
ITDHNFNNEQ EVKPQKDEKT LSVSDLKNNQ KSPVEPTKDN DKKNGLNLLK SSAVATLPNK   240
GTKELTAKAK GDQTNKVAKQ GQYKNQDPIV LVHGFNGFTD DINPSVLAHY WGGNKMNIRQ   300
DLEENGYKAY EASISAFGSN YDRAVELYYY IKGGRVDYGA AHAAKYGHER YGKTYEGIYK   360
DWKPGQKVHL VGHSMGGQTI RQLEELLRNG SREEIEYQKK HSGEISPLFK GNNDNMISSI   420
TTLGTPHNGT HASDLAGNEA L                                            441

SEQ ID NO: 96               moltype = AA  length = 365
FEATURE                     Location/Qualifiers
source                      1..365
                            mol_type = protein
                            organism = Staphylococcus aureus
SEQUENCE: 96
GFLNKSKNEQ AALKAQQAAI KEEASANNLS DTSQEAQEIQ EAKREAQAEA DKSVAVSNKE    60
SKAVALKAQQ AAIKEEASAN NLSDTSQEAQ EIQEAKKEAQ AETDKSAAVS NEEPKAVALK   120
AQQAAIKEEA SANNLSDISQ EAQEVQEAKK EAQAEKDSDT LTKDASAAKV EVSKPESQAE   180
RLANAAKQKQ AKLTPGSKES QLTEALFAEK PVAKNDLKEI PQLVTKKNDV SETETVNIDN   240
KDTVKQKEAK FENGVITRKA DEKTTNNTAV DKKSGKQSKK TTPSNKRNAS KASTNKTSGQ   300
KKQHNKKSSQ GAKKQSSSSK STQKNNQTSN KNSKTTNAKS SNASKTPNAK VEKAKSKIEK   360
RTFND                                                              365

SEQ ID NO: 97               moltype = AA  length = 351
FEATURE                     Location/Qualifiers
source                      1..351
                            mol_type = protein
                            organism = Staphylococcus aureus
SEQUENCE: 97
KDNLNGEKPT TNLNHNITSP SVNSEMNNNE TGTPHESNQT GNEGTGSNSR DANPDSNNVK    60
PDSNNQNPST DSKPDPNNQN PSPNPKPDPD NPKPKPDPKP DPDKPKPNPD PKPDPDNPKP   120
NPDPKPDPNK PNPDKPDPD KPKPNPNPKP DPNKPNPNPS PDPDQPGDSN HSGGSKNGGT   180
WNPNASDGSN QGQWQPNGNQ GNSQNPTGND FVSQRFLALA NGAYKYNPYI LNQINKLGKD   240
YGEVTDEDIY NIIRKQNFSG NAYLNGLQQQ SNYFRFQYFN PLKSERYYRN LDEQVLALIT   300
GEIGSMPDLK KPEDKPDSKQ RSFEPHEKDD FTVVKKQEDN KKSASTAYSK S            351

SEQ ID NO: 98               moltype = AA  length = 412
FEATURE                     Location/Qualifiers
source                      1..412
                            mol_type = protein
                            organism = Staphylococcus aureus
SEQUENCE: 98
IDSKNKPANS DIKFEVTQKS DAVKALKELP KSENVKNIYQ DYAVTDVKTD KKGFTHYTLQ    60
PSVDGVHAPD KEVKVHADKS GKVVLINGDT DAKKVKPTNK VTLSKDDAAD KAFKAVKIDK   120
NKAKNLKDKV IKENKVEIDG DSNKYVYNVE LITVTPEISH WKVKIDAQTG EILEKMNLVK   180
EAAETGKGKG VLGDTKDINI NSIDGGFSLE DLTHQGKLSA FSFNDQTGQA TLITNEDENF   240
VKDEQRAGVD ANYYAKQTYD YYKDTFGRES YDNQGSPIVS LTHVNNYGGQ DNRNNAAWIG   300
DKMIYGDGDG RTFTSLSGAN DVVAHELTHG VTQETANLEY KDQSGALNES FSDVFGYFVD   360
DEDFLMGEDV YTPGKEGDAL RSMSNPEQFG QPAHMKDYVF TEKDNGGVHT NS           412

SEQ ID NO: 99               moltype = DNA  length = 1872
FEATURE                     Location/Qualifiers
misc_feature                1..1872
                            note = DNA construct
source                      1..1872
                            mol_type = other DNA
                            organism = synthetic construct
SEQUENCE: 99
aaacgtatca acaacatcc ggacgtacaa aaagttacag atgctacaag taaagttgct     60
tcaaaaacat ctgcagcaat cagtaacaca gcgagtgatg ttaaagaata tgtcggcgat   120
aaaaaacaag attttgaaaa taagcgtgaa cttaaaagt tgctagaga acatgatcct    180
gcctatattg agaaaaaagg cgaaaaatta gctaaacaaa atcgtaaaga cgctgataaa   240
atgaataaaa tacttcaaaa aaatatcgaa aagcgtcata agaagagca aaaagcccgc   300
gaaaagaatg aaatacaacg tattaaagat atgaaaaagt cacaaaaata cgaagtaaaa   360
gcaggcttaa caccttaataa attagatgag aaaactgaga aaaaaggcga taaactagct   420
gaaaaaaatc gcaaagaaat cgctaaaatg aataaaaagt tacaaaaaaa tattgaaaaa   480
cgacacaaag aagaacaaaa acgccaacaa gaagctgata agcacgcat caagtcattt    540
aaaaaatata aagattatgt tgccaaaagc gcctctcaac aaaataaaga aaacaataca   600
gaggcaggtt ctggcggagg ggctggaagt ggtgggggcg ccatggatat tggtaaaaaa   660
catgtaattc ctaaaagtca gtaccgacgt aagcgtcgtg aattcttcca caacgaagac   720
agagaagaaa atttaaatca acatcaagat aacaaaata tagtaatac aacatcaaa    780
aaagcagata agcaaataca taaagattca attgataagc acgaacgttt taaaaatagt   840
ttatcatcgc atttagaaca gagaaaccgt gatgttaatg agaataaagc tgaagaaagt   900
aaaagtaatc aggatagtaa gtcagctat aacagagatc attatttaac agacgatgta   960
tctaaaaaac aaaattcatt agattcagtg gaccaagata cagagaaatc aaaatattat  1020
gagcaaaatt ctgaagcgac tttatcaact aaaatcaaccg ataagtaga atcaactgaa  1080
```

```
atgagaaagc taagttcaga taaaaacaaa gttggtcatg aagagcaaca tgtactttct  1140
aaaccttcag aacatgataa agagactaga attgattctg agtcttcaag aactgattca  1200
gacagctcga tgcagacaga gaaaataaaa aagacagtt  cagatggaaa taaaagtagt  1260
aatctgaaat ctgaagtaat atcagacaaa tcaaatacag taccaaaatt gtcggaatct  1320
gatgatgaag taaataatca gaagccatta actttaccgg aagaacagaa attgaaaaga  1380
cagcaaagtc aaaatgagca aacaaaaacc tatacatatg gtgatagcga acaaaatgac  1440
aagtctaatc atgaaaatga tttaagtcat catataccat cgataagtga tgataaagat  1500
aacgtcatga gagaaaatca tattgttgac gataatcctg ataatgatat caatacacca  1560
tcattatcaa aaacagatga cgatcgaaaa cttgatgaaa aaattcatgt tgaagataaa  1620
cataaacaaa atgcagactc gtctgaaacg gtgggatatc aaagtcagtc aactgcatct  1680
catcgtagca ctgaaaaaag aaatatttct attaatgacc atgataaatt aaacggtcaa  1740
aaaacaaata caaagacatc ggcaaataat aatcaaaaaa aggctacatc aaaattgaac  1800
aaagggcgcg ctacgaataa taattatagt gacattttga aaaagttttg gatgatgtat  1860
tggcctaaat aa                                                      1872
```

```
SEQ ID NO: 100        moltype = DNA  length = 1872
FEATURE               Location/Qualifiers
misc_feature          1..1872
                      note = DNA construct
source                1..1872
                      mol_type = other DNA
                      organism = synthetic construct
SEQUENCE: 100
atggatattg gtaaaaaaca tgtaattcct aaaagtcagt accgacgtaa gcgtcgtgaa    60
ttcttccaca acgaagacag agaagaaaat ttaaatcaac atcaagataa acaaaatata   120
gataatacaa catcaaaaaa agcagataag caaatacata aagattcaat tgataagcac   180
gaacgtttta aaaatagttt atcatcgcat ttagaacaga gaaaccgtga tgttaatgag   240
aataaagctg aagaaagtaa aagtaatcag gatagtaagt cagcatataa cagagatcat   300
tatttaacag acgatgtatc taaaaaacaa aattcattag attcagtgga ccaagataca   360
gagaaatcaa aatattatga gcaaaattct gaagcgactt tatcaactaa atcaaccgat   420
aaagtagaat caactgaaat gagaaagcta agttcagata aaaacaaagt tggtcatgaa   480
gagcaacatg tactttctaa accttcagaa catgataaag agactagaat tgattctgag   540
tcttcaagaa ctgattcaga cagctcgatg cagacagaga aaataaaaaa agacagttca   600
gatggaaata aaagtagtaa tctgaaatct gaagtaatat cagcaaatc  aaatacagta   660
ccaaaattgt cggaatctga tgatgaagta aataatcaga agccattaac tttaccggaa   720
gaacagaaat tgaaaagaca gcaaagtcaa aatgagcaaa caaaaaccta tacatatggt   780
gatagcgaac aaaatgacaa gtctaatcat gaaaatgatt taagtcatca tataccatcg   840
ataagtgatg ataaagataa cgtcatgaga gaaaatcata ttgttgacga taatcctgat   900
aatgatatca ataccaccatc attatcaaaa acagatgacg atcgaaaact tgatgaaaaa   960
attcatgttg aagataaaca taaacaaaat gcagactcgt ctgaaacggt gggatatcaa  1020
agtcagtcaa ctgcatctca tcgtagcact gaaaaaagaa atatttctat taatgaccat  1080
gataaattaa acggtcaaaa acaaatacaa agacatcgg  caaataataa tcaaaaaaag  1140
gctacatcaa aattgaacaa agggcgcgct acgaataaat aattatagtg acttttgaa  1200
aagttttgga tgatgtattg gcctaaaggt tctggcggag gggctggaag tggtgggggc  1260
gccaaacgta tcaacaaca  tccggacgta caaaaagtta cagatgctac aagtaaagtt  1320
gcttcaaaaa catctgcagc aatcagtaac acagcgagtg atgttaaaga atatgtcggc  1380
gataaaaaac aagattttga aaataagcgt gaacttaaaa agtttgctag agaacatgat  1440
cctgcctata ttgagaaaaa aggcgaaaaa ttagctaaac aaaatcgtaa agacgctgat  1500
aaaatgaata aaatacttca aaaaaatatc gaaaagcgtc ataaagaaga gcaaaaagcc  1560
cgcgaaaaga tgaaaataca acgtattaaa gatatgaaaa agtcacaaaa atacgaagta  1620
aaagcaggct taacacctaa taaattagat gagaaaaacg agaaaaaagg cgataaacta  1680
gctgaaaaaa atcgcaaaga aatcgctaaa atgaataaaa agttacaaaa aatattgaa   1740
aaacgacaca agaagaaca  aaaacgccaa caagaagctg ataaagcacg catcaagtca  1800
tttaaaaaat ataagaatta tgttgccaaa agcgcctctc aacaaaataa agaaaacaat  1860
acagaggcat aa                                                     1872
```

```
SEQ ID NO: 101        moltype = DNA  length = 1854
FEATURE               Location/Qualifiers
misc_feature          1..1854
                      note = DNA construct
source                1..1854
                      mol_type = other DNA
                      organism = synthetic construct
SEQUENCE: 101
atggatattg gtaaaaaaca tgtaattcct aaaagtcagt accgacgtaa gcgtcgtgaa    60
ttcttccaca acgaagacag agaagaaaat ttaaatcaac atcaagataa acaaaatata   120
gataatacaa catcaaaaaa agcagataag caaatacata aagattcaat tgataagcac   180
gaacgtttta aaaatagttt atcatcgcat ttagaacaga gaaaccgtga tgttaatgag   240
aataaagctg aagaaagtaa aagtaatcag gatagtaagt cagcatataa cagagatcat   300
tatttaacag acgatgtatc taaaaaacaa aattcattag attcagtgga ccaagataca   360
gagaaatcaa aatattatga gcaaaattct gaagcgactt tatcaactaa atcaaccgat   420
aaagtagaat caactgaaat gagaaagcta agttcagata aaaacaaagt tggtcatgaa   480
gagcaacatg tactttctaa accttcagaa catgataaag agactagaat tgattctgag   540
tcttcaagaa ctgattcaga cagctcgatg cagacagaga aaataaaaaa agacagttca   600
gatggaaata aaagtagtaa tctgaaatct gaagtaatat cagcaaatc  aaatacagta   660
ccaaaattgt cggaatctga tgatgaagta aataatcaga agccattaac tttaccggaa   720
gaacagaaat tgaaaagaca gcaaagtcaa aatgagcaaa caaaaaccta tacatatggt   780
gatagcgaac aaaatgacaa gtctaatcat gaaaatgatt taagtcatca tataccatcg   840
ataagtgatg ataaagataa cgtcatgaga gaaaatcata ttgttgacga taatcctgat   900
```

```
aatgatatca ataccaccatc attatcaaaa acagatgacg atcgaaaact tgatgaaaaa   960
attcatgttg aagataaaca taaacaaaat gcagactcgt ctgaaacggt gggatatcaa  1020
agtcagtcaa ctgcatctca tcgtagcact gaaaaaagaa atatttctat taatgaccat  1080
gataaattaa acggtcaaaa aacaaataca aagacatcgg caaataataa tcaaaaaaag  1140
gctacatcaa aattgaacaa agggcgcgct acgaataata attatagtga cattttgaaa  1200
aagttttgga tgatgtattg gcctaaaggt tctggcggag gggctaaacg tatcaaacaa  1260
catccggacg tacaaaaagt tacagatgct acaagtaaag ttgcttcaaa acatctgca   1320
gcaatcagta acacagcgag tgatgttaaa gaatatgtcg gcgataaaaa acaagatttt  1380
gaaaataagc gtgaacttaa aaagtttgct agagaacatg atcctgccta tattgagaaa  1440
aaaggcgaaa aattagctaa acaaaatcgt aaagacgctg ataaaatgaa taaaatactt  1500
caaaaaaata tcgaaaagcg tcataaagaa gagcaaaaag cccgcgaaaa gaatgaaata  1560
caacgtatta aagatatgaa aaagtcacaa aaatacgaag taaagcagg cttaacacct   1620
aataaattag atgagaaaac tgagaaaaaa ggcgataaat agctgaaaa aaatcgcaaa   1680
gaaatcgcta aaatgaataa aaagttacaa aaaaatattg aaaaacgaca caagaagaa   1740
caaaaacgcc aacaagaagc tgataaagca cgcatcaagt catttaaaaa atataaagat  1800
tatgttgcca aaagcgcctc tcaacaaaat aaagaaaaca atacagaggc ataa        1854

SEQ ID NO: 102           moltype = DNA  length = 1863
FEATURE                  Location/Qualifiers
misc_feature             1..1863
                         note = DNA construct
source                   1..1863
                         mol_type = other DNA
                         organism = synthetic construct
SEQUENCE: 102
atggatattg gtaaaaaaca tgtaattcct aaaagtcagt accgacgtaa gcgtcgtgaa    60
ttcttccaca acgaagacag agaagaaaat ttaaatcaac atcaagataa acaaaatata   120
gataatacaa catcaaaaaa agcagataag caaatacata agattcaat tgataagcac    180
gaacgtttta aaaatagttt atcatcgcat ttagaacaga gaaaccgtga tgttaatgag   240
aataaagctg aagaaagtaa aagtaatcag gatagtaagt cagcatataa cagagatcat   300
tatttaacag acgatgtatc taaaaaacaa aattcattag attcagtgga ccaagataca   360
gagaaatcaa aatattatga gcaaaattct gaagcgactt tatcaactaa atcaaccgat   420
aaagtagaat caactgaaat gagaaagcta agttcagata aaaacaaagt tggtcatgaa   480
gagcaacatg tactttctaa accttcagaa catgataaag agactagaat tgattctgag   540
tcttcaagaa ctgattcaga cagctcgatg cagacagaga aaataaaaaa agacagttca   600
gatgggaaata aaagtagtaa tctgaaatct gaagtaatat cagacaaatc aaatacagta   660
ccaaaattgt cggaatctga tgatgaagta aataatcaga agccattaac tttaccggaa   720
gaacagaaat tgaaaagaca gcaagtcaa aatgagcaaa caaaaaccta tacatatggt    780
gatagcgaac aaaatgacaa gtctaatcat gaaaatgatt taagtcatca tataccatcg   840
ataagtgatg ataaagataa cgtcatgaga gaaaatcata ttgttgacga taatcctgat   900
aatgatatca ataccaccatc attatcaaaa acagatgacg atcgaaaact tgatgaaaaa   960
attcatgttg aagataaaca taaacaaaat gcagactcgt ctgaaacggt gggatatcaa  1020
agtcagtcaa ctgcatctca tcgtagcact gaaaaaagaa atatttctat taatgaccat  1080
gataaattaa acggtcaaaa aacaaataca aagacatcgg caaataataa tcaaaaaaag  1140
gctacatcaa aattgaacaa agggcgcgct acgaataata attatagtga cattttgaaa  1200
aagttttgga tgatgtattg gcctaaaggt tctggcggag gggctggaag tggtgggggc  1260
gccatgactg aaaaagaaaa aatgttagca gaaaaatggt acgatgcaaa ctttgatcaa  1320
gacttaatca atgaacgtgc acgagcgaaa gatatttgct ttgaattaaa tcatacaaag  1380
ccgagtgaca aaaataaaag aaaggaatta atcgatgaat tattttcaaac aacaacagac  1440
aatgtaagta tttcgattcc ttttgataca gattatggtt ggaacgttaa actaggaaaa  1500
aatgtctatg taaacaccaa ttgttatttt atggatggtg gacagattac aattggcagt  1560
aatgttttta taggacctaa ttgtggattc tacacagcaa cacatccact taatttttcat  1620
catagaaatg aaggatttga aaagcagga ccaattaata ttggcagtaa tacttggttt    1680
ggcggacatg tagccgtgct tccgggagtg acgattggag aaggcagtgt gattggtgct  1740
ggtagtgttg tcaccaaaga tattccgcca cacagtttga cggttggaaa ccctttgtaaa  1800
gtcgttcgta aaattgataa tgaggtacca tcagaagcat gaacgatga aacactaaat   1860
tag                                                                 1863

SEQ ID NO: 103           moltype = DNA  length = 1845
FEATURE                  Location/Qualifiers
misc_feature             1..1845
                         note = DNA construct
source                   1..1845
                         mol_type = other DNA
                         organism = synthetic construct
SEQUENCE: 103
atggatattg gtaaaaaaca tgtaattcct aaaagtcagt accgacgtaa gcgtcgtgaa    60
ttcttccaca acgaagacag agaagaaaat ttaaatcaac atcaagataa acaaaatata   120
gataatacaa catcaaaaaa agcagataag caaatacata agattcaat tgataagcac    180
gaacgtttta aaaatagttt atcatcgcat ttagaacaga gaaaccgtga tgttaatgag   240
aataaagctg aagaaagtaa aagtaatcag gatagtaagt cagcatataa cagagatcat   300
tatttaacag acgatgtatc taaaaaacaa aattcattag attcagtgga ccaagataca   360
gagaaatcaa aatattatga gcaaaattct gaagcgactt tatcaactaa atcaaccgat   420
aaagtagaat caactgaaat gagaaagcta agttcagata aaaacaaagt tggtcatgaa   480
gagcaacatg tactttctaa accttcagaa catgataaag agactagaat tgattctgag   540
tcttcaagaa ctgattcaga cagctcgatg cagacagaga aaataaaaaa agacagttca   600
gatgggaaata aaagtagtaa tctgaaatct gaagtaatat cagacaaatc aaatacagta   660
ccaaaattgt cggaatctga tgatgaagta aataatcaga agccattaac tttaccggaa   720
gaacagaaat tgaaaagaca gcaaagtcaa aatgagcaaa caaaaaccta tacatatggt    780
```

```
gatagcgaac aaaatgacaa gtctaatcat gaaaatgatt taagtcatca tataccatcg    840
ataagtgatg ataaagataa cgtcatgaga gaaaatcata ttgttgacga taatcctgat    900
aatgatatca atacaccatc attatcaaaa acagatgacg atcgaaaact tgatgaaaaa    960
attcatgttg aagataaaca taaacaaaat gcagactcgt ctgaaacggt gggatatcaa   1020
agtcagtcaa ctgcatctca tcgtagcact gaaaaaagaa atatttctat taatgaccat   1080
gataaattaa acggtcaaaa aacaaataca aagacatcgg caaataataa tcaaaaaaag   1140
gctacatcaa aattgaacaa agggcgcgct acgaataata attatagtga cattttgaaa   1200
aagttttgga tgatgtattg gcctaaaggt tctggcggag gggctatgac tgaaaaagaa   1260
aaaatgttag cagaaaaatg gtacgatgca aactttgatc aagacttaat caatgaacgt   1320
gcacgagcga aagatatttg cttttgaatta aatcatacaa agccgagtga caaaaataaa   1380
agaaaggaat taatcgatga attatttcaa acaacaacag acaatgtaag tatttcgatt   1440
ccttttgata cagattatgg ttggaacgtt aaactaggaa aaaatgtcta tgtaaacacc   1500
aattgttatt ttatggatgg tggacagatt acaattggcg ataatgtttt tataggacct   1560
aattgtggat tctacacagc aacacatcca cttaattttc atcatagaaa tgaaggattt   1620
gaaaaagcag gaccaattaa tattggcagt aatacttggt ttggcggaca tgtagccgtg   1680
cttccgggag tgacgattgg agaaggcagt gtgattggtg ctggtagtgt tgtcaccaaa   1740
gatattccgc cacacagttt agcggttgga aacccttgta aagtcgttcg taaaattgat   1800
aatgaggtac catcagaagc attgaacgat gaaacactaa attag                   1845
```

SEQ ID NO: 104        moltype = DNA  length = 2418
FEATURE                Location/Qualifiers
misc_feature       1..2418
                        note = DNA construct
source                 1..2418
                        mol_type = other DNA
                        organism = synthetic construct

```
SEQUENCE: 104
atggatattg gtaaaaaaca tgtaattcct aaaagtcagt accgacgtaa gcgtcgtgaa     60
ttcttccaca acgaagacag agaagaaaat ttaaatcaac atcaagataa acaaaatata    120
gataatacaa catcaaaaaa agcagataag caaatacata aagattcaat tgataagcac    180
gaacgtttta aaaatagttt atcatcgcat ttagaacaga gaaaccgtga tgttaatgag    240
aataaagctg aagaaagtaa aagtaatcag gatagtaagt cagcatataa cagagatcat    300
tatttaacag acgatgtatc taaaaaacaa aattcattag attcagtgga ccaagataca    360
gagaaatcaa aatattatga gcaaaattct gaagcgactt tatcaactaa atcaaccgat    420
aaagtagaat caactgaaat gagaaagcta agttcagata aaaacaaagt tggtcatgaa    480
gagcaacatg tactttctaa accttcagaa catgataaag agactagaat tgattctgag    540
tcttcaagaa ctgattcaga cagctcgatg cagacagaga aaataaaaaa agacagttca    600
gatggaaata aaagtagtaa tctgaaatct gaagtaataa cagacaaatc aaatacagta    660
ccaaaattgt cggaatctga tgatgaagta aataatcaga agccattaac tttaccggaa    720
gaacagaaat tgaaaagaca gcaaagtcaa aatgagcaaa caaaacctaa acatatggtt    780
gatagcgaac aaaatgacaa gtctaatcat gaaaatgatt taagtcatca tataccatcg    840
ataagtgatg ataaagataa cgtcatgaga gaaaatcata ttgttgacga taatcctgat    900
aatgatatca atacaccatc attatcaaaa acagatgacg atcgaaaact tgatgaaaaa    960
attcatgttg aagataaaca taaacaaaat gcagactcgt ctgaaacggt gggatatcaa   1020
agtcagtcaa ctgcatctca tcgtagcact gaaaaaagaa atatttctat taatgaccat   1080
gataaattaa acggtcaaaa aacaaataca aagacatcgg caaataataa tcaaaaaaag   1140
gctacatcaa aattgaacaa agggcgcgct acgaataata attatagtga cattttgaaa   1200
aagttttgga tgatgtattg gcctaaaggt tctggcggag gggctaaagt tgccaaacaa   1260
gggcagtata aaaatcaaga ccctatcgtg ttagtgcatg gtttcaatgg atttacagat   1320
gatattaatc cttcagtgtt agctcattat tggggcggta taaaaatgaa cattcgccaa   1380
gatttagaag aaaatggtta caaagcttat gaagcaagta taagtcttt tggaagtaac   1440
tatgaccgcg cagttgaact ttattattat atcaaaggcg gtcgtgtaga ttatggtgca   1500
gcacatgcag caaaatatgg acatgaacgt tatggaaaaa catacgaagg aatttacaaa   1560
gactggaaaac caggacagaa ggtacaccta gttggacata gtatgggtgg tcaaacgata   1620
cgtcaactag aagaattact gcgtaatggt agtcgtgaaa aatagagta tcaaaagaaa   1680
catggtggcg aaatttctcc actattcaaa ggtaataatg acaatatgat ttcatcaatt   1740
actactttag gaacgccaca taatggaacg catgcttcag atttagctgg taatgaagct   1800
ttagtgagac aaaattgtat tgatatcggt aaaatgtttg gtaataaaaa ctctagagta   1860
gacttcgggt tggctcaatg gggtctaaaa cagaagccaa atgaatcata cattgattat   1920
gtcaaacgcg ttaaacaatc taattatgg aaatcaaaag ataatggatt ttacgatctg   1980
acgcgtgagg gtgcaacaga tttaaatcgt aaaacgtcgt tgaaccctaa cattgtgtat   2040
aaaacataca ctggtgaagc aacgcacaaa gcattaaata gcgatagaca aaaagcagac   2100
ttaaatatgt ttttcccatt tgtgattact ggtaacttaa tcggtaaagc tactgaaaaa   2160
gaatggcgag aaaacgatgg tttagtatcc gttattctct ctcagcatcc atttaatcaa   2220
gcttatacaa atgcgacgga taaaattcaa aaaggcattt ggcaagtaac gcctacaaaa   2280
catgattggg atcatgttga ttttgtcgga caagatagtt ctgatacagt gcgcacaaga   2340
gaagaattac aagattttg gcatcattta gcagacgatt tagtgaaaac tgaaaaggtg   2400
actgatacta agcaataa                                                 2418
```

SEQ ID NO: 105        moltype = DNA  length = 3012
FEATURE                Location/Qualifiers
misc_feature       1..3012
                        note = DNA construct
source                 1..3012
                        mol_type = other DNA
                        organism = synthetic construct

```
SEQUENCE: 105
cgaaatttgt tgcttcaaaa gcaatcacaa gctagacaaa ctgccgaaga tattgtaaat     60
caagcacata aagaagctga caatatcaaa aaagagaaat tacttgaggc aaaagaagaa    120
```

```
aaccaaatcc taagagaaca aaactgaagca gaactacgag aaagacgtag cgaacttcaa    180
agacaagaaa cccgacttct tcaaaaagaa gaaaacttag agcgtaaatc tgatctatta    240
gataaaaaag atgagatttt agagcaaaaa gaatcaaaaa ttgaagaaaa acaacaacaa    300
gtagatgcaa aagagagtag tgttcaaacg ttaataatga agcatgaaca agaattagaa    360
cgcatctccg gtctcactca agaagaagct attaatgagc aacttcaaag agtagaggaa    420
gaactgtcac aagatattgc agtacttgtt aaagaaaaag aaaaagaagc taaagaaaaa    480
gttgataaaa cagcaaaaga attattagct acagcagtac aaagattagc agcagatcac    540
acaagtgaat caacggtatc agtagttaac ttacctaatg atgagatgaa aggtcgaatc    600
attgacgtg aaggacgaaa catccgtaca cttgaaactt taactggcat tgatttaatt    660
attgatgaca caccagaagc agttatatta tctggttttg atccaataag aagagaaatt    720
gctagaacag cacttgttaa cttagtatct gatggacgta ttcatccagg tagaattgaa    780
gatatggtcg aaaaagctag aaaagaagta gacgatatta aagagaagc aggtgaacaa    840
gctacatttg aagtgaacgc acataatatg catcctgact tagtaaaaat tgtagggcgt    900
ttaaactatc gtacaagtta cggtcaaaat gtacttaaaa attcaattga agttgcgcat    960
cttgctagta tgttagctgc tgagctaggc gaagatgaga cattagcgaa acgagctgga   1020
cttttacatg atgttggtaa agcaattgat catgaagtag aaggtagtca tgttgaaatc   1080
ggtgtagaat tagcgaaaaa atatggtgaa aatgaaacag ttattaatgc aatccattct   1140
caccatggtg atgttgaacc tacatctatt atatctatcc ttgttgctgc tgcagatgca   1200
ttgtctgcgg ctcgtccagg tgcaagaaaa gaaaccattag agaattatat cgtcgatta   1260
gaacgtttag aaacgttatc agaaagttat gatggtgtag aaaaagcatt tgcgattcag   1320
gcaggtagag aaatccgagt gattgtatct cctgaagaaa ttgatgattt aaaatcttat   1380
cgattggcta gagatattaa aaatcagatt gaagtgaat tacaatatcc tggtcatatc   1440
aaggtgacag ttgttcgaga gactagagca gtagaatatg cgaaaaaacc tgagccgaaa   1500
ccagctccg ccctaagcc agcatgtggg aatgatgatg gaaaagataa agatggcaag   1560
gtaacaatta aaacgacagt ttatccattg caatcatttg cagagcaaat tggtggaaaa   1620
cacgtgaagg tatcatcaat ctatccagca gggacagatt tacatagcta tgaaccaaca   1680
caaaagata tattaagtgc aagcaaatca gacttgttta tgtatacagg ggataatta   1740
gatccggttg ctaagaaagt tgcatctact atcaaagata aagataaaa actgtcttta   1800
gaagataaat tagataagc aaagcttta actgatcaac acgaacatgg tgaagagcat   1860
gaacatggg gacatgatca tgagaaagaa gaacatcatc atcatggcgg atatgatcca   1920
cacgtatggt tagatcctaa aattaaccaa actttcgcta aagaaattaa agataattta   1980
gtgaagaaag atccaaaaca taagatgac tatgagaaaa actacaaaaa attaaacgac   2040
gatcttaaga aaattgataa cgatatgaag caagttacaa aagataagca aggtaatgca   2100
gtattcattt cacatgaatc aattggatac ttagctgatc gttaggttt tgttcaaaaa   2160
ggtattcaaa acatgaatgc tgaagatcca tcacaaaaag aattaactaa aattgttaaa   2220
gaaattagag atagcaatgc aaaatatatt ctttatgaag ataatgttgc gaataaagtg   2280
actgaaacaa ttcgtaaaga aacagatgcg aagcctttaa aattctacaa catggagtct   2340
ttaaataaag aacaacagaa aaagataat attacgtatc aatcattaat gaaatcgaat   2400
attgagaata tcggtaaagc tttagacagt ggtgttaaaa tgaaagacga taaagctgaa   2460
agtaaacacg acaaagcaat ttctgatggg tatttttaaag atgagcaagt taaagaccgt   2520
gaattaagcg attatgctgg tgaatggcaa tctgtttacc cttacttaaa agacggtacg   2580
cttgatgaag tgatggaaca taaagctgaa aatgatccga gaaatctgc taaagattta   2640
aaagcttatt atgacaaagg atataaaact gatattacta acattgatat aaaaaggaaat   2700
gaaattacat ttactaaaga tggtaagaaa cacactggta aatatgaata caatggtaag   2760
aaaacattga aatatcctaa aggtaaccgt ggcgtgagat ttatgtttaa attggtcgat   2820
ggtaatgata aagacttacc gaaattcatc caatttagcg atcacaacat tgcacctaaa   2880
aaggcagaac acttccatat ctttatgggt aatgataatg acgcgttatt aaaagaaatg   2940
gataactggc caacatatta tccttcaaaa ttaaataaag accaaatcaa agaagaaatg   3000
ttagcgcatt aa                                                        3012

SEQ ID NO: 106          moltype = DNA   length = 3030
FEATURE                 Location/Qualifiers
misc_feature            1..3030
                        note = DNA construct
source                  1..3030
                        mol_type = other DNA
                        organism = synthetic construct
SEQUENCE: 106
atgaatgaaa aagtagaagg catgaccttg gagctgaaat tagaccattt aggtgtccaa     60
gaaggcatga aaggtttaaa gcgacaatta ggtgttgtta atagtgaaat gaaagctaat    120
ctgtcagcat ttgataagtc tgaaaaatca atggaaaaat atcaggcgag aattaaggg    180
ttaaatgata ggcttaaagt tcaaaaaaag atgtattctc aagtagaaga tgagcttaaa    240
caagttaacg ctaattacca aaaagctaaa tccagtgtaa aagatgttga gaaagcatat    300
ttaaagttag tagaagccaa taaaaaagaa aaattagctc ttgtaaatc taagaagcc    360
ttaaaatcat cgaatacaga acttaaaaaa gctgaaaatc aatataaacg tacaaatcaa    420
cgtaaacaag atgcgtatca aaacttaaa cagttgagag atgcagaaca aaagcttaag    480
aatagtaacc aagctactac tgcacaacta aaaagagcaa gtgacgcagt acagaagcag    540
tccgctaagc ataaagcact tgttgaacaa tataaacaag aaggcaatca agttcaaaaa    600
ctaaagtgc aaaatgacaa tcttttcaaa tcaatgataa aattgaaag ttcttacgct    660
aaaactaata ctaaattaaa gcaaacagaa aaagaattta atgatttaaa caatactatt    720
aagaatcata gcgctaatgt cgcaaaagct gaaacagctg ttaataagaa aaaagctgct    780
ttaaataatt tggagcgttc aatagataaa gcttcatccg aaatgaagac ttttaacaaa    840
gaacaaatga tagctcaaag tcatttcggt aaacttgcaa gtcaagcgga tgtcatgtca    900
aagaaattta gttctattgg agacaaaatg acttcccctgg tgcgtacaat gacgatggc    960
gtatctacac caattacttt agggttaggt gcagcattaa aaacaagtgc agactttgg   1020
ggccaaatgt ctcgagttgg agcgattgcg caagcaagca gtaaagactt gaaaagcatg   1080
tctaatcaag cagttgactt aggagctaaa accagtaaaa gtgctaacga agttgctaaa   1140
ggtatggaag aattggcagc tttaggcttt aatgccaaac aaacaatgga ggctatgcca   1200
ggtgttatca gtgcagcaga agcaagtggg gcagaaatgg ctacaactgc aactgtaatg   1260
```

```
gcttcagcga ttaactcttt cggtttaaaa gcatctgatg caaatcatgt tgctgattta  1320
cttgcgagat cagcaaatga tagtgctgca gatattcagt acatgggaga tgcattgaag  1380
tatgctggta ctcctgcaaa agcattagga gtttcaatag aggacacttc cgcagcaatt  1440
gaagttttat ctaactcagg tttagagggt tctcaagcag gtactgccct aagagcttca  1500
tttatcaggc tagctaatcc aagtaaaaat acagctcagg aaatgaaaaa attaggtatt  1560
catttgtctg atgctaaagg tcaatttgtt ggcatgggtg aattgattag acagttccaa  1620
gataatatga aaggcatgac gagagaacaa aaactagcta cagtggctac aatagttggt  1680
actgaagcag caagtggatt tttagccttg attgaagcgg gaccagataa aattaatagc  1740
tatagtaaat ccttaaagaa ttccaatggc gaaagtaaaa aagcagcaga tttgatgaaa  1800
gataatctca aaggcgctct ggaacaatta ggtggcgctt ttgaatcatt agcaatcgaa  1860
gtcggtaaag atttaacgcc tatgattaga gcaggagcgg aaggtttaac aaaattagtt  1920
gatggattta cacatctccc tggttgggtt agaaaaggtt ctggcggagg ggctgcaaag  1980
gataacttaa atggagaaaa gccaacgact aatttgaatc ataatgtaac ttcaccatca  2040
gtaaatagtg aaatgaataa taatgagact gggacacctc acgaatcaaa tcaagctggt  2100
aatgaaggaa ctggttcgaa tagtcgtgat gctaatcctg attcgaataa tgtgaagcca  2160
gactcaaaca accaaaaccc aagtccagat tcaaacctg acccaaataa cccaaaccca  2220
ggtccgaatc cgaagccaga cccagataag ccgaaaccaa atccggaacc aaagccagac  2280
ccaaagccag acccagataa accaaagcca aatccggatc caaagccaga cccagataag  2340
ccgaaaccaa atccggatcc aaaaccagat ccagacaaac cgaagccaaa tccggatcca  2400
aaaccagatc caaatccgaa tccaaaacca gaccctaata agccaaatcc aaatccgtct  2460
ccaaatccca atcaacctgg ggattccaat caatctggtg gctcgaaaaa tggggggaca  2520
tgaacccaaa atgcttcaga tggatctaat caaggtcaat ggcaaccaaa tggaaatcaa  2580
ggaaactcac aaaatcctac tggtaatgat tttgtatccc aacgattttt agccttggcg  2640
aatggggctt acaagtataa tccgtatatt ttaaatcaaa ttaatcaatt ggggaaagaa  2700
tatggtgagg taactgatga agatatctac aatatcatcc gtaaacaaaa cttcagcgga  2760
aatgcatatt taaatggatt acaacagcaa tcgaattact ttagattcca atatttcaat  2820
ccattgaaat cagaaaggta ctatcgtaat ttagatgaac aagtactcgc attaattact  2880
ggcgaaattg gatcaatgcc agatttgaaa aagcccgaag ataagccgga ttcaaaacaa  2940
cgttcatttg agcctcatga aaaagatgat tttacagttg taaaaaaaca agaagataat  3000
aagaaaagtg cgtcaactgc atatagttaa                                   3030
```

```
SEQ ID NO: 107          moltype = DNA   length = 2187
FEATURE                 Location/Qualifiers
misc_feature            1..2187
                        note = DNA construct
source                  1..2187
                        mol_type = other DNA
                        organism = synthetic construct
SEQUENCE: 107
ggatttttaa acaaatctaa aaatgagcaa gcggcattaa aggcacaaca agcagcgata  60
aaagaagaag caagtgcaaa taatttaagt gatacatcac aagaagcaca agagattcaa  120
gaagctaaaa gagaagcaca agcagaagcg ataaaagtg tggctgtatc aaataaagaa  180
tcaaaagcag tggcattgaa agcacaacaa gcagcgataa aagaagaagc aagtgcaaat  240
aatttgagtg atacatcaca agaggcacaa gagattcaag aagctaaaaa agaagcacaa  300
gcagaaacag ataaaagtgc agctgtatca aatgaagaac caaaagcagt ggcattgaaa  360
gcacaacaag cagcgataaa agaagaagca agtgcaaata atttaagtga tatatccaca  420
gaggcacaag aggttcaaga agctaaaaaa gaagcacaag cagtgacaca  480
ttaactaaag atgcaagtgc agcaaaggta gaagtatcaa aaccagagtc acaagctgaa  540
agattagcaa acgctgcaaa acagaagcaa gctaaattaa caccaggttc aaaagagagt  600
caattaactg aagcgttatt tgcagaaaaa ccagttgcta aaaatgactt gaagaaatt  660
cctcaattag ttactaaaaa gaatgatgta tcagagacag agacggttaa tatagataat  720
aaagacactg ttaaacaaaa agaagctaaa tttgaaaatg gtgttattac acgtaaagct  780
gatgaaaaaa caactaataa tacagctgtt gacaagaaat caggtaaaca atctaaaaaa  840
acaacacctt caaataaacg aaatgcatca aaagcatcta caaataaaac ttcaggtcag  900
aaaaagcaac ataataagaa atcatcacaa ggtgcaaaga aacaaagtg ttcaagtaag  960
tcaactcaaa agaataatca aactagtaat aagaattcaa aaacaacaaa tgctaaatca  1020
tccaatgcat caaaaacgcc aaatgctaaa gttgagaaag ctaaagtaa aatagagaaa  1080
cgtacattca atgacggttc tggcggaggg gctggaagtg gtggggcgcg cgcaaaggat  1140
aactaaatg gagaaaagcc aacgactaat ttgaatcata atgtaacttc accatcagta  1200
aatagtgaaa tgaataataa tgagactggg cacctcacg aatcaaatca agctggtaat  1260
gaaggaactg gttcgaatag tcgtgatgct aatcctgatt cgaataatgt gaagccagac  1320
tcaaacaacc aaaacccaag tccagattca aaacctgacc caaataaccc aaacccaggt  1380
ccgaatccga agccagaccc agataagccg aaaccaaatc cggaaccaaa gccagaccca  1440
aagccagacc cagataaacc aaagccaaat ccggatccaa agccagaccc agataagccg  1500
aaaccaaatc cggatccaaa accagatcca gacaaccga agccaaatcc ggatccaaaa  1560
ccagatccaa atccgaatcc aaaaccagac cctaataagc caaatccaaa tccgtctcca  1620
aatcccaatc aacctgggga ttccaatcaa tctggtggct cgaaaaatgg ggggacatgg  1680
aacccaaatg cttcagatgg atctaatcaa ggtcaatggc aaccaaatgg aaatcaagga  1740
aactcacaaa atcctactgg taatgatttt gtatcccaac gatttttagc cttggcgaat  1800
ggggcttaca gtataatcc gtatatttta aatcaaatta atcaattggg gaaagaatat  1860
ggtgaggtaa ctgatgaaga tatctacaat atcatccgta aacaaaactt cagcggaaat  1920
gcatatttaa atggattaca acagcaatcg aattacttta gattccaata tttcaatcca  1980
ttgaaatcag aaaggtacta tcgtaattta gatgaacaag tactcgcatt aattactggc  2040
gaaattggat caatgccaga tttgaaaaag cccgaagata agccggattc aaaacaacgt  2100
tcatttgagc ctcatgaaaa agatgatttt acagttgtaa aaaacaagaa gataataag  2160
aaaagtgcgt caactgcata tagttaa                                      2187
```

```
SEQ ID NO: 108          moltype = DNA   length = 2169
FEATURE                 Location/Qualifiers
```

```
misc_feature         1..2169
                     note = DNA construct
source               1..2169
                     mol_type = other DNA
                     organism = synthetic construct
SEQUENCE: 108
gcaaaggata acttaaatgg agaaaagcca acgactaatt tgaatcataa tgtaacttca    60
ccatcagtaa atagtgaaat gaataataat gagactggga cacctcacga atcaaatcaa   120
gctggtaatg aaggaactgg ttcgaatagt cgtgatgcta atcctgattc gaataatgtg   180
aagccagact caaacaacca aacccaagt ccagattcaa aacctgaccc aaataaccca    240
aacccaggtc cgaatccgaa gccagaccca gataagccga aaccaaatcc ggaaccaaag   300
ccagacccaa agccagaccc agataaacca agccaaatc cggatccaaa gccagaccca    360
gataagccga aaccaaatcc ggatccaaaa ccagatccag acaaaccgaa gccaaatccg   420
gatccaaaac cagatccaaa tccgaatcca aaaccagacc ctaataagcc aaatccaaat   480
ccgtctccaa atcccaatca acctgggat tccaatcaat ctggtggctc gaaaaatggg    540
gggacatgga acccaaatgc ttcagatgga tctaatcaag gtcaatggca accaaatgga   600
aatcaaggaa actcacaaaa tcctactggt aatgattttg tatcccaacg attttttagcc 660
ttggcgaatg gggcttacaa gtataatccg tatattttaa atcaaattaa tcaattgggg   720
aaagaatatg gtgaggtaac tgatgaagat atctacaata tcatccgtaa acaaaacttc   780
agcggaaatg catatttaaa tggattacaa cagcaatcga attactttag attccaaatat  840
ttcaatccat tgaaatcaga aaggtactat cgtaatttag atgaacaagt actcgcatta   900
attactggcg aaattggatc aatgccagat ttgaaaaagc ccgaagataa gccggattca   960
aaacaacgtt catttgagcc tcatgaaaaa gatgatttta cagttgtaaa aaacaagaa   1020
gataataaga aaagtgcgtc aactgcatat agtggttctg gcggagggc tggatttta   1080
aacaaatcta aaaatgagca agcggcatta aaggcacaac aagcagcgat aaagaagaa   1140
gcaagtgcaa ataatttaag tgatacatca caagaagcac aagagattca agaagctaaa  1200
agagaagcac aagcagaagc ggataaaagt gtggctgtat caaataaaga atcaaaagca  1260
gtggcattga agcacaaca agcagcgata aagaagaag caagtgcaaa taatttgagt   1320
gatacatcac aagaggcaca agagattcaa gaagctaaaa agaagcaca agcagaaaca  1380
gataaaagtg cagctgtatc aaatgaagaa ccaaaagcag tggcattgaa agcacaacaa  1440
gcagcgataa agaagaagc aagtgcaaat aatttaagtg atatatcaca agaggcacaa   1500
gaggttcaag aagctaaaaa agaagcacaa gcagagaaaa cagtgacac attaactaaa   1560
gatgcaagtc agcaaaggt agaagtatca aaaccagagt cacaagctga agattagca   1620
aacgctgcaa aacagaagca agctaaatta acaccaggtt caaaagagag tcaattaact  1680
gaagcgttat ttgcagaaaa accagttgct aaaaaatgact tgaaagaaat tcctcaatta  1740
gttactaaaa agaatgatgt atcagagaca gagacggtta atatagataa taaagacact  1800
gttaaacaaa aagaagctaa atttgaaaat ggtgttatta cacgtaaagc tgatgaaaaa  1860
acaactaata atacagctgt tgacaagaaa tcaggtaaac aatctaaaaa aacaacacct  1920
tcaaataaac gaaatgcatc aaaagatct acaaataaac cttcaggtca gaaaagcaa   1980
cataatagaa aatcatcaca aggtgcaaag aaacaaagta gttcaagtaa gtcaactcaa  2040
aagaataatc aaactagtaa taagaattca aaaacaacaa atgctaaatc atccaatgca  2100
tcaaaacgc caaatgctaa agttgagaaa gctaaaagta aaatagagaa acgtacattc  2160
aatgactaa                                                          2169

SEQ ID NO: 109          moltype = DNA   length = 2604
FEATURE                 Location/Qualifiers
misc_feature            1..2604
                        note = DNA construct
source                  1..2604
                        mol_type = other DNA
                        organism = synthetic construct
SEQUENCE: 109
gcatgtggga atgatgatgg aaaagataaa gatggcaagg taacaattaa aacgacagtt    60
tatccattgc aatcatttgc agagcaaatt ggtggaaaac acgtgaaggt atcatcaatc   120
tatccagcag ggacagattt acatagctat gaaccaacaa aaaaagatat attaagtgca   180
agcaaatcag acttgtttat gtatacaggg gataatttag atccggttgc taagaaagtt   240
gcatctacta tcaaagataa agataaaaaa ctgtctttag aagataaatt agataaagca   300
aagcttttaa ctgatcaaca cgaacatggt gaagagcatg aacatgaggg acatgatcat   360
gagaaagaag aacatcatca tcatggcgga tatgatccaa acgtatggtt agatcctaaa   420
attaaccaaa ctttcgctaa ggaaattaaa gatgaattag tgaagaaaga tccaaaacat   480
aaagatgact atgagaaaaa ctacaaaaaa ttaaacgacg atcttaagaa aattgataac   540
gatatgaagc aagttacaaa agataagcaa ggtaatgcag tattcatttc acatgaatca   600
attggatact tagctgatcg ttatggttt gttcaaaaag gtattcaaaa catgaatgct   660
gaagatccat cacaaaaaga attaactaaa attgttaaga tagaga tagcaatgca    720
aaatatattc tttatgaaga taatgttgcg aataaagtga ctgaaacaat tcgtaaagaa   780
acagatgcga agcctttaaa aattctacaac atggagtctt taaataaaga acaacagaaa   840
aaagataata ttacgtatca atcattaatg aaatcgaata ttgaaaatat cggtaaagct   900
ttagacagtg gtgttaaagt gaaagacgat aaagctgaaa gtaaacgag caaagcaatt   960
tctgatgggt atttaagaa tgagcaagtt aaagaccgtg aattaagca ttatgctgat  1020
gaatggcaat ctgtttaccc ttacttaaaa aagcggtacgc ttgatgaagt gatgaacat   1080
aaagctgaaa atgatccgaa gaaatctgct aaagatttaa agcttatta tgacaaagga   1140
tataaaactg atattactaa cattgatata aaggaaatg aaattacatt tactaaagat   1200
ggtaagaaac acactggtaa atatgaatac aatggtaaga aacattgaa atatcctaaa   1260
ggtaaccgtg gcgtgagatt tatgtttaaa ttggtcgata gtaatgataa agacttaccg  1320
aaattcatcc aatttagcga tcacaacatt gcacctaaaa aggcagaaca cttccatatc   1380
tttatgggta atgataatga cgcgttatta aagaaatgg ataactggcc aacatattat   1440
ccttcaaaat taaataaaga ccaaatcaaa gaagaaatgt tagcgcatgg ttctggcgga   1500
ggggctggat tttaaacaa atctaaaaat gagcaagcgg cattaaaggc acaacaagca   1560
gcgataaaag aagaagcaag tgcaaataat ttaagtgata catcacaaga agcacaagag  1620
```

```
attcaagaag ctaaaagaga agcacaagca gaagcggata aaagtgtggc tgtatcaaat   1680
aaagaatcaa aagcagtggc attgaaagca caacaagcag cgataaaaga agaagcaagt   1740
gcaaataatt tgagtgatac atcacaagag gcacaagaga ttcaagaagc taaaaaagaa   1800
gcacaagcag aaacagataa aagtgcagct gtatcaaatg aagaaccaaa agcagtggca   1860
ttgaaagcac aacaagcagc gataaaagaa gaagcaagtg caaataattt aagtgataaa   1920
tcacaagagg cacaagaggt tcaagaagct aaaaaagaag cacaagcaga gaaagacagt   1980
gacacattaa ctaaagatgc aagtgcagca aaggtagaaa tatcaaaacc agagtcacaa   2040
gctgaaagat tagcaaacgc tgcaaaacag aagcaagcta aattaacacc aggttcaaaa   2100
gagagtcaat taactgaagc gttatttgca gaaaaaccag ttgctaaaaa tgacttgaaa   2160
gaaattcctc aattagttac taaaaagaat gatgtatcag agacagagac ggttaatata   2220
gataataaag acactgttaa acaaaaagaa gctaaatttg aaaatggtgt tattacacgt   2280
aaagctgatg aaaaaacaac taataataca gctgttgaca agaaatcagg taaacaatct   2340
aaaaaaacaa caccttcaaa taaacgaaat gcatcaaaag catctacaaa taaaacttca   2400
ggtcagaaaa agcaacataa taagaaatca tcacaaggtg caaagaaaca aagtagttca   2460
agtaagtcaa ctcaaaagaa taatcaaact agtaataaga attcaaaaac aacaaatgct   2520
aaaatcatcca atgcatcaaa aacgccaaat gctaaagttg agaaagctaa aagtaaaata   2580
gagaaacgta cattcaatga ctaa                                          2604
```

SEQ ID NO: 110      moltype = DNA length = 2394
FEATURE      Location/Qualifiers
misc_feature      1..2394
     note = DNA construct
source      1..2394
     mol_type = other DNA
     organism = synthetic construct
SEQUENCE: 110

```
atgactgaaa aagaaaaaat gttagcagaa aaatggtacg atgcaaactt tgatcaagac   60
ttaatcaatg aacgtgcacg agcgaaagat atttgctttg aattaaatca tacaaagccg   120
agtgacaaaa ataaaagaaa ggaattaatc gatgaattat tcaaacaac aacagacaat   180
gtaagtattt cgattccttt tgatacagat tatggttgga acgttaaact aggaaaaaat   240
gtctatgtaa acaccaattg ttattttatg gatggttgga agattacaat tggcgataat   300
gttttttatag gacctaattg tggattctac acagcaacac atccacttaa ttttcatcat   360
agaaatgaag gatttgaaaa agcaggacca attaatattg gcagtaatac ttggtttggc   420
ggacatgtag ccgtgcttcc gggagtgacg attggagaag gcagtgtgat tggtgctggt   480
agtgttgtca ccaaagatat tccgccacac agtttagcgg ttggaaaccc ttgtaaagtc   540
gttcgtaaaa ttgataatga ggtaccatca gaagcattga acgatgaaac actaaatggt   600
tctggcggag gggctgatac acctcaaaaa gatactacag ctaagacaac atctcatgat   660
tcaaaaaaat ctaatgacga tgaaacttct aaggatacta caagtaaaga tattgataaa   720
gcagacaaca ataacaag taaccaagac aataacgaca aaaaatttaa aactatagac   780
gacagcactt cagactctaa caatatcatt gattttattt ataagaattt accacaaacc   840
aatataaaacc aattgctaac caaaaataaa tacgatgata attactcatt aacaactta   900
atccaaaacc tattcaattt aaattcggat atttctgatt acgaacaacc tcgtaatggc   960
gaaagtcaa caaatgattc gaataaaaac agtgacaata tgatcaaaaa tgacactgat   1020
acgcaatcat ctaaacaaga taaagcagac aatcaaaaag cacctaaatc aaacaataca   1080
aaaccaagta catctaataa gcaaccaaat tcgccaaagc caacacaacc taatcaatca   1140
aatagtcaac cagcaagtga cgataaagca atcaaaaaat cttcatcgaa agataatcaa   1200
tcaatgtcag attcggtttt agactctatt ttggatcaat acagtgaaga tgcaaagaaa   1260
acacaaaaag attatgcatc tcaatctaaa aaagacaaaa atgaaaaatc taatacaaag   1320
aatccacagt taccaacaca agtgaattg aaacataaat ctaaacctgc tcaatcattc   1380
aataacgatg ttaatcaaaa ggatacacgt gcaacatcat tattcgaaac agatcctagt   1440
atatctaaca atgatgatag cggacaattt aacgttgttg actcaaaaga tacacgtcaa   1500
tttgtcaaat caattgctaa agatgcacat cgcattggtc aagataacga tatttatgcg   1560
tctgtcatga ttgcccaagc aatcttagaa tctgactcag gtcgtagtgc tttagctaag   1620
tcaccaaacc ataatttatt cggtatcaaa ggtgcttttg aagggaattc tgttcctttt   1680
aacacattag aagctgatgg taataaattg tatagtatta atgctggatt ccgaaaatat   1740
ccaagcacga aagaatcact aaaagattac tctgacctta ttaaaaatgg tattgatggc   1800
aatcgaacaa tttataaacc aacatggaaa tcggaagccg attcttataa agatgcaaca   1860
tcacacttat ctaaaacata tgctacagat ccaaactatg ctaagaaatt aaacagtatt   1920
attaaacact atcaattaac tcagtttgac gatgaacgca tgccagattt agataaatat   1980
gaacgttcta tcaaggatta tgatgattca tcagatgaat tcaaaccttt ccgtgaggta   2040
tctgatagta tgccatatcc acatggtcaa tgtacttggt acgtatataa ccgtatgaaa   2100
caatttggta catctatctc aggtgattta ggtgatgcac ataattggaa taatcgagct   2160
caataccgtg attatcaagt aagtcataca ccaaaacgtc atgctgctgt tgtatttgag   2220
gctggacaat ttggtgcaga tcaacattac ggtcatgtag cattgttgaaagtgtttaac   2280
agtgatggtt ctatcgttat ttcagaatcc aatgttaaag gattaggtat catttctcat   2340
agaactatca atgcagctgc cgctgaagaa ttatcatata ttacaggtaa ataa           2394
```

SEQ ID NO: 111      moltype = DNA length = 2352
FEATURE      Location/Qualifiers
misc_feature      1..2352
     note = DNA construct
source      1..2352
     mol_type = other DNA
     organism = synthetic construct
SEQUENCE: 111

```
attgattcaa aaaataaacc agctaattct gatattaaat tgaggtgac tcaaaagagt   60
gatgcggtca agcattaaa agaattgcct aaatccgaaa atgtaaaaaa tatttatcaa   120
gattacgctg ttactgatgt aaaaactgat aaaaaaggat ttacgcatta tacattgcaa   180
ccgagtgttg atggtgttca tgcacctgac aaagaagtga agtacacgc agacaaatca   240
```

-continued

```
ggaaaagtcg ttttaatcaa tggggatact gatgcgaaga agtaaagcc aacgaataaa    300
gtgacattaa gtaaagatga cgcagccgac aaagcattta aagcagttaa gattgataag   360
aataaagcga aaaatcttaa agataaagtc attaaagaaa acaaagttga aatcgatggt   420
gacagtaata aatacgttta taatgttgag ttaattacag tgacaccaga aatttcacat   480
tggaaagtta aaattgatgc tcaaactggc gaaattttag aaaaaatgaa cttagttaaa   540
gaagctgcag aaactggtaa aggaaaaggt gtacttggcg atacaaaaga tatcaatatc   600
aatagtattg acggtggatt tagcctagaa gatttaacgc atcaaggtaa attatcagca   660
tttagcttta atgatcaaac aggtcaagca acattgatta ctaatgaaga tgaaaacttc   720
gtaaaagatg agcaacgtgc tggcgtagat gcaaattatt acgctaaaca aacatatgat   780
tattacaaag acacatttgg tcgtgaatca tatgacaacc aaggtagtcc aattgtttca   840
ttaacgcatg ttaataacta cggtggtcaa gataacagaa ataatgccgc atggatcggt   900
gacaaaatga tctatggtga tggtgatggt cgcacattca aagtttatc gggtgcaaat    960
gacgtagtag cacacgaatt aacacacggt gtgacacaag agacagcgaa cttagaatat  1020
aaggaccagt caggcgctct aaatgaaagc ttttcagatg ttttttggata ctttgtagat  1080
gacgaggatt tcttaatggg tgaagatgtc tacacacctg gaaagagggg agacgcttta  1140
cgcagcatgt caaacccaga acaatttggt caaccagctc atatgaaaga ctatgtattc  1200
actgaaaaag ataatggtgg cgtacatacg aattctggtt ctggcggagg ggctggattt  1260
ttaaacaaat ctaaaaatga gcaagcggca taaaggcaac aacaagcagc gataaaagaa  1320
gaagcaagtg caaataattt aagtgataca tcacaagaag cacaagagat tcaagaagct  1380
aaaagagaag cacaagcaga agcggataaa agtgtggctg tatcaaataa agaatcaaaa  1440
gcagtggcat tgaaagcaca acaagcagcg ataaaagaag aagcaagtgc aaataatttg  1500
agtgatacat cacaagaggc aaagaagatt caagaagcta aaaaagaagc acaagcagaa  1560
acagataaaa gtgcagctgt atcaaatgaa gaaccaaaag cagtggcatt gaaagcacaa  1620
caagcagcga taaaagaaga agcaagtgca aataatttaa gtgatatatc acaagaggca  1680
caagaggttc aagaagctaa aaaagaagca caagcagaga agacagtgaa cacattaact  1740
aaagatgcaa gtgcagcaaa ggtagaagta tcaaaaccag agtcacaagc tgaaagatta  1800
gcaaacgctg caaaacagaa gcaagctaaa ttaaccacag gttcaaaaga gagtcaatta  1860
actgaagcgt tatttgcaga aaaaccagtt gctaaaaatg acttgaaaga aattcctcaa  1920
ttagttacta aaaagaatga tgtatcagag acagagacgg ttaatataga taataaagac  1980
actgttaaac aaaaagaagc taaatttgaa aatggtgtta ttacacgtaa agctgatgaa  2040
aaaacaacta ataatacagc tgttgacaag aaatcaggta aacaatctaa aaaaacaaca  2100
ccttcaaata aacgaaatgc atcaaaagca tctacaaata aaacttcagg tcagaaaaag  2160
caacataata agaaatcatc acaaggtgca agaaacaaa gtagttcaag taagtcaact   2220
caaaagaata atcaaactag taataagaat tcaaaaacaa caaatgctaa atcatccaat  2280
gcatcaaaaa cgccaaatgc taaagttgag aaagctaaaa gtaaaataga gaaacgtaca  2340
ttcaatgact aa                                                     2352
```

SEQ ID NO: 112      moltype = DNA length = 2310
FEATURE      Location/Qualifiers
misc_feature      1..2310
      note = DNA construct
source      1..2310
      mol_type = other DNA
      organism = synthetic construct
SEQUENCE: 112

```
attgattcaa aaaataaacc agctaattct gatattaaat ttgaggtgac tcaaaagagt     60
gatgcggtca aagcattaaa agaattgcct aaatccgaaa atgtaaaaaa tatttatcaa    120
gattacgctg ttactgatgt aaaaactgat aaaaaaggat ttacgcatta tacattgcaa    180
ccgagtgttg atggtgttca tgcacctgac aaagaagtga agtcacacgc agacaaatca    240
ggaaaagtcg ttttaatcaa tggggatact gatgcgaaga agtaaagcc aacgaataaa     300
gtgacattaa gtaaagatga cgcagccgac aaagcattta aagcagttaa gattgataag    360
aataaagcga aaaatcttaa agataaagtc attaaagaaa acaaagttga aatcgatggt    420
gacagtaata aatacgttta taatgttgag ttaattacag tgacaccaga aatttcacat    480
tggaaagtta aaattgatgc tcaaactggc gaaattttag aaaaaatgaa cttagttaaa    540
gaagctgcag aaactggtaa aggaaaaggt gtacttggcg atacaaaaga tatcaatatc    600
aatagtattg acggtggatt tagcctagaa gatttaacgc atcaaggtaa attatcagca    660
tttagcttta atgatcaaac aggtcaagca acattgatta ctaatgaaga tgaaaacttc    720
gtaaaagatg agcaacgtgc tggcgtagat gcaaattatt acgctaaaca aacatatgat    780
tattacaaag acacatttgg tcgtgaatca tatgacaacc aaggtagtcc aattgtttca    840
ttaacgcatg ttaataacta cggtggtcaa gataacagaa ataatgccgc atggatcggt    900
gacaaaatga tctatggtga tggtgatggt cgcacattca aagtttatc gggtgcaaat     960
gacgtagtag cacacgaatt aacacacggt gtgacacaag agacagcgaa cttagaatat   1020
aaggaccagt caggcgctct aaatgaaagc ttttcagatg ttttggata ctttgtagat    1080
gacgaggatt tcttaatggg tgaagatgtc tacacacctg gaaagagggg agacgcttta   1140
cgcagcatgt caaacccaga acaatttggt caaccagctc atatgaaaga ctatgtattc   1200
actgaaaaag ataatggtgg cgtacatacg aattctggtt ctggcggagg ggctgcaaag   1260
gataacttaa atggagaaaa gccaacgact aatttgaatc ataatgtaac ttcaccatca   1320
gtaaatagtg aaatgaataa taatgagact gggacacctc acgaatcaaa tcaagctggt   1380
aatgaaggaa ctggttcgaa tagtcgtgat gctaatcctg attcgaataa tgtgaagcca   1440
gactcaaaca accaaaaccc aagtccagat tcaaaacctg acccaaataa cccaaaccca   1500
ggtccgaatc cgaagccaga cccagataag ccgaaaccaa atccggaacc aaagccagac   1560
ccaaagccag acccagataa accaaagcca atccggatcc caaagccaga cccagataag   1620
ccgaaaccaa atccggatcc aaaaccagat ccagacaaac cgaagccaaa tccggatcca   1680
aaaccagatc ccaaaaccga tccaaaacca gaccctaata agcaaatcc aaatccgtct   1740
ccaaatccca atcaacctgg ggattccaat caatctggtg gctcgaaaaa tgggggaca   1800
tggaacccaa atgcttcaga tggatctaat caaggtcaat ggcaaccaaa tggaaatcaa   1860
ggaaactcac aaaatcctac tggtaatgat tttgtatccc aacgattttt agccttggcg   1920
aatgggcttt acaagtataa tccgtatatt ttaaatcaaa ttaatcaatt ggggaaagaa   1980
tatggtgagg taactgatga agatatctac aatatcatcg taaacaaaa cttcagcgga   2040
```

```
aatgcatatt taaatggatt acaacagcaa tcgaattact ttagattcca atatttcaat  2100
ccattgaaat cagaaaggta ctatcgtaat ttagatgaac aagtactcgc attaattact  2160
ggcgaaattg gatcaatgcc agatttgaaa aagcccgaag ataagccgga ttcaaaacaa  2220
cgttcatttg agcctcatga aaaagatgat tttacagttg taaaaaaaca agaagataat  2280
aagaaaagtg cgtcaactgc atatagttaa                                   2310
```

| | |
|---|---|
| SEQ ID NO: 113 | moltype = DNA   length = 2445 |
| FEATURE | Location/Qualifiers |
| misc_feature | 1..2445 |
| | note = DNA construct |
| source | 1..2445 |
| | mol_type = other DNA |
| | organism = synthetic construct |

SEQUENCE: 113
```
attgattcaa aaaataaacc agctaattct gatattaaat ttgaggtgac tcaaaagagt    60
gatgcgtca  aagcattaaa agaattgcct aaatccgaaa atgtaaaaaa tatttatcaa   120
gattacgctg ttactgatgt aaaaactgat aaaaaaggat ttacgcatta tacattgcaa   180
ccgagtgttg atggtgttca tgcacctgac aaagaagtga aagtacacgc agacaaatca   240
ggaaaagtcg ttttaatcaa tggggatact gatgcgaaga agtaaagcc  aacgaataaa   300
gtgacattaa gtaaagatga cgcagccgac aaagcattta aagcagttaa gattgataag   360
aataaagcga aaaatcttaa agataaagtc attaaagaaa caaagttga  aatcgatggt   420
gacagtaata aatacgtttta taatgttgag ttaattacag tgacaccaga aatttcacat   480
tggaaagtta aaattgatgc tcaaactggc gaaattttag aaaaaatgaa cttagttaaa   540
gaagctgcag aaactggtaa aggaaaaggt gtacttggcg atacaaaaga tatcaatatc   600
aatagtattg acgtggatt  tagcctagaa gatttaacgc atcaaggtaa attatcagca   660
tttagcttta atgatcaaac aggtcaagca acattgatta ctgatgaaga tgaaaacttc   720
gtaaaagatg agcaacgtgc tggcgtagat gcaattatt  acgctaaaca aacatatgat   780
tattacaaag acacatttgg tcgtgaatca tatgacaacc aaggtagtcc aattgtttca   840
ttaacgcatg ttaataacta cggtggtcaa gataacagaa ataatgccgc atggatcggt   900
gacaaaatga tctatggtga tggtgatggt cgcacattca caagtttatc gggtgcaaat   960
gacgtagtag cacacgaatt aacacacggt gtgacacaag agacagcgaa cttagaaat   1020
aaggaccagt caggcgctct aaatgaaagc ttttcagatg ttttttggata ctttgtagat  1080
gacgaggatt tcttaatggg tgaagatgtc tacacacctg gaaaagaggg agacgcttta  1140
cgcacgcatgt caaacccaga acaatttggt caaccagctc atatgaaaga ctatgtattc  1200
actgaaaaag ataatggtgg cgtacatacg aattctggtt ctggcggagg ggctggaagt  1260
ggtgggggcg ccaaagttgc caaacaaggg cagtataaaa atcaagaccc tatcgtgtta  1320
gtgcatggtt tcaatggatt tacagatgat attaatcctt cagtgttagc tcattattgg  1380
ggcggtaata aaatgaacat tcgccaagat ttagaagaaa atggttacaa agcttatgaa  1440
gcaagtataa gtgcttttgg aagtaactat gaccgcgcag ttgaactttta ttattatatc  1500
aaaggcggtc gtgtagatta tggtgcagca catgcagcaa aatatggaca tgaacgttat  1560
ggaaaaacat acgaaggaat ttacaaagac tggaaaccag acagaaggt  acacctagtt  1620
ggacatagta tgggtggtca aacgatacgt caactagaag aattactgcg taatggtagt  1680
cgtgaagaaa tagagtatca aaagaaacat ggtggcgaaa tttctccact attcaaaggt  1740
aataatgaca atatgatttc atcaattact actttaggaa cgccacataa tggaacgcat  1800
gcttcagatt tagctggtaa tgaagcttta gtgagacaaa ttgtatttga tatcggtaaa  1860
atgtttggta ataaaaactc tagagtagac ttcgggttgg ctcaatgggg tctaaaacag  1920
aagccaaatg aatcatacat tgattatgtc aaacgcgtta aacaatcaa  tttatggaaa  1980
tcaaaagata atggatttta cgatctgacg cgtgagggtg caacagattt aaatcgtaaa  2040
acgtcgttga accctaacat tgtgtataaa acatacactg gtgaagcaac gcacaaagca  2100
ttaaatagca atagacaaaa agcagactta aatatgtttt tcccatttgt gattactggt  2160
aacttaatcg gtaaagctac tgaaaaagaa tggcgagaaa acgatggttt agtatccgtt  2220
atttcttctc agcatccatt taatcaagct tatacaaatg cgacggataa aattcaaaaa  2280
ggcatttggc aagtaacgcc tacaaaacat gattgggatc atgttgattt tgtcggacaa  2340
gatagttctg atacagtgcg cacaagagaa gaattacaag ttttttggca tcatttagca  2400
gacgatttag tgaaactgaa aaaggtgact gatactaagc aataa         2445
```

| | |
|---|---|
| SEQ ID NO: 114 | moltype = DNA   length = 2394 |
| FEATURE | Location/Qualifiers |
| misc_feature | 1..2394 |
| | note = DNA construct |
| source | 1..2394 |
| | mol_type = other DNA |
| | organism = synthetic construct |

SEQUENCE: 114
```
gatacacctc aaaagatac  tacagctaag acaacatctc atgattcaaa aaatctaat    60
gacgatgaaa cttctaagga tactacaagt aaagatattg ataaagcaga caacaataat   120
acaagtaacc aagacaataa cgacaaaaaa tttaaaacta tagacgacag cacttcagac   180
tctaacaata tcattgattt tatttataag aatttaccac aaaccaatat aaaccaattg   240
ctaaccaaaa ataaatacga tgataattac tcattaacac cttttaatcca aaacctattc   300
aatttaaatt cggatatttc tgattacgaa caacctcgta atggcgaaaa gtcaacaaat   360
gattcgaata aaaacagtga caatagcatc aaaaatgaca ctgatacgca atcatctaaa   420
caagataaag cagacaatca aaaagcacct aaatcaaaca atacaaaacc aagtacatct   480
aataagcaac caaattcgcc aaagccaaca caacctaatc aatcaaatag tcaaccagca   540
agtacgacaa aacaaatca  aaaatcttca tcgaaagata atcaatcaat gtcagattcg   600
gctttagact ctattttgga tcaatacagt gaagatgcaa agaaaacaca aaaagattat   660
gcatctcaat ctaaaaaaga caaaaatgaa aaatctaata caaagaatcc acagttacca   720
acacaagatg aattgaaaca taatctaaa  cctgctcaat cattcaataa cgatgttaat   780
caaaaggata cacgtgcaac atcattattc gaaacagatc ctagtatatc taacaatgat   840
gatagcggac aatttaacgt tgttgactca aaagatacac gtcaatttgt caaatcaatt   900
```

```
gctaaagatg cacatcgcat tggtcaagat aacgatattt atgcgtctgt catgattgcc    960
caagcaatct tagaatctga ctcaggtcgt agtgctttag ctaagtcacc aaaccataat   1020
ttattcggta tcaaaggtgc ttttgaaggg aattctgttc cttttaacac attagaagct   1080
gatggtaata aattgtatag tattaatgct ggattccgaa aatatccaag cacgaaagaa   1140
tcactaaaag attactctga ccttattaaa aatggtattg atggcaatcg aacaatttat   1200
aaaccaacat ggaaatcgga agccgattct tataaagatg caacatcaca cttatctaaa   1260
acatatgcta cagatccaaa ctatgctaag aaattaaaca gtattattaa acactatcaa   1320
ttaactcagt ttgacgatga acgcatgcca gatttagata aatatgaacg ttctatcaag   1380
gattatgatg attcatcaga tgaattcaaa cctttccgtg aggtatctga tagtatgcca   1440
tatccacatg gtcaatgtac ttggtacgta tataaccgta tgaaacaatt tggtacatct   1500
atctcaggtg atttaggtga tgcacataat tggaataatc gagctcaata ccgtgattat   1560
caagtaagtc atacaccaaa acgtcatgct gctgttgtat ttgaggctgg acaatttggt   1620
gcagatcaac attacggtca tgtagcattt gttgaaaaag ttaacagtga tggttctatc   1680
gttatttcag aatccaatgt taaaggatta ggtatcattt ctcatagaac tatcaatgca   1740
gctgccgctg aagaattatc atatattaca ggtaaaggtt ctggcggagg gctatgact    1800
gaaaagaaa aatgttagc agaaaaatgg tacgatgcaa actttgatca agacttaatc   1860
aatgaacgtg cacgagcgaa agatatttgc tttgaattaa atcatacaaa gccgagtgac   1920
aaaaataaaa gaaaggaatt aatcgatgaa ttatttcaaa caacaacaga caatgtaagt   1980
atttcgattc cttttgatac agattatggt tggaacgtta aactaggaaa aaatgtctat   2040
gtaaacacca attgttattt tatggatggt ggacagatta caattggcga taatgttttt   2100
ataggaccta attgtggatt ctacacagca acacatccac ttaattttca tcatagaaat   2160
gaaggatttg aaaaagcagg accaattaat attggcagta atcttggtt tggcggacat   2220
gtagccgtgc ttccgggagt gacgattgga gaaggcagtg tgattggtgc tggtagtgtt   2280
gtcaccaaag atattccgcc acacagttta gcggttggaa acccttgtaa agtcgttcgt   2340
aaaattgata atgaggtacc atcagaagca ttgaacgatg aaacactaaa ttag         2394

SEQ ID NO: 115        moltype = DNA  length = 2412
FEATURE               Location/Qualifiers
misc_feature          1..2412
                      note = DNA construct
source                1..2412
                      mol_type = other DNA
                      organism = synthetic construct
SEQUENCE: 115
gatacacctc aaaagatac tacagctaag acaacatctc atgattcaaa aaatctaat     60
gacgatgaaa cttctaagga tactacaagt aaagatattg ataaagcaga caacaataat   120
acaagtaacc aagacaataa cgacaaaaaa tttaaaacta tagacgacag cacttcagac   180
tctaacaata tcattgattt tatttataag aatttaccac aaaccaatat aaaccaattg   240
ctaaccaaca ataaatacga tgataattac tcattaatcca aaacctattc                300
aattaaaatt cggatatttc tgattacgaa caacctcgta atggcgaaaa gtcaacaaat   360
gattcgaata aaaacagtga caatagcatc aaaaatgaca ctgatacgca atcatctaaa   420
caagataaag cagacaatca aaaagcacct aaatcaaaca atacaaaaacc aagtacatct   480
aataagcaac caaattcgcc aaagccaaca caacctaatc aatcaaatg tcaaccagca   540
agtgacgata aagcaaatca aaaatcttca tcgaaagata atcaatcaat gtcagattcg   600
gctttagact ctatttttgga tcaatacagt gaagatgcaa agaaaacaca aaaagattat   660
gcatctcaat ctaaaaaaga caaaaatgaa aaatctaata caaagaatcc acagttacca   720
acacaagatg aattgaaaca taatctaaa cctgctcaata cattcaataa cgatgttaat   780
caaaaggata cacgtgcaac atcattattc gaaacagatc ctagtatatc taacaatgat   840
gatagcggac aatttaacgt tgttgactca aaagatacac gtcaatttgt caaatcaatt   900
gctaaagatg cacatcgcat tggtcaagat aacgatattt atgcgtctgt catgattgcc    960
caagcaatct tagaatctga ctcaggtcgt agtgctttag ctaagtcacc aaaccataat   1020
ttattcggta tcaaaggtgc ttttgaaggg aattctgttc cttttaacac attagaagct   1080
gatggtaata aattgtatag tattaatgct ggattccgaa aatatccaag cacgaaagaa   1140
tcactaaaag attactctga ccttattaaa aatggtattg atggcaatcg aacaatttat   1200
aaaccaacat ggaaatcgga agccgattct tataaagatg caacatcaca cttatctaaa   1260
acatatgcta cagatccaaa ctatgctaag aaattaaaca gtattattaa acactatcaa   1320
ttaactcagt ttgacgatga acgcatgcca gatttagata aatatgaacg ttctatcaag   1380
gattatgatg attcatcaga tgaattcaaa cctttccgtg aggtatctga tagtatgcca   1440
tatccacatg gtcaatgtac ttggtacgta tataaccgta tgaaacaatt tggtacatct   1500
atctcaggtg atttaggtga tgcacataat tggaataatc gagctcaata ccgtgattat   1560
caagtaagtc atacaccaaa acgtcatgct gctgttgtat ttgaggctgg acaatttggt   1620
gcagatcaac attacggtca tgtagcattt gttgaaaaag ttaacagtga tggttctatc   1680
gttatttcag aatccaatgt taaaggatta ggtatcattt ctcatagaac tatcaatgca   1740
gctgccgctg aagaattatc atatattaca ggtaaaggtc tgagccgaag accagctccc   1800
gcccctaagc caatgactga aaaagaaaaa atgttagcag aaaaatggta cgatgcaaac   1860
tttgatcaag acttaatcaa tgaacgtgca cgagcgaaag atatttgctt tgaattaaat   1920
catacaaagc cgagtgacaa aaataaaaga aggaattaa tcgatgaatt atttcaaaca   1980
acaacagaca atgtaagtat ttcgattcct tttgatacag attatggttg gaacgttaaa   2040
ctaggaaaaa atgtctatgt aaacaccaat tgttatttta tggatggtgg acagattaca   2100
attggcgata atgtttttat aggacctaat tgtggattct acacagcaac acatccactt   2160
aattttcatc atagaaatga aggatttgaa aaagcaggac caattaatat tggcagtaat   2220
cttggttttg gcggacatgt agccgtgctt ccgggagtga cgattggaga aggcagtgtg   2280
attggtgctg gtagtgttgt caccaaagat attccgccac acagtttagc ggttggaaac   2340
ccttgtaaag tcgttcgtaa aattgataat gaggtaccat cagaagcatt gaacgatgaa   2400
acactaaatt ag                                                       2412

SEQ ID NO: 116        moltype = DNA  length = 2967
FEATURE               Location/Qualifiers
misc_feature          1..2967
```

|  | note = DNA construct |  |
| --- | --- | --- |
| source | 1..2967 |  |
|  | mol_type = other DNA |  |
|  | organism = synthetic construct |  |

SEQUENCE: 116

```
gatacacctc aaaagatac  tacagctaag  acaacatctc  atgattcaaa  aaaatctaat   60
gacgatgaaa cttctaagga tactacaagt  aaagatattg  ataaagcaga  caacaataat  120
acaagtaacc aagacaataa cgacaaaaaa  tttaaaacta  tagacgacag  cacttcgagac 180
tctaacaata tcattgattt tatttataag  aatttaccac  aaaccaatat  aaaccaattg  240
ctaaccaaaa ataaatacga tgataattac  tcattaacaa  ctttaatcca  aaacctattc  300
aatttaaatt cggatatttc tgattacgaa  caacctcgta  atggcgaaaa  gtcaacaaat  360
gattcgaata aaaacagtga caatagcatc  aaaaatgaca  ctgatacgca  atcatctaaa  420
caagataaag cagacaatca aaaagcacct  aaatcaaaca  atacaaaacc  aagtacatct  480
aataagcaac caaattcgcc aaagccaaca  caacctaatc  aatcaaatag  tcaaccagca  540
agtgacgata aagcaaatca aaaatcttca  tcgaaagata  atcaatcaat  gtcagattcg  600
gctttagact ctattttgga tcaatacagt  gaagatgcaa  agaaaacaca  aaaagattat  660
gcatctcaat ctaaaaaaga caaaaatgaa  aaatctaata  caaagaatcc  acagttacca  720
acacaagatg aattgaaaca taaatctaaa  cctgctcaat  cattcaataa  cgatgttaat  780
caaaaggata cacgtgcaac atcattattc  gaaacagatc  ctagtatatc  taacaatgat  840
gatagcggac aatttaacgt tgttgactca  aaagatacac  gtcaatttgt  caaatcaatt  900
gctaaagatg cacatcgcat tggtcaagat  aacgatattt  atgcgtctgt  catgattgcc  960
caagcaatct tagaatctga ctcaggtcgt  agtgcttag  ctaagtcacc  aaaccataat 1020
ttattcggta tcaaaggtgc ttttgaaggg  aattctgttc  cttttaacac  attagaagct 1080
gatggtaata aattgtatag tattaatgct  ggattccgaa  aatatccaag  cacgaaagaa 1140
tcactaaaag attactctga ccttattaaa  aatggtattg  atggcaatcg  aacaatttat 1200
aaaccaacat ggaaatcgga agccgattct  tataaagatg  caacatcaca  cttatctaaa 1260
acatatgcta cagatccaaa ctatgctaag  aaattaaaca  gtattattaa  acactatcaa 1320
ttaactcagt ttgacgatga acgcatgcca  gatttagata  aatatgaacg  ttctatcaag 1380
gattatgatg attcatcaga tgaattcaaa  cctttccgtg  aggtatctga  tagtatgcca 1440
tatccacatg gtcaatgtac ttggtacgta  tataaccgta  tgaaacaatt  tggtacatct 1500
atctcaggtg atttaggtga tgcacataat  tggaataatc  gagctcaata  ccgtgattat 1560
caagtaagtc atacaccaaa acgtcatgct  gctgttgtat  ttgaggctgg  acaatttggt 1620
gcagatcaac attacggtca tgtagcattt  gttgaaaaag  ttaacagtga  tggttctatc 1680
gttatttcag aatccaatgt taaaggatta  ggtatcctt  ctcatagaac  tatcaatgca 1740
gctgccgctg aagaattatc atatattaca  ggtaaaggtt  ctggcggagg  ggctaaagtt 1800
gccaaacaag gcagtataa aaatcaagac  cctatcgtgt  tagtgcatgg  tttcaatgga 1860
tttacagatg atattaatcc ttcagtgtta  gctcattatt  ggggcggtaa  taaaatgaac 1920
attcgccaag atttagaaga aaatggttac  aaagcttatg  aagcaagtat  aagtgctttt 1980
ggaagtaact atgaccgcgc agttgaactt  tattattata  tcaaaggcgg  tcgtgtagat 2040
tatggtgcag cacatgcagc aaaatatgga  catgaacgtt  atggaaaaac  atacgaagga 2100
atttacaaag actggaaacc aggacagaag  gtacacctag  ttggacatag  tatgggtggt 2160
caaacgatac gtcaactaga agaattactg  cgtaatggta  gtcgtgaaga  aatagagtat 2220
caaaagaaac atggtggcga aatttctcca  ctattcaagg  taataatga  caatatgatt 2280
tcatcaatta ctactttagg aacgccacat  aatggaacgc  atgcttcaga  tttagctggt 2340
aatgaagctt tagtgagaca aattgtattt  gatatcggta  aatgtttgg  taataaaaac 2400
tctagagtag acttcgggtt ggctcaatgg  ggtcaaaaac  agaagccaaa  tgaatcatac 2460
attgattatg tcaaacgcgt taaacaatct  aatttatgga  aatcaaaaga  taatggattt 2520
tacgatctga cgcgtgaggg tgcaacagat  ttaaatcgta  aacgtcgtt  gaaccctaac 2580
attgtgtata aaacatacac tggtgaagca  acgcacaaag  cattaaatag  cgatagacaa 2640
aaagcagact taaatatgtt tttccctttt  gtgattactg  gtaacttaat  cggtaaagct 2700
actgaaaaag aatggcgaga aaacgatggt  ttagtatccg  ttattcttc  tcagcatcca 2760
tttaatcaag cttatacaaa tgcgacggat  aaaattcaa  aaggcatttg  gcaagtaacg 2820
cctacaaaac atgattggga tcatgttgat  tttgtcggac  aagatagttc  tgatacagtg 2880
cgcacaagag aagaattaca agattttttgg catcatttag  cagacgattt  agtgaaaact 2940
gaaaaggtga ctgatactaa gcaataa                                        2967
```

| SEQ ID NO: 117 | moltype = DNA length = 2355 |
| --- | --- |
| FEATURE | Location/Qualifiers |
| misc_feature | 1..2355 |
|  | note = DNA construct |
| source | 1..2355 |
|  | mol_type = other DNA |
|  | organism = synthetic construct |

SEQUENCE: 117

```
gatacacctc aaaagatac  tacagctaag  acaacatctc  atgattcaaa  aaaatctaat   60
gacgatgaaa cttctaagga tactacaagt  aaagatattg  ataaagcaga  caacaataat  120
acaagtaacc aagacaataa cgacaaaaaa  tttaaaacta  tagacgacag  cacttcgagac 180
tctaacaata tcattgattt tatttataag  aatttaccac  aaaccaatat  aaaccaattg  240
ctaaccaaaa ataaatacga tgataattac  tcattaacaa  ctttaatcca  aaacctattc  300
aatttaaatt cggatatttc tgattacgaa  caacctcgta  atggcgaaaa  gtcaacaaat  360
gattcgaata aaaacagtga caatagcatc  aaaaatgaca  ctgatacgca  atcatctaaa  420
caagataaag cagacaatca aaaagcacct  aaatcaaaca  atacaaaacc  aagtacatct  480
aataagcaac caaattcgcc aaagccaaca  caacctaatc  aatcaaatag  tcaaccagca  540
agtgacgata aagcaaatca aaaatcttca  tcgaaagata  atcaatcaat  gtcagattcg  600
gctttagact ctattttgga tcaatacagt  gaagatgcaa  agaaaacaca  aaaagattat  660
gcatctcaat ctaaaaaaga caaaaatgaa  aaatctaata  caaagaatcc  acagttacca  720
acacaagatg aattgaaaca taaatctaaa  cctgctcaat  cattcaataa  cgatgttaat  780
caaaaggata cacgtgcaac atcattattc  gaaacagatc  ctagtatatc  taacaatgat  840
gatagcggac aatttaacgt tgttgactca  aaagatacac  gtcaatttgt  caaatcaatt  900
```

```
gctaaagatg cacatcgcat tggtcaagat aacgatattt atgcgtctgt catgattgcc    960
caagcaatct tagaatctga ctcaggtcgt agtgctttag ctaagtcacc aaaccataat   1020
ttattcggta tcaaaggtgc ttttgaaggg aattctgttc cttttaacac attagaagct   1080
gatggtaata aattgtatag tattaatgct ggattccgaa atatccaag cacgaaagaa   1140
tcactaaaag attactctga ccttattaaa aatggtattg atggcaatcg aacaatttat   1200
aaaccaacat ggaaatcgga agccgattct tataaagatg caacatcaca cttatctaaa   1260
acatatgcta cagatccaaa ctatgctaag aaattaaaca gtattattaa acactatcaa   1320
ttaactcagt ttgacgatga acgcatgcca gatttagata aatatgaacg ttctatcaag   1380
gattatgatg attcatcaga tgaattcaaa cctttccgtg aggtatctga tagtatgcca   1440
tatccacatg gtcaatgtac ttggtacgta tataaccgta tgaaacaatt tggtacatct   1500
atctcaggtg atttaggtga tgcacataat tggaataatc gagctcaata ccgtgattat   1560
caagtaagtc atacaccaaa acgtcatgct gctgttgtat ttgaggctgg acaatttggt   1620
gcagatcaac attacggtca tgtagcattt gttgaaaaag ttaacagtga tggttctatc   1680
gttatttcag aatccaatgt taaggatta ggtatcattt ctcatagaac tatcaatgca   1740
gctgccgctg aagaattatc atatattaca ggtaaaggtt ctggcggagg ggctaaagtt   1800
gccaaacaag ggcagtataa aaatcaagac cctatcgtgt tagtgcatgg tttcaatgga   1860
tttacagatg atattaatcc ttcagtgtta gctcattatt ggggcggtaa taaatgaac   1920
attcgccaag atttagaaga aaatggttac aaagcttatg aagcaagtat aagtgctttt   1980
ggaagtaact atgaccgcgc agttgaactt tattattata tcaaaggcgg tcgtgtagat   2040
tatggtgcag cacatgcagc aaaatatgga catgaacgtt atggaaaaac atacgaagga   2100
atttacaaag actggaaacc aggacagaag gtacacctag ttggacatag tatgggtggt   2160
caaacgatac gtcaactaga agaattactg cgtaatgata gtcgtgaaga aatagagtat   2220
caaaagaaac atggtggcga aatttctcca ctattcaaag gtaataatga caatatgatt   2280
tcatcaatta ctactttagg aacgccacat aatggaacgc atgcttcaga tttagctggt   2340
aatgaagctt tataa                                                   2355

SEQ ID NO: 118        moltype = DNA  length = 1506
FEATURE               Location/Qualifiers
misc_feature          1..1506
                      note = DNA construct
source                1..1506
                      mol_type = other DNA
                      organism = synthetic construct
SEQUENCE: 118
gcagattctg atattaatat taaaaccggt actacagata ttggaagcaa tactacagta     60
aaaacaggtg atttagtcac ttatgataaa gaaaatggca tgttaaaaaa agtattttat    120
agttttatcg atgataaaaa tcataataaa aaactgctag ttattagaac gaaaggtacc    180
attgctggtc aatatagagt ttatagcgaa gaaggtgcta caaaagtgg tttagcctgg    240
ccttcagcct ttaaggtaca gttgcaacta cctgataatg aagtagctca aatatctgat    300
tactatccaa gaaattcgat tgatacaaaa gagtatatga gtactttaac ttatggattc    360
aacggtaatg ttactggtga tgatacagga aaaattggcg gccttattgg tgcaaatgtt    420
tcgattggtc atacactgaa atatgttcaa cctgatttca aaacaatttt agagagccca    480
actgataaaa aagtaggctg gaaagtgata tttaacaata tggtgaatca aaattgggga    540
ccatatgata gagattcttg gaacccggta tatggcaatc aacttttcat gaaaactaga    600
aatggctcta tgaaagcagc agataacttc cttgatccta caaagcaag ttctctatta    660
tcttcagggt tttcaccaga cttcgctaca gttattacta tggatagaaa agcatccaaa    720
caacaaacaa atatagatgt aatatacgaa cgagttcgta gtgactacca attgcactgg    780
acttcaacaa attggaaagg taccaatact aaagataaat ggatagatcg ttcttcagaa    840
agatataaaa tcgattggga aaaagaagaa atgacaaatg ttctggcgg aggggctaaa    900
cgtatcaaac aacatccgga cgtacaaaaa gttacagatg ctacaagtaa agttgcttca    960
aaaacatctg cagcaatcag taacacagcg agtgatgtta aagaatatgt cggcgataaa   1020
aaacaagatt ttgaaaataa gcgtgaactt aaaaagtttg ctagagaaca tgatcctgcc   1080
tatattgaga aaaaggcga aaaattagct aaacaaaatc gtaaagacgc tgataaaatg   1140
aataaaatac ttcaaaaaaa tatcgaaaag cgtcataaag aagagcaaaa agcccgcgaa   1200
aagaatgaaa tacaacgtat taaagatatg aaaaagtcac aaaaatacga agtaaaagca   1260
ggcttaacac ctaataaatt agatgagaaa actgagaaaa aaggcgataa actagctgaa   1320
aaaaatcgca agaaatcgc taaatgaat aaaaagttac aaaaaatat tgaaaacga    1380
cacaaagaag aacaaaaacg ccaacaagaa gctgataaag cacgcatcaa gtcatttaaa   1440
aaatataaag attatgttgc caaagcgcc tctcaacaaa ataagaaaa caatacagag   1500
gcataa                                                              1506

SEQ ID NO: 119        moltype = DNA  length = 1497
FEATURE               Location/Qualifiers
misc_feature          1..1497
                      note = DNA construct
source                1..1497
                      mol_type = other DNA
                      organism = synthetic construct
SEQUENCE: 119
gcagattctg atattaatat taaaaccggt actacagata ttggaagcaa tactacagta     60
aaaacaggtg atttagtcac ttatgataaa gaaaatggca tgttaaaaaa agtattttat    120
agttttatcg atgataaaaa tcataataaa aaactgctag ttattagaac gaaaggtacc    180
attgctggtc aatatagagt ttatagcgaa gaaggtgcta caaaagtgg tttagcctgg    240
ccttcagcct ttaaggtaca gttgcaacta cctgataatg aagtagctca aatatctgat    300
tactatccaa gaaattcgat tgatacaaaa gagtatatga gtactttaac ttatggattc    360
aacggtaatg ttactggtga tgatacagga aaaattggcg gccttattgg tgcaaatgtt    420
tcgattggtc atacactgaa atatgttcaa cctgatttca aaacaatttt agagagccca    480
actgataaaa aagtaggctg gaaagtgata tttaacaata tggtgaatca aaattgggga    540
ccatatgata gagattcttg gaacccggta tatggcaatc aacttttcat gaaaactaga    600
```

```
aatggctcta tgaaagcagc agataacttc cttgatccta acaaagcaag ttctctatta     660
tcttcagggt tttcaccaga cttcgctaca gttattacta tggatagaaa agcatccaaa     720
caacaaacaa atatagatgt aatatacgaa cgagttcgtg atgactacca attgcactgg     780
acttcaacaa attggaaagg taccaatact aaagataaat ggatagatcg ttcttcagaa     840
agatataaaa tcgattggga aaaagaagaa atgacaaatg gttctggcgg aggggctatg     900
actgaaaaag aaaaaatgtt agcagaaaaa tggtacgatg caaactttga tcaagactta     960
atcaatgaac gtgcacgagc gaaagatatt tgctttgaat taaatcatac aaagccgagt    1020
gacaaaaata aaagaaagga attaatcgat gaattatttc aaacaacaac agacaatgta    1080
agtatttcga ttccttttga tacagattat ggttggaacg ttaaactagg aaaaaatgtc    1140
tatgtaaaca ccaattgtta ttttatggat ggtggacaga ttacaattgg cgataatgtt    1200
tttataggac taattgtgg attctacaca gcaacacatc cacttaattt tcatcataga    1260
aatgaaggat ttgaaaaagc aggaccaatt aatattggca gtaatacttg gtttggcgga    1320
catgtagccg tgcttccggg agtgacgatt ggagaaggca gtgtgattgg tgctggtagt    1380
gttgtcacca aagatattcc gccacacagt ttagcgtgca aacccctg taaagtcgtt    1440
cgtaaaattg ataatgaggt accatcagaa gcattgaacg atgaaacact aaattag      1497

SEQ ID NO: 120          moltype = DNA   length = 2070
FEATURE                 Location/Qualifiers
misc_feature            1..2070
                        note = DNA construct
source                  1..2070
                        mol_type = other DNA
                        organism = synthetic construct
SEQUENCE: 120
gcagattctg atattaatat taaaaccggt actacagata ttggaagcaa tactacagta     60
aaaacaggtg atttagtcac ttatgataaa gaaaatgaca tgttaaaaaa agtatttat    120
agttttatcg atgataaaaa tcataataaa aaactgctag ttattagaac gaaaggtacc    180
attgctggtc aatatagagt ttatagcgaa gaaggtgcta acaaaagtgg tttagcctgg    240
ccttcagcct ttaaggtaca gttgcaacta cctgataatg aagtagctca atatctgat    300
tactatccaa gaaattcgat tgatacaaaa gagtatatga gtactttaac ttatgtgatt    360
aacggtaatg ttactggtga tgatacagga aaaattggcg gccttattgg tgcaaatgtt    420
tcgattggtc atacactgaa atatgttcaa cctgatttca aaacaatttt agagagccca    480
actgataaaa aagtaggctg aaagtgata tttaacaata tggtgaatca aaattgggga    540
ccatatgata gagattcttg gaacccggta tatgccaatc aacttttcat gaaaactaga    600
aatggctcta tgaaagcagc agataacttc cttgatccta acaaagcaag ttctctatta    660
tcttcagggt tttcaccaga cttcgctaca gttattacta tggatagaaa agcatccaaa    720
caacaaacaa atatagatgt aatatacgaa cgagttcgtg atgactacca attgcactgg    780
acttcaacaa attggaaagg taccaatact aaagataaat ggatagatcg ttcttcagaa    840
agatataaaa tcgattggga aaaagaagaa atgacaaatg gttctggcgg aggggctaaa    900
gttgccaaac aagggcagta taaaatcaa gaccctatcg tgttagtgca tggtttcaat    960
ggatttacag atgatattaa tccttcagtg ttagctcatt attggggcgg taataaaatg   1020
aacattcgcc aagatttaga agaaaatggt tacaagctt atgaagcaag tataagtgct   1080
tttggaagta actatgaccg cgcagttgaa cttattatt atatcaaagg cggtcgtgta   1140
gattatggtg cagcacatgc agcaaaatat ggacatgaac gttatggaaa acatacgaa   1200
ggaattaca aagactggaa accaggacag aaggtaccc tagttggaca tagtatggt   1260
ggtcaaacga tacgtcaact agaagaatta ctgcgtaatg gtagtcgtga agaaataagag   1320
tatcaaaaga aacatggtgg cgaaattct ccactattca aaggtataaa tgacaatatg   1380
atttcatcaa ttactacttt aggaacgca ccataatggaa cgcatgcttc agatttagct   1440
ggtaatgaag ctttagtgag acaaattgta tttgatatcg gtaaatgtt tggtaatanaa   1500
aactctagag tagcttcgg gttggctcaa tggggtctaa acagaagcc aaatgaatca   1560
tacattgatt atgtcaaacg cgttaaacaa tctaattat ggaaatcaaa agataatgga   1620
ttttacgatc tgacgcgtga gggtgcaaca gatttaaatc gtaaacgtc gttgaaccct   1680
aacattgtgt ataaaacata cactggtgaa gcaacgcaca aagcattaaa tagcgataga   1740
caaaaagcag acttaaatat gttttcccca tttgtgatta ctggtaactt aatcggtaaa   1800
gctactgaaa aagaatggcg agaaaacgat ggtttagtat ccgttatttc ttctcagcat   1860
ccatttaatc aagcttatac aaatgcgacg gataaaattc aaaaaggcat ttggcaagta   1920
acgcctacaa aacatgattg ggatcatgtt gattttgtcg acaagatag ttctgataca   1980
gtgcgcacaa gagaagaatt acaagatttt tggcatcatt tagcagacga tttagtgaaa   2040
actgaaaagg tgactgatac taagcaataa                                    2070

SEQ ID NO: 121          moltype = DNA   length = 1173
FEATURE                 Location/Qualifiers
misc_feature            1..1173
                        note = DNA construct
source                  1..1173
                        mol_type = other DNA
                        organism = synthetic construct
SEQUENCE: 121
aaagttgcca acaagggca gtataaaaat caagcccta tcgtgttagt gcatggtttc     60
aatggattta cagatgatat taatccttca gtgttagctc attattgggg cggtaataaa    120
atgaacattc gccaagattt agaagaaat ggttacaaag cttatgaagc aagtataagt    180
gcttttggaa gtaactatga ccgcgcagtt gaactttatt attatatcaa aggcggtcgt    240
gtagattatg gtgcagcaca tgcagcaaaa tatggacatg aacgttatgg aaaacatacg    300
gaaggaattt acaaagactg gaaaccagga cagaaggttg acatagtatg    360
ggtggtcaaa cgatacgtca actagaagaa ttactgcgta atggtagtcg tgaagaaata    420
gagtatcaaa agaacatgg tggcgaaatt ctccactat tcaaaggtaa taatgacaat    480
atgattcat caattactac tttaggaacg ccacataatg gaacgcatgc ttcagattta    540
gctggtaatg aagctttagt gagacaaatt gtatttgata tcggtaaaat gtttggtaat    600
aaaaactcta gagtagactt cgggttggct caatggggtc taaaacagaa gccaaatgaa    660
```

```
tcatacattg attatgtcaa acgcgttaaa caatctaatt tatgaaaatc aaaagataat  720
ggattttacg atctgacgcg tgagggtgca acagatttaa atcgtaaaac gtcgttgaac  780
cctaacattg tgtataaaac atacactggt gaagcaacgc acaaagcatt aaatagcgat  840
agacaaaaag cagacttaaa tatgtttttc ccatttgtga ttactggtaa cttaatcggt  900
aaagctactg aaaaagaatg gcgagaaaac gatggtttag tatccgttat ttcttctcag  960
catccattta atcaagctta tacaaatgcg acggataaaa ttcaaaaagg catttggcaa 1020
gtaacgccta caaaacatga ttgggatcat gttgattttg tcggacaaga tagttctgat 1080
acagtgcgca caagagaaga attacaagat ttttggcatc atttagcaga cgatttagtg 1140
aaaactgaaa aggtgactga tactaagcaa taa                              1173

SEQ ID NO: 122         moltype = DNA   length = 561
FEATURE                Location/Qualifiers
misc_feature           1..561
                       note = DNA construct
source                 1..561
                       mol_type = other DNA
                       organism = synthetic construct
SEQUENCE: 122
aaagttgcca acaagggca gtataaaaat caagaccta tcgtgttagt gcatggtttc   60
aatggattta cagatgatat taatccttca gtgttagctc attattgggg cggtaataaa  120
atgaacattc gccaagattt agaagaaaat ggttacaaag cttatgaagc aagtataagt  180
gcttttggaa gtaactatga ccgcgcagtt gaactttatt attatatcaa aggcggtcgt  240
gtagattatg gtgcagcaca tgcagcaaaa tatggacata aacgttatgg aaaaacatac  300
gaaggaattt acaaagactg gaaaccagga cagaaggtac acctagttgg acatagtatg  360
ggtggtcaaa cgatacgtca actagaagaa ttactgcgta atggtagtcg tgaagaaata  420
gagtatcaaa agaaacatgg tggcgaaatt tctccactat tcaaaggtaa taatgacaat  480
atgatttcat caattactac tttaggaacg ccacataatg gaacgcatgc ttcagattta  540
gctggtaatg aagctttata a                                           561

SEQ ID NO: 123         moltype = DNA   length = 882
FEATURE                Location/Qualifiers
misc_feature           1..882
                       note = DNA construct
source                 1..882
                       mol_type = other DNA
                       organism = synthetic construct
SEQUENCE: 123
gcagattctg atattaatat taaaaccggt actacagata ttggaagcaa tactacagta   60
aaaacaggtg atttagtcac ttatgataaa gaaaatgca tgttaaaaaa agtatttat   120
agttttatcg atgataaaaa tcataataaa aaactgctag ttattagaac gaaaggtacc  180
attgctggtc aatatagagt ttatagcgaa gaaggtgcta caaaaagtgg tttagcctgg  240
ccttcagcct taaggtaca gttgcaacta cctgataatg aagtagctca aatatctgat  300
tactatccaa gaaatttcgat tgatacaaaa gagtatatga gtactttaac ttatgattc  360
aacggtaatg ttactggtga tgatacagga aaaattggcg gccttattgg tgcaaatgtt  420
tcgattggtc atacactgaa atatgttcaa cctgatttca aaacaatttt agagagccca  480
actgataaaa aagtaggctg gaaagtgata tttaacaata tggtgaatca aaattgggga  540
ccatatgata gagattcttg gaacccggta tatggcaatc aacttttcat gaaaactaga  600
aatggctcta tgaaagcagc agataactc cttgatccta caaaagcaag ttctctatta  660
tcttcagggt tttcaccaga cttcgctaca gttattacta tggatagaaa agcatccaaa  720
caacaaaaca atatagatgt aatatacgaa cgagttcgtg atgactacca attgcactgg  780
acttcaacaa attggaaagg taccaatact aaagataaat ggatagatcg ttcttcagaa  840
agatataaaa tcgattggga aaaagaagaa atgacaaatt aa                     882

SEQ ID NO: 124         moltype = DNA   length = 1722
FEATURE                Location/Qualifiers
misc_feature           1..1722
                       note = DNA construct
source                 1..1722
                       mol_type = other DNA
                       organism = synthetic construct
SEQUENCE: 124
gcagctgaag aaacaggtgg tacaaataca gaagcacaac caaaaactga agcagttgca   60
agtccaacaa caacatctga aaaagctcca gaaactaaac cagtagctaa tgctgtctca  120
gtatctaata aagaagttga ggcccctact tctgaaacaa agaagctaa agaagttaaa  180
gaagttaaag cccctaagga aacaaaagaa gttaaaccag cagcaaaagc cactaacaat  240
acatatccta tttttgaatca ggaacttaga gaagcgatta aaaaccctgc aataaaaagac  300
aaagatcata gcgcaccaaa ctctcgtcca attgattttg aaatgaaaaa gaagatgga  360
actcaacagt tttatcatta tgcaagttct gttaaacg ctagagttaa tttcactgat  420
tcaaaaccag aaattgaatt aggattacaa tcaggtcaat tttggagaa atttgaagtt  480
tatgaaggtg acaaaaagtt gccaattaaa ttagtatcat acgatactgt taagattat  540
gcttacattc gcttctctgt atcaaacgga acaaagctg ttaaattgt tagttcaaca  600
cacttcaata acaagaaga aaaatacgat tacacattaa tggaattcgc acaaccaatt  660
tataacagtg cagataaatt caaaactgaa gaagattata agctgaaaaa attattagcg  720
ccatataaaa agcgaaaac actagaaaga caagttataa aattcaagat  780
aaacttcctg aaaattaaa ggctgagtac aagaagaaat tagaggatac aaagaaagct  840
ttagatgagc aagtgaaatc agctattact gaattccaaa atgtacaacc aacaaatgaa  900
aaaatgactg atttacaaga tacaaaaatat gttgtttatg aaagtgttga gaataacgaa  960
tctatgatgg atacttttgt taaacacct attaaaacag gtatgcttaa cggcaaaaaa 1020
tatatggtca tggaaactac taatgacgat tactggaaag atttcatggt tgaaggtcaa 1080
```

```
cgtgttagaa ctataagcaa agatgctaaa aataatacta gaacaattat tttcccatat   1140
gttgaaggta aaactctata tgatgctatc gttaaagttc acgtaaaaac gattgattat   1200
gatggacaat accatgtcag aatcgttgat aaagaagcat ttacaaaagc caataccgat   1260
aaatctaaca aaaagaaca acaagataac tcagctaaga aggaagctac tccagctacg    1320
cctagcaaac caacaccatc acctgttgaa aaagaatcac aaaaacaaga cagccaaaaa   1380
gatgacaata aacaattacc aagtgttgaa aaagaaaatg acgcatctag tgagtcaggt   1440
aaagacaaaa cgcctgctac aaaaccaact aaaggtgaag tagaatcaag tagtacaact   1500
ccaactaagg tagtatctac gactcaaaat gttgcaaaac caacaactgc ttcatcaaaa   1560
acaacaaaag atgttgttca aacttcagca ggttctagcg aagcaaaaga tagtgctcca   1620
ttacaaaaag caacattaa aaacacaaat gatggacaca ctcaaagcca aaacaataaa    1680
aatacacaag aaaataaagc aaaatcatta ccacaaactt aa                      1722

SEQ ID NO: 125          moltype = DNA  length = 1230
FEATURE                 Location/Qualifiers
misc_feature            1..1230
                        note = DNA construct
source                  1..1230
                        mol_type = other DNA
                        organism = synthetic construct
SEQUENCE: 125
atggatattg gtaaaaaaca tgtaattcct aaaagtcagt accgacgtaa gcgtcgtgaa   60
ttcttccaca acgaagacag agaagaaaat ttaaatcaac atcaagataa acaaaatata   120
gataatacaa catcaaaaaa agcagataag caaatacata aagattcaat tgataagcac   180
gaacgtttta aaaatagttt atcatcgcat ttagaacaga gaaaccgtga tgttaatgag   240
aataaagctg aagaaagtaa aagtaatcag gatagtaagt cagcatataa cagagatcat   300
tatttaacag acgatgtatc taaaaaacaa aattcattag attcagtgga ccaagataca   360
gagaaatcaa aatattatga gcaaaattct gaagcgactt tatcaactaa atcaaccgat   420
aaagtagaat caactgaaat gagaaagcta agttcagata aaacaaagt tggtcatgaa   480
gagcaacatg tactttctaa accttcagaa catgataaag agactagaat tgattctgag   540
tcttcaagaa ctgattcaga cagctcgatg cagacagaa aataaaaaa agacagttca   600
gatggaaata aaagtagtaa tctgaaatct gaagtaatat cagacaaatc aaatacagta   660
ccaaaattgt cggaatctga tgatgaagta aataatcaga agccattaac tttaccggaa   720
gaacagaaat tgaaaagaca gcaaagtcaa aatgagcaaa caaaaaccta tacatatggt   780
gatagcgaac aaaatgacaa gtctaatcat gaaaatgatt taagtcatca tataccatcg   840
ataagtgatg ataaagataa cgtcatgaga gaaaatatca ttgttgacga taatcctgat   900
aatgatatca atacaccatc attatcaaaa acagatgacg atcgaaaact tgatgaaaaa   960
attcatgttg aagataaaca taaacaaaat gcagactcgt ctgaaacggt gggatatcaa  1020
agtcagtcaa ctgcatctca tcgtagcact gaaaaagaa atatttctat taatgaccat  1080
gataaattaa acggtcaaaa aacaaataca aagacatcgg caaataataa tcaaaaaaag  1140
gctacatcaa aattgaacaa agggcgcgct acgaataata attatagtga catttgaaa   1200
aagtttggga tgatgtattg gcctaaataa                                    1230

SEQ ID NO: 126          moltype = DNA  length = 1779
FEATURE                 Location/Qualifiers
misc_feature            1..1779
                        note = DNA construct
source                  1..1779
                        mol_type = other DNA
                        organism = synthetic construct
SEQUENCE: 126
gatacacctc aaaagatac tacagctaag acaacatctc atgattcaaa aaaatctaat    60
gacgatgaaa cttctaagga tactacaagt aaagatattg ataaagcaga caacaataat   120
acaagtaacc aagacaataa cgacaaaaaa tttaaaacta tagacgacag cacttcagac   180
tctaacaata tcattgattt tatttataag aatttaccac aaaccaatat aaaccaattg   240
ctaaccaaaa ataaatacga tgtaattac tcattaacaa ctttaatcca aaacctattc   300
aattaaatt cggatatttc tgattacgaa caacctcgta atggcgaaaa gtcaacaaat   360
gattcgaata aaaacagtga caatagcatc aaaaatgaca ctgatacgca atcatctaaa   420
caagataaag cagacaatca aaaagcacct aaatcaaaca atacaaaacc aagtacatct   480
aataagcaac caaattcgcc aaagccaaca caacctaatc aatcaaatag tcaaccagca   540
agtgacgata agcaaatca aaatcttca tcgaaagata atcaatcaat gtcagattcg   600
gctttagact ctattttgga tcaatacagt gaagatgcaa agaaacaca aaaagattat   660
gcatctcaat ctaaaaaaga caaaaatgaa aaatctaata caagaatcc acagttacca   720
acacaagatg aattgaaaca taaatctaaa cctgctcaat cattcaataa cgatgttaat   780
caaaaggata cacgtgcaac atcattattc gaaacagatc ctagtatac taacaatgat   840
gatagcggac aatttaacgt tgttgactca aaagatacac gtcaatttgt caaatcaatt   900
gctaaagatg cacatcgcat tggtcaagat aacgatattt atgcgtctgt catgattgcc   960
caagcaatct tagaatctga ctcaggtcgt agtgctttag ctaagtcacc aaaccataat  1020
ttattcggta tcaaaggtgc ttttgaaggg aattctgttc cttttaacac attagaagct  1080
gatggtaata aattgtatag tattaatgct ggattccgaa aatatccaag cacgaaagta  1140
tcactaaaag attactctga ccttattaaa aatggtattg atggcaatcg aacaatttat  1200
aaaccaacat ggaaatcgga agccgattct tataaagatg caacatcaca cttatctaaa  1260
acatatgcta cagatccaaa ctatgctaag aaattaaaca gtattattaa acactatcaa  1320
ttaactcagt ttgacgatga acgcatgcca gatttagata aatatgaacg ttctatcaag  1380
gattatgatg attcatcaga tgaattcaaa cctttccgtg aggtatctga tagtatgcca  1440
tatccacatg gtcaatgtac ttggtacgta tataaccgta tgaaacaatt tggtacatct  1500
atctcaggtg atttaggtga tgcacataat tggaataatc gagctcaata ccgtgattat  1560
caagtaagtc atacaccaaa acgtcatgct gctgttgtat ttgaggctgg acaatttggt  1620
gcagatcaac attacggtca tgtagcattt gttgaaaaag ttaacagtga tggttctatc  1680
gttatttcag aatccaatgt taaaggatta ggtatcattt ctcatagaac tatcaatgca  1740
```

```
gctgccgctg aagaattatc atatattaca ggtaaataa                            1779

SEQ ID NO: 127          moltype = DNA   length = 2382
FEATURE                 Location/Qualifiers
misc_feature            1..2382
                        note = DNA construct
source                  1..2382
                        mol_type = other DNA
                        organism = synthetic construct
SEQUENCE: 127
caaacaaaat atggagatca atcagaaaaa ggatcccaaa gtgtaagtaa taaaaataat     60
aaaatacata tcgcaattgt taacgaggat caaccaacga catataacgg taaaaaggtt    120
gagctgggtc aagcatttat taaaaggtta gcaaatgaga aaaactataa atttgaaaca    180
gtaacaagaa acgttgctga gtctggtttg aaaaatggcg gataccaagt catgattgtt    240
atcccagaaa actttctcaaa attggcaatg caattagacg ctaaaacacc atcgaaaata    300
tcactacagt ataaaacagc tgtaggacaa aagaagaag tagctaaaaa cacagaaaaa    360
gttgtaagta atgtacttaa cgactttaac aaaaacttgg tcgaaattta tttaacaagc    420
atcattgata atttacataa tgcacaaaaa aatgttgacg ctattatgac gcgtgaacat    480
ggtgtgaata gtaaattctc gaattactta ttaaatccaa ttaacgactt cccggaatta    540
tttacagata cgcttgtaaa ttcgatttct gcaaacaaag atattacaaa atggttccaa    600
acatacaata aatcattact gagtgcgaat tcagatacat tcagagtgaa cacagattat    660
aatgtttcga ctttaattga aaaacaaaat tcattatttg acgaacacaa tcagcgatg    720
gataaaatgt tacaagatta taatcgcaa aaagatagcg tggaacttga taactatatc    780
aatgcattaa aacagatgga cagccaaatt gatcaacaat caagtatgca agatacaggt    840
aaagaagaat aaaacaaac tgttaaagaa aacttagata aattaagaga atcattcaa    900
tcacaagagt caccattttc aaaaggtatg attgaagaat atcgtaagca attaacagaa    960
tcactccaag atgagcttgc aaacaacaaa gacttacaag atgcgctaaa tagcattaaa   1020
atgaacaatg ctcaattcgc tgaaaactta gagaacaaac ttcatgatga tatttgtcaaa   1080
gaacctgatt cagatacaac atttatctat aacatgtcta acaagactt tatagctgca   1140
ggtttaaatg aggatgaagc taataaatac gaagcaattg tcaaagaagc aaaacgttat   1200
aaaaacgaat ataatttgaa aaaaccgtta gcagaacaca ttaatttaac agattacgat   1260
aaccaagttg cgcaagacac aagtagtttt attaatgatg gtgtgaaagt gcaacgtact   1320
gaaacgatta aaagtaatga tattaatcaa ttaactgttg caacgatcc tcattttaat   1380
tttgaaggcg acattaaaat taatgtgaaa aaatatgaca ttaagaacaa aagtgttcaa   1440
ctcgatacat ctaacaagga atataagtt gaagtcaatg gcgttgctaa attgaaaag   1500
gatgctgaga aagattcctt aaaagataaa acaatgcatt acaattgtt atttggacaa   1560
gcaaatcgtc aagatgaacc aaatgataag aaagcaacga gtgttgtgga tgtaacattg   1620
aatcataacc ttgatggtcg cttatcgaaa gatgcattaa gccagcaatt gagtgcatta   1680
tctaggttg atgcgcatta taaaatgtac acagatacaa aaggcagaga gataaacca   1740
ttcgacaaca acgtttaat tgatatgatg gttgaccaag ttatcaatga catgaaagt   1800
ttcaaagacg ataaagtagc tgtgttacat caaattgatt caatgaaga aaactcagac   1860
aaaactgattg atgacatttt aaataacaaa aagaatacaa caaaaaataa agaagatatt   1920
tctaagctga ttgatcagtt agaaaacgtt aaaaagactt ttgctgaaga gccacaagaa   1980
ccaaaaattg ataaaggcaa aaatgatgaa tttaatacga tgtcttcaaa tttagataaa   2040
gaaattgta gaattctga gaaagtacg caattgctat cagatacaca agaatcaaaa   2100
acaattgcag attcagttag tggacaatta aatcaattag ataataatgt gaataaacta   2160
catgcgacag gtcgagcatt aggcgtaaga gcgaattgatt tgaaccgtca aatgctaaa   2220
aacgataaag ataatgagtt attcgctaaa gagtttaaaa aagtattaca aaattctaaa   2280
gatggcgaca gacaaaacca agcattaaaa gcattatgag gtaatccggt tcaaaagaaa   2340
aacttagaaa atgttttagc taataatggt aatacagact aa                       2382

SEQ ID NO: 128          moltype = DNA   length = 609
FEATURE                 Location/Qualifiers
misc_feature            1..609
                        note = DNA construct
source                  1..609
                        mol_type = other DNA
                        organism = synthetic construct
SEQUENCE: 128
aaacgtatca acaacatcc ggacgtacaa aaagttacag atgctacaag taaagttgct      60
tcaaaaacat ctgcagcaat cagtaacaca gcgagtgatg ttaaagaata tgtcggcgat    120
aaaaaacaag attttgaaaa taagcgtgaa cttaaaaagt ttgctagaga acatgatcct    180
gcctatattg agaaaaaagg cgaaaaatta gctaaacaaa atcgtaaaga cgctgataaa    240
atgaataaaa tacttcaaaa aaatatcgaa aagcgtcata aagaagaca aaaagcccgc    300
gaaagaatg aaatacaacg tattaaagat atgaaaagt cacaaaaata cgaagtaaaa    360
gcaggcttaa cacctaataa attagatgag aaaactgaga aaaaggcga taaactagct    420
gaaaaaaatc gcaagaaat cgctaaaatg aataaaaagt tacaaaaaaa tattgaaaaa    480
cgacacaaag aagaacaaaa acgccaacaa gaagctgata agcacgcat caagtctttt    540
aaaaaatata aagattatgt tgccaaaagc gcctctcaac aaaataaaga aacaataca    600
gaggcataa                                                             609

SEQ ID NO: 129          moltype = DNA   length = 1230
FEATURE                 Location/Qualifiers
misc_feature            1..1230
                        note = DNA construct
source                  1..1230
                        mol_type = other DNA
                        organism = synthetic construct
SEQUENCE: 129
```

```
gtggatattg gtaaaaaaca tgtaattcct aaaagtcagt accgacgtaa gcgtcgtgaa    60
ttcttccaca acgaagacag agaagaaaat ttaaatcaac atcaagataa acaaaatata   120
gataatacaa catcaaaaaa agcagataag caaatacata aagattcaat tgataagcac   180
gaacgtttta aaaatagttt atcatcgcat ttagaacaga gaaaccgtga tgtgaatgag   240
aacaaagctg aagaaagtaa aagtaatcag ggtagtaagt cagcatataa caaagatcat   300
tatttaacag acgatgtatc taaaaaacaa aattcattag attcagtaga ccaagataca   360
gagaaatcaa aatattatga gcaaaatact gaagcgactt tatcaactaa ttcaaccgat   420
aaagtagaat caactgacat gagaaagcta agttcagata aaaacaaagt tggtcatgaa   480
gagcaacatg tactttctaa accttcagaa catgataaag agactagaat tgattttgag   540
tcttcaagaa ctgattcaga cagctcgatg cagacagaga aaataaaaaa agacagttca   600
gatggaaata aaagtagtaa tctgaaatct gaagtaatat cagacaaatc aaattcagta   660
ccaatattgt cggaatctga tgatgaagta aataatcaga agccattaac tttgccggaa   720
gaacagaaat tgaaaaggca gcaaagtcaa aatgagcaaa caaaaactta tacatatggt   780
gatagcgaac aaaatgacaa gtctaatcat gaaaatgatt taagtcatca tacaccatcg   840
ataagtgatg ataaagatta cgttatgaga gaagatcata ttgttgacga taatcctgat   900
aatgatatca atacaccatc attatcaaaa atagatgacg atcgaaaact tgatgaaaaa   960
attcatgtcg aagataaaca taaacaaaat gcagactcat ctgaaacggt gggatatcaa  1020
agtcagtcaa gtgcatctca tcgtagcact gaaaaaagaa atatggctat taatgaccat  1080
gataaattaa acggtcaaaa accaaataca aagacatcgg caaataataa tcaaaaaaag  1140
gctacatcaa aattgaacaa agggcgcgct acaaataata attatagcgc cattttgaaa  1200
aagttttgga tgatgtattg gcctaaataa                                    1230

SEQ ID NO: 130           moltype = DNA   length = 1488
FEATURE                  Location/Qualifiers
misc_feature             1..1488
                         note = DNA construct
source                   1..1488
                         mol_type = other DNA
                         organism = synthetic construct
SEQUENCE: 130
cgaaatttgt tgcttcaaaa gcaatcacaa gctagacaaa ctgccgaaga tattgtaaat    60
caagcacata aagaagctga caatatcaaa aaagagaaat tacttgaggc aaaagaagaa   120
aaccaaatcc taagagaaca aactgaagca gaactacgag aaagacgtag cgaacttcaa   180
agacaagaaa cccgacttct tcaaaaagaa gaaaacttag agcgtaaatc tgatctatta   240
gataaaaaag atgagatttt agagcaaaaa gaatcaaaaa ttgaagaaaa acaacaacaa   300
gtagatgcaa aagagagtag tgttcaaacg ttaaataatga agcatgaaca agaattagaa   360
cgcatctccg gtctcactca agaagaagct attaatgagc aacttcaaag agtagagaaa   420
gaactgtcac aagatattgc agtacttgtt aagaaaaaaa aaagagagc taaagaaaaa   480
gttgataaaa cagcaaaaga attattagct acagcagtac aaagattagc agcagatcac   540
acaagtgaat caacggtatc agtagttaac ttacctaatg atgagatgaa aggtcgaatc   600
attggacgtg aaggacgaaa catccgtaca cttgaaactt taactggcat tgatttaatt   660
attgatgaca caccagaagc agttatatta tctggttttg atccaataag aagagaaatt   720
gctagaacag cacttgttaa cttagtatct gatggacgta ttcatccagg tagaattgaa   780
gatatggtcg aaaaagctag aaagaagta gacgatatta aagagaagc aggtgaacaa   840
gctacatttg aagtgaacgc acataatatg catcctgact tagtaaaaat tgtagggcgt   900
ttaaactatc gtacaagtta cggtcaaaat gtacttaaac attcaattga agttgcgcat   960
cttgctagta tgttagctgc tgagctaggc gaagatgaa cattagcgaa acgagctgga  1020
cttttacatg atgttggtaa agcaattgat catgaagtag aaggtagtca tgttgaaatc  1080
ggtgtagaat tagcgaaaaa atatggtgaa aatgaaacag ttattaatgc aatccattct  1140
caccatggtg atgttgaacc tacatctatt atatctatcc ttgttgctgc tgcagatgca  1200
ttgtctgcgg ctcgtccagg tgcaagaaaa gaaacattag agaattatat tcgtcgatta  1260
gaacgtttag aaacgttatc agaaagttat gatggtgtag aaaaagcatt tgcgattcag  1320
gcaggtagag aaatccgagt gattgtatct cctgaagaaa ttgatgattt aaaatcttat  1380
cgattggcta gagatattaa aaatcagatt gaagatgaat tacaatatcc tggtcatatc  1440
aaggtgcacag ttgttcgaga gactagagca gtagaatatg cgaaataa              1488

SEQ ID NO: 131           moltype = DNA   length = 435
FEATURE                  Location/Qualifiers
misc_feature             1..435
                         note = DNA construct
source                   1..435
                         mol_type = other DNA
                         organism = synthetic construct
SEQUENCE: 131
aacaatcata ataatggtac aaaagaaaat aaaatcgcga atacaaataa aaataatgct    60
gatgaaagta agataaaga cacatctaaa gacgcttcta aagataaatc aaaatctaca   120
gacagtgata atcaaaaga tgatcaagac aaagcgacta agatgaatc tgataatgat   180
caaaacaacg ctaatcaa gaacaatcaa gcacaaaata caaaatcaca acaacaagct   240
aatcaaaatc aacaacagca acaacaacgt caaggtggtg gccaaagaca tacagtgaat   300
ggtcaagaaa acttataccg tatcgcaatt caatactacg gttcaggttc accgaaaaat   360
gttgaaaaaa ttagacctgc caatggttta agtggtaaca atattagaaa cggtcaacaa   420
atcgttattc cataa                                                    435

SEQ ID NO: 132           moltype = DNA   length = 1959
FEATURE                  Location/Qualifiers
misc_feature             1..1959
                         note = DNA construct
source                   1..1959
                         mol_type = other DNA
```

```
                    organism = synthetic construct
SEQUENCE: 132
atgaatgaaa aagtagaagg catgaccttg gagctgaaat tagaccattt aggtgtccaa    60
gaaggcatga aaggtttaaa gcgacaatta ggtgttgtta atagtgaaat gaaagctaat   120
ctgtcagcat ttgataagtc tgaaaaatca atggaaaaat atcaggcgag aattaagggg   180
ttaaatgata ggcttaaagt tcaaaaaaag atgtattctc aagtagaaga tgagcttaaa   240
caagttaacg ctaattacca aaaagctaaa tccagtgtaa aagatgttga aaagcatat    300
ttaaagttag tagaagccaa taaaaaagaa aaattagctc ttgataaatc taagaagcc    360
ttaaaatcat cgaatacaga acttaaaaaa gctgaaaatc aatataaacg tacaaatcaa   420
cgtaaacaag atgcgtatca aaaacttaaa cagttgagag atgcagaaca aaagcttaag   480
aatagtaacc aagctactac tgcacaacta aaaagagcaa gtgacgcagt acagaagcag   540
tccgctaagc ataaagcact tgttgaacaa tataaacaag aaggcaatca agttcaaaaa   600
ctaaaagtgc aaaatgacaa tctttcaaaa tcaaatgata aaattgaaag ttcttacgct   660
aaaactaata ctaaattaaa gcaaacagaa aaagaattta atgatttaaa caatactatt   720
aagaatcata gcgctaatgt cgcaaaagct gaaacagctg ttaataaaga aaaagctgct   780
ttaaataatt tggagcgttc aatagataaa gcttcatccg aaatgaagac ttttaacaaa   840
gaacaaatga tagctcaaag tcatttcggt aaacttgcaa gtcaagcgga tgtcatgtca   900
aagaaattta gttctattgg agacaaaatg acttccctgg tacgtacaat gacgatgggc   960
gtatctacac caattacttt agggttaggt gcagcattaa aaacaagtgc agactttgaa  1020
ggccaaatgt ctcgagttgg agcgattgcg caagcaagca gtaaagactt gaaaagcatg  1080
tctaatcaag cagttgactt aggagctaaa accagtaaaa gtgctaacga agttgctaaa  1140
ggtatggaag aattggcagc tttaggcttt aatgccaaac aaacaattgga ggctatgcca  1200
ggtgttatca gtgcagcaga agcaagtggt gcagaaatgg ctacaactgc aactgtaatg  1260
gcttcagcga ttaactcttt cggtttaaaa gcatctgatg caaatcatgt tgctgattta  1320
cttgcgagat cagcaaatga tagtgctgca gatattcagt acatgggaga tgcattgaag  1380
tatgctggta ctcctgcaaa agcattagga gtttcaatag ggacacttc cgcagcaatt  1440
gaagttttat ctaactcagg tttagaggt tctcaagcag gtactgccct aagagcttca  1500
tttatcaggc tagctaatcc aagtaaaaat acagctaagg aaatgaaaaa attaggtatt  1560
catttgtctg atgctaaagg tcaatttgtt ggcatgggtg aattgattag acagttccaa  1620
gataaatga aaggcatgac gagagaacaa aaactagctca cagtggctac aatagtttggt  1680
actgaagcag caagtggatt tttagccttg attgaagcgg gaccagataa aattaatagc  1740
tatagtaaat ccttaaagaa ttccaatggc gaaagtaaaa aagcagcaga tttgatgaaa  1800
gataatctca aaggcgctct ggaacaatta ggtggcgctt ttgaatcatt agcaatcgaa  1860
gtcggtaaag atttaacgcc tatgattaga gcaggagcga aaggtttaac aaaattagtt  1920
gatggattta cacatctccc tggttgggtt agaaaataa                          1959

SEQ ID NO: 133         moltype = DNA   length = 600
FEATURE                Location/Qualifiers
misc_feature           1..600
                       note = DNA construct
source                 1..600
                       mol_type = other DNA
                       organism = synthetic construct
SEQUENCE: 133
atgactgaaa aagaaaaaat gttagcagaa aaatggtacg atgcaaactt tgatcaagac    60
ttaatcaatg aacgtgcacg agcgaaagat atttgctttg aattaaatca tacaaagccg   120
agtgacaaaa ataaaagaaa ggaattaatc gatgaattac ttcaaacaac aacagacaat   180
gtaagtattt cgattccttt tgatacagat tatggttgga acgttaaact aggaaaaaat   240
gtctatgtaa acaccaattg ttatttatg gatggtggac agattacaat tggcgataat   300
gttttttatg gacctaattg tggattctac acagcaacac atccacttaa ttttcatcat   360
agaaatgaag gatttgaaaa agcaggacca attaatattg gcagtaatac ttggttttgg   420
ggacatgtag ccgtgcttcc gggagtgacg attggagaag gcagtgtgat tggtgctggt   480
agtgttgtca ccaaagatat tccgccacac agtttagcgg ttggaaaccc ttgtaaagtc   540
gttcgtaaaa ttgataatga ggtaccatca gaagcattga acgatgaaac actaaattag   600

SEQ ID NO: 134         moltype = DNA   length = 1779
FEATURE                Location/Qualifiers
misc_feature           1..1779
                       note = DNA construct
source                 1..1779
                       mol_type = other DNA
                       organism = synthetic construct
SEQUENCE: 134
gacacacctc aaaagatac tacagctaag acaacatctc atgattccaa aaaatctact    60
gatgatgaaa cttctaagga tactacaagt aaagatattg ataaagcaga caacaataat   120
actagtaacc aagacaataa cgacaaaaaa gttaaaacta tagcgacag cacttcagac   180
tctaacaata tcattgattt tatttataag aatttaccac aaaccaatat aaaccaattg   240
ctaaccaaaa ataaatacga tgtaattac tcattaacaa ctttaatcca aaacttattc   300
aatttaaatt cggatatttc tgattacgaa caacctcgta atggtgaaaa gtcaacaat    360
gattcgaata aaaacagtga taatagcatc aaaaatgata cggatacgca atcatctaaa   420
caagataaag cagacaatca aaaagcccct aaatcaaaca atacaaaacc aagtacatct   480
aataagcaac caaattcgcc aaagccaaca caaccaaatc aatcaaatag tcaaccagca   540
agtgacgata aagtaaatca aaaatcttca tcgaaagata tcaatcaat gtcagattcg   600
gctttagatt ctattttgga tcaatacagt gaagatgaa agaaaacaca aaaagattac   660
gcatctcaat ctaaaaaaga caaaatgaa aaatctaata caagaatcc acagttacca   720
acacaagatg aattgaaaca taaatctaaa cctgctcaat cattcaataa cgatgttaat   780
caaaaggata cacgtgcaac atcactattc gaaacagatc ctagtatatc taacaatgat   840
gatagtggac aatttaacgt tgttgactca aaagatacac gtcaatttgt caaatcaatt   900
gctaaagatg cacaccgcat tggtcaagat aacgatattt atgcgtctgt catgattgcc   960
```

```
caagcaatct tagaatctga ctcaggtcgt agtgctttag ctaagtcacc aaaccataat   1020
ttattcggta tcaaaggtgc ttttgaaggg aattctgttc cttttaacac attagaagct   1080
gatggtaatc aattgtatag tattaatgct ggattccgaa aatatccaag cacgaaagaa   1140
tcactaaaag attactctga ccttattaaa aatggtattg atggcaatcg aacaatttat   1200
aaaccaacat ggaaatcgga agccgattct tataaagata aacatcaca cttatctaaa   1260
acatatgcta cagatccaaa ctatgctaag aaattaaaca gtattattaa acactatcaa   1320
ttaactcagt tgacgatga acgtatgcca gatttagata aatatgaacg ttctatcaag   1380
gattatgatg attcatcaga tgaattcaaa cctttccgcg aggtatctga taatatgcca   1440
tatccacatg gccaatgtac ttggtacgta tataaccgta tgaaacaatt tggtacatct   1500
atctcaggtg atttaggtga tgcacataat tggaataatc gagctcaata ccgtgattat   1560
caagtaagtc atacaccaaa acgtcatgct gctgttgtat ttgaggctgg acaatttggt   1620
gcagatcaac attacggtca tgtagcattt gttgaaaaag ttaacagtga tggttctatc   1680
gttatttcag aatccaatgt taaggatta ggtatcattt ctcatagaac tatcaatgca   1740
gctgccgctg aagaattatc atatattaca ggtaaataa                         1779
```

SEQ ID NO: 135            moltype = DNA   length = 1326
FEATURE                   Location/Qualifiers
misc_feature              1..1326
                          note = DNA construct
source                    1..1326
                          mol_type = other DNA
                          organism = synthetic construct
SEQUENCE: 135
```
gctgagaagc aagtgaatat gggaaattca caggaggata cagttacagc acaatctatt    60
ggggatcaac aaactaggga aaatgctaat tatcaacgtg aaaacggtgt tgacgaacag   120
caacatactg aaaatttaac taagaacttg cataatgata aacaatatc agaagaaaat   180
catcgtaaaa cagatgattt gaataaagat caactaaagg atgataaaaa atcatcgctt   240
aataataaaa atattcaacg tgatacaaca aaaaataaca atgctaatcc tagggatgta   300
aatcaagggt tagaacaggc tattaatgat ggcaaacaaa gtaaagtggc gtcacagcaa   360
cagtcaaaag aggcagataa tagtcaagac ttaaacgcta aacaatct accttccaa     420
agtcgaacaa aggtatcacc atcattaaat aagtcagatc aaacaagtca acgagaaatt   480
gttaatgaga cagaaataga gaaagtacaa ccgcaacaaa agaatcaagc gaatgataaa   540
attactgacc acaattttaa caatgaacaa gaagtgaaac ctcaaaaaga cgaaaaaaca   600
ctatcagttt cagatttaaa aaacaatcaa aaatcaccag ttgaaccaac aaaggacaat   660
gacaagaaaa atggattaaa tttattaaaa agtagtgcag tagcaacgtt accaaacaaa   720
gggacaaagg aacttactgc aaaagcgaaa ggtgatcaaa cgaataaagt tgccaaacaa   780
gggcagtata aaaatcaaga tcctatagtt ttagtgcatg gtttcaatgg gtttacagat   840
gatattaatc cttcagtgtt agctcattat tggggcggta ataaaatgaa cattcgccaa   900
gatttagaag aaaatggtta caaagcttat gaagcaagta taagtgcttt tggaagtaac   960
tatgaccgcg cagttgaact ttattattat atcaaaggcg gtcgtgtaga ttatggtgca  1020
gcacatgcag caaaatatgg acatgaacgt tatggaaaaa catacgaagg aatttacaaa  1080
gactggaaac caggacagaa ggtacacctt gttggacata gtatgggtgg tcaaacgata  1140
cgtcaactag aagaattact gcgtaatggt agtcgtgaag atagagta ttcaaagaaa    1200
catagtggcg aaatttctcc actattcaaa ggtaataatg acaatatgat ttcatcaatt  1260
actactttag gaacgccaca taatggaacg catgcttcag atttagctgg taatgaagct  1320
ttataa                                                             1326
```

SEQ ID NO: 136            moltype = DNA   length = 1098
FEATURE                   Location/Qualifiers
misc_feature              1..1098
                          note = DNA construct
source                    1..1098
                          mol_type = other DNA
                          organism = synthetic construct
SEQUENCE: 136
```
ggatttttaa acaaatctaa aaatgagcaa gcggcattaa aggcacaaca agcagcgata    60
aaagaagaag caagtgcaaa taatttaagt gatacatcac aagaagcaca agagattcaa   120
gaagctaaaa gagaagcaca agcagaagcg ataaaagtg tggctgtatc aaataaagaa    180
tcaaaagcag tggcattgaa agcacaacaa gcagcgataa aagaaagc aagtgcaaat    240
aatttgagtg atacatcaca agaggcacaa gagattcaag aagctaaaaa agaagcacaa   300
gcagaaacag ataaaagtgc agctgtatca aatgaagaac caaaagcagt ggcattgaaa   360
gcacaacaag cagcgataaa agaagaagca agtgcaaata tttaagtga tatatcacaa    420
gaggcacaag aggttcaaga agctaaaaaa gaagcacaag cagagaaaga cagtgacaca   480
ttaactaaag atgcaagtgc agcaaaggta gaagtatcaa aaccagagtc acaagctgaa   540
agattagcaa acgctgcaaa acagaagcaa gctaaattaa caccaggttc aaaagagagt   600
caattaactg aagcgttatt tgcagaaaaa ccagttgcta aaaatgactt gaaagaaatt   660
cctcaattag ttactaaaaa gaatgatgta tcagagacag agacggttaa tatagataat   720
aaagcacactg ttaaacaaaa agaagctaaa tttgaaaatg gtgttattac acgtaaagct  780
gatgaaaaaa caactaataa tacagctgtt gacaagaaat caggtaaaca atctaaaaat   840
acaacaccctt caaatatttt gaaatgtcaa aaagcatcta caaataatt tttcaggtcag  900
aaaaagcaac ataataagaa atcatcacaa ggtgcaaaga aacaaagtag ttcaagtaag   960
tcaactcaaa agaataatca aactagtaat aagaattcaa aaacaaaca tgctaaatca   1020
tccaatgcat caaaaacgcc aaatgctaaa gttgagaaag ctaaagtaa aatagagaaa   1080
cgtacattca atgactaa                                                1098
```

SEQ ID NO: 137            moltype = DNA   length = 1056
FEATURE                   Location/Qualifiers
misc_feature              1..1056
                          note = DNA construct

```
source                        1..1056
                              mol_type = other DNA
                              organism = synthetic construct
SEQUENCE: 137
aaggataact taaatggaga aaaaccaact actaatttga atcataatat aacttcacca    60
tcagtaaata gtgaaatgaa taataatgag actgggacac ctcacgaatc aaatcaaacg   120
ggtaatgaag gaacaggttc gaatagtcgt gatgctaatc ctgattcgaa taatgtgaag   180
ccagactcaa acaaccaaaa cccaagtaca gattcaaaac cagacccaaa taaccaaaac   240
ccaagtccga atcctaaacc agatccagat aacccgacaa caaaaccgga tccaaaacca   300
gacccagata aaccaaagcc aaatccggat ccaaaaccag atccagataa cccgaaacca   360
aatccagatc caaaaccaga ccctaataag ccaaatccgg atccaaaacc agatccagat   420
aaaccaaagc caaatccgaa tccaaaacca gaccctaata agccaaatcc taacccgtca   480
ccagatcccg atcaacctgg ggattccaat cattctggtg gctcgaaaaa tgggggggaca   540
tggaaccaaa atgcttcaga tggatctaat caaggtcaat ggcaaccaaa tgggaatcaa   600
ggaaactcac aaaatcctac tggtaatgat tttgtatccc aacgattttt agccttggca   660
aatggggctt acaagtataa tccgtatatt ttaaatcaaa ttaataagtt gggcaaagat   720
tatggagaag ttactgatga agacatttat aatattattc gaaaacaaaa tttcagcgga   780
aatgcatatt taaatggatt acaacagcaa tcgaattact ttagattcca atatttcaat   840
ccattgaaat cagaaggta ctatcgtaat ttagatgaac aagtactcgc attaattact   900
ggtgaaattg gatcaatgcc agatttgaaa agcccgaag ataagccgga ttcaaaacaa   960
cgctcatttg aaccgcatga aaaagacgat tttacagtag ttaaaaaaca agaagataat  1020
aagaaaagtg cgtcaactgc atatagtaaa agttaa                            1056

SEQ ID NO: 138                moltype = DNA  length = 1239
FEATURE                       Location/Qualifiers
misc_feature                  1..1239
                              note = DNA construct
source                        1..1239
                              mol_type = other DNA
                              organism = synthetic construct
SEQUENCE: 138
attgattcaa aaaataaacc agctaattct gatattaaat ttgaggtgac tcaaaagagt    60
gatgcggtca aagcattaaa agaattgcct aaatccgaaa atgtaaaaaa tatttatcaa   120
gattacgctg ttactgatgt aaaaaactgat aaaaaaggat ttacgcatta tacattgcaa   180
ccgagtgttg atggtgttca tgcacctgac aaagaagtga aagtacacgc agacaaatca   240
ggaaaagtcg tttaatcaa tggggatact gatgcgaaga aagtaaagcc aacgaataaa   300
gtgacattaa gtaagatga cgcagccgac aaagcattta agcagttaa gattgataag   360
aataaagcga aaatcttaa agataaagtc attaaagaaa caaagttga atcgatggt   420
gacagtaata aatacgttta taatgttgag ttaattacag tgacaccgaa aatttcacat   480
tggaaagtta aaattgatgc tcaaactggc gaaattttag aaaaaatgaa cttagttaaa   540
gaagctgcag aaactggtaa aggaaaaggt gtacttggcg atacaaaaga tatcaatatc   600
aatagtattg acggtggatt tagcctagaa gatttaacgc atcaaggtaa attatcagca   660
tttagcttta tgatcaaac aggtcaagca acattgatta ctaatgaaga tgaaaacttc   720
gtaaaagatg agcaacgtgc tggcgtagat gcaattatt acgctaaaca aacatatgat   780
tattacaaag acacatttgg tcgtgaatca tatgacaacc aaggtagtcc aattgtttca   840
ttaacgcatg ttaataacta cggtggtcaa gataacagaa ataatgccgc atggatcggt   900
gacaaaatga tctcatggtga tggtgatggt cgcacattca caagtttatc gggtgcaaat   960
gacgtagtag cacacgaatt aacacacggt gtgacacaag agacagcgaa cttagaaat  1020
aaggaccagt caggcgctct aaatgaaagc ttttcagatg tttttggata ctttgtagat  1080
gacgaggatt tcttaatggg tgaagatgtc tacacacctg aaaagaggg agacgcttta  1140
cgcagcatgt caaacccaga acaatttggt caaccagctc atatgaaaga ctatgtattc  1200
actgaaaaag ataatggtgg cgtacatacg aattcttaa                         1239

SEQ ID NO: 139                moltype = AA  length = 319
FEATURE                       Location/Qualifiers
source                        1..319
                              mol_type = protein
                              organism = Staphylococcus aureus
SEQUENCE: 139
MKTRIVSSVT TTLLLGSILM NPVANAADSD INIKTGTTDI GSNTTVKTGD LVTYDKENGM    60
LKKVFYSFID DKNHNKKLLV IRTKGTIAGQ YRVYSEEGAN KSGLAWPSAF KVQLQLPDNE   120
VAQISDYYPR NSIDTKEYMS TLTYGFNGNV TGDDTGKIGG LIGANVSIGH TLKYVQPDFK   180
TILESPTDKK VGWKVIFNNM VNQNWGPYDR DSWNPVYGNQ LFMKTRNGSM KAADNFLDPN   240
KASSLLSSGF SPDFATVITM DRKASKQQTN IDVIYERVRD DYQLHWTSTN WKGTNTKDKW   300
IDRSSERYKI DWEKEEMTN                                                319

SEQ ID NO: 140                moltype = AA  length = 515
FEATURE                       Location/Qualifiers
source                        1..515
                              mol_type = protein
                              organism = Staphylococcus aureus
SEQUENCE: 140
MKKKLGMLLL VPAVTLSLAA CGNDDGKDKD GKVTIKTTVY PLQSFAEQIG GKHVKVSSIY    60
PAGTDLHSYE PTQKDILSAS KSDLFMYTGD NLDPVAKKVA STIKDKDKKL SLEDKLDKAK   120
LLTDQHEHGE EHEHEGHDHG KEEHHHHGGY DPHVWLDPKI NQTFAKEIKD ELVKKDPKHK   180
DDYEKNYKKL NDDLKKIDND MKQVTKDKQG NAVFISHESI GYLADRYGFV QKGIQNMNAE   240
DPSQKELTKI VKEIRDSNAK YILYEDNVAN KVTETIRKET DAKPLKFYNM ESLNKEQQKK   300
DNITYQSLMK SNIENIGKAL DSGVKVKDDK AESKHDKAIS DGYFKDEQVK DRELSDYAGE   360
WQSVYPYLKD GTLDEVMEHK AENDPKKSAK DLKAYYDKGY KTDITNIDIK GNEITFTKDG   420
```

```
TKHTGKYEYN GKKTLKYPKG NRGVRFMFKL VDGNDKDLPK FIQFSDHNIA PKKAEHFHIF   480
MGNDNDALLK EMDNWPTYYP SKLNKDQIKE EMLAH                              515

SEQ ID NO: 141          moltype = AA  length = 519
FEATURE                 Location/Qualifiers
source                  1..519
                        mol_type = protein
                        organism = Staphylococcus aureus
SEQUENCE: 141
MNLLSLLLIL LGIILGVVGG YVVARNLLLQ KQSQARQTAE DIVNQAHKEA DNIKKEKLLE    60
AKEENQILRE QTEAELRERR SELQRQETRL LQKEENLERK SDLLDKKDEI LEQKESKIEE   120
KQQQVDAKES SVQTLIMKHE QELERISGLT QEEAINEQLQ RVEEELSQDI AVLVKEKEKE   180
AKEKVDKTAK ELLATAVQRL AADHTSESTV SVVNLPNDEM KGRIIGREGR NIRTLETLTG   240
IDLIIDDTPE AVILSGFDPI RREIARTALV NLVSDGRIHP GRIEDMVEKA RKEVDDIIRE   300
AGEQATFEVN AHNMHPDLVK IVGRLNYRTS YGQNVLKHSI EVAHLASMLA AELGEDETLA   360
KRAGLLHDVG KAIDHEVEGS HVEIGVELAK KYGENETVIN AIHSHHGDVE PTSIISILVA   420
AADALSAARP GARKETLENY IRRLERLETL SESYDGVEKA FAIQAGREIR VIVSPEEIDD   480
LKSYRLARDI KNQIEDELQY PGHIKVTVVR ETRAVEYAK                          519

SEQ ID NO: 142          moltype = AA  length = 619
FEATURE                 Location/Qualifiers
source                  1..619
                        mol_type = protein
                        organism = Staphylococcus aureus
SEQUENCE: 142
MPKNKILIYL LSTTLVLPTL VSPTAYADTP QKDTTAKTTS HDSKKSNDDE TSKDTTSKDI    60
DKADNNNTSN QDNNDKKFKT IDDSTSDSNN IIDFIYKNLP QTNINQLLTK NKYDDNYSLT   120
TLIQNLFNLN SDISDYEQPR NGEKSTNDSN KNSDNSIKND TDTQSSKQDK ADNQKAPKSN   180
NTKPSTSNKQ PNSPKPTQPN QSNSQPASDD KANQKSSSKD NQSMSDSALD SILDQYSEDA   240
KKTQKDYASQ SKKDKNEKSN TKNPQLPTQD ELKHKSKPAQ SFNNDVNQKD TRATSLFETD   300
PSISNNDDSG QFNVVDSKDT RQFVKSIAKD AHRIGQDNDI YASVMIAQAI LESDSGRSAL   360
AKSPNHNLFG IKGAFEGNSV PFNTLEADGN KLYSINAGFR KYPSTKESLK DYSDLIKNGI   420
DGNRTIYKPT WKSEADSYKD ATSHLSKTYA TDPNYAKKLN SIIKHYQLTQ FDDERMPDLD   480
KYERSIKDYD DSSDEFKPFR EVSDSMPYPH GQCTWYVYNR MKQFGTSISG DLGDAHNWNN   540
RAQYRDYQVS HTPKRHAAVV FEAGQFGADQ HYGHVAFVEK VNSDGSIVIS ESNVKGLGII   600
SHRTINAAAA EELSYITGK                                                619

SEQ ID NO: 143          moltype = AA  length = 645
FEATURE                 Location/Qualifiers
source                  1..645
                        mol_type = protein
                        organism = Staphylococcus aureus
SEQUENCE: 143
MNKQQKEFKS FYSIRKSSLG VASVAISTLL LLMSNGEAQA AAEETGGTNT EAQPKTEAVA    60
SPTTTSEKAP ETKPVANAVS VSNKEVEAPT SETKEAKEVK EVKAPKETKE VKPAAKATNN   120
TYPILNQELR EAIKNPAIKD KDHSAPNSRP IDFEMKKKDG TQQFYHYASS VKPARVIFTD   180
SKPEIELGLQ SGQFWRKFEV YEGDKKLPIK LVSYDTVKDY AYIRFSVSNG TKAVKIVSST   240
HFNNKEEKYD YTLMEFAQPI YNSADKFKTE EDYKAEKLLA PYKKAKTLER QVYELNKIQD   300
KLPEKLKAEY KKKLEDTKKA LDEQVKSAIT EFQNVQPTNE KMTDLQDTKY VVYESVENNE   360
SMMDTFVKHP IKTGMLNGKK YMVMETTNDD YWKDFMVEGQ RVRTISKDAK NNTRTIIFPY   420
VEGKTLYDAI VKVHVKTIDY DGQYHVRIVD KEAFTKANTD KSNKKEQQDN SAKKEATPAT   480
PSKPTPSPVE KESQKQDSQK DDNKQLPSVE KENDASSESG KDKTPATKPT KGEVESSSTT   540
PTKVSTTQN VAKPTTASSK TTKDVVQTSA GSSEAKDSAP LQKANIKNTN DGHTQSQNNK   600
NTQENKAKSL PQTGEESNKD MTLPLMALLA LSSIVAFVLP RKRKN                   645

SEQ ID NO: 144          moltype = AA  length = 681
FEATURE                 Location/Qualifiers
source                  1..681
                        mol_type = protein
                        organism = Staphylococcus aureus
SEQUENCE: 144
MMKSQNKYSI RKFSVGASSI LIATLLFLSG GQAQAAEKQV NMGNSQEDTV TAQSIGDQQT    60
RENANYQREN GVDEQQHTEN LTKNLHNDKT ISEENHRKTD DLNKDQLKDD KKSSRNNKNI   120
QRDTTKNNNA NPSDVNQGLE QAINDGKQSK VASQQQSKEA DNSQDSNANN NLPSQSRTKE   180
APSLNKLDQT SQREIVNETE IEKVQPQQNN QANDKITNYN FNNEQEVKPQ KDEKTLSVSD   240
LKNNQKSPVE PTKDNDKKNG LNLLKSSAVA TLPNKGTKEL TAKAKDDQTN KVAKQGQYKN   300
QDPIVLVHGF NGFTDDINPS VLAHYWGGNK MNIRQDLEEN GYKAYEASIS AFGSNYDRAV   360
ELYYYIKGGR VDYGAAHAAK YGHERYGKTY EGIYKDWKPG QKVHLVGHSM GGQTIRQLEE   420
LLRNGSREEI EYQKKHGGEI SPLFKGNNDN MISSITTLGT PHNGTHASDL AGNEALVRQI   480
VFDIGKMFGN KNSRVDFGLA QWGLKQKPNE SYIDYVKRVK QSNLWKSKDN GFYDLTREGA   540
TDLNRKTSLN PNIVYKTYTG EATHKALNSD RQKADLNMFF PFVITGNLIG KATEKEWREN   600
DGLVSVISSQ HPFNQAYTNA TDKIQKGIWQ VTPTKHDWDH VDFVGQDSSD TVRTREELQD   660
FWHHLADDLV KTEKVTDTKQ A                                             681

SEQ ID NO: 145          moltype = AA  length = 769
FEATURE                 Location/Qualifiers
source                  1..769
                        mol_type = protein
                        organism = Staphylococcus aureus
```

```
SEQUENCE: 145
MDIGKKHVIP KSQYRRKRRE FFHNEDREEN LNQHQDKQNI DNTTSKKADK QIHKDSIDKH    60
ERFKNSLSSH LEQRNRDVNE NKAEESKSNQ DSKSAYNRDH YLTDDVSKKQ NSLDSVDQDT   120
EKSKYYEQNS EATLSTKSTD KVESTEMRKL SSDKNKVGHE EQHVLSKPSE HDKETRIDSE   180
SSRTDSDSSM QTEKIKKDSS DGNKSSNLKS EVISDKSNTV PKLSESDDEV NNQKPLTLPE   240
EQKLKRQQSQ NEQTKTYTYG DSEQNDKSNH ENDLSHHIPS ISDDKDNVMR ENHIVDDNPD   300
NDINTPSLSK TDDDRKLDEK IHVEDKHKQN ADSSETVGYQ SQSTASHRST EKRNISINDH   360
DKLNGQKTNT KTSANNNQKK ATSKLNKGRA TNNNYSDILK KFWMMYWPKL VILMGIIILI   420
VILNAIFNNV NKNDRMNDNN DADAQKYTTT MKNANNTVKS VVTVENETSK DSSLPKDKAS   480
QDEVGSGVVY KKSGDTLYIV TNAHVVGDKE NQKITFSNNK SVVGKVLGKD KWSDLAVVKA   540
TSSDSSVKEI AIGDSNNLVL GEPILVVGNP LGVDFKGTVT EGIISGLNRN VPIDFDKDNK   600
YDMLMKAFQI DASVNPGNSG GAVVNREGKL IGVVAAKISM PNVENMSFAI PVNEVQKIVK   660
DLETKGKIDY PDVGVKMKNI ASLNSFERQA VKLPGKVKNG VVVDQVDNNG LADQSGLKKG   720
DVITELDGKL LEDDLRFRQI IFSHKDDLKS ITAKIYRDGK EKEINIKLK              769

SEQ ID NO: 146        moltype = AA  length = 2066
FEATURE               Location/Qualifiers
source                1..2066
                      mol_type = protein
                      organism = Staphylococcus aureus
SEQUENCE: 146
MNEKVEGMTL ELKLDHLGVQ EGMKGLKRQL GVVNSEMKAN LSAFDKSEKS MEKYQARIKG    60
LNDRLKVQKK MYSQVEDELK QVNANYQKAK SSVKDVEKAY LKLVEANKKE KLALDKSKEA   120
LKSSNTELKK AENQYKRTNQ RKQDAYQKLK QLRDAEQKLK NSNQATTAQL KRASDAVQKQ   180
SAKHKALVEQ YKQEGNQVQK LKVQNDNLSK SNDKIESSYA KTNTKLKQTE KEFNDLNNTI   240
KNHSANVAKA ETAVNKEKAA LNNLERSIDK ASSEMKTFNK EQMIAQSHFG KLASQADVMS   300
KKFSSIGDKM TSLGRTMTMG VSTPITLGLG AALKTSADFE GQMSRVGAIA QASSKDLKSM   360
SNQAVDLGAK TSKSANEVAK GMEELAALGF NAKQTMEAMP GVISAAEASG AEMATTATVM   420
ASAINSFGLK ASDANHVADL LARSANDSAA DIQYMGDALK YAGTPAKALG VSIEDTSAAI   480
EVLSNSGLEG SQAGTALRAS FIRLANPSKN TAKEMKKLGI HLSDAKGQFV GMGELIRQFQ   540
DNMKGMTREQ KLATVATIVG TEAASGFLAL IEAGPDKINS YSKSLKNSNG ESKKAADLMK   600
DNLKGALEQL GGAFESLAIE VGKDLTPMIR AGAEGLTKLV DGFTHLPGWV RKASVGLALF   660
GASIGPAVLA GGLLIRAVGS AAKGYASLNR RIAENTILSN TNSKAMKSLG LQTLFLGSTT   720
GKTSKGFKGL AGAMLFNLKP INVLKNSAKL AILPFKLLKN GGLAAKSLF AVSGGARFAG    780
VALKFLTGPI GATITAITIA YKVFKTAYDR VEWFRNGING LGETIKFFGG KIIGGAVRKL   840
GEFKNYLGSI GKSFKEKFSK DMKDGYKSLS DDDLLKVGVN KFKGFMQTMG TASKKASDTV   900
KVLGKGVSKE TEKALEKYVH YSEENNRIME KVRLNSGQIT EDKAKKLLKI EADLSNNLIA   960
EIEKRNKKEL EKTQELIDKY SAFDEQEKQN ILTRTKEKND LRIKKEQELN QKIKELKEKA  1020
LSDGQISENE RKEIEKLENQ RRDITVKELS KTEKEQERIL VRMQRNRNSY SIDEASKAIK  1080
EAEKARKAKK KEVDKQYEDD VIAIKNNVNL SKSEKDKLLA IADQRHKDEV RKAKSKKDAV  1140
VDVVKKQNKD IDKEMDLSSG RVYKNTEKWW NGLKSWWSNF REDQKKKSDK YAKEQEETAR  1200
RNRENIKKWF GNAWDGVKSK TGEAFSKMGR NANHFGGEMK KMWSGIKGIP SKLSSGWSSA  1260
KSSVGYHTKA IANSTGKWFG KAWQSVKSTT GSIYNQTKQK YSDASDKAWA HSKSIWKGTS  1320
KWFSNAYKSA KGWLTDMANK SRSKWDNISS TAWSNAKSVW KGTSKWFSNS YKSLKGWTGD  1380
MYSRAHDRFD AISSSAWSNA KSVFNGFRKW LSRTYEWIRD IGKDMGRAAA DLGKNVANKA  1440
IGGLNSMIGG INKISKAITD KNLIKPIPTL STGTLAGKGV ATDNSGALTQ PTFAVLNDRG  1500
SGNAPGGGVQ EVIHRADGTF HAPQGRDVVV PLGVGDSVIN ANDTLKLQRM GVLPKFHGGT  1560
KKKKWMEQVT ENLGKKAGDF GSKAKNTAHN IKKGAEEMVE AAGDKIKDGA SWLGDKIGDV  1620
WDYVQHPGKL VNKVMSGLNI NFGGGANATV KIAKGAYSLL KKKLVDKVKS WFEDFGGGGD  1680
GSYLFDHPIW QRFGSYTGGL NFNGGRHYGI DFQMPTGTNI YAVKGGIADK VWTDYGGGNS  1740
IQIKTGANEW NWYMHLSKQL ARQGQRIKAG QLIGKSGATG NFVRGAHLHF QLMQGSHPGN  1800
DTAKDPEKWL KSLKGSGVRS GSGVNKAASA WAGDIRRAAK RMGVNVTSGD VGNIISLIQH  1860
ESGGNAGITQ SSALRDINVL QGNPAKGLLQ YIPQTFRHYA VRGHNNIYSG YDQLLAFFNN  1920
SYWRSQFNPR GGWSPSGPRR YANGGLITKH QLAEVGEGDK QEMVIPLTRR KRAIQLTEQV  1980
MRIIGMDGKP NNITVNNDTS TVEKLLKQIV MLSDKGNKLT DALIQTVSSQ DNNLGSNDAI  2040
RGLEKILSKQ SGHRANANNY MGGLTN                                     2066
```